US007083931B2

(12) United States Patent
Gurtu

(10) Patent No.: US 7,083,931 B2
(45) Date of Patent: Aug. 1, 2006

(54) ***RENILLA* GFP MUTANTS WITH INCREASED FLUORESCENT INTENSITY AND SPECTRAL SHIFT**

(75) Inventor: Vanessa Elaine Gurtu, Carlsbad, CA (US)

(73) Assignee: Stratagene California, La Jolla, CA (US)

( * ) Notice: Subject to any disclaimer, the term of this patent is extended or adjusted under 35 U.S.C. 154(b) by 211 days.

(21) Appl. No.: 10/815,337

(22) Filed: Apr. 1, 2004

(65) Prior Publication Data

US 2005/0014223 A1 Jan. 20, 2005

Related U.S. Application Data

(60) Provisional application No. 60/460,432, filed on Apr. 4, 2003.

(51) Int. Cl.

| | |
|---|---|
| ***C12Q 1/68*** | (2006.01) |
| ***G01N 33/66*** | (2006.01) |
| ***C12P 21/02*** | (2006.01) |
| ***C12N 5/10*** | (2006.01) |
| ***C07K 14/435*** | (2006.01) |
| ***C07H 21/04*** | (2006.01) |

(52) U.S. Cl. .......................... 435/6; 435/7.1; 435/69.1; 435/252.3; 435/254.11; 435/325; 530/350; 536/23.5

(58) Field of Classification Search ..................... None
See application file for complete search history.

(56) References Cited

U.S. PATENT DOCUMENTS

| | | | | |
|---|---|---|---|---|
| 5,625,048 | A | 4/1997 | Tsien et al. | 536/23.4 |
| 5,777,079 | A | 7/1998 | Tsien et al. | 530/350 |
| 5,804,387 | A | 9/1998 | Cormack et al. | 435/6 |
| 5,874,304 | A | 2/1999 | Zolotukhin et al. | 435/366 |
| 5,968,738 | A | 10/1999 | Anderson et al. | 435/6 |
| 5,968,750 | A | 10/1999 | Zolotukhin et al. | 435/6 |
| 6,172,188 | B1 | 1/2001 | Thastrup et al. | 530/350 |
| 6,232,107 | B1 | 5/2001 | Bryan et al. | 435/189 |
| 2002/0064842 | A1 | 5/2002 | Sorge et al. | 435/183 |
| 2002/0132318 | A1 | 9/2002 | Zhao et al. | 435/183 |

FOREIGN PATENT DOCUMENTS

| | | |
|---|---|---|
| WO | WO 97/11094 | 3/1997 |
| WO | WO 97/20078 | 6/1997 |
| WO | WO 97/42320 | 11/1997 |
| WO | WO 98/06737 | 2/1998 |
| WO | WO 98/21355 | 5/1998 |
| WO | WO 01/64843 A1 | 9/2001 |
| WO | WO 01/68824 A2 | 9/2001 |
| WO | WO 02/048174 A2 | 6/2002 |
| WO | WO 03/033650 A2 | 4/2003 |

OTHER PUBLICATIONS

Chalfie, et al.; "Green Fluorescent Protein as a Marker for Gene Expression"; (1994); *Science*; 263: 802-805.

Tsien; "The Green Fluorescent Protein"; (1998); *Annu. Rev. Biochem.*; 67: 509-544.

Ward; "Energy Transfer Processes in Bioluminescence"; (1979); *Photochem. Photobiol. Rev.*; 4: 1-57.

Ward, et al.; "Spectral Perturbations of the Aequorea Green-Fluorescent Protein"; (1982); *Photochem. Photobiol.*; 35: 803-808.

Heim, et al., "Improved Green Fluorescence"; (1995); *Nature*; 373: 663-664.

Chalfie; "Green Fluorescent Protein"; (1995); *Photochemistry and Photobiology*; 62(4): 651-656.

Ehrig, et al.; "Green-fluorescent protein mutants with altered fluorescence excitation spectra"; (1995); *FEBS Lett.*; 367: 163-166.

Surpin, et al.; "Development of Monoclonal Antibodies to Aequorea Green-Fluorescent Protein and their Cross Reaction with Renilla Green-Fluorescent Protein"; (1987); *Photochem. Photobiol.*; 45(Supp.): 95S.

Delagrave, et al.; "Red-Shifted Excitation Mutants of the Green Fluorescent Protein"; (1995); *Biotechnology*; 13: 151-154.

Yang, et al.; "Dual color microscopic imagery of cells expressing the green fluorescent protein and a red-shifted variant"; (1996); *Gene*; 173: 19-23.

Ward and Cormier; "An Energy Transfer Protein in Coelenterate Bioluminescence"; *The Journal of Biological Chemistry*; (1979); 254 (3): 781-788.

Copy of International Search Report dated Aug. 18, 2004.

*Primary Examiner*—Robert A. Wax
(74) *Attorney, Agent, or Firm*—Kathlinee M. Williams; Edward Angell Palmer & Dodge, LLP

(57) ABSTRACT

The present invention provides a polynucleotides encoding mutants of green fluorescent protein from *Renilla reniformis*, including humanized sequences which permit enhanced expression of the encoded polypeptides in mammalian cells.

29 Claims, 40 Drawing Sheets

Figure 2. Expression of hrGFP wild-type or hrGFP GM2 Mutant in CHO Cells hrGFP wild-type hrGFP GM2

```
atg gtg agc aag cag atc ctg aag aac acc ggc ctg cag gag atc atg         48
Met Val Ser Lys Gln Ile Leu Lys Asn Thr Gly Leu Gln Glu Ile Met
1               5                   10                  15
agc ttc aag gtg aac ctg gag ggc gtg gtg aac aac cac gtg ttc acc         96
Ser Phe Lys Val Asn Leu Glu Gly Val Val Asn Asn His Val Phe Thr
            20                  25                  30
atg gag ggc tgc ggc aag ggc aac atc ctg ttc ggc aac cag ctg gtg        144
Met Glu Gly Cys Gly Lys Gly Asn Ile Leu Phe Gly Asn Gln Leu Val
        35                  40                  45
cag atc cgc gtg acc aag ggc gcc ccc ctg ccc ttc gcc ttc gac atc        192
Gln Ile Arg Val Thr Lys Gly Ala Pro Leu Pro Phe Ala Phe Asp Ile
    50                  55                  60
ctg agc ccc gcc ttc cag tac ggc aac cgc acc ttc acc aag tac ccc        240
Leu Ser Pro Ala Phe Gln Tyr Gly Asn Arg Thr Phe Thr Lys Tyr Pro
65                  70                  75                  80
gag gac atc agc gac ttc ttc atc cag agc ttc ccc gcc ggc ttc gtg        288
Glu Asp Ile Ser Asp Phe Phe Ile Gln Ser Phe Pro Ala Gly Phe Val
                85                  90                  95
tac gag cgc acc ctg cgc tac gag gac ggc ggc ctg gtg gag atc cgc        336
Tyr Glu Arg Thr Leu Arg Tyr Glu Asp Gly Gly Leu Val Glu Ile Arg
            100                 105                 110
agc gac atc aac ctg atc gag gag atg ttc gtg tac cgc gtg gag tac        384
Ser Asp Ile Asn Leu Ile Glu Glu Met Phe Val Tyr Arg Val Glu Tyr
        115                 120                 125
aag ggc cgc aac ttc ccc aac gac ggc ccc gtg atg aag aag acc atc        432
Lys Gly Arg Asn Phe Pro Asn Asp Gly Pro Val Met Lys Lys Thr Ile
    130                 135                 140
acc ggc ctg cag ccc agc ttc gag gtg gtg tac atg aac gac ggc gtg        480
Thr Gly Leu Gln Pro Ser Phe Glu Val Val Tyr Met Asn Asp Gly Val
145                 150                 155                 160
ctg gtg ggc cag gtg atc ctg gtg tac cgc ctg aac agc ggc aag ttc        528
Leu Val Gly Gln Val Ile Leu Val Tyr Arg Leu Asn Ser Gly Lys Phe
                165                 170                 175
tac agc tgc cac atg cgc acc ctg atg aag agc aag ggc gtg gtg aag        576
Tyr Ser Cys His Met Arg Thr Leu Met Lys Ser Lys Gly Val Val Lys
            180                 185                 190
gac ttc ccc gag tac cac ttc atc cag cac cgc ctg gag aag acc tac        624
Asp Phe Pro Glu Tyr His Phe Ile Gln His Arg Leu Glu Lys Thr Tyr
        195                 200                 205
gtg gag gac ggc ggc ttc gtg gag cag cac gag acc gcc atc gcc cag        672
Val Glu Asp Gly Gly Phe Val Glu Gln His Glu Thr Ala Ile Ala Gln
    210                 215                 220
ctg acc agc ctg ggc aag ccc ctg ggc agc ctg cac gag tgg gtg taa        720
Leu Thr Ser Leu Gly Lys Pro Leu Gly Ser Leu His Glu Trp Val SEQ ID NO:1
225                 230                 235                     SEQ ID NO:2
```

Fig. 4

```
atg gtg agc aag cag atc ctg aag aac acc ggc ctg cag gag atc atg          48
Met Val Ser Lys Gln Ile Leu Lys Asn Thr Gly Leu Gln Glu Ile Met
1               5                   10                  15
agc ttc aag gtg aac ctg gag ggc gtg gtg aac aac cac gtg ttc acc          96
Ser Phe Lys Val Asn Leu Glu Gly Val Val Asn Asn His Val Phe Thr
            20                  25                  30
atg gag ggc tgc ggc aag ggc aac atc ctg tta ggc aac cag ctg gtg         144
Met Glu Gly Cys Gly Lys Gly Asn Ile Leu Leu Gly Asn Gln Leu Val
        35                  40                  45
cag atc cgc gtg acc aag ggc gcc ccc ctg ccc ttc gcc ttc gac atc         192
Gln Ile Arg Val Thr Lys Gly Ala Pro Leu Pro Phe Ala Phe Asp Ile
    50                  55                  60
ctg agc ccc gcc ttc cag tac ggc aac cgc acc ttc acc aag tac ccc         240
Leu Ser Pro Ala Phe Gln Tyr Gly Asn Arg Thr Phe Thr Lys Tyr Pro
65                  70                  75                  80
gag gac atc agc gac ttc ttc atc cag agc ttc ccc gcc ggc ttc gtg         288
Glu Asp Ile Ser Asp Phe Phe Ile Gln Ser Phe Pro Ala Gly Phe Val
                85                  90                  95
tac gag cgc acc ctg cgc tac gag gac ggc ggc ctg gtg gag atc cgc         336
Tyr Glu Arg Thr Leu Arg Tyr Glu Asp Gly Gly Leu Val Glu Ile Arg
            100                 105                 110
agc gac atc aac ctg atc gag gag atg ttc gtg tac cgc gtg gag tac         384
Ser Asp Ile Asn Leu Ile Glu Glu Met Phe Val Tyr Arg Val Glu Tyr
        115                 120                 125
aag ggc cgc aac ttc ccc aac gac ggc ccc gtg atg aag aag acc atc         432
Lys Gly Arg Asn Phe Pro Asn Asp Gly Pro Val Met Lys Lys Thr Ile
    130                 135                 140
acc ggc ctg cag ccc agc ttc gag gtg gtg tac atg aac gac ggc gtg         480
Thr Gly Leu Gln Pro Ser Phe Glu Val Val Tyr Met Asn Asp Gly Val
145                 150                 155                 160
ctg gtg ggc cag gtg atc ctg gtg tac cgc ctg aac agc ggc aag ttc         528
Leu Val Gly Gln Val Ile Leu Val Tyr Arg Leu Asn Ser Gly Lys Phe
                165                 170                 175
tac agc tgc cac atg cgc acc ctg atg aag agc aag ggc gtg gtg aag         576
Tyr Ser Cys His Met Arg Thr Leu Met Lys Ser Lys Gly Val Val Lys
            180                 185                 190
gac ttc ccc gag tac cac ttc atc cag cac cgc ctg gag aag acc tac         624
Asp Phe Pro Glu Tyr His Phe Ile Gln His Arg Leu Glu Lys Thr Tyr
        195                 200                 205
gtg gag gac ggc ggc ttc gtg gag cag cac gag acc gcc atc gcc cag         672
Val Glu Asp Gly Gly Phe Val Glu Gln His Glu Thr Ala Ile Ala Gln
    210                 215                 220
ctg acc agc ctg ggc aag ccc ctg ggc agc ctg cac gag tgg gtg taa         720
Leu Thr Ser Leu Gly Lys Pro Leu Gly Ser Leu His Glu Trp Val SEQ ID NO:3
225                 230                 235                     SEQ ID NO:4
```

Fig. 5

```
atg gtg agc aag cag atc ctg aag aac acc ggc ctg cag gag atc atg        48
Met Val Ser Lys Gln Ile Leu Lys Asn Thr Gly Leu Gln Glu Ile Met
1               5                   10                  15
agc ttc aag gtg aac ctg gag ggc gtg gtg aac aac cac gtg ttc acc        96
Ser Phe Lys Val Asn Leu Glu Gly Val Val Asn Asn His Val Phe Thr
            20                  25                  30
atg gag ggc tgc ggc aag ggc aac atc ctg ttc ggc aac cag ctg gtg       144
Met Glu Gly Cys Gly Lys Gly Asn Ile Leu Phe Gly Asn Gln Leu Val
        35                  40                  45
cag atc cgc gtg acc aag ggc gcc ccc ctg ccc ttc gcc ttc gac atc       192
Gln Ile Arg Val Thr Lys Gly Ala Pro Leu Pro Phe Ala Phe Asp Ile
    50                  55                  60
ctg agc ccc gcc ttc cag tac ggc aac cgc acc ttc acc aag tac ccc       240
Leu Ser Pro Ala Phe Gln Tyr Gly Asn Arg Thr Phe Thr Lys Tyr Pro
65                  70                  75                  80
gag gac atc agc gac ttc ttc atc cag agc ttc ccc gcc ggc ttc gtg       288
Glu Asp Ile Ser Asp Phe Phe Ile Gln Ser Phe Pro Ala Gly Phe Val
                85                  90                  95
tac gag cgc acc ctg cgc tac gag gac ggc ggc ctg gtg gag atc cgc       336
Tyr Glu Arg Thr Leu Arg Tyr Glu Asp Gly Gly Leu Val Glu Ile Arg
            100                 105                 110
agc gac atc aac ctg atc gag ggg atg ttc gtg tac cgc gtg gag tac       384
Ser Asp Ile Asn Leu Ile Glu Gly Met Phe Val Tyr Arg Val Glu Tyr
        115                 120                 125
aag ggc cgc aac ttc ccc aac gac ggc ccc gtg atg aag aag acc atc       432
Lys Gly Arg Asn Phe Pro Asn Asp Gly Pro Val Met Lys Lys Thr Ile
    130                 135                 140
acc ggc ctg cag ccc agc ttc gag gtg gtg tac atg aac gac ggc gtg       480
Thr Gly Leu Gln Pro Ser Phe Glu Val Val Tyr Met Asn Asp Gly Val
145                 150                 155                 160
ctg gtg ggc cag gtg atc ctg gtg tac cgc ctg aac agc ggc aag ttc       528
Leu Val Gly Gln Val Ile Leu Val Tyr Arg Leu Asn Ser Gly Lys Phe
                165                 170                 175
tac agc tgc cac atg cgc acc ctg atg aag agc aag ggc gtg gtg aag       576
Tyr Ser Cys His Met Arg Thr Leu Met Lys Ser Lys Gly Val Val Lys
            180                 185                 190
gac ttc ccc gag tac cac ttc atc cag cac cgc ctg gag aag acc tac       624
Asp Phe Pro Glu Tyr His Phe Ile Gln His Arg Leu Glu Lys Thr Tyr
        195                 200                 205
gtg gag gac ggc ggc ttc gta gag cag cac gag acc gcc atc gcc cag       672
Val Glu Asp Gly Gly Phe Val Glu Gln His Glu Thr Ala Ile Ala Gln
    210                 215                 220
ctg acc agc ctg ggc aag ccc ctg ggc agc ctg cac gag tgg gtg taa       720
Leu Thr Ser Leu Gly Lys Pro Leu Gly Ser Leu His Glu Trp Val SEQ ID NO:5
225                 230                 235                         SEQ ID NO:6
```

Fig. 6

```
atg gtg agc aag cag atc ctg aag aac acc ggc ctg cag gag atc atg       48
Met Val Ser Lys Gln Ile Leu Lys Asn Thr Gly Leu Gln Glu Ile Met
1               5                   10                  15
agc ttc aag gtg aac ctg gag ggc gtg gtg aac aac cac gtg ttc acc       96
Ser Phe Lys Val Asn Leu Glu Gly Val Val Asn Asn His Val Phe Thr
            20                  25                  30
atg gag ggc tgc ggc aag ggc aac atc ctg ttc ggc aac cag ctg gtg      144
Met Glu Gly Cys Gly Lys Gly Asn Ile Leu Phe Gly Asn Gln Leu Val
        35                  40                  45
cag atc cgc gtg acc aag ggc gcc ccc ctg ccc ttc gcc ttc gac atc      192
Gln Ile Arg Val Thr Lys Gly Ala Pro Leu Pro Phe Ala Phe Asp Ile
    50                  55                  60
ctg agc ccc gcc ttc cag tac ggc aac cgc acc ttc acc aag tac ccc      240
Leu Ser Pro Ala Phe Gln Tyr Gly Asn Arg Thr Phe Thr Lys Tyr Pro
65                  70                  75                  80
gag gac atc agc gac ttc ttc atc cag agc ttc ccc gcc ggc ttc gtg      288
Glu Asp Ile Ser Asp Phe Phe Ile Gln Ser Phe Pro Ala Gly Phe Val
                85                  90                  95
tac gag cgc acc atg cgc tac gag gac ggc ggc ctg gtg gag atc cgc      336
Tyr Glu Arg Thr Met Arg Tyr Glu Asp Gly Gly Leu Val Glu Ile Arg
            100                 105                 110
agc gac atc aac ctg atc gag gag atg ttc gtg tac cgc gtg gag tac      384
Ser Asp Ile Asn Leu Ile Glu Glu Met Phe Val Tyr Arg Val Glu Tyr
        115                 120                 125
aag ggc cgc aac ttc ccc aac gac ggc ccc gtg atg aag aag acc atc      432
Lys Gly Arg Asn Phe Pro Asn Asp Gly Pro Val Met Lys Lys Thr Ile
    130                 135                 140
acc ggc ctg cag ccc agc ttc gag gtg gtg tac atg aac gac ggc gtg      480
Thr Gly Leu Gln Pro Ser Phe Glu Val Val Tyr Met Asn Asp Gly Val
145                 150                 155                 160
ctg gtg ggc cag gtg atc ctg gtg tac cgc ctg aac agc ggc aag ttc      528
Leu Val Gly Gln Val Ile Leu Val Tyr Arg Leu Asn Ser Gly Lys Phe
                165                 170                 175
tac agc tgc cac atg cgc acc ctg atg aag agc aag ggc gtg gtg aag      576
Tyr Ser Cys His Met Arg Thr Leu Met Lys Ser Lys Gly Val Val Lys
            180                 185                 190
gac ttc ccc gag tac cac ttc atc cag cac cgc ctg gag aag acc tac      624
Asp Phe Pro Glu Tyr His Phe Ile Gln His Arg Leu Glu Lys Thr Tyr
        195                 200                 205
gtg gag gac ggc ggc ttc gtg gag cag cac gag acc gcc atc gcc cag      672
Val Glu Asp Gly Gly Phe Val Glu Gln His Glu Thr Ala Ile Ala Gln
    210                 215                 220
ctg acc agc ctg ggc aag ccc ctg ggc agc ctg cac gag tgg gtg taa      720
Leu Thr Ser Leu Gly Lys Pro Leu Gly Ser Leu His Glu Trp Val SEQ ID NO:7
225                 230                 235                     SEQ ID NO:8
```

Fig. 7

```
atg gtg agc aag cag atc ctg aag aac acc ggc ctg cag gag atc atg       48
Met Val Ser Lys Gln Ile Leu Lys Asn Thr Gly Leu Gln Glu Ile Met
1               5                   10                  15
agc ttc aag gtg aac ctg gag ggc gtg gtg aac aac cac gtg ttc acc       96
Ser Phe Lys Val Asn Leu Glu Gly Val Val Asn Asn His Val Phe Thr
            20                  25                  30
atg gag ggc tgc ggc aag ggc aac atc ctg tcc ggc aac cag ctg gtg      144
Met Glu Gly Cys Gly Lys Gly Asn Ile Leu Ser Gly Asn Gln Leu Val
        35                  40                  45
cag atc cgc gtg acc aag ggc gcc ccc ctg ccc ttc gcc ttc gac atc      192
Gln Ile Arg Val Thr Lys Gly Ala Pro Leu Pro Phe Ala Phe Asp Ile
    50                  55                  60
ctg agc ccc gcc ttc cag tac ggc aac cgc acc ttc acc aag tac ccc      240
Leu Ser Pro Ala Phe Gln Tyr Gly Asn Arg Thr Phe Thr Lys Tyr Pro
65                  70                  75                  80
gag gac atc agc gac ttc ttc atc cag agc ttc ccc gcc ggc ttc gtg      288
Glu Asp Ile Ser Asp Phe Phe Ile Gln Ser Phe Pro Ala Gly Phe Val
                85                  90                  95
tac gag cgc acc ctg cgc tac gag gac ggc ggc ctg gtg gag atc cgc      336
Tyr Glu Arg Thr Leu Arg Tyr Glu Asp Gly Gly Leu Val Glu Ile Arg
            100                 105                 110
agc gac atc aac ctg atc gag gag atg ttc gtg tac cgc gtg gag tac      384
Ser Asp Ile Asn Leu Ile Glu Glu Met Phe Val Tyr Arg Val Glu Tyr
        115                 120                 125
aag ggc cgc aac ttc ccc aac gac ggc ccc gtg atg aag aag acc atc      432
Lys Gly Arg Asn Phe Pro Asn Asp Gly Pro Val Met Lys Lys Thr Ile
    130                 135                 140
acc ggc ctg cag ccc agc ttc gag gtg gtg tac atg aac gac ggc gtg      480
Thr Gly Leu Gln Pro Ser Phe Glu Val Val Tyr Met Asn Asp Gly Val
145                 150                 155                 160
ctg gtg ggc cag gtg atc ctg gtg tac cgc ctg aac agc ggc aag ttc      528
Leu Val Gly Gln Val Ile Leu Val Tyr Arg Leu Asn Ser Gly Lys Phe
                165                 170                 175
tac agc tgc cac atg cgc acc ctg atg aag agc aag ggc gtg gtg aag      576
Tyr Ser Cys His Met Arg Thr Leu Met Lys Ser Lys Gly Val Val Lys
            180                 185                 190
gac ttc ccc gag tac cac ttc atc cag cac cgc ctg gag aag acc tac      624
Asp Phe Pro Glu Tyr His Phe Ile Gln His Arg Leu Glu Lys Thr Tyr
        195                 200                 205
gtg gag gac ggc ggc ttc gtg gag cag cac gag acc gcc atc gcc cag      672
Val Glu Asp Gly Gly Phe Val Glu Gln His Glu Thr Ala Ile Ala Gln
    210                 215                 220
ctg acc agc ctg ggc aag ccc ctg ggc agc ctg cac gag tgg gtg taa      720
Leu Thr Ser Leu Gly Lys Pro Leu Gly Ser Leu His Glu Trp Val SEQ ID NO:9
225                 230                 235                         SEQ ID NO:10
```

Fig. 8

```
atg gtg agc aag cag atc ctg aag aac acc ggc ctg cag gag atc atg        48
Met Val Ser Lys Gln Ile Leu Lys Asn Thr Gly Leu Gln Glu Ile Met
1               5                   10                  15
agc ttc aag gtg aac ctg gag ggc gtg gtg aac aac cac gtg ttc acc        96
Ser Phe Lys Val Asn Leu Glu Gly Val Val Asn Asn His Val Phe Thr
            20                  25                  30
atg gag ggc tgc ggc aag ggc aac atc ctg ttc ggc aac cag ctg gtg       144
Met Glu Gly Cys Gly Lys Gly Asn Ile Leu Phe Gly Asn Gln Leu Val
        35                  40                  45
cag atc cgc gtg acc aag ggc gcc ccc ctg ccc ttc gcc ttc gac atc       192
Gln Ile Arg Val Thr Lys Gly Ala Pro Leu Pro Phe Ala Phe Asp Ile
    50                  55                  60
ctg agc ccc gcc ttc cag tac ggc aac cgc acc ttc acc aag tac ccc       240
Leu Ser Pro Ala Phe Gln Tyr Gly Asn Arg Thr Phe Thr Lys Tyr Pro
65                  70                  75                  80
gag gac atc agc gac ttc ttc atc cag agc ttc ccc gcc ggc ttc gtg       288
Glu Asp Ile Ser Asp Phe Phe Ile Gln Ser Phe Pro Ala Gly Phe Val
                85                  90                  95
tac gag cgc acc ctg ctc tac gag gac ggc ggc ctg gtg gag atc cgc       336
Tyr Glu Arg Thr Leu Cys Tyr Glu Asp Gly Gly Leu Val Glu Ile Arg
            100                 105                 110
agc gac atc aac ctg atc gag gag atg ttc gtg tac cac gtg gag tac       384
Ser Asp Ile Asn Leu Ile Glu Glu Met Phe Val Tyr His Val Glu Tyr
        115                 120                 125
aag ggc cgc aac ttc ccc aac gac ggc ccc gtg atg aag aag acc atc       432
Lys Gly Arg Asn Phe Pro Asn Asp Gly Pro Val Met Lys Lys Thr Ile
    130                 135                 140
acc ggc ctg cag ccc agc ttc gag gtg gtg tac atg aac gac ggc gtg       480
Thr Gly Leu Gln Pro Ser Phe Glu Val Val Tyr Met Asn Asp Gly Val
145                 150                 155                 160
ctg gtg ggc cag gtg atc ctg gtg tac cgc ctg aac agc ggc aag ttc       528
Leu Val Gly Gln Val Ile Leu Val Tyr Arg Leu Asn Ser Gly Lys Phe
                165                 170                 175
tac agc tgc cac atg cgc acc ctg atg aag agc aag ggc gtg gtg aag       576
Tyr Ser Cys His Met Arg Thr Leu Met Lys Ser Lys Gly Val Val Lys
            180                 185                 190
gac ttc ccc gag tac cac ttc atc cag cac cgc ctg gag aag acc tac       624
Asp Phe Pro Glu Tyr His Phe Ile Gln His Arg Leu Glu Lys Thr Tyr
        195                 200                 205
gtg gag gac ggc ggc ttc gtg gag cag cac gag acc gcc atc gcc cag       672
Val Glu Asp Gly Gly Phe Val Glu Gln His Glu Thr Ala Ile Ala Gln
    210                 215                 220
ctg acc agc ctg ggc aat ccc ctg ggc agc ctg cac gag tgg gtg taa       720
Leu Thr Ser Leu Gly Tyr Pro Leu Gly Ser Leu His Glu Trp Val SEQ ID NO:11
225                 230                 235                     SEQ ID NO:12
```

Fig. 9

```
atg gtg agc aag cag atc ctg aag aac acc ggc ctg cag gag atc atg          48
Met Val Ser Lys Gln Ile Leu Lys Asn Thr Gly Leu Gln Glu Ile Met
1               5                   10                  15
agc ttc aag gtg atc ctg gag ggc gtg gtg aac aac cac gtg ttc acc          96
Ser Phe Lys Val Ile Leu Glu Gly Val Val Asn Asn His Val Phe Thr
            20                  25                  30
atg gag ggc tgc ggc aag ggc aac atc ctg ttc ggc aac cag ctg gtg         144
Met Glu Gly Cys Gly Lys Gly Asn Ile Leu Phe Gly Asn Gln Leu Val
        35                  40                  45
cag atc cgc gtg acc aag ggc gcc ccc ctg ccc ttc gcc ttc gac atc         192
Gln Ile Arg Val Thr Lys Gly Ala Pro Leu Pro Phe Ala Phe Asp Ile
    50                  55                  60
ctg agc ccc gcc ttc cag tac ggc aac cgc acc ttc acc aag tac ccc         240
Leu Ser Pro Ala Phe Gln Tyr Gly Asn Arg Thr Phe Thr Lys Tyr Pro
65                  70                  75                  80
gag gac atc agc gac ttc ttc atc cag agc ttc ccc gcc ggc ttc gtg         288
Glu Asp Ile Ser Asp Phe Phe Ile Gln Ser Phe Pro Ala Gly Phe Val
                85                  90                  95
tac gag cgc acc ctg cgc tac gag gac ggc ggc ctg gtg gag atc cgc         336
Tyr Glu Arg Thr Leu Arg Tyr Glu Asp Gly Gly Leu Val Glu Ile Arg
            100                 105                 110
agc gac atc aac ctg atc gag ggg atg ttc gtg tac cgc gtg gag tac         384
Ser Asp Ile Asn Leu Ile Glu Gly Met Phe Val Tyr Arg Val Glu Tyr
        115                 120                 125
aag ggc cgc aac ttc ccc aac gac ggc ccc gtg atg aag aat acc atc         432
Lys Gly Arg Asn Phe Pro Asn Asp Gly Pro Val Met Lys Asn Thr Ile
    130                 135                 140
acc ggc ctg cag ccc agc ttc gag gtg gtg tac atg aac gac ggc gtg         480
Thr Gly Leu Gln Pro Ser Phe Glu Val Val Tyr Met Asn Asp Gly Val
145                 150                 155                 160
ctg gtg ggc cag gtg atc ctg gtg tac cgc ctg aac agc ggc aag ttc         528
Leu Val Gly Gln Val Ile Leu Val Tyr Arg Leu Asn Ser Gly Lys Phe
                165                 170                 175
tac agc tgc cac atg cgc acc ctg atg aag agc aag ggc gtg gtg aag         576
Tyr Ser Cys His Met Arg Thr Leu Met Lys Ser Lys Gly Val Val Lys
            180                 185                 190
gac ttc ccc gag tac cac ttc atc cag cac cgc ctg gag aag acc tac         624
Asp Phe Pro Glu Tyr His Phe Ile Gln His Arg Leu Glu Lys Thr Tyr
        195                 200                 205
gtg gag gac ggc ggc ttc gtg gag cag cac gag acc gcc atc gcc cag         672
Val Glu Asp Gly Gly Phe Val Glu Gln His Glu Thr Ala Ile Ala Gln
    210                 215                 220
ctg acc agc ctg ggc aag ccc ctg ggc agc ctg cac gag tgg gtg taa         720
Leu Thr Ser Leu Gly Lys Pro Leu Gly Ser Leu His Glu Trp Val SEQ ID NO:13
225                 230                 235                     SEQ ID NO:14
```

Fig. 10

```
atg gtg agc aag cag atc ctg aag aac acc ggc ctg cag gag atc atg        48
Met Val Ser Lys Gln Ile Leu Lys Asn Thr Gly Leu Gln Glu Ile Met
1               5                   10                  15
agc ttc aag gtg aac ctg gag ggc gtg gtg aac aac cac gtg ttc acc        96
Ser Phe Lys Val Asn Leu Glu Gly Val Val Asn Asn His Val Phe Thr
            20                  25                  30
atg gag ggc tgc ggc aag ggc aac atc ctg ttc ggc aac cag ctg gtg       144
Met Glu Gly Cys Gly Lys Gly Asn Ile Leu Phe Gly Asn Gln Leu Val
        35                  40                  45
cag atc cgc gtg acc aag ggc gcc ccc ctg ccc ttc gcc ttc gac atc       192
Gln Ile Arg Val Thr Lys Gly Ala Pro Leu Pro Phe Ala Phe Asp Ile
    50                  55                  60
ctg agc ccc gcc ttc cag tac ggc aac cgc acc ttc acc aag tac ccc       240
Leu Ser Pro Ala Phe Gln Tyr Gly Asn Arg Thr Phe Thr Lys Tyr Pro
65                  70                  75                  80
gag gac atc agc gac ttc ttc atc cag agc ttc ccc gcc ggc ttc gtg       288
Glu Asp Ile Ser Asp Phe Phe Ile Gln Ser Phe Pro Ala Gly Phe Val
                85                  90                  95
tac gag cgc acc ctg cgc ttc gag gac ggc ggc ctg gtg gag atc cgc       336
Tyr Glu Arg Thr Leu Arg Phe Glu Asp Gly Gly Leu Val Glu Ile Arg
            100                 105                 110
agc gac atc aac ctg atc gag gag atg ttc gtg tac cgc gtg gag tac       384
Ser Asp Ile Asn Leu Ile Glu Glu Met Phe Val Tyr Arg Val Glu Tyr
        115                 120                 125
aag ggc cgc aac ttc ccc aac gac ggc ccc gtg atg aag aag acc atc       432
Lys Gly Arg Asn Phe Pro Asn Asp Gly Pro Val Met Lys Lys Thr Ile
    130                 135                 140
acc ggc ctg cag ccc agc ttc gag gtg gtg tac atg aac gac ggc gtg       480
Thr Gly Leu Gln Pro Ser Phe Glu Val Val Tyr Met Asn Asp Gly Val
145                 150                 155                 160
ctg gtg ggc cag gtg atc ctg gtg tac cgc ctg aac agc ggc aag ttc       528
Leu Val Gly Gln Val Ile Leu Val Tyr Arg Leu Asn Ser Gly Lys Phe
                165                 170                 175
tac agc tgc cac atg cgc acc ctg atg aag agc aag ggc gtg gtg aag       576
Tyr Ser Cys His Met Arg Thr Leu Met Lys Ser Lys Gly Val Val Lys
            180                 185                 190
gac ttc ccc gag tac cac ttc atc cag cac cgc ctg gag aag acc tac       624
Asp Phe Pro Glu Tyr His Phe Ile Gln His Arg Leu Glu Lys Thr Tyr
        195                 200                 205
gtg gag gac ggc ggc ttc gtg gag cag cac gag acc gcc atc gcc cag       672
Val Glu Asp Gly Gly Phe Val Glu Gln His Glu Thr Ala Ile Ala Gln
    210                 215                 220
ctg acc agc ctg ggc aag ccc ctg ggc agc ctg cac gag tgg gtg taa       720
Leu Thr Ser Leu Gly Lys Pro Leu Gly Ser Leu His Glu Trp Val SEQ ID NO:15
225                 230                 235                         SEQ ID NO:16
```

Fig. 11

```
atg gtg agc aag cag atc ctg aag aac acc ggc ctg cag gag atc atg        48
Met Val Ser Lys Gln Ile Leu Lys Asn Thr Gly Leu Gln Glu Ile Met
1               5                   10                  15
agc ttc aag gtg aac ctg gag ggc gtg gtg aac aac cac gtg ttc ccc        96
Ser Phe Lys Val Asn Leu Glu Gly Val Val Asn Asn His Val Phe Pro
            20                  25                  30
atg gag ggc tgc ggc aag ggc aac atc ctg ttc ggc aac cag ctg gtg       144
Met Glu Gly Cys Gly Lys Gly Asn Ile Leu Phe Gly Asn Gln Leu Val
        35                  40                  45
cag atc cgc gtg acc aag ggc gcc ccc ctg ccc ttc gcc ttc gac atc       192
Gln Ile Arg Val Thr Lys Gly Ala Pro Leu Pro Phe Ala Phe Asp Ile
    50                  55                  60
ctg agc ccc gcc ttc cag tac ggc aac cgc acc ttc acc aag tac ccc       240
Leu Ser Pro Ala Phe Gln Tyr Gly Asn Arg Thr Phe Thr Lys Tyr Pro
65                  70                  75                  80
gag gac atc agc gac ttc ttc atc cag agc ttc ccc gcc ggc ttc gtg       288
Glu Asp Ile Ser Asp Phe Phe Ile Gln Ser Phe Pro Ala Gly Phe Val
                85                  90                  95
tac gag cgc acc ctg cgc ttc gag gac ggc ggc ctg gtg gag atc cgc       336
Tyr Glu Arg Thr Leu Arg Phe Glu Asp Gly Gly Leu Val Glu Ile Arg
            100                 105                 110
agc gac atc aac ctg atc gag gag atg ttc gtg tac cgc gtg gag tac       384
Ser Asp Ile Asn Leu Ile Glu Glu Met Phe Val Tyr Arg Val Glu Tyr
        115                 120                 125
aag ggc cgc aac ttc ccc aac gac ggc ccc gtg atg aag aag acc atc       432
Lys Gly Arg Asn Phe Pro Asn Asp Gly Pro Val Met Lys Lys Thr Ile
    130                 135                 140
acc ggc ctg cag ccc agc ttc gag gtg gtg tac atg aac gac ggc gtg       480
Thr Gly Leu Gln Pro Ser Phe Glu Val Val Tyr Met Asn Asp Gly Val
145                 150                 155                 160
ctg gtg ggc cag gtg atc ctg gtg tac cgc ctg aac agc ggc aag ttc       528
Leu Val Gly Gln Val Ile Leu Val Tyr Arg Leu Asn Ser Gly Lys Phe
                165                 170                 175
tac agc tgc cac atg cgc acc ctg atg aag agc aag ggc gtg gtg aag       576
Tyr Ser Cys His Met Arg Thr Leu Met Lys Ser Lys Gly Val Val Lys
            180                 185                 190
gac ttc ccc gag tac cac ttc atc cag cac cgc ctg gag aag acc tac       624
Asp Phe Pro Glu Tyr His Phe Ile Gln His Arg Leu Glu Lys Thr Tyr
        195                 200                 205
gtg gag gac ggc ggc ttc gtg gag cag cac gag acc gcc atc gcc cag       672
Val Glu Asp Gly Gly Phe Val Glu Gln His Glu Thr Ala Ile Ala Gln
    210                 215                 220
ctg acc agc ctg ggc aag ccc ctg ggc agc ctg cac gag tgg gtg taa       720
Leu Thr Ser Leu Gly Lys Pro Leu Gly Ser Leu His Glu Trp Val SEQ ID NO:17
225                 230                 235                     SEQ ID NO:18
```

Fig. 12

```
atg gtg agc aag cag atc ctg aag aac acc ggc ctg cag gag atc atg         48
Met Val Ser Lys Gln Ile Leu Lys Asn Thr Gly Leu Gln Glu Ile Met
1               5                   10                  15
agc ttc aag gtg aac ctg gag ggc gtg gtg aac aac cac gtg ttc acc         96
Ser Phe Lys Val Asn Leu Glu Gly Val Val Asn Asn His Val Phe Thr
            20                  25                  30
atg gag ggc tgc ggc aag ggc aac atc ctg ttc ggc aac cag ctg gtg        144
Met Glu Gly Cys Gly Lys Gly Asn Ile Leu Phe Gly Asn Gln Leu Val
        35                  40                  45
cag atc cgc gtg acc aag ggc gcc ccc ctg ccc ttc gcc ttc gac atc        192
Gln Ile Arg Val Thr Lys Gly Ala Pro Leu Pro Phe Ala Phe Asp Ile
    50                  55                  60
ctg agc ccc gcc ttc cag tac ggc aac cgc acc ttc acc aag tac ccc        240
Leu Ser Pro Ala Phe Gln Tyr Gly Asn Arg Thr Phe Thr Lys Tyr Pro
65                  70                  75                  80
gag gac atc agc gac ttc ttc atc cag agc ttc ccc gcc ggc ttc gtg        288
Glu Asp Ile Ser Asp Phe Phe Ile Gln Ser Phe Pro Ala Gly Phe Val
                85                  90                  95
tac gag cgc acc ctg cgc tac gag gac ggc ggc ctg gtg gag atc cgc        336
Tyr Glu Arg Thr Leu Arg Tyr Glu Asp Gly Gly Leu Val Glu Ile Arg
            100                 105                 110
agc gac atc aac ctg atc gag ggg atg ttc gtg tac cgc gtg gag tac        384
Ser Asp Ile Asn Leu Ile Glu Gly Met Phe Val Tyr Arg Val Glu Tyr
        115                 120                 125
aag ggc cgc aac ttc ccc aac gac ggc ccc gtg atg aag aag acc atc        432
Lys Gly Arg Asn Phe Pro Asn Asp Gly Pro Val Met Lys Lys Thr Ile
    130                 135                 140
acc ggc ctg cag ccc agc ttc gag gtg gtg tac atg aac gac ggc gtg        480
Thr Gly Leu Gln Pro Ser Phe Glu Val Val Tyr Met Asn Asp Gly Val
145                 150                 155                 160
ctg gtg ggc cag gtg atc ctg gtg tac cgc ctg aac agc ggc aag ttc        528
Leu Val Gly Gln Val Ile Leu Val Tyr Arg Leu Asn Ser Gly Lys Phe
                165                 170                 175
tac agc tgc cac atg cgc acc ctg atg aag agc aag ggc gtg gtg aag        576
Tyr Ser Cys His Met Arg Thr Leu Met Lys Ser Lys Gly Val Val Lys
            180                 185                 190
gac ttc ccc gag tac cac ttc atc cag cac cgc ctg gag aag acc tac        624
Asp Phe Pro Glu Tyr His Phe Ile Gln His Arg Leu Glu Lys Thr Tyr
        195                 200                 205
gtg gag gac ggc ggc ttc gtg gag cag cac gag acc gcc atc gcc cag        672
Val Glu Asp Gly Gly Phe Val Glu Gln His Glu Thr Ala Ile Ala Gln
    210                 215                 220
ctg acc agc ctg ggc aag ccc ctg ggc agc ctg cac gag tgg gtg taa        720
Leu Thr Ser Leu Gly Lys Pro Leu Gly Ser Leu His Glu Trp Val   SEQ ID NO:19
225                 230                 235                       SEQ ID NO:20
```

Fig. 13

```
atg gtg agc aag cag atc ctg aag aac acc ggc ctg cag gag atc atg        48
Met Val Ser Lys Gln Ile Leu Lys Asn Thr Gly Leu Gln Glu Ile Met
1               5                   10                  15
agc ttc aag gtg aac ctg gag ggc gtg gtg aac aac cac gtg ttc acc        96
Ser Phe Lys Val Asn Leu Glu Gly Val Val Asn Asn His Val Phe Thr
            20                  25                  30
atg gag ggc tgc ggc aag ggc aac atc ctg tcc ggc aac cag ctg gtg       144
Met Glu Gly Cys Gly Lys Gly Asn Ile Leu Ser Gly Asn Gln Leu Val
        35                  40                  45
cag atc cgc gtg acc aag ggc gcc ccc ctg ccc ttc gcc ttc gac atc       192
Gln Ile Arg Val Thr Lys Gly Ala Pro Leu Pro Phe Ala Phe Asp Ile
    50                  55                  60
ctg agc ccc gcc ttc cag tac ggc aac cgc acc ttc acc aag tac ccc       240
Leu Ser Pro Ala Phe Gln Tyr Gly Asn Arg Thr Phe Thr Lys Tyr Pro
65                  70                  75                  80
gag gac atc agc gac ttc ttc atc cag agc ttc ccc gcc ggc ttc gtg       288
Glu Asp Ile Ser Asp Phe Phe Ile Gln Ser Phe Pro Ala Gly Phe Val
                85                  90                  95
tac gag cgc acc ctg cgc ttc gag gac ggc ggc ctg gtg gag atc cgc       336
Tyr Glu Arg Thr Leu Arg Phe Glu Asp Gly Gly Leu Val Glu Ile Arg
            100                 105                 110
agc gac atc aac ctg atc gag gag atg ttc gag tac cgc gtg gag tac       384
Ser Asp Ile Asn Leu Ile Glu Glu Met Phe Glu Tyr Arg Val Glu Tyr
        115                 120                 125
aag ggc cgc aac ttc ccc aac gac ggc ccc gtg atg aag aag acc atc       432
Lys Gly Arg Asn Phe Pro Asn Asp Gly Pro Val Met Lys Lys Thr Ile
    130                 135                 140
acc ggc ctg cag ccc agc ttc gag gtg gtg tac atg aac gac ggc gtg       480
Thr Gly Leu Gln Pro Ser Phe Glu Val Val Tyr Met Asn Asp Gly Val
145                 150                 155                 160
ctg gtg ggc cag gtg atc ctg gtg tac cgc ctg aac agc ggc aag ttc       528
Leu Val Gly Gln Val Ile Leu Val Tyr Arg Leu Asn Ser Gly Lys Phe
                165                 170                 175
tac agc tgc cac atg cgc acc ctg atg aag agc aag ggc gtg gtg aag       576
Tyr Ser Cys His Met Arg Thr Leu Met Lys Ser Lys Gly Val Val Lys
            180                 185                 190
gac ttc ccc gag tac cac ttc atc cag cac cgc ctg gag aag acc tac       624
Asp Phe Pro Glu Tyr His Phe Ile Gln His Arg Leu Glu Lys Thr Tyr
        195                 200                 205
gtg gag gac ggc ggc ttc gta gag cag cac gag acc gcc atc gcc cag       672
Val Glu Asp Gly Gly Phe Val Glu Gln His Glu Thr Ala Ile Ala Gln
    210                 215                 220
ctg acc agc ctg ggc aag ccc ctg ggc agc ctg cac gag tgg gtg taa       720
Leu Thr Ser Leu Gly Lys Pro Leu Gly Ser Leu His Glu Trp Val SEQ ID NO:21
225                 230                 235                         SEQ ID NO:22
```

Fig. 14

```
atg gtg agc aag cag atc ctg aag aac acc ggc ctg cag gag atc atg         48
Met Val Ser Lys Gln Ile Leu Lys Asn Thr Gly Leu Gln Glu Ile Met
1               5                   10                  15
agc ttc aag gtg aac ctg gag ggc gtg gtg aac aac cac gtg ttc acc         96
Ser Phe Lys Val Asn Leu Glu Gly Val Val Asn Asn His Val Phe Thr
            20                  25                  30
atg gag ggc tgc ggc aag ggc aac atc ctg tcc ggc aac cag ctg gtg        144
Met Glu Gly Cys Gly Lys Gly Asn Ile Leu Ser Gly Asn Gln Leu Val
        35                  40                  45
cag atc cgc gtg acc aag ggc gcc ccc ctg ccc ttc gcc ttc gac atc        192
Gln Ile Arg Val Thr Lys Gly Ala Pro Leu Pro Phe Ala Phe Asp Ile
    50                  55                  60
ctg agc ccc gcc ttc cag tac ggc aac cgc acc ttc acc aag tac ccc        240
Leu Ser Pro Ala Phe Gln Tyr Gly Asn Arg Thr Phe Thr Lys Tyr Pro
65                  70                  75                  80
gag gac atc agc gac ttc ttc atc cag agc ttc ccc gcc ggc ttc gtg        288
Glu Asp Ile Ser Asp Phe Phe Ile Gln Ser Phe Pro Ala Gly Phe Val
                85                  90                  95
tac gag cgc acc ctg cgc ttc gag gac ggc ggc ctg gtg gag atc cgc        336
Tyr Glu Arg Thr Leu Arg Phe Glu Asp Gly Gly Leu Val Glu Ile Arg
            100                 105                 110
agc gac atc aac ctg atc gag gag atg ttc ggg tac cgc gtg gag tac        384
Ser Asp Ile Asn Leu Ile Glu Glu Met Phe Glu Tyr Arg Val Glu Tyr
        115                 120                 125
aag ggc cgc aac ttc ccc aac gac ggc ccc gtg atg aag aag acc atc        432
Lys Gly Arg Asn Phe Pro Asn Asp Gly Pro Val Met Lys Lys Thr Ile
    130                 135                 140
acc ggc ctg cag ccc agc ttc gag gtg gtg tac atg aac gac ggc gtg        480
Thr Gly Leu Gln Pro Ser Phe Glu Val Val Tyr Met Asn Asp Gly Val
145                 150                 155                 160
ctg gtg ggc cag gtg atc ctg gtg tac cgc ctg aac agc ggc aag ttc        528
Leu Val Gly Gln Val Ile Leu Val Tyr Arg Leu Asn Ser Gly Lys Phe
                165                 170                 175
tac agc tgc cac atg cgc acc ctg atg aag agc aag ggc gtg gtg aag        576
Tyr Ser Cys His Met Arg Thr Leu Met Lys Ser Lys Gly Val Val Lys
            180                 185                 190
gac ttc ccc gag tac cac ttc atc cag cac cgc ctg gag aag acc tac        624
Asp Phe Pro Glu Tyr His Phe Ile Gln His Arg Leu Glu Lys Thr Tyr
        195                 200                 205
gtg gag gac ggc ggc ttc gtg gag cag cac gag acc gcc atc gcc cag        672
Val Glu Asp Gly Gly Phe Val Glu Gln His Glu Thr Ala Ile Ala Gln
    210                 215                 220
ctg acc agc ctg ggc aag ccc ctg ggc agc ctg cac gag tgg gtg taa        720
Leu Thr Ser Leu Gly Lys Pro Leu Gly Ser Leu His Glu Trp Val SEQ ID NO:23
225                 230                 235                     SEQ ID NO:24
```

Fig. 15

```
atg gtg agc aag cag atc ctg aag aac acc ggc ctg cag gag atc atg        48
Met Val Ser Lys Gln Ile Leu Lys Asn Thr Gly Leu Gln Glu Ile Met
1               5                   10                  15
agc ttc aag gtg atc ctg gag ggc gtg gtg aac aac cac gtg ttc acc        96
Ser Phe Lys Val Ile Leu Glu Gly Val Val Asn Asn His Val Phe Thr
            20                  25                  30
atg gag ggc tgc ggc aag ggc aac atc ctg ttc ggc aac cag ctg gtg       144
Met Glu Gly Cys Gly Lys Gly Asn Ile Leu Phe Gly Asn Gln Leu Val
        35                  40                  45
cag atc cgc gtg acc aag ggc gcc ccc ctg ccc ttc gcc ttc gac atc       192
Gln Ile Arg Val Thr Lys Gly Ala Pro Leu Pro Phe Ala Phe Asp Ile
    50                  55                  60
ctg agc ccc gcc ttc cag tac ggc aac cgc acc ttc acc aag tac ccc       240
Leu Ser Pro Ala Phe Gln Tyr Gly Asn Arg Thr Phe Thr Lys Tyr Pro
65                  70                  75                  80
gag gac atc agc gac ttc ttc atc cag agc ttc ccc gcc ggc ttc gtg       288
Glu Asp Ile Ser Asp Phe Phe Ile Gln Ser Phe Pro Ala Gly Phe Val
                85                  90                  95
tac gag cgc acc ctg cgc ttc gag gac ggc ggc ctg gtg gag atc cgc       336
Tyr Glu Arg Thr Leu Arg Phe Glu Asp Gly Gly Leu Val Glu Ile Arg
            100                 105                 110
agc gac atc aac ctg atc gag ggg atg ttc gtg tac cgc gtg gag tac       384
Ser Asp Ile Asn Leu Ile Glu Gly Met Phe Val Tyr Arg Val Glu Tyr
        115                 120                 125
aag ggc cgc aac ttc ccc aac gac ggc ccc gtg atg aag aat acc atc       432
Lys Gly Arg Asn Phe Pro Asn Asp Gly Pro Val Met Lys Asn Thr Ile
    130                 135                 140
acc ggc ctg cag ccc agc ttc gag gtg gtg tac atg aac gac ggc gtg       480
Thr Gly Leu Gln Pro Ser Phe Glu Val Val Tyr Met Asn Asp Gly Val
145                 150                 155                 160
ctg gtg ggc cag gtg atc ctg gtg tac cgc ctg aac agc ggc aag ttc       528
Leu Val Gly Gln Val Ile Leu Val Tyr Arg Leu Asn Ser Gly Lys Phe
                165                 170                 175
tac agc tgc cac atg cgc acc ctg atg aag agc aag ggc gtg gtg aag       576
Tyr Ser Cys His Met Arg Thr Leu Met Lys Ser Lys Gly Val Val Lys
            180                 185                 190
gac ttc ccc gag tac cac ttc atc cag cac cgc ctg gag aag gcc tac       624
Asp Phe Pro Glu Tyr His Phe Ile Gln His Arg Leu Glu Lys Ala Tyr
        195                 200                 205
gtg gag gac ggc ggc atc gtg gag cag cac gag acc gcc atc gcc cag       672
Val Glu Asp Gly Gly Ile Val Glu Gln His Glu Thr Ala Ile Ala Gln
    210                 215                 220
ctg acc agc ctg ggc aag ccc ctg ggc agc ctg cac gag tgg gtg taa       720
Leu Thr Ser Leu Gly Lys Pro Leu Gly Ser Leu His Glu Trp Val SEQ ID NO:25
225                 230                 235                     SEQ ID NO:26
```

Fig. 16

```
atg gtg agc aag cag atc ctg aag aac acc ggc ctg cag gag atc atg        48
Met Val Ser Lys Gln Ile Leu Lys Asn Thr Gly Leu Gln Glu Ile Met
1               5                   10                  15
agc ttc aag gtg aac ctg gag ggc gtg gtg aac aac cac gtg ttc acc        96
Ser Phe Lys Val Asn Leu Glu Gly Val Val Asn Asn His Val Phe Thr
            20                  25                  30
atg gag ggc tgc ggc aag ggc aac atc ctg ttc ggc aac cag ctg gtg       144
Met Glu Gly Cys Gly Lys Gly Asn Ile Leu Phe Gly Asn Gln Leu Val
        35                  40                  45
cag atc cgc gtg acc aag ggc gcc ccc ctg ccc ttc gcc ttc gac atc       192
Gln Ile Arg Val Thr Lys Gly Ala Pro Leu Pro Phe Ala Phe Asp Ile
    50                  55                  60
ctg agc ccc gcc ttc cag tac ggc aac cgc acc ttc acc aag tac ccc       240
Leu Ser Pro Ala Phe Gln Tyr Gly Asn Arg Thr Phe Thr Lys Tyr Pro
65                  70                  75                  80
gag gac atc agc gac ttc ttc atc cag agc ttc ccc gcc ggc ttc gtg       288
Glu Asp Ile Ser Asp Phe Phe Ile Gln Ser Phe Pro Ala Gly Phe Val
                85                  90                  95
tac gag cgc acc ctg cgc tac gag gac ggc ggc ctg gcg gag atc cgc       336
Tyr Glu Arg Thr Leu Arg Tyr Glu Asp Gly Gly Leu Ala Glu Ile Arg
            100                 105                 110
agc gac atc aac ctg atc gag ggg atg ttc gtg tac cgc gtg gag tac       384
Ser Asp Ile Asn Leu Ile Glu Gly Met Phe Val Tyr Arg Val Glu Tyr
        115                 120                 125
aag ggc cgc aac ttc ccc aac gac ggc ccc gtg atg aag aat acc atc       432
Lys Gly Arg Asn Phe Pro Asn Asp Gly Pro Val Met Lys Asn Thr Ile
    130                 135                 140
acc ggc ctg cag ccc agc ttc gag gtg gtg tac atg aac gac ggc gtg       480
Thr Gly Leu Gln Pro Ser Phe Glu Val Val Tyr Met Asn Asp Gly Val
145                 150                 155                 160
ctg gtg ggc cag gtg atc ctg gtg tac cgc ctg aac agc ggc aag ttc       528
Leu Val Gly Gln Val Ile Leu Val Tyr Arg Leu Asn Ser Gly Lys Phe
                165                 170                 175
tac agc tgc cac atg cgc acc ctg atg aag agc aag ggc gtg gtg aag       576
Tyr Ser Cys His Met Arg Thr Leu Met Lys Ser Lys Gly Val Val Lys
            180                 185                 190
gac ttc ccc gag tac cac ttc atc cag cac cgc ctg gag aag acc tac       624
Asp Phe Pro Glu Tyr His Phe Ile Gln His Arg Leu Glu Lys Thr Tyr
        195                 200                 205
gtg gag gac ggc ggc ttc gtg gag cag cac gag acc gcc atc gcc cag       672
Val Glu Asp Gly Gly Phe Val Glu Gln His Glu Thr Ala Ile Ala Gln
    210                 215                 220
ctg acc agc ctg ggc aag ccc ctg ggc agc ctg cac gag tgg gtg taa       720
Leu Thr Ser Leu Gly Lys Pro Leu Gly Ser Leu His Glu Trp Val SEQ ID NO:27
225                 230                 235                     SEQ ID NO:28
```

Fig. 17

```
atg gtg agc aag cag atc ctg aag aac acc ggc ctg cag gag atc gtg        48
Met Val Ser Lys Gln Ile Leu Lys Asn Thr Gly Leu Gln Glu Ile Val
1               5                   10                  15
agc ttc aag gtg atc ctg gag ggc gtg gtg aac aac cac gtg ttc acc        96
Ser Phe Lys Val Ile Leu Glu Gly Val Val Asn Asn His Val Phe Thr
            20                  25                  30
atg gag ggc tgc ggc aag ggc aac atc ctg ttc ggc aac cag ctg gtg       144
Met Glu Gly Cys Gly Lys Gly Asn Ile Leu Phe Gly Asn Gln Leu Val
        35                  40                  45
cag atc cgc gtg acc aag ggc gcc ccc ctg ccc ttc gcc ttc gac atc       192
Gln Ile Arg Val Thr Lys Gly Ala Pro Leu Pro Phe Ala Phe Asp Ile
    50                  55                  60
ctg agc ccc gcc ttc cag tac ggc aac cgc acc ttc acc aag tac ccc       240
Leu Ser Pro Ala Phe Gln Tyr Gly Asn Arg Thr Phe Thr Lys Tyr Pro
65                  70                  75                  80
gag gac atc agc gac ttc ttc atc cag agc ttc ccc gcc ggc ttc gtg       288
Glu Asp Ile Ser Asp Phe Phe Ile Gln Ser Phe Pro Ala Gly Phe Val
                85                  90                  95
tac gag cgc acc ctg cgc tac gag gac ggc ggc ctg gtg gag atc cgc       336
Tyr Glu Arg Thr Leu Arg Tyr Glu Asp Gly Gly Leu Val Glu Ile Arg
            100                 105                 110
agc gac atc aac ctg atc gag ggg atg ttc gtg tac cgc gtg gag tac       384
Ser Asp Ile Asn Leu Ile Glu Gly Met Phe Val Tyr Arg Val Glu Tyr
        115                 120                 125
aag ggc cgc aac ttc ccc aac gac ggc ccc gtg atg aag aat acc atc       432
Lys Gly Arg Asn Phe Pro Asn Asp Gly Pro Val Met Lys Asn Thr Ile
    130                 135                 140
acc ggc ctg cag ccc agc ttc gag gtg gtg tac atg aac gac ggc gtg       480
Thr Gly Leu Gln Pro Ser Phe Glu Val Val Tyr Met Asn Asp Gly Val
145                 150                 155                 160
ctg gtg ggc cag gtg atc ctg gtg tac cgc ctg aac tgc ggc aag ttc       528
Leu Val Gly Gln Val Ile Leu Val Tyr Arg Leu Asn Cys Gly Lys Phe
                165                 170                 175
tac agc tgc cac atg cgc acc ctg atg aag agc aag ggc gtg gtg aag       576
Tyr Ser Cys His Met Arg Thr Leu Met Lys Ser Lys Gly Val Val Lys
            180                 185                 190
gac ttc ccc gag tac cac ttc atc cag cac cgc ctg gag aag acc tac       624
Asp Phe Pro Glu Tyr His Phe Ile Gln His Arg Leu Glu Lys Thr Tyr
        195                 200                 205
gtg gag gac ggc ggc ttc gtg gag cag cac gag acc gcc atc gcc cag       672
Val Glu Asp Gly Gly Phe Val Glu Gln His Glu Thr Ala Ile Ala Gln
    210                 215                 220
ctg acc agc ctg ggc aag ccc ctg ggc agc ctg cac gag tgg gtg taa       720
Leu Thr Ser Leu Gly Lys Pro Leu Gly Ser Leu His Glu Trp Val SEQ ID NO:29
225                 230                 235                     SEQ ID NO:30
```

Fig. 18

```
atg agt aaa caa ata ttg aag aac act gga ttg cag gag atc atg tcg       48
Met Ser Lys Gln Ile Leu Lys Asn Thr Gly Leu Gln Glu Ile Met Ser
1               5                   10                  15
ttt aaa gtg aat ctg gaa ggt gta gta aac aat cat gtg ttc aca atg       96
Phe Lys Val Asn Leu Glu Gly Val Val Asn Asn His Val Phe Thr Met
            20                  25                  30
gaa ggt tgt gga aaa gga aat att tta ttc gga aac caa ctg gtt cag      144
Glu Gly Cys Gly Lys Gly Asn Ile Leu Phe Gly Asn Gln Leu Val Gln
        35                  40                  45
att cgt gtc aca aaa ggg gct ccg ctt cca ttt gca ttt gat att ctc      192
Ile Arg Val Thr Lys Gly Ala Pro Leu Pro Phe Ala Phe Asp Ile Leu
    50                  55                  60
tca cca gct ttc caa tac ggc aac cgt aca ttc acg aaa tac ccg gag      240
Ser Pro Ala Phe Gln Tyr Gly Asn Arg Thr Phe Thr Lys Tyr Pro Glu
65                  70                  75                  80
gat ata tca gac ttt ttt ata caa tca ttt cca gcg gga ttt gta tac      288
Asp Ile Ser Asp Phe Phe Ile Gln Ser Phe Pro Ala Gly Phe Val Tyr
                85                  90                  95
gaa aga acg ttg cgt tac gaa gat ggt gga ctg gtt gaa atc cgt tca      336
Glu Arg Thr Leu Arg Tyr Glu Asp Gly Gly Leu Val Glu Ile Arg Ser
            100                 105                 110
gat ata aat tta atc gag gag atg ttt gtc tac aga gtg gaa tat aaa      384
Asp Ile Asn Leu Ile Glu Glu Met Phe Val Tyr Arg Val Glu Tyr Lys
        115                 120                 125
ggt agt aac ttc ccg aat gat ggt cca gtg atg aag aag aca atc aca      432
Gly Ser Asn Phe Pro Asn Asp Gly Pro Val Met Lys Lys Thr Ile Thr
    130                 135                 140
gga tta caa cct tcg ttc gaa gtt gtg tat atg aac gat ggc gtc ttg      480
Gly Leu Gln Pro Ser Phe Glu Val Val Tyr Met Asn Asp Gly Val Leu
145                 150                 155                 160
gtt ggc caa gtc att ctt gtt tat aga tta aac tct ggc aaa ttt tat      528
Val Gly Gln Val Ile Leu Val Tyr Arg Leu Asn Ser Gly Lys Phe Tyr
                165                 170                 175
tcg tgt cac atg aga aca ctg atg aaa tca aag ggt gta gtg aag gat      576
Ser Cys His Met Arg Thr Leu Met Lys Ser Lys Gly Val Val Lys Asp
            180                 185                 190
ttt ccc gaa tac cat ttc att caa cat cgt tta gag aag acg tat gtg      624
Phe Pro Glu Tyr His Phe Ile Gln His Arg Leu Glu Lys Thr Tyr Val
        195                 200                 205
gaa gac gga ggt ttt gtt gag gaa cac gag acg gcc att gct caa ctg      672
Glu Asp Gly Gly Phe Val Glu Glu His Glu Thr Ala Ile Ala Gln Leu
    210                 215                 220
aca tcg ctg ggg aaa cca ctt gga tcc tta cac gaa tgg gtt              714
Thr Ser Leu Gly Lys Pro Leu Gly Ser Leu His Glu Trp Val      SEQ ID NO:31
225                 230                 235                          SEQ ID NO:32
```

Fig. 19

```
atg agt aaa caa ata ttg aag aac act gga ttg cag gag atc atg tcg       48
Met Ser Lys Gln Ile Leu Lys Asn Thr Gly Leu Gln Glu Ile Met Ser
1               5                   10                  15
ttt aaa gtg aat ctg gaa ggt gta gta aac aat cat gtg ttc aca atg       96
Phe Lys Val Asn Leu Glu Gly Val Val Asn Asn His Val Phe Thr Met
            20                  25                  30
gaa ggt tgt gga aaa gga aat att tta tta gga aac caa ctg gtt cag      144
Glu Gly Cys Gly Lys Gly Asn Ile Leu Leu Gly Asn Gln Leu Val Gln
        35                  40                  45
att cgt gtc aca aaa ggg gct ccg ctt cca ttt gca ttt gat att ctc      192
Ile Arg Val Thr Lys Gly Ala Pro Leu Pro Phe Ala Phe Asp Ile Leu
    50                  55                  60
tca cca gct ttc caa tac ggc aac cgt aca ttc acg aaa tac ccg gag      240
Ser Pro Ala Phe Gln Tyr Gly Asn Arg Thr Phe Thr Lys Tyr Pro Glu
65                  70                  75                  80
gat ata tca gac ttt ttt ata caa tca ttt cca gcg gga ttt gta tac      288
Asp Ile Ser Asp Phe Phe Ile Gln Ser Phe Pro Ala Gly Phe Val Tyr
                85                  90                  95
gaa aga acg ttg cgt tac gaa gat ggt gga ctg gtt gaa atc cgt tca      336
Glu Arg Thr Leu Arg Tyr Glu Asp Gly Gly Leu Val Glu Ile Arg Ser
            100                 105                 110
gat ata aat tta atc gag gag atg ttt gtc tac aga gtg gaa tat aaa      384
Asp Ile Asn Leu Ile Glu Glu Met Phe Val Tyr Arg Val Glu Tyr Lys
        115                 120                 125
ggt agt aac ttc ccg aat gat ggt cca gtg atg aag aag aca atc aca      432
Gly Ser Asn Phe Pro Asn Asp Gly Pro Val Met Lys Lys Thr Ile Thr
    130                 135                 140
gga tta caa cct tcg ttc gaa gtt gtg tat atg aac gat ggc gtc ttg      480
Gly Leu Gln Pro Ser Phe Glu Val Val Tyr Met Asn Asp Gly Val Leu
145                 150                 155                 160
gtt ggc caa gtc att ctt gtt tat aga tta aac tct ggc aaa ttt tat      528
Val Gly Gln Val Ile Leu Val Tyr Arg Leu Asn Ser Gly Lys Phe Tyr
                165                 170                 175
tcg tgt cac atg aga aca ctg atg aaa tca aag ggt gta gtg aag gat      576
Ser Cys His Met Arg Thr Leu Met Lys Ser Lys Gly Val Val Lys Asp
            180                 185                 190
ttt ccc gaa tac cat ttc att caa cat cgt tta gag aag acg tat gtg      624
Phe Pro Glu Tyr His Phe Ile Gln His Arg Leu Glu Lys Thr Tyr Val
        195                 200                 205
gaa gac gga ggt ttt gtt gag gaa cac gag acg gcc att gct caa ctg      672
Glu Asp Gly Gly Phe Val Glu Glu His Glu Thr Ala Ile Ala Gln Leu
    210                 215                 220
aca tcg ctg ggg aaa cca ctt gga tcc tta cac gaa tgg gtt              714
Thr Ser Leu Gly Lys Pro Leu Gly Ser Leu His Glu Trp Val       SEQ ID NO:33
225                 230                 235                       SEQ ID NO:34
```

Fig. 20

```
atg agt aaa caa ata ttg aag aac act gga ttg cag gag atc atg tcg       48
Met Ser Lys Gln Ile Leu Lys Asn Thr Gly Leu Gln Glu Ile Met Ser
1               5                   10                  15
ttt aaa gtg aat ctg gaa ggt gta gta aac aat cat gtg ttc aca atg       96
Phe Lys Val Asn Leu Glu Gly Val Val Asn Asn His Val Phe Thr Met
            20                  25                  30
gaa ggt tgt gga aaa gga aat att tta ttc gga aac caa ctg gtt cag      144
Glu Gly Cys Gly Lys Gly Asn Ile Leu Phe Gly Asn Gln Leu Val Gln
        35                  40                  45
att cgt gtc aca aaa ggg gct ccg ctt cca ttt gca ttt gat att ctc      192
Ile Arg Val Thr Lys Gly Ala Pro Leu Pro Phe Ala Phe Asp Ile Leu
    50                  55                  60
tca cca gct ttc caa tac ggc aac cgt aca ttc acg aaa tac ccg gag      240
Ser Pro Ala Phe Gln Tyr Gly Asn Arg Thr Phe Thr Lys Tyr Pro Glu
65                  70                  75                  80
gat ata tca gac ttt ttt ata caa tca ttt cca gcg gga ttt gta tac      288
Asp Ile Ser Asp Phe Phe Ile Gln Ser Phe Pro Ala Gly Phe Val Tyr
                85                  90                  95
gaa aga acg ttg cgt tac gaa gat ggt gga ctg gtt gaa atc cgt tca      336
Glu Arg Thr Leu Arg Tyr Glu Asp Gly Gly Leu Val Glu Ile Arg Ser
            100                 105                 110
gat ata aat tta atc gag ggg atg ttt gtc tac aga gtg gaa tat aaa      384
Asp Ile Asn Leu Ile Glu Gly Met Phe Val Tyr Arg Val Glu Tyr Lys
        115                 120                 125
ggt agt aac ttc ccg aat gat ggt cca gtg atg aag aag aca atc aca      432
Gly Ser Asn Phe Pro Asn Asp Gly Pro Val Met Lys Lys Thr Ile Thr
    130                 135                 140
gga tta caa cct tcg ttc gaa gtt gtg tat atg aac gat ggc gtc ttg      480
Gly Leu Gln Pro Ser Phe Glu Val Val Tyr Met Asn Asp Gly Val Leu
145                 150                 155                 160
gtt ggc caa gtc att ctt gtt tat aga tta aac tct ggc aaa ttt tat      528
Val Gly Gln Val Ile Leu Val Tyr Arg Leu Asn Ser Gly Lys Phe Tyr
                165                 170                 175
tcg tgt cac atg aga aca ctg atg aaa tca aag ggt gta gtg aag gat      576
Ser Cys His Met Arg Thr Leu Met Lys Ser Lys Gly Val Val Lys Asp
            180                 185                 190
ttt ccc gaa tac cat ttc att caa cat cgt tta gag aag acg tat gtg      624
Phe Pro Glu Tyr His Phe Ile Gln His Arg Leu Glu Lys Thr Tyr Val
        195                 200                 205
gaa gac gga ggt ttt gta gag gaa cac gag acg gcc att gct caa ctg      672
Glu Asp Gly Gly Phe Val Glu Glu His Glu Thr Ala Ile Ala Gln Leu
    210                 215                 220
aca tcg ctg ggg aaa cca ctt gga tcc tta cac gaa tgg gtt              714
Thr Ser Leu Gly Lys Pro Leu Gly Ser Leu His Glu Trp Val       SEQ ID NO:35
225                 230                 235                       SEQ ID NO:36
```

Fig. 21

```
atg agt aaa caa ata ttg aag aac act gga ttg cag gag atc atg tcg        48
Met Ser Lys Gln Ile Leu Lys Asn Thr Gly Leu Gln Glu Ile Met Ser
1               5                   10                  15
ttt aaa gtg aat ctg gaa ggt gta gta aac aat cat gtg ttc aca atg        96
Phe Lys Val Asn Leu Glu Gly Val Val Asn Asn His Val Phe Thr Met
            20                  25                  30
gaa ggt tgt gga aaa gga aat att tta ttc gga aac caa ctg gtt cag       144
Glu Gly Cys Gly Lys Gly Asn Ile Leu Phe Gly Asn Gln Leu Val Gln
        35                  40                  45
att cgt gtc aca aaa ggg gct ccg ctt cca ttt gca ttt gat att ctc       192
Ile Arg Val Thr Lys Gly Ala Pro Leu Pro Phe Ala Phe Asp Ile Leu
    50                  55                  60
tca cca gct ttc caa tac ggc aac cgt aca ttc acg aaa tac ccg gag       240
Ser Pro Ala Phe Gln Tyr Gly Asn Arg Thr Phe Thr Lys Tyr Pro Glu
65                  70                  75                  80
gat ata tca gac ttt ttt ata caa tca ttt cca gcg gga ttt gta tac       288
Asp Ile Ser Asp Phe Phe Ile Gln Ser Phe Pro Ala Gly Phe Val Tyr
                85                  90                  95
gaa aga acg atg cgt tac gaa gat ggt gga ctg gtt gaa atc cgt tca       336
Glu Arg Thr Met Arg Tyr Glu Asp Gly Gly Leu Val Glu Ile Arg Ser
            100                 105                 110
gat ata aat tta atc gag gag atg ttt gtc tac aga gtg gaa tat aaa       384
Asp Ile Asn Leu Ile Glu Glu Met Phe Val Tyr Arg Val Glu Tyr Lys
        115                 120                 125
ggt agt aac ttc ccg aat gat ggt cca gtg atg aag aag aca atc aca       432
Gly Ser Asn Phe Pro Asn Asp Gly Pro Val Met Lys Lys Thr Ile Thr
    130                 135                 140
gga tta caa cct tcg ttc gaa gtt gtg tat atg aac gat ggc gtc ttg       480
Gly Leu Gln Pro Ser Phe Glu Val Val Tyr Met Asn Asp Gly Val Leu
145                 150                 155                 160
gtt ggc caa gtc att ctt gtt tat aga tta aac tct ggc aaa ttt tat       528
Val Gly Gln Val Ile Leu Val Tyr Arg Leu Asn Ser Gly Lys Phe Tyr
                165                 170                 175
tcg tgt cac atg aga aca ctg atg aaa tca aag ggt gta gtg aag gat       576
Ser Cys His Met Arg Thr Leu Met Lys Ser Lys Gly Val Val Lys Asp
            180                 185                 190
ttt ccc gaa tac cat ttc att caa cat cgt tta gag aag acg tat gtg       624
Phe Pro Glu Tyr His Phe Ile Gln His Arg Leu Glu Lys Thr Tyr Val
        195                 200                 205
gaa gac gga ggt ttt gtt gag gaa cac gag acg gcc att gct caa ctg       672
Glu Asp Gly Gly Phe Val Glu Glu His Glu Thr Ala Ile Ala Gln Leu
    210                 215                 220
aca tcg ctg ggg aaa cca ctt gga tcc tta cac gaa tgg gtt               714
Thr Ser Leu Gly Lys Pro Leu Gly Ser Leu His Glu Trp Val      SEQ ID NO:37
225                 230                 235                          SEQ ID NO:38
```

Fig. 22

```
atg agt aaa caa ata ttg aag aac act gga ttg cag gag atc atg tcg          48
Met Ser Lys Gln Ile Leu Lys Asn Thr Gly Leu Gln Glu Ile Met Ser
1               5                   10                  15
ttt aaa gtg aat ctg gaa ggt gta gta aac aat cat gtg ttc aca atg          96
Phe Lys Val Asn Leu Glu Gly Val Val Asn Asn His Val Phe Thr Met
            20                  25                  30
gaa ggt tgt gga aaa gga aat att tta tcc gga aac caa ctg gtt cag         144
Glu Gly Cys Gly Lys Gly Asn Ile Leu Ser Gly Asn Gln Leu Val Gln
        35                  40                  45
att cgt gtc aca aaa ggg gct ccg ctt cca ttt gca ttt gat att ctc         192
Ile Arg Val Thr Lys Gly Ala Pro Leu Pro Phe Ala Phe Asp Ile Leu
    50                  55                  60
tca cca gct ttc caa tac ggc aac cgt aca ttc acg aaa tac ccg gag         240
Ser Pro Ala Phe Gln Tyr Gly Asn Arg Thr Phe Thr Lys Tyr Pro Glu
65                  70                  75                  80
gat ata tca gac ttt ttt ata caa tca ttt cca gcg gga ttt gta tac         288
Asp Ile Ser Asp Phe Phe Ile Gln Ser Phe Pro Ala Gly Phe Val Tyr
                85                  90                  95
gaa aga acg ttg cgt tac gaa gat ggt gga ctg gtt gaa atc cgt tca         336
Glu Arg Thr Leu Arg Tyr Glu Asp Gly Gly Leu Val Glu Ile Arg Ser
            100                 105                 110
gat ata aat tta atc gag gag atg ttt gtc tac aga gtg gaa tat aaa         384
Asp Ile Asn Leu Ile Glu Glu Met Phe Val Tyr Arg Val Glu Tyr Lys
        115                 120                 125
ggt agt aac ttc ccg aat gat ggt cca gtg atg aag aag aca atc aca         432
Gly Ser Asn Phe Pro Asn Asp Gly Pro Val Met Lys Lys Thr Ile Thr
    130                 135                 140
gga tta caa cct tcg ttc gaa gtt gtg tat atg aac gat ggc gtc ttg         480
Gly Leu Gln Pro Ser Phe Glu Val Val Tyr Met Asn Asp Gly Val Leu
145                 150                 155                 160
gtt ggc caa gtc att ctt gtt tat aga tta aac tct ggc aaa ttt tat         528
Val Gly Gln Val Ile Leu Val Tyr Arg Leu Asn Ser Gly Lys Phe Tyr
                165                 170                 175
tcg tgt cac atg aga aca ctg atg aaa tca aag ggt gta gtg aag gat         576
Ser Cys His Met Arg Thr Leu Met Lys Ser Lys Gly Val Val Lys Asp
            180                 185                 190
ttt ccc gaa tac cat ttc att caa cat cgt tta gag aag acg tat gtg         624
Phe Pro Glu Tyr His Phe Ile Gln His Arg Leu Glu Lys Thr Tyr Val
        195                 200                 205
gaa gac gga ggt ttt gtt gag gaa cac gag acg gcc att gct caa ctg         672
Glu Asp Gly Gly Phe Val Glu Glu His Glu Thr Ala Ile Ala Gln Leu
    210                 215                 220
aca tcg ctg ggg aaa cca ctt gga tcc tta cac gaa tgg gtt                 714
Thr Ser Leu Gly Lys Pro Leu Gly Ser Leu His Glu Trp Val      SEQ ID NO:39
225                 230                 235                          SEQ ID NO:40
```

Fig. 23

```
atg agt aaa caa ata ttg aag aac act gga ttg cag gag atc atg tcg        48
Met Ser Lys Gln Ile Leu Lys Asn Thr Gly Leu Gln Glu Ile Met Ser
1               5                   10                  15
ttt aaa gtg aat ctg gaa ggt gta gta aac aat cat gtg ttc aca atg        96
Phe Lys Val Asn Leu Glu Gly Val Val Asn Asn His Val Phe Thr Met
            20                  25                  30
gaa ggt tgt gga aaa gga aat att tta ttc gga aac caa ctg gtt cag       144
Glu Gly Cys Gly Lys Gly Asn Ile Leu Phe Gly Asn Gln Leu Val Gln
        35                  40                  45
att cgt gtc aca aaa ggg gct ccg ctt cca ttt gca ttt gat att ctc       192
Ile Arg Val Thr Lys Gly Ala Pro Leu Pro Phe Ala Phe Asp Ile Leu
    50                  55                  60
tca cca gct ttc caa tac ggc aac cgt aca ttc acg aaa tac ccg gag       240
Ser Pro Ala Phe Gln Tyr Gly Asn Arg Thr Phe Thr Lys Tyr Pro Glu
65                  70                  75                  80
gat ata tca gac ttt ttt ata caa tca ttt cca gcg gga ttt gta tac       288
Asp Ile Ser Asp Phe Phe Ile Gln Ser Phe Pro Ala Gly Phe Val Tyr
                85                  90                  95
gaa aga acg ttg tgt tac gaa gat ggt gga ctg gtt gaa atc cgt tca       336
Glu Arg Thr Leu Cys Tyr Glu Asp Gly Gly Leu Val Glu Ile Arg Ser
            100                 105                 110
gat ata aat tta atc gag gag atg ttt gtc tac cat gtg gaa tat aaa       384
Asp Ile Asn Leu Ile Glu Glu Met Phe Val Tyr His Val Glu Tyr Lys
        115                 120                 125
ggt agt aac ttc ccg aat gat ggt cca gtg atg aag aag aca atc aca       432
Gly Ser Asn Phe Pro Asn Asp Gly Pro Val Met Lys Lys Thr Ile Thr
    130                 135                 140
gga tta caa cct tcg ttc gaa gtt gtg tat atg aac gat ggc gtc ttg       480
Gly Leu Gln Pro Ser Phe Glu Val Val Tyr Met Asn Asp Gly Val Leu
145                 150                 155                 160
gtt ggc caa gtc att ctt gtt tat aga tta aac tct ggc aaa ttt tat       528
Val Gly Gln Val Ile Leu Val Tyr Arg Leu Asn Ser Gly Lys Phe Tyr
                165                 170                 175
tcg tgt cac atg aga aca ctg atg aaa tca aag ggt gta gtg aag gat       576
Ser Cys His Met Arg Thr Leu Met Lys Ser Lys Gly Val Val Lys Asp
            180                 185                 190
ttt ccc gaa tac cat ttc att caa cat cgt tta gag aag acg tat gtg       624
Phe Pro Glu Tyr His Phe Ile Gln His Arg Leu Glu Lys Thr Tyr Val
        195                 200                 205
gaa gac gga ggt ttt gtt gag gaa cac gag acg gcc att gct caa ctg       672
Glu Asp Gly Gly Phe Val Glu Glu His Glu Thr Ala Ile Ala Gln Leu
    210                 215                 220
aca tcg ctg ggg aat cca ctt gga tcc tta cac gaa tgg gtt               714
Thr Ser Leu Gly Tyr Pro Leu Gly Ser Leu His Glu Trp Val      SEQ ID NO:41
225                 230                 235                          SEQ ID NO:42
```

Fig. 24

```
atg agt aaa caa ata ttg aag aac act gga ttg cag gag atc atg tcg        48
Met Ser Lys Gln Ile Leu Lys Asn Thr Gly Leu Gln Glu Ile Met Ser
1               5                   10                  15
ttt aaa gtg att ctg gaa ggt gta gta aac aat cat gtg ttc aca atg        96
Phe Lys Val Ile Leu Glu Gly Val Val Asn Asn His Val Phe Thr Met
            20                  25                  30
gaa ggt tgt gga aaa gga aat att tta ttc gga aac caa ctg gtt cag       144
Glu Gly Cys Gly Lys Gly Asn Ile Leu Phe Gly Asn Gln Leu Val Gln
        35                  40                  45
att cgt gtc aca aaa ggg gct ccg ctt cca ttt gca ttt gat att ctc       192
Ile Arg Val Thr Lys Gly Ala Pro Leu Pro Phe Ala Phe Asp Ile Leu
    50                  55                  60
tca cca gct ttc caa tac ggc aac cgt aca ttc acg aaa tac ccg gag       240
Ser Pro Ala Phe Gln Tyr Gly Asn Arg Thr Phe Thr Lys Tyr Pro Glu
65                  70                  75                  80
gat ata tca gac ttt ttt ata caa tca ttt cca gcg gga ttt gta tac       288
Asp Ile Ser Asp Phe Phe Ile Gln Ser Phe Pro Ala Gly Phe Val Tyr
                85                  90                  95
gaa aga acg ttg cgt tac gaa gat ggt gga ctg gtt gaa atc cgt tca       336
Glu Arg Thr Leu Arg Tyr Glu Asp Gly Gly Leu Val Glu Ile Arg Ser
            100                 105                 110
gat ata aat tta atc gag ggg atg ttt gtc tac aga gtg gaa tat aaa       384
Asp Ile Asn Leu Ile Glu Gly Met Phe Val Tyr Arg Val Glu Tyr Lys
        115                 120                 125
ggt agt aac ttc ccg aat gat ggt cca gtg atg aag aat aca atc aca       432
Gly Ser Asn Phe Pro Asn Asp Gly Pro Val Met Lys Asn Thr Ile Thr
    130                 135                 140
gga tta caa cct tcg ttc gaa gtt gtg tat atg aac gat ggc gtc ttg       480
Gly Leu Gln Pro Ser Phe Glu Val Val Tyr Met Asn Asp Gly Val Leu
145                 150                 155                 160
gtt ggc caa gtc att ctt gtt tat aga tta aac tct ggc aaa ttt tat       528
Val Gly Gln Val Ile Leu Val Tyr Arg Leu Asn Ser Gly Lys Phe Tyr
                165                 170                 175
tcg tgt cac atg aga aca ctg atg aaa tca aag ggt gta gtg aag gat       576
Ser Cys His Met Arg Thr Leu Met Lys Ser Lys Gly Val Val Lys Asp
            180                 185                 190
ttt ccc gaa tac cat ttc att caa cat cgt tta gag aag acg tat gtg       624
Phe Pro Glu Tyr His Phe Ile Gln His Arg Leu Glu Lys Thr Tyr Val
        195                 200                 205
gaa gac gga ggt ttt gtt gag gaa cac gag acg gcc att gct caa ctg       672
Glu Asp Gly Gly Phe Val Glu Glu His Glu Thr Ala Ile Ala Gln Leu
    210                 215                 220
aca tcg ctg ggg aaa cca ctt gga tcc tta cac gaa tgg gtt               714
Thr Ser Leu Gly Lys Pro Leu Gly Ser Leu His Glu Trp Val      SEQ ID NO:43
225                 230                 235                          SEQ ID NO:44
```

Fig. 25

```
atg agt aaa caa ata ttg aag aac act gga ttg cag gag atc atg tcg        48
Met Ser Lys Gln Ile Leu Lys Asn Thr Gly Leu Gln Glu Ile Met Ser
1               5                   10                  15
ttt aaa gtg aat ctg gaa ggt gta gta aac aat cat gtg ttc aca atg        96
Phe Lys Val Asn Leu Glu Gly Val Val Asn Asn His Val Phe Thr Met
            20                  25                  30
gaa ggt tgt gga aaa gga aat att tta ttc gga aac caa ctg gtt cag       144
Glu Gly Cys Gly Lys Gly Asn Ile Leu Phe Gly Asn Gln Leu Val Gln
        35                  40                  45
att cgt gtc aca aaa ggg gct ccg ctt cca ttt gca ttt gat att ctc       192
Ile Arg Val Thr Lys Gly Ala Pro Leu Pro Phe Ala Phe Asp Ile Leu
    50                  55                  60
tca cca gct ttc caa tac ggc aac cgt aca ttc acg aaa tac ccg gag       240
Ser Pro Ala Phe Gln Tyr Gly Asn Arg Thr Phe Thr Lys Tyr Pro Glu
65                  70                  75                  80
gat ata tca gac ttt ttt ata caa tca ttt cca gcg gga ttt gta tac       288
Asp Ile Ser Asp Phe Phe Ile Gln Ser Phe Pro Ala Gly Phe Val Tyr
                85                  90                  95
gaa aga acg ttg cgt ttc gaa gat ggt gga ctg gtt gaa atc cgt tca       336
Glu Arg Thr Leu Arg Phe Glu Asp Gly Gly Leu Val Glu Ile Arg Ser
            100                 105                 110
gat ata aat tta atc gag gag atg ttt gtc tac aga gtg gaa tat aaa       384
Asp Ile Asn Leu Ile Glu Glu Met Phe Val Tyr Arg Val Glu Tyr Lys
        115                 120                 125
ggt agt aac ttc ccg aat gat ggt cca gtg atg aag aag aca atc aca       432
Gly Ser Asn Phe Pro Asn Asp Gly Pro Val Met Lys Lys Thr Ile Thr
    130                 135                 140
gga tta caa cct tcg ttc gaa gtt gtg tat atg aac gat ggc gtc ttg       480
Gly Leu Gln Pro Ser Phe Glu Val Val Tyr Met Asn Asp Gly Val Leu
145                 150                 155                 160
gtt ggc caa gtc att ctt gtt tat aga tta aac tct ggc aaa ttt tat       528
Val Gly Gln Val Ile Leu Val Tyr Arg Leu Asn Ser Gly Lys Phe Tyr
                165                 170                 175
tcg tgt cac atg aga aca ctg atg aaa tca aag ggt gta gtg aag gat       576
Ser Cys His Met Arg Thr Leu Met Lys Ser Lys Gly Val Val Lys Asp
            180                 185                 190
ttt ccc gaa tac cat ttc att caa cat cgt tta gag aag acg tat gtg       624
Phe Pro Glu Tyr His Phe Ile Gln His Arg Leu Glu Lys Thr Tyr Val
        195                 200                 205
gaa gac gga ggt ttt gtt gag gaa cac gag acg gcc att gct caa ctg       672
Glu Asp Gly Gly Phe Val Glu Glu His Glu Thr Ala Ile Ala Gln Leu
    210                 215                 220
aca tcg ctg ggg aaa cca ctt gga tcc tta cac gaa tgg gtt               714
Thr Ser Leu Gly Lys Pro Leu Gly Ser Leu His Glu Trp Val      SEQ ID NO:45
225                 230                 235                          SEQ ID NO:46
```

Fig. 26

```
atg agt aaa caa ata ttg aag aac act gga ttg cag gag atc atg tcg        48
Met Ser Lys Gln Ile Leu Lys Asn Thr Gly Leu Gln Glu Ile Met Ser
1               5                   10                  15
ttt aaa gtg aat ctg gaa ggt gta gta aac aat cat gtg ttc cca atg        96
Phe Lys Val Asn Leu Glu Gly Val Val Asn Asn His Val Phe Pro Met
            20                  25                  30
gaa ggt tgt gga aaa gga aat att tta ttc gga aac caa ctg gtt cag       144
Glu Gly Cys Gly Lys Gly Asn Ile Leu Phe Gly Asn Gln Leu Val Gln
        35                  40                  45
att cgt gtc aca aaa ggg gct ccg ctt cca ttt gca ttt gat att ctc       192
Ile Arg Val Thr Lys Gly Ala Pro Leu Pro Phe Ala Phe Asp Ile Leu
    50                  55                  60
tca cca gct ttc caa tac ggc aac cgt aca ttc acg aaa tac ccg gag       240
Ser Pro Ala Phe Gln Tyr Gly Asn Arg Thr Phe Thr Lys Tyr Pro Glu
65                  70                  75                  80
gat ata tca gac ttt ttt ata caa tca ttt cca gcg gga ttt gta tac       288
Asp Ile Ser Asp Phe Phe Ile Gln Ser Phe Pro Ala Gly Phe Val Tyr
                85                  90                  95
gaa aga acg ttg cgt ttc gaa gat ggt gga ctg gtt gaa atc cgt tca       336
Glu Arg Thr Leu Arg Phe Glu Asp Gly Gly Leu Val Glu Ile Arg Ser
            100                 105                 110
gat ata aat tta atc gag gag atg ttt gtc tac aga gtg gaa tat aaa       384
Asp Ile Asn Leu Ile Glu Glu Met Phe Val Tyr Arg Val Glu Tyr Lys
        115                 120                 125
ggt agt aac ttc ccg aat gat ggt cca gtg atg aag aag aca atc aca       432
Gly Ser Asn Phe Pro Asn Asp Gly Pro Val Met Lys Lys Thr Ile Thr
    130                 135                 140
gga tta caa cct tcg ttc gaa gtt gtg tat atg aac gat ggc gtc ttg       480
Gly Leu Gln Pro Ser Phe Glu Val Val Tyr Met Asn Asp Gly Val Leu
145                 150                 155                 160
gtt ggc caa gtc att ctt gtt tat aga tta aac tct ggc aaa ttt tat       528
Val Gly Gln Val Ile Leu Val Tyr Arg Leu Asn Ser Gly Lys Phe Tyr
                165                 170                 175
tcg tgt cac atg aga aca ctg atg aaa tca aag ggt gta gtg aag gat       576
Ser Cys His Met Arg Thr Leu Met Lys Ser Lys Gly Val Val Lys Asp
            180                 185                 190
ttt ccc gaa tac cat ttc att caa cat cgt tta gag aag acg tat gtg       624
Phe Pro Glu Tyr His Phe Ile Gln His Arg Leu Glu Lys Thr Tyr Val
        195                 200                 205
gaa gac gga ggt ttt gtt gag gaa cac gag acg gcc att gct caa ctg       672
Glu Asp Gly Gly Phe Val Glu Glu His Glu Thr Ala Ile Ala Gln Leu
    210                 215                 220
aca tcg ctg ggg aaa cca ctt gga tcc tta cac gaa tgg gtt               714
Thr Ser Leu Gly Lys Pro Leu Gly Ser Leu His Glu Trp Val      SEQ ID NO:47
225                 230                 235                          SEQ ID NO:48
```

Fig. 27

```
atg agt aaa caa ata ttg aag aac act gga ttg cag gag atc atg tcg        48
Met Ser Lys Gln Ile Leu Lys Asn Thr Gly Leu Gln Glu Ile Met Ser
1               5                   10                  15
ttt aaa gtg aat ctg gaa ggt gta gta aac aat cat gtg ttc aca atg        96
Phe Lys Val Asn Leu Glu Gly Val Val Asn Asn His Val Phe Thr Met
            20                  25                  30
gaa ggt tgt gga aaa gga aat att tta ttc gga aac caa ctg gtt cag       144
Glu Gly Cys Gly Lys Gly Asn Ile Leu Phe Gly Asn Gln Leu Val Gln
        35                  40                  45
att cgt gtc aca aaa ggg gct ccg ctt cca ttt gca ttt gat att ctc       192
Ile Arg Val Thr Lys Gly Ala Pro Leu Pro Phe Ala Phe Asp Ile Leu
    50                  55                  60
tca cca gct ttc caa tac ggc aac cgt aca ttc acg aaa tac ccg gag       240
Ser Pro Ala Phe Gln Tyr Gly Asn Arg Thr Phe Thr Lys Tyr Pro Glu
65                  70                  75                  80
gat ata tca gac ttt ttt ata caa tca ttt cca gcg gga ttt gta tac       288
Asp Ile Ser Asp Phe Phe Ile Gln Ser Phe Pro Ala Gly Phe Val Tyr
                85                  90                  95
gaa aga acg ttg cgt tac gaa gat ggt gga ctg gtt gaa atc cgt tca       336
Glu Arg Thr Leu Arg Tyr Glu Asp Gly Gly Leu Val Glu Ile Arg Ser
            100                 105                 110
gat ata aat tta atc gag ggg atg ttt gtc tac aga gtg gaa tat aaa       384
Asp Ile Asn Leu Ile Glu Gly Met Phe Val Tyr Arg Val Glu Tyr Lys
        115                 120                 125
ggt agt aac ttc ccg aat gat ggt cca gtg atg aag aag aca atc aca       432
Gly Ser Asn Phe Pro Asn Asp Gly Pro Val Met Lys Lys Thr Ile Thr
    130                 135                 140
gga tta caa cct tcg ttc gaa gtt gtg tat atg aac gat ggc gtc ttg       480
Gly Leu Gln Pro Ser Phe Glu Val Val Tyr Met Asn Asp Gly Val Leu
145                 150                 155                 160
gtt ggc caa gtc att ctt gtt tat aga tta aac tct ggc aaa ttt tat       528
Val Gly Gln Val Ile Leu Val Tyr Arg Leu Asn Ser Gly Lys Phe Tyr
                165                 170                 175
tcg tgt cac atg aga aca ctg atg aaa tca aag ggt gta gtg aag gat       576
Ser Cys His Met Arg Thr Leu Met Lys Ser Lys Gly Val Val Lys Asp
            180                 185                 190
ttt ccc gaa tac cat ttc att caa cat cgt tta gag aag acg tat gtg       624
Phe Pro Glu Tyr His Phe Ile Gln His Arg Leu Glu Lys Thr Tyr Val
        195                 200                 205
gaa gac gga ggt ttt gtt gag gaa cac gag acg gcc att gct caa ctg       672
Glu Asp Gly Gly Phe Val Glu Glu His Glu Thr Ala Ile Ala Gln Leu
    210                 215                 220
aca tcg ctg ggg aaa cca ctt gga tcc tta cac gaa tgg gtt               714
Thr Ser Leu Gly Lys Pro Leu Gly Ser Leu His Glu Trp Val      SEQ ID NO:49
225                 230                 235                          SEQ ID NO:50
```

Fig. 28

```
atg agt aaa caa ata ttg aag aac act gga ttg cag gag atc atg tcg        48
Met Ser Lys Gln Ile Leu Lys Asn Thr Gly Leu Gln Glu Ile Met Ser
1               5                   10                  15
ttt aaa gtg aat ctg gaa ggt gta gta aac aat cat gtg ttc aca atg        96
Phe Lys Val Asn Leu Glu Gly Val Val Asn Asn His Val Phe Thr Met
            20                  25                  30
gaa ggt tgt gga aaa gga aat att tta tcc gga aac caa ctg gtt cag       144
Glu Gly Cys Gly Lys Gly Asn Ile Leu Ser Gly Asn Gln Leu Val Gln
        35                  40                  45
att cgt gtc aca aaa ggg gct ccg ctt cca ttt gca ttt gat att ctc       192
Ile Arg Val Thr Lys Gly Ala Pro Leu Pro Phe Ala Phe Asp Ile Leu
    50                  55                  60
tca cca gct ttc caa tac ggc aac cgt aca ttc acg aaa tac ccg gag       240
Ser Pro Ala Phe Gln Tyr Gly Asn Arg Thr Phe Thr Lys Tyr Pro Glu
65                  70                  75                  80
gat ata tca gac ttt ttt ata caa tca ttt cca gcg gga ttt gta tac       288
Asp Ile Ser Asp Phe Phe Ile Gln Ser Phe Pro Ala Gly Phe Val Tyr
                85                  90                  95
gaa aga acg ttg cgt ttc gaa gat ggt gga ctg gtt gaa atc cgt tca       336
Glu Arg Thr Leu Arg Phe Glu Asp Gly Gly Leu Val Glu Ile Arg Ser
            100                 105                 110
gat ata aat tta atc gag gag atg ttt gag tac aga gtg gaa tat aaa       384
Asp Ile Asn Leu Ile Glu Glu Met Phe Glu Tyr Arg Val Glu Tyr Lys
        115                 120                 125
ggt agt aac ttc ccg aat gat ggt cca gtg atg aag aag aca atc aca       432
Gly Ser Asn Phe Pro Asn Asp Gly Pro Val Met Lys Lys Thr Ile Thr
    130                 135                 140
gga tta caa cct tcg ttc gaa gtt gtg tat atg aac gat ggc gtc ttg       480
Gly Leu Gln Pro Ser Phe Glu Val Val Tyr Met Asn Asp Gly Val Leu
145                 150                 155                 160
gtt ggc caa gtc att ctt gtt tat aga tta aac tct ggc aaa ttt tat       528
Val Gly Gln Val Ile Leu Val Tyr Arg Leu Asn Ser Gly Lys Phe Tyr
                165                 170                 175
tcg tgt cac atg aga aca ctg atg aaa tca aag ggt gta gtg aag gat       576
Ser Cys His Met Arg Thr Leu Met Lys Ser Lys Gly Val Val Lys Asp
            180                 185                 190
ttt ccc gaa tac cat ttc att caa cat cgt tta gag aag acg tat gtg       624
Phe Pro Glu Tyr His Phe Ile Gln His Arg Leu Glu Lys Thr Tyr Val
        195                 200                 205
gaa gac gga ggt ttt gta gag gaa cac gag acg gcc att gct caa ctg       672
Glu Asp Gly Gly Phe Val Glu Glu His Glu Thr Ala Ile Ala Gln Leu
    210                 215                 220
aca tcg ctg ggg aaa cca ctt gga tcc tta cac gaa tgg gtt               714
Thr Ser Leu Gly Lys Pro Leu Gly Ser Leu His Glu Trp Val     SEQ ID NO:51
225                 230                 235                             SEQ ID NO:52
```

Fig. 29

```
atg agt aaa caa ata ttg aag aac act gga ttg cag gag atc atg tcg       48
Met Ser Lys Gln Ile Leu Lys Asn Thr Gly Leu Gln Glu Ile Met Ser
1               5                   10                  15
ttt aaa gtg aat ctg gaa ggt gta gta aac aat cat gtg ttc aca atg       96
Phe Lys Val Asn Leu Glu Gly Val Val Asn Asn His Val Phe Thr Met
            20                  25                  30
gaa ggt tgt gga aaa gga aat att tta tcc gga aac caa ctg gtt cag      144
Glu Gly Cys Gly Lys Gly Asn Ile Leu Ser Gly Asn Gln Leu Val Gln
        35                  40                  45
att cgt gtc aca aaa ggg gct ccg ctt cca ttt gca ttt gat att ctc      192
Ile Arg Val Thr Lys Gly Ala Pro Leu Pro Phe Ala Phe Asp Ile Leu
    50                  55                  60
tca cca gct ttc caa tac ggc aac cgt aca ttc acg aaa tac ccg gag      240
Ser Pro Ala Phe Gln Tyr Gly Asn Arg Thr Phe Thr Lys Tyr Pro Glu
65                  70                  75                  80
gat ata tca gac ttt ttt ata caa tca ttt cca gcg gga ttt gta tac      288
Asp Ile Ser Asp Phe Phe Ile Gln Ser Phe Pro Ala Gly Phe Val Tyr
                85                  90                  95
gaa aga acg ttg cgt ttc gaa gat ggt gga ctg gtt gaa atc cgt tca      336
Glu Arg Thr Leu Arg Phe Glu Asp Gly Gly Leu Val Glu Ile Arg Ser
            100                 105                 110
gat ata aat tta atc gag gag atg ttt gag tac aga gtg gaa tat aaa      384
Asp Ile Asn Leu Ile Glu Glu Met Phe Glu Tyr Arg Val Glu Tyr Lys
        115                 120                 125
ggt agt aac ttc ccg aat gat ggt cca gtg atg aag aag aca atc aca      432
Gly Ser Asn Phe Pro Asn Asp Gly Pro Val Met Lys Lys Thr Ile Thr
    130                 135                 140
gga tta caa cct tcg ttc gaa gtt gtg tat atg aac gat ggc gtc ttg      480
Gly Leu Gln Pro Ser Phe Glu Val Val Tyr Met Asn Asp Gly Val Leu
145                 150                 155                 160
gtt ggc caa gtc att ctt gtt tat aga tta aac tct ggc aaa ttt tat      528
Val Gly Gln Val Ile Leu Val Tyr Arg Leu Asn Ser Gly Lys Phe Tyr
                165                 170                 175
tcg tgt cac atg aga aca ctg atg aaa tca aag ggt gta gtg aag gat      576
Ser Cys His Met Arg Thr Leu Met Lys Ser Lys Gly Val Val Lys Asp
            180                 185                 190
ttt ccc gaa tac cat ttc att caa cat cgt tta gag aag acg tat gtg      624
Phe Pro Glu Tyr His Phe Ile Gln His Arg Leu Glu Lys Thr Tyr Val
        195                 200                 205
gaa gac gga ggt ttt gtt gag gaa cac gag acg gcc att gct caa ctg      672
Glu Asp Gly Gly Phe Val Glu Glu His Glu Thr Ala Ile Ala Gln Leu
    210                 215                 220
aca tcg ctg ggg aaa cca ctt gga tcc tta cac gaa tgg gtt              714
Thr Ser Leu Gly Lys Pro Leu Gly Ser Leu His Glu Trp Val    SEQ ID NO:53
225                 230                 235                        SEQ ID NO:54
```

Fig. 30

```
atg agt aaa caa ata ttg aag aac act gga ttg cag gag atc atg tcg          48
Met Ser Lys Gln Ile Leu Lys Asn Thr Gly Leu Gln Glu Ile Met Ser
1               5                   10                  15
ttt aaa gtg att ctg gaa ggt gta gta aac aat cat gtg ttc aca atg          96
Phe Lys Val Ile Leu Glu Gly Val Val Asn Asn His Val Phe Thr Met
            20                  25                  30
gaa ggt tgt gga aaa gga aat att tta ttc gga aac caa ctg gtt cag         144
Glu Gly Cys Gly Lys Gly Asn Ile Leu Phe Gly Asn Gln Leu Val Gln
        35                  40                  45
att cgt gtc aca aaa ggg gct ccg ctt cca ttt gca ttt gat att ctc         192
Ile Arg Val Thr Lys Gly Ala Pro Leu Pro Phe Ala Phe Asp Ile Leu
    50                  55                  60
tca cca gct ttc caa tac ggc aac cgt aca ttc acg aaa tac ccg gag         240
Ser Pro Ala Phe Gln Tyr Gly Asn Arg Thr Phe Thr Lys Tyr Pro Glu
65                  70                  75                  80
gat ata tca gac ttt ttt ata caa tca ttt cca gcg gga ttt gta tac         288
Asp Ile Ser Asp Phe Phe Ile Gln Ser Phe Pro Ala Gly Phe Val Tyr
                85                  90                  95
gaa aga acg ttg cgt ttc gaa gat ggt gga ctg gtt gaa atc cgt tca         336
Glu Arg Thr Leu Arg Phe Glu Asp Gly Gly Leu Val Glu Ile Arg Ser
            100                 105                 110
gat ata aat tta atc gag ggg atg ttt gtc tac aga gtg gaa tat aaa         384
Asp Ile Asn Leu Ile Glu Gly Met Phe Val Tyr Arg Val Glu Tyr Lys
        115                 120                 125
ggt agt aac ttc ccg aat gat ggt cca gtg atg aag aat aca atc aca         432
Gly Ser Asn Phe Pro Asn Asp Gly Pro Val Met Lys Asn Thr Ile Thr
    130                 135                 140
gga tta caa cct tcg ttc gaa gtt gtg tat atg aac gat ggc gtc ttg         480
Gly Leu Gln Pro Ser Phe Glu Val Val Tyr Met Asn Asp Gly Val Leu
145                 150                 155                 160
gtt ggc caa gtc att ctt gtt tat aga tta aac tct ggc aaa ttt tat         528
Val Gly Gln Val Ile Leu Val Tyr Arg Leu Asn Ser Gly Lys Phe Tyr
                165                 170                 175
tcg tgt cac atg aga aca ctg atg aaa tca aag ggt gta gtg aag gat         576
Ser Cys His Met Arg Thr Leu Met Lys Ser Lys Gly Val Val Lys Asp
            180                 185                 190
ttt ccc gaa tac cat ttc att caa cat cgt tta gag aag gcg tat gtg         624
Phe Pro Glu Tyr His Phe Ile Gln His Arg Leu Glu Lys Ala Tyr Val
        195                 200                 205
gaa gac gga ggt att gtt gag gaa cac gag acg gcc att gct caa ctg         672
Glu Asp Gly Gly Ile Val Glu Glu His Glu Thr Ala Ile Ala Gln Leu
    210                 215                 220
aca tcg ctg ggg aaa cca ctt gga tcc tta cac gaa tgg gtt                 714
Thr Ser Leu Gly Lys Pro Leu Gly Ser Leu His Glu Trp Val       SEQ ID NO:55
225                 230                 235                       SEQ ID NO:56
```

Fig. 31

```
atg agt aaa caa ata ttg aag aac act gga ttg cag gag atc atg tcg          48
Met Ser Lys Gln Ile Leu Lys Asn Thr Gly Leu Gln Glu Ile Met Ser
1               5                   10                  15
ttt aaa gtg aat ctg gaa ggt gta gta aac aat cat gtg ttc aca atg          96
Phe Lys Val Asn Leu Glu Gly Val Val Asn Asn His Val Phe Thr Met
            20                  25                  30
gaa ggt tgt gga aaa gga aat att tta ttc gga aac caa ctg gtt cag         144
Glu Gly Cys Gly Lys Gly Asn Ile Leu Phe Gly Asn Gln Leu Val Gln
        35                  40                  45
att cgt gtc aca aaa ggg gct ccg ctt cca ttt gca ttt gat att ctc         192
Ile Arg Val Thr Lys Gly Ala Pro Leu Pro Phe Ala Phe Asp Ile Leu
    50                  55                  60
tca cca gct ttc caa tac ggc aac cgt aca ttc acg aaa tac ccg gag         240
Ser Pro Ala Phe Gln Tyr Gly Asn Arg Thr Phe Thr Lys Tyr Pro Glu
65                  70                  75                  80
gat ata tca gac ttt ttt ata caa tca ttt cca gcg gga ttt gta tac         288
Asp Ile Ser Asp Phe Phe Ile Gln Ser Phe Pro Ala Gly Phe Val Tyr
                85                  90                  95
gaa aga acg ttg cgt tac gaa gat ggt gga ctg gct gaa atc cgt tca         336
Glu Arg Thr Leu Arg Tyr Glu Asp Gly Gly Leu Ala Glu Ile Arg Ser
            100                 105                 110
gat ata aat tta atc gag ggg atg ttt gtc tac aga gtg gaa tat aaa         384
Asp Ile Asn Leu Ile Glu Gly Met Phe Val Tyr Arg Val Glu Tyr Lys
        115                 120                 125
ggt agt aac ttc ccg aat gat ggt cca gtg atg aag aat aca atc aca         432
Gly Ser Asn Phe Pro Asn Asp Gly Pro Val Met Lys Asn Thr Ile Thr
    130                 135                 140
gga tta caa cct tcg ttc gaa gtt gtg tat atg aac gat ggc gtc ttg         480
Gly Leu Gln Pro Ser Phe Glu Val Val Tyr Met Asn Asp Gly Val Leu
145                 150                 155                 160
gtt ggc caa gtc att ctt gtt tat aga tta aac tct ggc aaa ttt tat         528
Val Gly Gln Val Ile Leu Val Tyr Arg Leu Asn Ser Gly Lys Phe Tyr
                165                 170                 175
tcg tgt cac atg aga aca ctg atg aaa tca aag ggt gta gtg aag gat         576
Ser Cys His Met Arg Thr Leu Met Lys Ser Lys Gly Val Val Lys Asp
            180                 185                 190
ttt ccc gaa tac cat ttc att caa cat cgt tta gag aag acg tat gtg         624
Phe Pro Glu Tyr His Phe Ile Gln His Arg Leu Glu Lys Thr Tyr Val
        195                 200                 205
gaa gac gga ggt ttt gtt gag gaa cac gag acg gcc att gct caa ctg         672
Glu Asp Gly Gly Phe Val Glu Glu His Glu Thr Ala Ile Ala Gln Leu
    210                 215                 220
aca tcg ctg ggg aaa cca ctt gga tcc tta cac gaa tgg gtt                 714
Thr Ser Leu Gly Lys Pro Leu Gly Ser Leu His Glu Trp Val       SEQ ID NO:57
225                 230                 235                           SEQ ID NO:58
```

Fig. 32

```
atg agt aaa caa ata ttg aag aac act gga ttg cag gag atc gtg tcg        48
Met Ser Lys Gln Ile Leu Lys Asn Thr Gly Leu Gln Glu Ile Val Ser
1               5                   10                  15
ttt aaa gtg att ctg gaa ggt gta gta aac aat cat gtg ttc aca atg        96
Phe Lys Val Ile Leu Glu Gly Val Val Asn Asn His Val Phe Thr Met
            20                  25                  30
gaa ggt tgt gga aaa gga aat att tta ttc gga aac caa ctg gtt cag       144
Glu Gly Cys Gly Lys Gly Asn Ile Leu Phe Gly Asn Gln Leu Val Gln
        35                  40                  45
att cgt gtc aca aaa ggg gct ccg ctt cca ttt gca ttt gat att ctc       192
Ile Arg Val Thr Lys Gly Ala Pro Leu Pro Phe Ala Phe Asp Ile Leu
    50                  55                  60
tca cca gct ttc caa tac ggc aac cgt aca ttc acg aaa tac ccg gag       240
Ser Pro Ala Phe Gln Tyr Gly Asn Arg Thr Phe Thr Lys Tyr Pro Glu
65                  70                  75                  80
gat ata tca gac ttt ttt ata caa tca ttt cca gcg gga ttt gta tac       288
Asp Ile Ser Asp Phe Phe Ile Gln Ser Phe Pro Ala Gly Phe Val Tyr
                85                  90                  95
gaa aga acg ttg cgt tac gaa gat ggt gga ctg gtt gaa atc cgt tca       336
Glu Arg Thr Leu Arg Tyr Glu Asp Gly Gly Leu Val Glu Ile Arg Ser
            100                 105                 110
gat ata aat tta atc gag ggg atg ttt gtc tac aga gtg gaa tat aaa       384
Asp Ile Asn Leu Ile Glu Gly Met Phe Val Tyr Arg Val Glu Tyr Lys
        115                 120                 125
ggt agt aac ttc ccg aat gat ggt cca gtg atg aag aat aca atc aca       432
Gly Ser Asn Phe Pro Asn Asp Gly Pro Val Met Lys Asn Thr Ile Thr
    130                 135                 140
gga tta caa cct tcg ttc gaa gtt gtg tat atg aac gat ggc gtc ttg       480
Gly Leu Gln Pro Ser Phe Glu Val Val Tyr Met Asn Asp Gly Val Leu
145                 150                 155                 160
gtt ggc caa gtc att ctt gtt tat aga tta aac tgt ggc aaa ttt tat       528
Val Gly Gln Val Ile Leu Val Tyr Arg Leu Asn Cys Gly Lys Phe Tyr
                165                 170                 175
tcg tgt cac atg aga aca ctg atg aaa tca aag ggt gta gtg aag gat       576
Ser Cys His Met Arg Thr Leu Met Lys Ser Lys Gly Val Val Lys Asp
            180                 185                 190
ttt ccc gaa tac cat ttc att caa cat cgt tta gag aag acg tat gtg       624
Phe Pro Glu Tyr His Phe Ile Gln His Arg Leu Glu Lys Thr Tyr Val
        195                 200                 205
gaa gac gga ggt ttt gtt gag gaa cac gag acg gcc att gct caa ctg       672
Glu Asp Gly Gly Phe Val Glu Glu His Glu Thr Ala Ile Ala Gln Leu
    210                 215                 220
aca tcg ctg ggg aaa cca ctt gga tcc tta cac gaa tgg gtt               714
Thr Ser Leu Gly Lys Pro Leu Gly Ser Leu His Glu Trp Val      SEQ ID NO:59
225                 230                 235                          SEQ ID NO:60
```

Fig. 33

```
atg agt aaa caa ata ttg aag aac act gga ttg cag gag atc atg tcg        48
Met Ser Lys Gln Ile Leu Lys Asn Thr Gly Leu Gln Glu Ile Met Ser
1               5                   10                  15
ttt aaa gtg aat ctg gaa ggt gta gta aac aat cat gtg ttc aca atg        96
Phe Lys Val Asn Leu Glu Gly Val Val Asn Asn His Val Phe Thr Met
            20                  25                  30
gaa ggt tgt gga aaa gga aat att tta ttc gga aac caa ctg gtt cag       144
Glu Gly Cys Gly Lys Gly Asn Ile Leu Phe Gly Asn Gln Leu Val Gln
        35                  40                  45
att cgt gtc aca aaa ggg gct ccg ctt cca ttt gca ttt gat att ctc       192
Ile Arg Val Thr Lys Gly Ala Pro Leu Pro Phe Ala Phe Asp Ile Leu
    50                  55                  60
tca cca gcc ttc caa tac ggc aac cgt aca ttc acg aaa tac ccg gag       240
Ser Pro Ala Phe Gln Tyr Gly Asn Arg Thr Phe Thr Lys Tyr Pro Glu
65                  70                  75                  80
gat ata tca gac ttt ttt ata caa tca ttt cca gcg gga ttt gta tac       288
Asp Ile Ser Asp Phe Phe Ile Gln Ser Phe Pro Ala Gly Phe Val Tyr
                85                  90                  95
gaa aga gcg ttg cgt tac gaa gat ggt gga ctg gtt gaa atc cgt tca       336
Glu Arg Ala Leu Arg Tyr Glu Asp Gly Gly Leu Val Glu Ile Arg Ser
            100                 105                 110
gat ata aat tta atc gag gag atg ttt gtc tac aga gtg gaa tat aaa       384
Asp Ile Asn Leu Ile Glu Glu Met Phe Val Tyr Arg Val Glu Tyr Lys
        115                 120                 125
ggt agt aac ttc ccg aat gat ggt cca gtg atg aag aag aca atc aca       432
Gly Ser Asn Phe Pro Asn Asp Gly Pro Val Met Lys Lys Thr Ile Thr
    130                 135                 140
gga tta caa cct tcg ttc gaa gtt gtg tat atg aac gat ggc gtc ttg       480
Gly Leu Gln Pro Ser Phe Glu Val Val Tyr Met Asn Asp Gly Val Leu
145                 150                 155                 160
gtt ggc caa gtc att ctt gtt tat aga tta aac tct ggc aaa ttt tat       528
Val Gly Gln Val Ile Leu Val Tyr Arg Leu Asn Ser Gly Lys Phe Tyr
                165                 170                 175
tcg tgt cac atg aga aca ctg atg aaa tca aag ggt gta gtg aag gat       576
Ser Cys His Met Arg Thr Leu Met Lys Ser Lys Gly Val Val Lys Asp
            180                 185                 190
ttt ccc gaa tac cat ttc att caa cat cgt tta gag aag acg tat gtg       624
Phe Pro Glu Tyr His Phe Ile Gln His Arg Leu Glu Lys Thr Tyr Val
        195                 200                 205
gaa gac gga ggt ttt gtt gag gaa cac gag acg gcc att gct caa ctg       672
Glu Asp Gly Gly Phe Val Glu Glu His Glu Thr Ala Ile Ala Gln Leu
    210                 215                 220
aca tcg ctg ggg aaa cca ctt gga tcc tta cac gaa tgg gtt               714
Thr Ser Leu Gly Lys Pro Leu Gly Ser Leu His Glu Trp Val      SEQ ID NO:61
225                 230                 235                      SEQ ID NO:62
```

Fig. 34

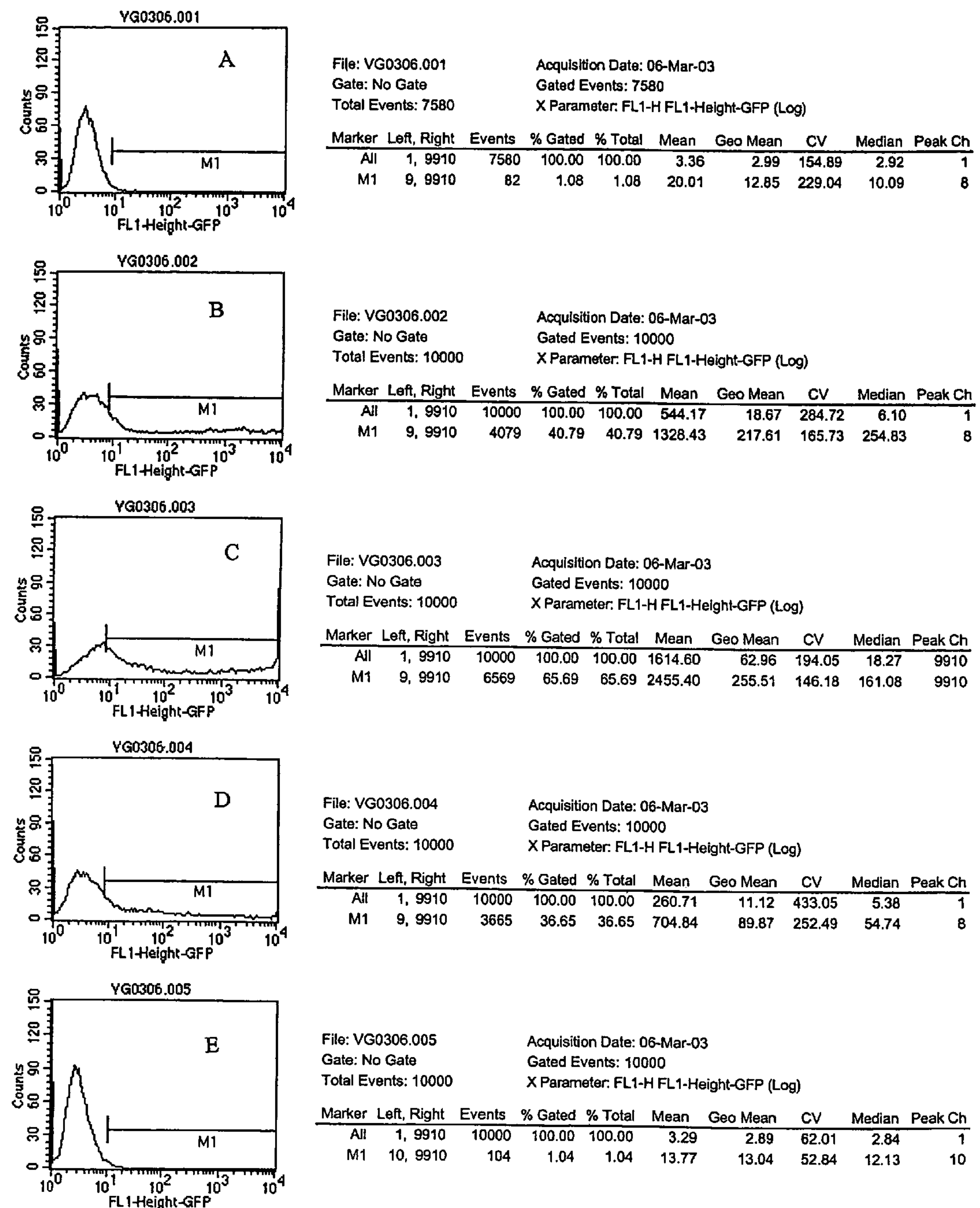

File: VG0306.001 Acquisition Date: 06-Mar-03
Gate: No Gate Gated Events: 7580
Total Events: 7580 X Parameter: FL1-H FL1-Height-GFP (Log)

| Marker | Left, Right | Events | % Gated | % Total | Mean | Geo Mean | CV | Median | Peak Ch |
|---|---|---|---|---|---|---|---|---|---|
| All | 1, 9910 | 7580 | 100.00 | 100.00 | 3.36 | 2.99 | 154.89 | 2.92 | 1 |
| M1 | 9, 9910 | 82 | 1.08 | 1.08 | 20.01 | 12.85 | 229.04 | 10.09 | 8 |

File: VG0306.002 Acquisition Date: 06-Mar-03
Gate: No Gate Gated Events: 10000
Total Events: 10000 X Parameter: FL1-H FL1-Height-GFP (Log)

| Marker | Left, Right | Events | % Gated | % Total | Mean | Geo Mean | CV | Median | Peak Ch |
|---|---|---|---|---|---|---|---|---|---|
| All | 1, 9910 | 10000 | 100.00 | 100.00 | 544.17 | 18.67 | 284.72 | 6.10 | 1 |
| M1 | 9, 9910 | 4079 | 40.79 | 40.79 | 1328.43 | 217.61 | 165.73 | 254.83 | 8 |

File: VG0306.003 Acquisition Date: 06-Mar-03
Gate: No Gate Gated Events: 10000
Total Events: 10000 X Parameter: FL1-H FL1-Height-GFP (Log)

| Marker | Left, Right | Events | % Gated | % Total | Mean | Geo Mean | CV | Median | Peak Ch |
|---|---|---|---|---|---|---|---|---|---|
| All | 1, 9910 | 10000 | 100.00 | 100.00 | 1614.60 | 62.96 | 194.05 | 18.27 | 9910 |
| M1 | 9, 9910 | 6569 | 65.69 | 65.69 | 2455.40 | 255.51 | 146.18 | 161.08 | 9910 |

File: VG0306.004 Acquisition Date: 06-Mar-03
Gate: No Gate Gated Events: 10000
Total Events: 10000 X Parameter: FL1-H FL1-Height-GFP (Log)

| Marker | Left, Right | Events | % Gated | % Total | Mean | Geo Mean | CV | Median | Peak Ch |
|---|---|---|---|---|---|---|---|---|---|
| All | 1, 9910 | 10000 | 100.00 | 100.00 | 260.71 | 11.12 | 433.05 | 5.38 | 1 |
| M1 | 9, 9910 | 3665 | 36.65 | 36.65 | 704.84 | 89.87 | 252.49 | 54.74 | 8 |

File: VG0306.005 Acquisition Date: 06-Mar-03
Gate: No Gate Gated Events: 10000
Total Events: 10000 X Parameter: FL1-H FL1-Height-GFP (Log)

| Marker | Left, Right | Events | % Gated | % Total | Mean | Geo Mean | CV | Median | Peak Ch |
|---|---|---|---|---|---|---|---|---|---|
| All | 1, 9910 | 10000 | 100.00 | 100.00 | 3.29 | 2.89 | 62.01 | 2.84 | 1 |
| M1 | 10, 9910 | 104 | 1.04 | 1.04 | 13.77 | 13.04 | 52.84 | 12.13 | 10 |

Fig. 35

SEQUENCE LISTING

```
<160> NUMBER OF SEQ ID NOS: 80

<210> SEQ ID NO 1
<211> LENGTH: 720
<212> TYPE: DNA
<213> ORGANISM: Renilla reniformis

<400> SEQUENCE: 1

atggtgagca agcagatcct gaagaacacc ggcctgcagg agatcatgag cttcaaggtg     60

aacctggagg gcgtggtgaa caaccacgtg ttcaccatgg agggctgcgg caagggcaac    120

atcctgttcg gcaaccagct ggtgcagatc cgcgtgacca agggcgcccc cctgcccttc    180

gccttcgaca tcctgagccc cgccttccag tacggcaacc gcaccttcac caagtacccc    240

gaggacatca gcgacttctt catccagagc ttccccgccg gcttcgtgta cgagcgcacc    300

ctgcgctacg aggacggcgg cctggtggag atccgcagcg acatcaacct gatcgaggag    360

atgttcgtgt accgcgtgga gtacaagggc cgcaacttcc ccaacgacgg ccccgtgatg    420

aagaagacca tcaccggcct gcagcccagc ttcgaggtgg tgtacatgaa cgacggcgtg    480

ctggtgggcc aggtgatcct ggtgtaccgc ctgaacagcg gcaagttcta cagctgccac    540

atgcgcaccc tgatgaagag caagggcgtg gtgaaggact tccccgagta ccacttcatc    600

cagcaccgcc tggagaagac ctacgtggag gacggcggct tcgtggagca gcacgagacc    660

gccatcgccc agctgaccag cctgggcaag cccctgggca gcctgcacga gtgggtgtaa    720


<210> SEQ ID NO 2
<211> LENGTH: 239
<212> TYPE: PRT
<213> ORGANISM: Renilla reniformis

<400> SEQUENCE: 2

Met Val Ser Lys Gln Ile Leu Lys Asn Thr Gly Leu Gln Glu Ile Met
1               5                   10                  15

Ser Phe Lys Val Asn Leu Glu Gly Val Val Asn Asn His Val Phe Thr
            20                  25                  30

Met Glu Gly Cys Gly Lys Gly Asn Ile Leu Phe Gly Asn Gln Leu Val
        35                  40                  45

Gln Ile Arg Val Thr Lys Gly Ala Pro Leu Pro Phe Ala Phe Asp Ile
    50                  55                  60

Leu Ser Pro Ala Phe Gln Tyr Gly Asn Arg Thr Phe Thr Lys Tyr Pro
65                  70                  75                  80

Glu Asp Ile Ser Asp Phe Phe Ile Gln Ser Phe Pro Ala Gly Phe Val
                85                  90                  95

Tyr Glu Arg Thr Leu Arg Tyr Glu Asp Gly Gly Leu Val Glu Ile Arg
            100                 105                 110
```

-continued

```
Ser Asp Ile Asn Leu Ile Glu Glu Met Phe Val Tyr Arg Val Glu Tyr
        115                 120                 125

Lys Gly Arg Asn Phe Pro Asn Asp Gly Pro Val Met Lys Lys Thr Ile
    130                 135                 140

Thr Gly Leu Gln Pro Ser Phe Glu Val Val Tyr Met Asn Asp Gly Val
145                 150                 155                 160

Leu Val Gly Gln Val Ile Leu Val Tyr Arg Leu Asn Ser Gly Lys Phe
                165                 170                 175

Tyr Ser Cys His Met Arg Thr Leu Met Lys Ser Lys Gly Val Val Lys
            180                 185                 190

Asp Phe Pro Glu Tyr His Phe Ile Gln His Arg Leu Glu Lys Thr Tyr
        195                 200                 205

Val Glu Asp Gly Gly Phe Val Glu Gln His Glu Thr Ala Ile Ala Gln
    210                 215                 220

Leu Thr Ser Leu Gly Lys Pro Leu Gly Ser Leu His Glu Trp Val
225                 230                 235


<210> SEQ ID NO 3
<211> LENGTH: 720
<212> TYPE: DNA
<213> ORGANISM: Renilla reniformis

<400> SEQUENCE: 3

atggtgagca agcagatcct gaagaacacc ggcctgcagg agatcatgag cttcaaggtg     60

aacctggagg gcgtggtgaa caaccacgtg ttcaccatgg agggctgcgg caagggcaac    120

atcctgttag gcaaccagct ggtgcagatc cgcgtgacca agggcgcccc cctgcccttc    180

gccttcgaca tcctgagccc cgccttccag tacggcaacc gcaccttcac caagtacccc    240

gaggacatca gcgacttctt catccagagc ttccccgccg gcttcgtgta cgagcgcacc    300

ctgcgctacg aggacggcgg cctggtggag atccgcagcg acatcaacct gatcgaggag    360

atgttcgtgt accgcgtgga gtacaagggc cgcaacttcc ccaacgacgg ccccgtgatg    420

aagaagacca tcaccggcct gcagcccagc ttcgaggtgg tgtacatgaa cgacggcgtg    480

ctggtgggcc aggtgatcct ggtgtaccgc ctgaacagcg gcaagttcta cagctgccac    540

atgcgcaccc tgatgaagag caagggcgtg gtgaaggact tccccgagta ccacttcatc    600

cagcaccgcc tggagaagac ctacgtggag gacggcggct tcgtggagca gcacgagacc    660

gccatcgccc agctgaccag cctgggcaag cccctgggca gcctgcacga gtgggtgtaa    720


<210> SEQ ID NO 4
<211> LENGTH: 239
<212> TYPE: PRT
<213> ORGANISM: Renilla reniformis

<400> SEQUENCE: 4

Met Val Ser Lys Gln Ile Leu Lys Asn Thr Gly Leu Gln Glu Ile Met
1               5                   10                  15

Ser Phe Lys Val Asn Leu Glu Gly Val Val Asn Asn His Val Phe Thr
            20                  25                  30

Met Glu Gly Cys Gly Lys Gly Asn Ile Leu Leu Gly Asn Gln Leu Val
        35                  40                  45

Gln Ile Arg Val Thr Lys Gly Ala Pro Leu Pro Phe Ala Phe Asp Ile
    50                  55                  60

Leu Ser Pro Ala Phe Gln Tyr Gly Asn Arg Thr Phe Thr Lys Tyr Pro
65                  70                  75                  80
```

-continued

```
Glu Asp Ile Ser Asp Phe Phe Ile Gln Ser Phe Pro Ala Gly Phe Val
                85                  90                  95

Tyr Glu Arg Thr Leu Arg Tyr Glu Asp Gly Gly Leu Val Glu Ile Arg
            100                 105                 110

Ser Asp Ile Asn Leu Ile Glu Glu Met Phe Val Tyr Arg Val Glu Tyr
        115                 120                 125

Lys Gly Arg Asn Phe Pro Asn Asp Gly Pro Val Met Lys Lys Thr Ile
    130                 135                 140

Thr Gly Leu Gln Pro Ser Phe Glu Val Val Tyr Met Asn Asp Gly Val
145                 150                 155                 160

Leu Val Gly Gln Val Ile Leu Val Tyr Arg Leu Asn Ser Gly Lys Phe
                165                 170                 175

Tyr Ser Cys His Met Arg Thr Leu Met Lys Ser Lys Gly Val Val Lys
            180                 185                 190

Asp Phe Pro Glu Tyr His Phe Ile Gln His Arg Leu Glu Lys Thr Tyr
        195                 200                 205

Val Glu Asp Gly Gly Phe Val Glu Gln His Glu Thr Ala Ile Ala Gln
    210                 215                 220

Leu Thr Ser Leu Gly Lys Pro Leu Gly Ser Leu His Glu Trp Val
225                 230                 235
```

<210> SEQ ID NO 5
<211> LENGTH: 720
<212> TYPE: DNA
<213> ORGANISM: Renilla reniformis

<400> SEQUENCE: 5

```
atggtgagca agcagatcct gaagaacacc ggcctgcagg agatcatgag cttcaaggtg      60

aacctggagg gcgtggtgaa caaccacgtg ttcaccatgg agggctgcgg caagggcaac     120

atcctgttcg gcaaccagct ggtgcagatc cgcgtgacca agggcgcccc cctgcccttc     180

gccttcgaca tcctgagccc cgccttccag tacggcaacc gcaccttcac caagtacccc     240

gaggacatca gcgacttctt catccagagc ttccccgccg gcttcgtgta cgagcgcacc     300

ctgcgctacg aggacggcgg cctggtggag atccgcagcg acatcaacct gatcgagggg     360

atgttcgtgt accgcgtgga gtacaagggc cgcaacttcc ccaacgacgg ccccgtgatg     420

aagaagacca tcaccggcct gcagcccagc ttcgaggtgg tgtacatgaa cgacggcgtg     480

ctggtgggcc aggtgatcct ggtgtaccgc ctgaacagcg gcaagttcta cagctgccac     540

atgcgcaccc tgatgaagag caagggcgtg gtgaaggact tccccgagta ccacttcatc     600

cagcaccgcc tggagaagac ctacgtggag gacggcggct tcgtagagca gcacgagacc     660

gccatcgccc agctgaccag cctgggcaag cccctgggca gcctgcacga gtgggtgtaa     720
```

<210> SEQ ID NO 6
<211> LENGTH: 239
<212> TYPE: PRT
<213> ORGANISM: Renilla reniformis

<400> SEQUENCE: 6

```
Met Val Ser Lys Gln Ile Leu Lys Asn Thr Gly Leu Gln Glu Ile Met
1               5                   10                  15

Ser Phe Lys Val Asn Leu Glu Gly Val Val Asn Asn His Val Phe Thr
            20                  25                  30

Met Glu Gly Cys Gly Lys Gly Asn Ile Leu Phe Gly Asn Gln Leu Val
        35                  40                  45
```

-continued

```
Gln Ile Arg Val Thr Lys Gly Ala Pro Leu Pro Phe Ala Phe Asp Ile
    50                  55                  60

Leu Ser Pro Ala Phe Gln Tyr Gly Asn Arg Thr Phe Thr Lys Tyr Pro
65                  70                  75                  80

Glu Asp Ile Ser Asp Phe Phe Ile Gln Ser Phe Pro Ala Gly Phe Val
                85                  90                  95

Tyr Glu Arg Thr Leu Arg Tyr Glu Asp Gly Gly Leu Val Glu Ile Arg
            100                 105                 110

Ser Asp Ile Asn Leu Ile Glu Gly Met Phe Val Tyr Arg Val Glu Tyr
        115                 120                 125

Lys Gly Arg Asn Phe Pro Asn Asp Gly Pro Val Met Lys Lys Thr Ile
    130                 135                 140

Thr Gly Leu Gln Pro Ser Phe Glu Val Val Tyr Met Asn Asp Gly Val
145                 150                 155                 160

Leu Val Gly Gln Val Ile Leu Val Tyr Arg Leu Asn Ser Gly Lys Phe
                165                 170                 175

Tyr Ser Cys His Met Arg Thr Leu Met Lys Ser Lys Gly Val Val Lys
            180                 185                 190

Asp Phe Pro Glu Tyr His Phe Ile Gln His Arg Leu Glu Lys Thr Tyr
        195                 200                 205

Val Glu Asp Gly Gly Phe Val Glu Gln His Glu Thr Ala Ile Ala Gln
    210                 215                 220

Leu Thr Ser Leu Gly Lys Pro Leu Gly Ser Leu His Glu Trp Val
225                 230                 235
```

```
<210> SEQ ID NO 7
<211> LENGTH: 720
<212> TYPE: DNA
<213> ORGANISM: Renilla reniformis

<400> SEQUENCE: 7

atggtgagca agcagatcct gaagaacacc ggcctgcagg agatcatgag cttcaaggtg     60

aacctggagg gcgtggtgaa caaccacgtg ttcaccatgg agggctgcgg caagggcaac    120

atcctgttcg gcaaccagct ggtgcagatc cgcgtgacca agggcgcccc cctgcccttc    180

gccttcgaca tcctgagccc cgccttccag tacggcaacc gcaccttcac caagtacccc    240

gaggacatca gcgacttctt catccagagc ttccccgccg gcttcgtgta cgagcgcacc    300

atgcgctacg aggacggcgg cctggtggag atccgcagcg acatcaacct gatcgaggag    360

atgttcgtgt accgcgtgga gtacaagggc cgcaacttcc ccaacgacgg ccccgtgatg    420

aagaagacca tcaccggcct gcagcccagc ttcgaggtgg tgtacatgaa cgacggcgtg    480

ctggtgggcc aggtgatcct ggtgtaccgc ctgaacagcg gcaagttcta cagctgccac    540

atgcgcaccc tgatgaagag caagggcgtg gtgaaggact tccccgagta ccacttcatc    600

cagcaccgcc tggagaagac ctacgtggag gacggcggct tcgtggagca gcacgagacc    660

gccatcgccc agctgaccag cctgggcaag cccctgggca gcctgcacga gtgggtgtaa    720
```

```
<210> SEQ ID NO 8
<211> LENGTH: 239
<212> TYPE: PRT
<213> ORGANISM: Renilla reniformis

<400> SEQUENCE: 8

Met Val Ser Lys Gln Ile Leu Lys Asn Thr Gly Leu Gln Glu Ile Met
1               5                   10                  15
```

-continued

```
Ser Phe Lys Val Asn Leu Glu Gly Val Val Asn Asn His Val Phe Thr
            20                  25                  30

Met Glu Gly Cys Gly Lys Gly Asn Ile Leu Phe Gly Asn Gln Leu Val
        35                  40                  45

Gln Ile Arg Val Thr Lys Gly Ala Pro Leu Pro Phe Ala Phe Asp Ile
    50                  55                  60

Leu Ser Pro Ala Phe Gln Tyr Gly Asn Arg Thr Phe Thr Lys Tyr Pro
65                  70                  75                  80

Glu Asp Ile Ser Asp Phe Phe Ile Gln Ser Phe Pro Ala Gly Phe Val
                85                  90                  95

Tyr Glu Arg Thr Met Arg Tyr Glu Asp Gly Gly Leu Val Glu Ile Arg
            100                 105                 110

Ser Asp Ile Asn Leu Ile Glu Glu Met Phe Val Tyr Arg Val Glu Tyr
        115                 120                 125

Lys Gly Arg Asn Phe Pro Asn Asp Gly Pro Val Met Lys Lys Thr Ile
    130                 135                 140

Thr Gly Leu Gln Pro Ser Phe Glu Val Val Tyr Met Asn Asp Gly Val
145                 150                 155                 160

Leu Val Gly Gln Val Ile Leu Val Tyr Arg Leu Asn Ser Gly Lys Phe
                165                 170                 175

Tyr Ser Cys His Met Arg Thr Leu Met Lys Ser Lys Gly Val Val Lys
            180                 185                 190

Asp Phe Pro Glu Tyr His Phe Ile Gln His Arg Leu Glu Lys Thr Tyr
        195                 200                 205

Val Glu Asp Gly Gly Phe Val Glu Gln His Glu Thr Ala Ile Ala Gln
    210                 215                 220

Leu Thr Ser Leu Gly Lys Pro Leu Gly Ser Leu His Glu Trp Val
225                 230                 235
```

<210> SEQ ID NO 9
<211> LENGTH: 720
<212> TYPE: DNA
<213> ORGANISM: Renilla reniformis

<400> SEQUENCE: 9

```
atggtgagca agcagatcct gaagaacacc ggcctgcagg agatcatgag cttcaaggtg      60

aacctggagg gcgtggtgaa caaccacgtg ttcaccatgg agggctgcgg caagggcaac     120

atcctgtccg gcaaccagct ggtgcagatc cgcgtgacca agggcgcccc cctgcccttc     180

gccttcgaca tcctgagccc cgccttccag tacggcaacc gcaccttcac caagtacccc     240

gaggacatca gcgacttctt catccagagc ttccccgccg gcttcgtgta cgagcgcacc     300

ctgcgctacg aggacggcgg cctggtggag atccgcagcg acatcaacct gatcgaggag     360

atgttcgtgt accgcgtgga gtacaagggc cgcaacttcc ccaacgacgg ccccgtgatg     420

aagaagacca tcaccggcct gcagcccagc ttcgaggtgg tgtacatgaa cgacggcgtg     480

ctggtgggcc aggtgatcct ggtgtaccgc ctgaacagcg gcaagttcta cagctgccac     540

atgcgcaccc tgatgaagag caagggcgtg gtgaaggact tccccgagta ccacttcatc     600

cagcaccgcc tggagaagac ctacgtggag gacggcggct tcgtggagca gcacgagacc     660

gccatcgccc agctgaccag cctgggcaag cccctgggca gcctgcacga gtgggtgtaa     720
```

<210> SEQ ID NO 10
<211> LENGTH: 239
<212> TYPE: PRT

-continued

<213> ORGANISM: Renilla reniformis

<400> SEQUENCE: 10

```
Met Val Ser Lys Gln Ile Leu Lys Asn Thr Gly Leu Gln Glu Ile Met
1               5                   10                  15

Ser Phe Lys Val Asn Leu Glu Gly Val Val Asn Asn His Val Phe Thr
            20                  25                  30

Met Glu Gly Cys Gly Lys Gly Asn Ile Leu Ser Gly Asn Gln Leu Val
        35                  40                  45

Gln Ile Arg Val Thr Lys Gly Ala Pro Leu Pro Phe Ala Phe Asp Ile
    50                  55                  60

Leu Ser Pro Ala Phe Gln Tyr Gly Asn Arg Thr Phe Thr Lys Tyr Pro
65                  70                  75                  80

Glu Asp Ile Ser Asp Phe Phe Ile Gln Ser Phe Pro Ala Gly Phe Val
                85                  90                  95

Tyr Glu Arg Thr Leu Arg Tyr Glu Asp Gly Gly Leu Val Glu Ile Arg
            100                 105                 110

Ser Asp Ile Asn Leu Ile Glu Glu Met Phe Val Tyr Arg Val Glu Tyr
        115                 120                 125

Lys Gly Arg Asn Phe Pro Asn Asp Gly Pro Val Met Lys Lys Thr Ile
    130                 135                 140

Thr Gly Leu Gln Pro Ser Phe Glu Val Val Tyr Met Asn Asp Gly Val
145                 150                 155                 160

Leu Val Gly Gln Val Ile Leu Val Tyr Arg Leu Asn Ser Gly Lys Phe
                165                 170                 175

Tyr Ser Cys His Met Arg Thr Leu Met Lys Ser Lys Gly Val Val Lys
            180                 185                 190

Asp Phe Pro Glu Tyr His Phe Ile Gln His Arg Leu Glu Lys Thr Tyr
        195                 200                 205

Val Glu Asp Gly Gly Phe Val Glu Gln His Glu Thr Ala Ile Ala Gln
    210                 215                 220

Leu Thr Ser Leu Gly Lys Pro Leu Gly Ser Leu His Glu Trp Val
225                 230                 235
```

<210> SEQ ID NO 11
<211> LENGTH: 720
<212> TYPE: DNA
<213> ORGANISM: Renilla reniformis

<400> SEQUENCE: 11

```
atggtgagca agcagatcct gaagaacacc ggcctgcagg agatcatgag cttcaaggtg     60

aacctggagg gcgtggtgaa caaccacgtg ttcaccatgg agggctgcgg caagggcaac    120

atcctgttcg gcaaccagct ggtgcagatc cgcgtgacca agggcgcccc cctgcccttc    180

gccttcgaca tcctgagccc cgccttccag tacggcaacc gcaccttcac caagtacccc    240

gaggacatca gcgacttctt catccagagc ttccccgccg gcttcgtgta cgagcgcacc    300

ctgctctacg aggacggcgg cctggtggag atccgcagcg acatcaacct gatcgaggag    360

atgttcgtgt accacgtgga gtacaagggc cgcaacttcc ccaacgacgg ccccgtgatg    420

aagaagacca tcaccggcct gcagcccagc ttcgaggtgg tgtacatgaa cgacggcgtg    480

ctggtgggcc aggtgatcct ggtgtaccgc ctgaacagcg gcaagttcta cagctgccac    540

atgcgcaccc tgatgaagag caagggcgtg gtgaaggact tccccgagta ccacttcatc    600

cagcaccgcc tggagaagac ctacgtggag gacggcggct tcgtggagca gcacgagacc    660
```

```
gccatcgccc agctgaccag cctgggcaat cccctgggca gcctgcacga gtgggtgtaa     720


<210> SEQ ID NO 12
<211> LENGTH: 239
<212> TYPE: PRT
<213> ORGANISM: Renilla reniformis

<400> SEQUENCE: 12

Met Val Ser Lys Gln Ile Leu Lys Asn Thr Gly Leu Gln Glu Ile Met
1               5                   10                  15

Ser Phe Lys Val Asn Leu Glu Gly Val Val Asn Asn His Val Phe Thr
            20                  25                  30

Met Glu Gly Cys Gly Lys Gly Asn Ile Leu Phe Gly Asn Gln Leu Val
        35                  40                  45

Gln Ile Arg Val Thr Lys Gly Ala Pro Leu Pro Phe Ala Phe Asp Ile
    50                  55                  60

Leu Ser Pro Ala Phe Gln Tyr Gly Asn Arg Thr Phe Thr Lys Tyr Pro
65                  70                  75                  80

Glu Asp Ile Ser Asp Phe Phe Ile Gln Ser Phe Pro Ala Gly Phe Val
                85                  90                  95

Tyr Glu Arg Thr Leu Cys Tyr Glu Asp Gly Gly Leu Val Glu Ile Arg
            100                 105                 110

Ser Asp Ile Asn Leu Ile Glu Glu Met Phe Val Tyr His Val Glu Tyr
        115                 120                 125

Lys Gly Arg Asn Phe Pro Asn Asp Gly Pro Val Met Lys Lys Thr Ile
    130                 135                 140

Thr Gly Leu Gln Pro Ser Phe Glu Val Val Tyr Met Asn Asp Gly Val
145                 150                 155                 160

Leu Val Gly Gln Val Ile Leu Val Tyr Arg Leu Asn Ser Gly Lys Phe
                165                 170                 175

Tyr Ser Cys His Met Arg Thr Leu Met Lys Ser Lys Gly Val Val Lys
            180                 185                 190

Asp Phe Pro Glu Tyr His Phe Ile Gln His Arg Leu Glu Lys Thr Tyr
        195                 200                 205

Val Glu Asp Gly Gly Phe Val Glu Gln His Glu Thr Ala Ile Ala Gln
    210                 215                 220

Leu Thr Ser Leu Gly Tyr Pro Leu Gly Ser Leu His Glu Trp Val
225                 230                 235


<210> SEQ ID NO 13
<211> LENGTH: 720
<212> TYPE: DNA
<213> ORGANISM: Renilla reniformis

<400> SEQUENCE: 13

atggtgagca agcagatcct gaagaacacc ggcctgcagg agatcatgag cttcaaggtg      60

atcctggagg gcgtggtgaa caaccacgtg ttcaccatgg agggctgcgg caagggcaac     120

atcctgttcg gcaaccagct ggtgcagatc cgcgtgacca agggcgcccc cctgcccttc     180

gccttcgaca tcctgagccc cgccttccag tacggcaacc gcaccttcac caagtacccc     240

gaggacatca gcgacttctt catccagagc ttccccgccg gcttcgtgta cgagcgcacc     300

ctgcgctacg aggacggcgg cctggtggag atccgcagcg acatcaacct gatcgagggg     360

atgttcgtgt accgcgtgga gtacaagggc cgcaacttcc ccaacgacgg ccccgtgatg     420

aagaatacca tcaccggcct gcagcccagc ttcgaggtgg tgtacatgaa cgacggcgtg     480
```

-continued

```
ctggtgggcc aggtgatcct ggtgtaccgc ctgaacagcg gcaagttcta cagctgccac    540

atgcgcaccc tgatgaagag caagggcgtg gtgaaggact tccccgagta ccacttcatc    600

cagcaccgcc tggagaagac ctacgtggag gacggcggct tcgtggagca gcacgagacc    660

gccatcgccc agctgaccag cctgggcaag cccctgggca gcctgcacga gtgggtgtaa    720


<210> SEQ ID NO 14
<211> LENGTH: 239
<212> TYPE: PRT
<213> ORGANISM: Renilla reniformis

<400> SEQUENCE: 14

Met Val Ser Lys Gln Ile Leu Lys Asn Thr Gly Leu Gln Glu Ile Met
1               5                   10                  15

Ser Phe Lys Val Ile Leu Glu Gly Val Val Asn Asn His Val Phe Thr
            20                  25                  30

Met Glu Gly Cys Gly Lys Gly Asn Ile Leu Phe Gly Asn Gln Leu Val
        35                  40                  45

Gln Ile Arg Val Thr Lys Gly Ala Pro Leu Pro Phe Ala Phe Asp Ile
    50                  55                  60

Leu Ser Pro Ala Phe Gln Tyr Gly Asn Arg Thr Phe Thr Lys Tyr Pro
65                  70                  75                  80

Glu Asp Ile Ser Asp Phe Phe Ile Gln Ser Phe Pro Ala Gly Phe Val
                85                  90                  95

Tyr Glu Arg Thr Leu Arg Tyr Glu Asp Gly Gly Leu Val Glu Ile Arg
            100                 105                 110

Ser Asp Ile Asn Leu Ile Glu Gly Met Phe Val Tyr Arg Val Glu Tyr
        115                 120                 125

Lys Gly Arg Asn Phe Pro Asn Asp Gly Pro Val Met Lys Asn Thr Ile
    130                 135                 140

Thr Gly Leu Gln Pro Ser Phe Glu Val Val Tyr Met Asn Asp Gly Val
145                 150                 155                 160

Leu Val Gly Gln Val Ile Leu Val Tyr Arg Leu Asn Ser Gly Lys Phe
                165                 170                 175

Tyr Ser Cys His Met Arg Thr Leu Met Lys Ser Lys Gly Val Val Lys
            180                 185                 190

Asp Phe Pro Glu Tyr His Phe Ile Gln His Arg Leu Glu Lys Thr Tyr
        195                 200                 205

Val Glu Asp Gly Gly Phe Val Glu Gln His Glu Thr Ala Ile Ala Gln
    210                 215                 220

Leu Thr Ser Leu Gly Lys Pro Leu Gly Ser Leu His Glu Trp Val
225                 230                 235


<210> SEQ ID NO 15
<211> LENGTH: 720
<212> TYPE: DNA
<213> ORGANISM: Renilla reniformis

<400> SEQUENCE: 15

atggtgagca agcagatcct gaagaacacc ggcctgcagg agatcatgag cttcaaggtg     60

aacctggagg gcgtggtgaa caaccacgtg ttcaccatgg agggctgcgg caagggcaac    120

atcctgttcg gcaaccagct ggtgcagatc cgcgtgacca agggcgcccc cctgcccttc    180

gccttcgaca tcctgagccc cgccttccag tacggcaacc gcaccttcac caagtacccc    240

gaggacatca gcgacttctt catccagagc ttccccgccg gcttcgtgta cgagcgcacc    300
```

```
ctgcgcttcg aggacggcgg cctggtggag atccgcagcg acatcaacct gatcgaggag    360

atgttcgtgt accgcgtgga gtacaagggc cgcaacttcc ccaacgacgg ccccgtgatg    420

aagaagacca tcaccggcct gcagcccagc ttcgaggtgg tgtacatgaa cgacggcgtg    480

ctggtgggcc aggtgatcct ggtgtaccgc ctgaacagcg gcaagttcta cagctgccac    540

atgcgcaccc tgatgaagag caagggcgtg gtgaaggact tccccgagta ccacttcatc    600

cagcaccgcc tggagaagac ctacgtggag gacggcggct tcgtggagca gcacgagacc    660

gccatcgccc agctgaccag cctgggcaag cccctgggca gcctgcacga gtgggtgtaa    720
```

<210> SEQ ID NO 16
<211> LENGTH: 239
<212> TYPE: PRT
<213> ORGANISM: Renilla reniformis

<400> SEQUENCE: 16

```
Met Val Ser Lys Gln Ile Leu Lys Asn Thr Gly Leu Gln Glu Ile Met
1               5                   10                  15

Ser Phe Lys Val Asn Leu Glu Gly Val Val Asn Asn His Val Phe Thr
            20                  25                  30

Met Glu Gly Cys Gly Lys Gly Asn Ile Leu Phe Gly Asn Gln Leu Val
        35                  40                  45

Gln Ile Arg Val Thr Lys Gly Ala Pro Leu Pro Phe Ala Phe Asp Ile
    50                  55                  60

Leu Ser Pro Ala Phe Gln Tyr Gly Asn Arg Thr Phe Thr Lys Tyr Pro
65                  70                  75                  80

Glu Asp Ile Ser Asp Phe Phe Ile Gln Ser Phe Pro Ala Gly Phe Val
                85                  90                  95

Tyr Glu Arg Thr Leu Arg Phe Glu Asp Gly Gly Leu Val Glu Ile Arg
            100                 105                 110

Ser Asp Ile Asn Leu Ile Glu Glu Met Phe Val Tyr Arg Val Glu Tyr
        115                 120                 125

Lys Gly Arg Asn Phe Pro Asn Asp Gly Pro Val Met Lys Lys Thr Ile
    130                 135                 140

Thr Gly Leu Gln Pro Ser Phe Glu Val Val Tyr Met Asn Asp Gly Val
145                 150                 155                 160

Leu Val Gly Gln Val Ile Leu Val Tyr Arg Leu Asn Ser Gly Lys Phe
                165                 170                 175

Tyr Ser Cys His Met Arg Thr Leu Met Lys Ser Lys Gly Val Val Lys
            180                 185                 190

Asp Phe Pro Glu Tyr His Phe Ile Gln His Arg Leu Glu Lys Thr Tyr
        195                 200                 205

Val Glu Asp Gly Gly Phe Val Glu Gln His Glu Thr Ala Ile Ala Gln
    210                 215                 220

Leu Thr Ser Leu Gly Lys Pro Leu Gly Ser Leu His Glu Trp Val
225                 230                 235
```

<210> SEQ ID NO 17
<211> LENGTH: 720
<212> TYPE: DNA
<213> ORGANISM: Renilla reniformis

<400> SEQUENCE: 17

```
atggtgagca agcagatcct gaagaacacc ggcctgcagg agatcatgag cttcaaggtg     60

aacctggagg gcgtggtgaa caaccacgtg ttccccatgg agggctgcgg caagggcaac    120
```

```
atcctgttcg gcaaccagct ggtgcagatc cgcgtgacca agggcgcccc cctgcccttc    180

gccttcgaca tcctgagccc cgccttccag tacggcaacc gcaccttcac caagtacccc    240

gaggacatca gcgacttctt catccagagc ttccccgccg gcttcgtgta cgagcgcacc    300

ctgcgcttcg aggacggcgg cctggtggag atccgcagcg acatcaacct gatcgaggag    360

atgttcgtgt accgcgtgga gtacaagggc cgcaacttcc ccaacgacgg ccccgtgatg    420

aagaagacca tcaccggcct gcagcccagc ttcgaggtgg tgtacatgaa cgacggcgtg    480

ctggtgggcc aggtgatcct ggtgtaccgc ctgaacagcg gcaagttcta cagctgccac    540

atgcgcaccc tgatgaagag caagggcgtg gtgaaggact tccccgagta ccacttcatc    600

cagcaccgcc tggagaagac ctacgtggag gacggcggct tcgtggagca gcacgagacc    660

gccatcgccc agctgaccag cctgggcaag cccctgggca gcctgcacga gtgggtgtaa    720
```

<210> SEQ ID NO 18
<211> LENGTH: 239
<212> TYPE: PRT
<213> ORGANISM: Renilla reniformis

<400> SEQUENCE: 18

```
Met Val Ser Lys Gln Ile Leu Lys Asn Thr Gly Leu Gln Glu Ile Met
1               5                   10                  15

Ser Phe Lys Val Asn Leu Glu Gly Val Val Asn Asn His Val Phe Pro
            20                  25                  30

Met Glu Gly Cys Gly Lys Gly Asn Ile Leu Phe Gly Asn Gln Leu Val
        35                  40                  45

Gln Ile Arg Val Thr Lys Gly Ala Pro Leu Pro Phe Ala Phe Asp Ile
    50                  55                  60

Leu Ser Pro Ala Phe Gln Tyr Gly Asn Arg Thr Phe Thr Lys Tyr Pro
65                  70                  75                  80

Glu Asp Ile Ser Asp Phe Phe Ile Gln Ser Phe Pro Ala Gly Phe Val
                85                  90                  95

Tyr Glu Arg Thr Leu Arg Phe Glu Asp Gly Gly Leu Val Glu Ile Arg
            100                 105                 110

Ser Asp Ile Asn Leu Ile Glu Glu Met Phe Val Tyr Arg Val Glu Tyr
        115                 120                 125

Lys Gly Arg Asn Phe Pro Asn Asp Gly Pro Val Met Lys Lys Thr Ile
    130                 135                 140

Thr Gly Leu Gln Pro Ser Phe Glu Val Val Tyr Met Asn Asp Gly Val
145                 150                 155                 160

Leu Val Gly Gln Val Ile Leu Val Tyr Arg Leu Asn Ser Gly Lys Phe
                165                 170                 175

Tyr Ser Cys His Met Arg Thr Leu Met Lys Ser Lys Gly Val Val Lys
            180                 185                 190

Asp Phe Pro Glu Tyr His Phe Ile Gln His Arg Leu Glu Lys Thr Tyr
        195                 200                 205

Val Glu Asp Gly Gly Phe Val Glu Gln His Glu Thr Ala Ile Ala Gln
    210                 215                 220

Leu Thr Ser Leu Gly Lys Pro Leu Gly Ser Leu His Glu Trp Val
225                 230                 235
```

<210> SEQ ID NO 19
<211> LENGTH: 720
<212> TYPE: DNA
<213> ORGANISM: Renilla reniformis

<400> SEQUENCE: 19

```
atggtgagca agcagatcct gaagaacacc ggcctgcagg agatcatgag cttcaaggtg     60

aacctggagg gcgtggtgaa caaccacgtg ttcaccatgg agggctgcgg caagggcaac    120

atcctgttcg gcaaccagct ggtgcagatc cgcgtgacca agggcgcccc cctgcccttc    180

gccttcgaca tcctgagccc cgccttccag tacggcaacc gcaccttcac caagtacccc    240

gaggacatca gcgacttctt catccagagc ttccccgccg gcttcgtgta cgagcgcacc    300

ctgcgctacg aggacggcgg cctggtggag atccgcagcg acatcaacct gatcgagggg    360

atgttcgtgt accgcgtgga gtacaagggc cgcaacttcc ccaacgacgg ccccgtgatg    420

aagaagacca tcaccggcct gcagcccagc ttcgaggtgg tgtacatgaa cgacggcgtg    480

ctggtgggcc aggtgatcct ggtgtaccgc ctgaacagcg gcaagttcta cagctgccac    540

atgcgcaccc tgatgaagag caagggcgtg gtgaaggact tccccgagta ccacttcatc    600

cagcaccgcc tggagaagac ctacgtggag gacggcggct tcgtggagca gcacgagacc    660

gccatcgccc agctgaccag cctgggcaag cccctgggca gcctgcacga gtgggtgtaa    720
```

<210> SEQ ID NO 20
<211> LENGTH: 239
<212> TYPE: PRT
<213> ORGANISM: Renilla reniformis

<400> SEQUENCE: 20

```
Met Val Ser Lys Gln Ile Leu Lys Asn Thr Gly Leu Gln Glu Ile Met
1               5                   10                  15

Ser Phe Lys Val Asn Leu Glu Gly Val Val Asn Asn His Val Phe Thr
            20                  25                  30

Met Glu Gly Cys Gly Lys Gly Asn Ile Leu Phe Gly Asn Gln Leu Val
        35                  40                  45

Gln Ile Arg Val Thr Lys Gly Ala Pro Leu Pro Phe Ala Phe Asp Ile
    50                  55                  60

Leu Ser Pro Ala Phe Gln Tyr Gly Asn Arg Thr Phe Thr Lys Tyr Pro
65                  70                  75                  80

Glu Asp Ile Ser Asp Phe Phe Ile Gln Ser Phe Pro Ala Gly Phe Val
                85                  90                  95

Tyr Glu Arg Thr Leu Arg Tyr Glu Asp Gly Gly Leu Val Glu Ile Arg
            100                 105                 110

Ser Asp Ile Asn Leu Ile Glu Gly Met Phe Val Tyr Arg Val Glu Tyr
        115                 120                 125

Lys Gly Arg Asn Phe Pro Asn Asp Gly Pro Val Met Lys Lys Thr Ile
    130                 135                 140

Thr Gly Leu Gln Pro Ser Phe Glu Val Val Tyr Met Asn Asp Gly Val
145                 150                 155                 160

Leu Val Gly Gln Val Ile Leu Val Tyr Arg Leu Asn Ser Gly Lys Phe
                165                 170                 175

Tyr Ser Cys His Met Arg Thr Leu Met Lys Ser Lys Gly Val Val Lys
            180                 185                 190

Asp Phe Pro Glu Tyr His Phe Ile Gln His Arg Leu Glu Lys Thr Tyr
        195                 200                 205

Val Glu Asp Gly Gly Phe Val Glu Gln His Glu Thr Ala Ile Ala Gln
    210                 215                 220

Leu Thr Ser Leu Gly Lys Pro Leu Gly Ser Leu His Glu Trp Val
225                 230                 235
```

-continued

<210> SEQ ID NO 21
<211> LENGTH: 720
<212> TYPE: DNA
<213> ORGANISM: Renilla reniformis

<400> SEQUENCE: 21
atggtgagca agcagatcct gaagaacacc ggcctgcagg agatcatgag cttcaaggtg 60
aacctggagg gcgtggtgaa caaccacgtg ttcaccatgg agggctgcgg caagggcaac 120
atcctgtccg gcaaccagct ggtgcagatc cgcgtgacca agggcgcccc cctgcccttc 180
gccttcgaca tcctgagccc cgccttccag tacggcaacc gcaccttcac caagtacccc 240
gaggacatca gcgacttctt catccagagc ttccccgccg gcttcgtgta cgagcgcacc 300
ctgcgcttcg aggacggcgg cctggtggag atccgcagcg acatcaacct gatcgaggag 360
atgttcgagt accgcgtgga gtacaagggc cgcaacttcc ccaacgacgg ccccgtgatg 420
aagaagacca tcaccggcct gcagcccagc ttcgaggtgg tgtacatgaa cgacggcgtg 480
ctggtgggcc aggtgatcct ggtgtaccgc ctgaacagcg gcaagttcta cagctgccac 540
atgcgcaccc tgatgaagag caagggcgtg gtgaaggact tccccgagta ccacttcatc 600
cagcaccgcc tggagaagac ctacgtggag gacggcggct tcgtagagca gcacgagacc 660
gccatcgccc agctgaccag cctgggcaag cccctgggca gcctgcacga gtgggtgtaa 720

<210> SEQ ID NO 22
<211> LENGTH: 239
<212> TYPE: PRT
<213> ORGANISM: Renilla reniformis

<400> SEQUENCE: 22

Met Val Ser Lys Gln Ile Leu Lys Asn Thr Gly Leu Gln Glu Ile Met
1 5 10 15

Ser Phe Lys Val Asn Leu Glu Gly Val Val Asn Asn His Val Phe Thr
20 25 30

Met Glu Gly Cys Gly Lys Gly Asn Ile Leu Ser Gly Asn Gln Leu Val
35 40 45

Gln Ile Arg Val Thr Lys Gly Ala Pro Leu Pro Phe Ala Phe Asp Ile
50 55 60

Leu Ser Pro Ala Phe Gln Tyr Gly Asn Arg Thr Phe Thr Lys Tyr Pro
65 70 75 80

Glu Asp Ile Ser Asp Phe Phe Ile Gln Ser Phe Pro Ala Gly Phe Val
85 90 95

Tyr Glu Arg Thr Leu Arg Phe Glu Asp Gly Gly Leu Val Glu Ile Arg
100 105 110

Ser Asp Ile Asn Leu Ile Glu Glu Met Phe Glu Tyr Arg Val Glu Tyr
115 120 125

Lys Gly Arg Asn Phe Pro Asn Asp Gly Pro Val Met Lys Lys Thr Ile
130 135 140

Thr Gly Leu Gln Pro Ser Phe Glu Val Val Tyr Met Asn Asp Gly Val
145 150 155 160

Leu Val Gly Gln Val Ile Leu Val Tyr Arg Leu Asn Ser Gly Lys Phe
165 170 175

Tyr Ser Cys His Met Arg Thr Leu Met Lys Ser Lys Gly Val Val Lys
180 185 190

Asp Phe Pro Glu Tyr His Phe Ile Gln His Arg Leu Glu Lys Thr Tyr
195 200 205

-continued

```
Val Glu Asp Gly Gly Phe Val Glu Gln His Glu Thr Ala Ile Ala Gln
    210                 215                 220

Leu Thr Ser Leu Gly Lys Pro Leu Gly Ser Leu His Glu Trp Val
225                 230                 235


<210> SEQ ID NO 23
<211> LENGTH: 720
<212> TYPE: DNA
<213> ORGANISM: Renilla reniformis

<400> SEQUENCE: 23

atggtgagca agcagatcct gaagaacacc ggcctgcagg agatcatgag cttcaaggtg      60

aacctggagg gcgtggtgaa caaccacgtg ttcaccatgg agggctgcgg caagggcaac     120

atcctgtccg gcaaccagct ggtgcagatc cgcgtgacca agggcgcccc cctgcccttc     180

gccttcgaca tcctgagccc cgccttccag tacggcaacc gcaccttcac caagtacccc     240

gaggacatca gcgacttctt catccagagc ttccccgccg gcttcgtgta cgagcgcacc     300

ctgcgcttcg aggacggcgg cctggtggag atccgcagcg acatcaacct gatcgaggag     360

atgttcgggt accgcgtgga gtacaagggc cgcaacttcc ccaacgacgg ccccgtgatg     420

aagaagacca tcaccggcct gcagcccagc ttcgaggtgg tgtacatgaa cgacggcgtg     480

ctggtgggcc aggtgatcct ggtgtaccgc ctgaacagcg gcaagttcta cagctgccac     540

atgcgcaccc tgatgaagag caagggcgtg gtgaaggact tccccgagta ccacttcatc     600

cagcaccgcc tggagaagac ctacgtggag gacggcggct tcgtggagca gcacgagacc     660

gccatcgccc agctgaccag cctgggcaag cccctgggca gcctgcacga gtgggtgtaa     720


<210> SEQ ID NO 24
<211> LENGTH: 239
<212> TYPE: PRT
<213> ORGANISM: Renilla reniformis

<400> SEQUENCE: 24

Met Val Ser Lys Gln Ile Leu Lys Asn Thr Gly Leu Gln Glu Ile Met
1               5                   10                  15

Ser Phe Lys Val Asn Leu Glu Gly Val Val Asn Asn His Val Phe Thr
            20                  25                  30

Met Glu Gly Cys Gly Lys Gly Asn Ile Leu Ser Gly Asn Gln Leu Val
        35                  40                  45

Gln Ile Arg Val Thr Lys Gly Ala Pro Leu Pro Phe Ala Phe Asp Ile
    50                  55                  60

Leu Ser Pro Ala Phe Gln Tyr Gly Asn Arg Thr Phe Thr Lys Tyr Pro
65                  70                  75                  80

Glu Asp Ile Ser Asp Phe Phe Ile Gln Ser Phe Pro Ala Gly Phe Val
                85                  90                  95

Tyr Glu Arg Thr Leu Arg Phe Glu Asp Gly Gly Leu Val Glu Ile Arg
            100                 105                 110

Ser Asp Ile Asn Leu Ile Glu Glu Met Phe Glu Tyr Arg Val Glu Tyr
        115                 120                 125

Lys Gly Arg Asn Phe Pro Asn Asp Gly Pro Val Met Lys Lys Thr Ile
    130                 135                 140

Thr Gly Leu Gln Pro Ser Phe Glu Val Val Tyr Met Asn Asp Gly Val
145                 150                 155                 160

Leu Val Gly Gln Val Ile Leu Val Tyr Arg Leu Asn Ser Gly Lys Phe
                165                 170                 175
```

-continued

```
Tyr Ser Cys His Met Arg Thr Leu Met Lys Ser Lys Gly Val Val Lys
            180                 185                 190

Asp Phe Pro Glu Tyr His Phe Ile Gln His Arg Leu Glu Lys Thr Tyr
        195                 200                 205

Val Glu Asp Gly Gly Phe Val Glu Gln His Glu Thr Ala Ile Ala Gln
    210                 215                 220

Leu Thr Ser Leu Gly Lys Pro Leu Gly Ser Leu His Glu Trp Val
225                 230                 235


<210> SEQ ID NO 25
<211> LENGTH: 720
<212> TYPE: DNA
<213> ORGANISM: Renilla reniformis

<400> SEQUENCE: 25

atggtgagca agcagatcct gaagaacacc ggcctgcagg agatcatgag cttcaaggtg      60

atcctggagg gcgtggtgaa caaccacgtg ttcaccatgg agggctgcgg caagggcaac     120

atcctgttcg gcaaccagct ggtgcagatc cgcgtgacca agggcgcccc cctgcccttc     180

gccttcgaca tcctgagccc cgccttccag tacggcaacc gcaccttcac caagtacccc     240

gaggacatca gcgacttctt catccagagc ttccccgccg gcttcgtgta cgagcgcacc     300

ctgcgcttcg aggacggcgg cctggtggag atccgcagcg acatcaacct gatcgagggg     360

atgttcgtgt accgcgtgga gtacaagggc cgcaacttcc ccaacgacgg ccccgtgatg     420

aagaatacca tcaccggcct gcagcccagc ttcgaggtgg tgtacatgaa cgacggcgtg     480

ctggtgggcc aggtgatcct ggtgtaccgc ctgaacagcg gcaagttcta cagctgccac     540

atgcgcaccc tgatgaagag caagggcgtg gtgaaggact tccccgagta ccacttcatc     600

cagcaccgcc tggagaaggc ctacgtggag gacggcggca tcgtggagca gcacgagacc     660

gccatcgccc agctgaccag cctgggcaag cccctgggca gcctgcacga gtgggtgtaa     720


<210> SEQ ID NO 26
<211> LENGTH: 239
<212> TYPE: PRT
<213> ORGANISM: Renilla reniformis

<400> SEQUENCE: 26

Met Val Ser Lys Gln Ile Leu Lys Asn Thr Gly Leu Gln Glu Ile Met
1               5                   10                  15

Ser Phe Lys Val Ile Leu Glu Gly Val Val Asn Asn His Val Phe Thr
            20                  25                  30

Met Glu Gly Cys Gly Lys Gly Asn Ile Leu Phe Gly Asn Gln Leu Val
        35                  40                  45

Gln Ile Arg Val Thr Lys Gly Ala Pro Leu Pro Phe Ala Phe Asp Ile
    50                  55                  60

Leu Ser Pro Ala Phe Gln Tyr Gly Asn Arg Thr Phe Thr Lys Tyr Pro
65                  70                  75                  80

Glu Asp Ile Ser Asp Phe Phe Ile Gln Ser Phe Pro Ala Gly Phe Val
                85                  90                  95

Tyr Glu Arg Thr Leu Arg Phe Glu Asp Gly Gly Leu Val Glu Ile Arg
            100                 105                 110

Ser Asp Ile Asn Leu Ile Glu Gly Met Phe Val Tyr Arg Val Glu Tyr
        115                 120                 125

Lys Gly Arg Asn Phe Pro Asn Asp Gly Pro Val Met Lys Asn Thr Ile
    130                 135                 140
```

-continued

```
Thr Gly Leu Gln Pro Ser Phe Glu Val Val Tyr Met Asn Asp Gly Val
145                 150                 155                 160

Leu Val Gly Gln Val Ile Leu Val Tyr Arg Leu Asn Ser Gly Lys Phe
                165                 170                 175

Tyr Ser Cys His Met Arg Thr Leu Met Lys Ser Lys Gly Val Val Lys
            180                 185                 190

Asp Phe Pro Glu Tyr His Phe Ile Gln His Arg Leu Glu Lys Ala Tyr
        195                 200                 205

Val Glu Asp Gly Gly Ile Val Glu Gln His Glu Thr Ala Ile Ala Gln
    210                 215                 220

Leu Thr Ser Leu Gly Lys Pro Leu Gly Ser Leu His Glu Trp Val
225                 230                 235


<210> SEQ ID NO 27
<211> LENGTH: 720
<212> TYPE: DNA
<213> ORGANISM: Renilla reniformis

<400> SEQUENCE: 27

atggtgagca agcagatcct gaagaacacc ggcctgcagg agatcatgag cttcaaggtg      60

aacctggagg gcgtggtgaa caaccacgtg ttcaccatgg agggctgcgg caagggcaac     120

atcctgttcg gcaaccagct ggtgcagatc cgcgtgacca agggcgcccc cctgcccttc     180

gccttcgaca tcctgagccc cgccttccag tacggcaacc gcaccttcac caagtacccc     240

gaggacatca gcgacttctt catccagagc ttccccgccg gcttcgtgta cgagcgcacc     300

ctgcgctacg aggacggcgg cctggcggag atccgcagcg acatcaacct gatcgagggg     360

atgttcgtgt accgcgtgga gtacaagggc cgcaacttcc ccaacgacgg ccccgtgatg     420

aagaatacca tcaccggcct gcagcccagc ttcgaggtgg tgtacatgaa cgacggcgtg     480

ctggtgggcc aggtgatcct ggtgtaccgc ctgaacagcg gcaagttcta cagctgccac     540

atgcgcaccc tgatgaagag caagggcgtg gtgaaggact tccccgagta ccacttcatc     600

cagcaccgcc tggagaagac ctacgtggag gacggcggct tcgtggagca gcacgagacc     660

gccatcgccc agctgaccag cctgggcaag cccctgggca gcctgcacga gtgggtgtaa     720


<210> SEQ ID NO 28
<211> LENGTH: 239
<212> TYPE: PRT
<213> ORGANISM: Renilla reniformis

<400> SEQUENCE: 28

Met Val Ser Lys Gln Ile Leu Lys Asn Thr Gly Leu Gln Glu Ile Met
1               5                   10                  15

Ser Phe Lys Val Asn Leu Glu Gly Val Val Asn Asn His Val Phe Thr
            20                  25                  30

Met Glu Gly Cys Gly Lys Gly Asn Ile Leu Phe Gly Asn Gln Leu Val
        35                  40                  45

Gln Ile Arg Val Thr Lys Gly Ala Pro Leu Pro Phe Ala Phe Asp Ile
    50                  55                  60

Leu Ser Pro Ala Phe Gln Tyr Gly Asn Arg Thr Phe Thr Lys Tyr Pro
65                  70                  75                  80

Glu Asp Ile Ser Asp Phe Phe Ile Gln Ser Phe Pro Ala Gly Phe Val
                85                  90                  95

Tyr Glu Arg Thr Leu Arg Tyr Glu Asp Gly Gly Leu Ala Glu Ile Arg
            100                 105                 110
```

-continued

```
Ser Asp Ile Asn Leu Ile Glu Gly Met Phe Val Tyr Arg Val Glu Tyr
        115                 120                 125

Lys Gly Arg Asn Phe Pro Asn Asp Gly Pro Val Met Lys Asn Thr Ile
    130                 135                 140

Thr Gly Leu Gln Pro Ser Phe Glu Val Val Tyr Met Asn Asp Gly Val
145                 150                 155                 160

Leu Val Gly Gln Val Ile Leu Val Tyr Arg Leu Asn Ser Gly Lys Phe
                165                 170                 175

Tyr Ser Cys His Met Arg Thr Leu Met Lys Ser Lys Gly Val Val Lys
            180                 185                 190

Asp Phe Pro Glu Tyr His Phe Ile Gln His Arg Leu Glu Lys Thr Tyr
        195                 200                 205

Val Glu Asp Gly Gly Phe Val Glu Gln His Glu Thr Ala Ile Ala Gln
    210                 215                 220

Leu Thr Ser Leu Gly Lys Pro Leu Gly Ser Leu His Glu Trp Val
225                 230                 235


<210> SEQ ID NO 29
<211> LENGTH: 720
<212> TYPE: DNA
<213> ORGANISM: Renilla reniformis

<400> SEQUENCE: 29

atggtgagca agcagatcct gaagaacacc ggcctgcagg agatcgtgag cttcaaggtg      60

atcctggagg gcgtggtgaa caaccacgtg ttcaccatgg agggctgcgg caagggcaac     120

atcctgttcg gcaaccagct ggtgcagatc cgcgtgacca agggcgcccc cctgcccttc     180

gccttcgaca tcctgagccc cgccttccag tacggcaacc gcaccttcac caagtacccc     240

gaggacatca gcgacttctt catccagagc ttccccgccg gcttcgtgta cgagcgcacc     300

ctgcgctacg aggacggcgg cctggtggag atccgcagcg acatcaacct gatcgagggg     360

atgttcgtgt accgcgtgga gtacaagggc cgcaacttcc ccaacgacgg ccccgtgatg     420

aagaatacca tcaccggcct gcagcccagc ttcgaggtgg tgtacatgaa cgacggcgtg     480

ctggtgggcc aggtgatcct ggtgtaccgc ctgaactgcg gcaagttcta cagctgccac     540

atgcgcaccc tgatgaagag caagggcgtg gtgaaggact tccccgagta ccacttcatc     600

cagcaccgcc tggagaagac ctacgtggag gacggcggct tcgtggagca gcacgagacc     660

gccatcgccc agctgaccag cctgggcaag cccctgggca gcctgcacga gtgggtgtaa     720


<210> SEQ ID NO 30
<211> LENGTH: 239
<212> TYPE: PRT
<213> ORGANISM: Renilla reniformis

<400> SEQUENCE: 30

Met Val Ser Lys Gln Ile Leu Lys Asn Thr Gly Leu Gln Glu Ile Val
1               5                   10                  15

Ser Phe Lys Val Ile Leu Glu Gly Val Val Asn Asn His Val Phe Thr
            20                  25                  30

Met Glu Gly Cys Gly Lys Gly Asn Ile Leu Phe Gly Asn Gln Leu Val
        35                  40                  45

Gln Ile Arg Val Thr Lys Gly Ala Pro Leu Pro Phe Ala Phe Asp Ile
    50                  55                  60

Leu Ser Pro Ala Phe Gln Tyr Gly Asn Arg Thr Phe Thr Lys Tyr Pro
65                  70                  75                  80
```

```
Glu Asp Ile Ser Asp Phe Phe Ile Gln Ser Phe Pro Ala Gly Phe Val
                85                  90                  95

Tyr Glu Arg Thr Leu Arg Tyr Glu Asp Gly Gly Leu Val Glu Ile Arg
            100                 105                 110

Ser Asp Ile Asn Leu Ile Glu Gly Met Phe Val Tyr Arg Val Glu Tyr
        115                 120                 125

Lys Gly Arg Asn Phe Pro Asn Asp Gly Pro Val Met Lys Asn Thr Ile
    130                 135                 140

Thr Gly Leu Gln Pro Ser Phe Glu Val Val Tyr Met Asn Asp Gly Val
145                 150                 155                 160

Leu Val Gly Gln Val Ile Leu Val Tyr Arg Leu Asn Cys Gly Lys Phe
                165                 170                 175

Tyr Ser Cys His Met Arg Thr Leu Met Lys Ser Lys Gly Val Val Lys
            180                 185                 190

Asp Phe Pro Glu Tyr His Phe Ile Gln His Arg Leu Glu Lys Thr Tyr
        195                 200                 205

Val Glu Asp Gly Gly Phe Val Glu Gln His Glu Thr Ala Ile Ala Gln
    210                 215                 220

Leu Thr Ser Leu Gly Lys Pro Leu Gly Ser Leu His Glu Trp Val
225                 230                 235


<210> SEQ ID NO 31
<211> LENGTH: 714
<212> TYPE: DNA
<213> ORGANISM: Renilla reniformis

<400> SEQUENCE: 31

atgagtaaac aaatattgaa gaacactgga ttgcaggaga tcatgtcgtt taaagtgaat      60

ctggaaggtg tagtaaacaa tcatgtgttc acaatggaag gttgtggaaa aggaaatatt     120

ttattcggaa accaactggt tcagattcgt gtcacaaaag gggctccgct tccatttgca     180

tttgatattc tctcaccagc tttccaatac ggcaaccgta cattcacgaa atacccggag     240

gatatatcag actttttat acaatcattt ccagcgggat ttgtatacga aagaacgttg     300

cgttacgaag atggtggact ggttgaaatc cgttcagata taaatttaat cgaggagatg     360

tttgtctaca gagtggaata taaaggtagt aacttcccga atgatggtcc agtgatgaag     420

aagacaatca caggattaca accttcgttc gaagttgtgt atatgaacga tggcgtcttg     480

gttggccaag tcattcttgt ttatagatta aactctggca aattttattc gtgtcacatg     540

agaacactga tgaaatcaaa gggtgtagtg aaggattttc ccgaatacca tttcattcaa     600

catcgtttag agaagacgta tgtggaagac ggaggttttg ttgaggaaca cgagacggcc     660

attgctcaac tgacatcgct ggggaaacca cttggatcct tacacgaatg ggtt           714


<210> SEQ ID NO 32
<211> LENGTH: 238
<212> TYPE: PRT
<213> ORGANISM: Renilla reniformis

<400> SEQUENCE: 32

Met Ser Lys Gln Ile Leu Lys Asn Thr Gly Leu Gln Glu Ile Met Ser
1               5                   10                  15

Phe Lys Val Asn Leu Glu Gly Val Val Asn Asn His Val Phe Thr Met
            20                  25                  30

Glu Gly Cys Gly Lys Gly Asn Ile Leu Phe Gly Asn Gln Leu Val Gln
        35                  40                  45
```

-continued

```
Ile Arg Val Thr Lys Gly Ala Pro Leu Pro Phe Ala Phe Asp Ile Leu
    50                  55                  60

Ser Pro Ala Phe Gln Tyr Gly Asn Arg Thr Phe Thr Lys Tyr Pro Glu
65                  70                  75                  80

Asp Ile Ser Asp Phe Phe Ile Gln Ser Phe Pro Ala Gly Phe Val Tyr
                85                  90                  95

Glu Arg Thr Leu Arg Tyr Glu Asp Gly Gly Leu Val Glu Ile Arg Ser
            100                 105                 110

Asp Ile Asn Leu Ile Glu Glu Met Phe Val Tyr Arg Val Glu Tyr Lys
        115                 120                 125

Gly Ser Asn Phe Pro Asn Asp Gly Pro Val Met Lys Lys Thr Ile Thr
    130                 135                 140

Gly Leu Gln Pro Ser Phe Glu Val Val Tyr Met Asn Asp Gly Val Leu
145                 150                 155                 160

Val Gly Gln Val Ile Leu Val Tyr Arg Leu Asn Ser Gly Lys Phe Tyr
                165                 170                 175

Ser Cys His Met Arg Thr Leu Met Lys Ser Lys Gly Val Val Lys Asp
            180                 185                 190

Phe Pro Glu Tyr His Phe Ile Gln His Arg Leu Glu Lys Thr Tyr Val
        195                 200                 205

Glu Asp Gly Gly Phe Val Glu Glu His Glu Thr Ala Ile Ala Gln Leu
    210                 215                 220

Thr Ser Leu Gly Lys Pro Leu Gly Ser Leu His Glu Trp Val
225                 230                 235
```

<210> SEQ ID NO 33
<211> LENGTH: 714
<212> TYPE: DNA
<213> ORGANISM: Renilla reniformis

<400> SEQUENCE: 33

```
atgagtaaac aaatattgaa gaacactgga ttgcaggaga tcatgtcgtt taaagtgaat     60

ctggaaggtg tagtaaacaa tcatgtgttc acaatggaag gttgtggaaa aggaaatatt    120

ttattaggaa accaactggt tcagattcgt gtcacaaaag ggctccgct tccatttgca    180

tttgatattc tctcaccagc tttccaatac ggcaaccgta cattcacgaa atacccggag    240

gatatatcag actttttat acaatcattt ccagcgggat ttgtatacga aagaacgttg    300

cgttacgaag atggtggact ggttgaaatc cgttcagata taaatttaat cgaggagatg    360

tttgtctaca gagtggaata taaaggtagt aacttcccga atgatggtcc agtgatgaag    420

aagacaatca caggattaca accttcgttc gaagttgtgt atatgaacga tggcgtcttg    480

gttggccaag tcattcttgt ttatagatta aactctggca aattttattc gtgtcacatg    540

agaacactga tgaaatcaaa gggtgtagtg aaggattttc ccgaatacca tttcattcaa    600

catcgtttag agaagacgta tgtggaagac ggaggttttg ttgaggaaca cgagacggcc    660

attgctcaac tgacatcgct ggggaaacca cttggatcct tacacgaatg ggtt          714
```

<210> SEQ ID NO 34
<211> LENGTH: 238
<212> TYPE: PRT
<213> ORGANISM: Renilla reniformis

<400> SEQUENCE: 34

```
Met Ser Lys Gln Ile Leu Lys Asn Thr Gly Leu Gln Glu Ile Met Ser
1               5                   10                  15
```

-continued

```
Phe Lys Val Asn Leu Glu Gly Val Val Asn Asn His Val Phe Thr Met
            20                  25                  30

Glu Gly Cys Gly Lys Gly Asn Ile Leu Leu Gly Asn Gln Leu Val Gln
        35                  40                  45

Ile Arg Val Thr Lys Gly Ala Pro Leu Pro Phe Ala Phe Asp Ile Leu
    50                  55                  60

Ser Pro Ala Phe Gln Tyr Gly Asn Arg Thr Phe Thr Lys Tyr Pro Glu
65                  70                  75                  80

Asp Ile Ser Asp Phe Phe Ile Gln Ser Phe Pro Ala Gly Phe Val Tyr
                85                  90                  95

Glu Arg Thr Leu Arg Tyr Glu Asp Gly Gly Leu Val Glu Ile Arg Ser
            100                 105                 110

Asp Ile Asn Leu Ile Glu Glu Met Phe Val Tyr Arg Val Glu Tyr Lys
        115                 120                 125

Gly Ser Asn Phe Pro Asn Asp Gly Pro Val Met Lys Lys Thr Ile Thr
    130                 135                 140

Gly Leu Gln Pro Ser Phe Glu Val Val Tyr Met Asn Asp Gly Val Leu
145                 150                 155                 160

Val Gly Gln Val Ile Leu Val Tyr Arg Leu Asn Ser Gly Lys Phe Tyr
                165                 170                 175

Ser Cys His Met Arg Thr Leu Met Lys Ser Lys Gly Val Val Lys Asp
            180                 185                 190

Phe Pro Glu Tyr His Phe Ile Gln His Arg Leu Glu Lys Thr Tyr Val
        195                 200                 205

Glu Asp Gly Gly Phe Val Glu Glu His Glu Thr Ala Ile Ala Gln Leu
    210                 215                 220

Thr Ser Leu Gly Lys Pro Leu Gly Ser Leu His Glu Trp Val
225                 230                 235
```

<210> SEQ ID NO 35
<211> LENGTH: 714
<212> TYPE: DNA
<213> ORGANISM: Renilla reniformis

<400> SEQUENCE: 35

```
atgagtaaac aaatattgaa gaacactgga ttgcaggaga tcatgtcgtt taaagtgaat     60

ctggaaggtg tagtaaacaa tcatgtgttc acaatggaag gttgtggaaa aggaaatatt    120

ttattcggaa accaactggt tcagattcgt gtcacaaaag ggctccgct tccatttgca    180

tttgatattc tctcaccagc tttccaatac ggcaaccgta cattcacgaa atacccggag    240

gatatatcag actttttat acaatcattt ccagcgggat ttgtatacga aagaacgttg    300

cgttacgaag atggtggact ggttgaaatc cgttcagata taaatttaat cgaggggatg    360

tttgtctaca gagtggaata taaaggtagt aacttcccga atgatggtcc agtgatgaag    420

aagacaatca caggattaca accttcgttc gaagttgtgt atatgaacga tggcgtcttg    480

gttggccaag tcattcttgt ttatagatta aactctggca aattttattc gtgtcacatg    540

agaacactga tgaaatcaaa gggtgtagtg aaggattttc ccgaatacca tttcattcaa    600

catcgtttag agaagacgta tgtggaagac ggaggttttg tagaggaaca cgagacggcc    660

attgctcaac tgacatcgct ggggaaacca cttggatcct tacacgaatg ggtt          714
```

<210> SEQ ID NO 36
<211> LENGTH: 238
<212> TYPE: PRT
<213> ORGANISM: Renilla reniformis

<400> SEQUENCE: 36

```
Met Ser Lys Gln Ile Leu Lys Asn Thr Gly Leu Gln Glu Ile Met Ser
1               5                   10                  15

Phe Lys Val Asn Leu Glu Gly Val Val Asn Asn His Val Phe Thr Met
            20                  25                  30

Glu Gly Cys Gly Lys Gly Asn Ile Leu Phe Gly Asn Gln Leu Val Gln
        35                  40                  45

Ile Arg Val Thr Lys Gly Ala Pro Leu Pro Phe Ala Phe Asp Ile Leu
    50                  55                  60

Ser Pro Ala Phe Gln Tyr Gly Asn Arg Thr Phe Thr Lys Tyr Pro Glu
65                  70                  75                  80

Asp Ile Ser Asp Phe Phe Ile Gln Ser Phe Pro Ala Gly Phe Val Tyr
                85                  90                  95

Glu Arg Thr Leu Arg Tyr Glu Asp Gly Gly Leu Val Glu Ile Arg Ser
            100                 105                 110

Asp Ile Asn Leu Ile Glu Gly Met Phe Val Tyr Arg Val Glu Tyr Lys
        115                 120                 125

Gly Ser Asn Phe Pro Asn Asp Gly Pro Val Met Lys Lys Thr Ile Thr
    130                 135                 140

Gly Leu Gln Pro Ser Phe Glu Val Val Tyr Met Asn Asp Gly Val Leu
145                 150                 155                 160

Val Gly Gln Val Ile Leu Val Tyr Arg Leu Asn Ser Gly Lys Phe Tyr
                165                 170                 175

Ser Cys His Met Arg Thr Leu Met Lys Ser Lys Gly Val Val Lys Asp
            180                 185                 190

Phe Pro Glu Tyr His Phe Ile Gln His Arg Leu Glu Lys Thr Tyr Val
        195                 200                 205

Glu Asp Gly Gly Phe Val Glu Glu His Glu Thr Ala Ile Ala Gln Leu
    210                 215                 220

Thr Ser Leu Gly Lys Pro Leu Gly Ser Leu His Glu Trp Val
225                 230                 235
```

<210> SEQ ID NO 37
<211> LENGTH: 714
<212> TYPE: DNA
<213> ORGANISM: Renilla reniformis

<400> SEQUENCE: 37

```
atgagtaaac aaatattgaa gaacactgga ttgcaggaga tcatgtcgtt taaagtgaat     60

ctggaaggtg tagtaaacaa tcatgtgttc acaatggaag gttgtggaaa aggaaatatt    120

ttattcggaa accaactggt tcagattcgt gtcacaaaag ggctccgct tccatttgca    180

tttgatattc tctcaccagc tttccaatac ggcaaccgta cattcacgaa atacccggag    240

gatatatcag actttttat acaatcattt ccagcgggat ttgtatacga aagaacgatg    300

cgttacgaag atggtggact ggttgaaatc cgttcagata taaatttaat cgaggagatg    360

tttgtctaca gagtggaata taaaggtagt aacttcccga atgatggtcc agtgatgaag    420

aagacaatca caggattaca accttcgttc gaagttgtgt atatgaacga tggcgtcttg    480

gttggccaag tcattcttgt ttatagatta aactctggca aattttattc gtgtcacatg    540

agaacactga tgaaatcaaa gggtgtagtg aaggattttc ccgaatacca tttcattcaa    600

catcgtttag agaagacgta tgtggaagac ggaggttttg ttgaggaaca cgagacggcc    660

attgctcaac tgacatcgct ggggaaacca cttggatcct tacacgaatg ggtt          714
```

<210> SEQ ID NO 38
<211> LENGTH: 238
<212> TYPE: PRT
<213> ORGANISM: Renilla reniformis

<400> SEQUENCE: 38

```
Met Ser Lys Gln Ile Leu Lys Asn Thr Gly Leu Gln Glu Ile Met Ser
1               5                   10                  15

Phe Lys Val Asn Leu Glu Gly Val Val Asn Asn His Val Phe Thr Met
            20                  25                  30

Glu Gly Cys Gly Lys Gly Asn Ile Leu Phe Gly Asn Gln Leu Val Gln
        35                  40                  45

Ile Arg Val Thr Lys Gly Ala Pro Leu Pro Phe Ala Phe Asp Ile Leu
    50                  55                  60

Ser Pro Ala Phe Gln Tyr Gly Asn Arg Thr Phe Thr Lys Tyr Pro Glu
65                  70                  75                  80

Asp Ile Ser Asp Phe Phe Ile Gln Ser Phe Pro Ala Gly Phe Val Tyr
                85                  90                  95

Glu Arg Thr Met Arg Tyr Glu Asp Gly Gly Leu Val Glu Ile Arg Ser
            100                 105                 110

Asp Ile Asn Leu Ile Glu Glu Met Phe Val Tyr Arg Val Glu Tyr Lys
        115                 120                 125

Gly Ser Asn Phe Pro Asn Asp Gly Pro Val Met Lys Lys Thr Ile Thr
    130                 135                 140

Gly Leu Gln Pro Ser Phe Glu Val Val Tyr Met Asn Asp Gly Val Leu
145                 150                 155                 160

Val Gly Gln Val Ile Leu Val Tyr Arg Leu Asn Ser Gly Lys Phe Tyr
                165                 170                 175

Ser Cys His Met Arg Thr Leu Met Lys Ser Lys Gly Val Val Lys Asp
            180                 185                 190

Phe Pro Glu Tyr His Phe Ile Gln His Arg Leu Glu Lys Thr Tyr Val
        195                 200                 205

Glu Asp Gly Gly Phe Val Glu Glu His Glu Thr Ala Ile Ala Gln Leu
    210                 215                 220

Thr Ser Leu Gly Lys Pro Leu Gly Ser Leu His Glu Trp Val
225                 230                 235
```

<210> SEQ ID NO 39
<211> LENGTH: 714
<212> TYPE: DNA
<213> ORGANISM: Renilla reniformis

<400> SEQUENCE: 39

```
atgagtaaac aaatattgaa gaacactgga ttgcaggaga tcatgtcgtt taaagtgaat     60

ctggaaggtg tagtaaacaa tcatgtgttc acaatggaag gttgtggaaa aggaaatatt    120

ttatccggaa accaactggt tcagattcgt gtcacaaaag gggctccgct tccatttgca    180

tttgatattc tctcaccagc tttccaatac ggcaaccgta cattcacgaa atacccggag    240

gatatatcag actttttat acaatcattt ccagcgggat ttgtatacga aagaacgttg    300

cgttacgaag atggtggact ggttgaaatc cgttcagata taaatttaat cgaggagatg    360

tttgtctaca gagtggaata taaaggtagt aacttcccga atgatggtcc agtgatgaag    420

aagacaatca caggattaca accttcgttc gaagttgtgt atatgaacga tggcgtcttg    480

gttggccaag tcattcttgt ttatagatta aactctggca aattttattc gtgtcacatg    540
```

agaacactga tgaaatcaaa gggtgtagtg aaggattttc ccgaatacca tttcattcaa 600
catcgtttag agaagacgta tgtggaagac ggaggttttg ttgaggaaca cgagacggcc 660
attgctcaac tgacatcgct ggggaaacca cttggatcct tacacgaatg ggtt 714

<210> SEQ ID NO 40
<211> LENGTH: 238
<212> TYPE: PRT
<213> ORGANISM: Renilla reniformis

<400> SEQUENCE: 40

Met Ser Lys Gln Ile Leu Lys Asn Thr Gly Leu Gln Glu Ile Met Ser
1 5 10 15

Phe Lys Val Asn Leu Glu Gly Val Val Asn Asn His Val Phe Thr Met
20 25 30

Glu Gly Cys Gly Lys Gly Asn Ile Leu Ser Gly Asn Gln Leu Val Gln
35 40 45

Ile Arg Val Thr Lys Gly Ala Pro Leu Pro Phe Ala Phe Asp Ile Leu
50 55 60

Ser Pro Ala Phe Gln Tyr Gly Asn Arg Thr Phe Thr Lys Tyr Pro Glu
65 70 75 80

Asp Ile Ser Asp Phe Phe Ile Gln Ser Phe Pro Ala Gly Phe Val Tyr
85 90 95

Glu Arg Thr Leu Arg Tyr Glu Asp Gly Gly Leu Val Glu Ile Arg Ser
100 105 110

Asp Ile Asn Leu Ile Glu Glu Met Phe Val Tyr Arg Val Glu Tyr Lys
115 120 125

Gly Ser Asn Phe Pro Asn Asp Gly Pro Val Met Lys Lys Thr Ile Thr
130 135 140

Gly Leu Gln Pro Ser Phe Glu Val Val Tyr Met Asn Asp Gly Val Leu
145 150 155 160

Val Gly Gln Val Ile Leu Val Tyr Arg Leu Asn Ser Gly Lys Phe Tyr
165 170 175

Ser Cys His Met Arg Thr Leu Met Lys Ser Lys Gly Val Val Lys Asp
180 185 190

Phe Pro Glu Tyr His Phe Ile Gln His Arg Leu Glu Lys Thr Tyr Val
195 200 205

Glu Asp Gly Gly Phe Val Glu Glu His Glu Thr Ala Ile Ala Gln Leu
210 215 220

Thr Ser Leu Gly Lys Pro Leu Gly Ser Leu His Glu Trp Val
225 230 235

<210> SEQ ID NO 41
<211> LENGTH: 714
<212> TYPE: DNA
<213> ORGANISM: Renilla reniformis

<400> SEQUENCE: 41
atgagtaaac aaatattgaa gaacactgga ttgcaggaga tcatgtcgtt taaagtgaat 60
ctggaaggtg tagtaaacaa tcatgtgttc acaatggaag gttgtggaaa aggaaatatt 120
ttattcggaa accaactggt tcagattcgt gtcacaaaag ggctccgct tccatttgca 180 tttgatattc tctcaccagc tttccaatac ggcaaccgta cattcacgaa atacccggag 240
gatatatcag actttttat acaatcattt ccagcgggat ttgtatacga aagaacgttg 300
tgttacgaag atggtggact ggttgaaatc cgttcagata taaatttaat cgaggagatg 360

-continued tttgtctacc atgtggaata taaaggtagt aacttcccga atgatggtcc agtgatgaag 420
aagacaatca caggattaca accttcgttc gaagttgtgt atatgaacga tggcgtcttg 480
gttggccaag tcattcttgt ttatagatta aactctggca aattttattc gtgtcacatg 540
agaacactga tgaaatcaaa gggtgtagtg aaggattttc ccgaatacca tttcattcaa 600
catcgtttag agaagacgta tgtggaagac ggaggttttg ttgaggaaca cgagacggcc 660
attgctcaac tgacatcgct ggggaatcca cttggatcct tacacgaatg ggtt 714

<210> SEQ ID NO 42
<211> LENGTH: 238
<212> TYPE: PRT
<213> ORGANISM: Renilla reniformis

<400> SEQUENCE: 42

Met Ser Lys Gln Ile Leu Lys Asn Thr Gly Leu Gln Glu Ile Met Ser
1 5 10 15

Phe Lys Val Asn Leu Glu Gly Val Val Asn Asn His Val Phe Thr Met
20 25 30

Glu Gly Cys Gly Lys Gly Asn Ile Leu Phe Gly Asn Gln Leu Val Gln
35 40 45

Ile Arg Val Thr Lys Gly Ala Pro Leu Pro Phe Ala Phe Asp Ile Leu
50 55 60

Ser Pro Ala Phe Gln Tyr Gly Asn Arg Thr Phe Thr Lys Tyr Pro Glu
65 70 75 80

Asp Ile Ser Asp Phe Phe Ile Gln Ser Phe Pro Ala Gly Phe Val Tyr
85 90 95

Glu Arg Thr Leu Cys Tyr Glu Asp Gly Gly Leu Val Glu Ile Arg Ser
100 105 110

Asp Ile Asn Leu Ile Glu Glu Met Phe Val Tyr His Val Glu Tyr Lys
115 120 125

Gly Ser Asn Phe Pro Asn Asp Gly Pro Val Met Lys Lys Thr Ile Thr
130 135 140

Gly Leu Gln Pro Ser Phe Glu Val Val Tyr Met Asn Asp Gly Val Leu
145 150 155 160

Val Gly Gln Val Ile Leu Val Tyr Arg Leu Asn Ser Gly Lys Phe Tyr
165 170 175

Ser Cys His Met Arg Thr Leu Met Lys Ser Lys Gly Val Val Lys Asp
180 185 190

Phe Pro Glu Tyr His Phe Ile Gln His Arg Leu Glu Lys Thr Tyr Val
195 200 205

Glu Asp Gly Gly Phe Val Glu Glu His Glu Thr Ala Ile Ala Gln Leu
210 215 220

Thr Ser Leu Gly Tyr Pro Leu Gly Ser Leu His Glu Trp Val
225 230 235

<210> SEQ ID NO 43
<211> LENGTH: 714
<212> TYPE: DNA
<213> ORGANISM: Renilla reniformis

<400> SEQUENCE: 43
atgagtaaac aaatattgaa gaacactgga ttgcaggaga tcatgtcgtt taaagtgatt 60
ctggaaggtg tagtaaacaa tcatgtgttc acaatggaag gttgtggaaa aggaaatatt 120
ttattcggaa accaactggt tcagattcgt gtcacaaaag ggctccgct tccatttgca 180

```
tttgatattc tctcaccagc tttccaatac ggcaaccgta cattcacgaa atacccggag    240

gatatatcag actttttttat acaatcattt ccagcgggat ttgtatacga aagaacgttg    300

cgttacgaag atggtggact ggttgaaatc cgttcagata taaatttaat cgaggggatg    360

tttgtctaca gagtggaata taaaggtagt aacttcccga atgatggtcc agtgatgaag    420

aatacaatca caggattaca accttcgttc gaagttgtgt atatgaacga tggcgtcttg    480

gttggccaag tcattcttgt ttatagatta aactctggca aattttattc gtgtcacatg    540

agaacactga tgaaatcaaa gggtgtagtg aaggattttc ccgaatacca tttcattcaa    600

catcgtttag agaagacgta tgtggaagac ggaggttttg ttgaggaaca cgagacggcc    660

attgctcaac tgacatcgct ggggaaacca cttggatcct tacacgaatg ggtt          714
```

```
<210> SEQ ID NO 44
<211> LENGTH: 238
<212> TYPE: PRT
<213> ORGANISM: Renilla reniformis

<400> SEQUENCE: 44

Met Ser Lys Gln Ile Leu Lys Asn Thr Gly Leu Gln Glu Ile Met Ser
1               5                   10                  15

Phe Lys Val Ile Leu Glu Gly Val Val Asn Asn His Val Phe Thr Met
            20                  25                  30

Glu Gly Cys Gly Lys Gly Asn Ile Leu Phe Gly Asn Gln Leu Val Gln
        35                  40                  45

Ile Arg Val Thr Lys Gly Ala Pro Leu Pro Phe Ala Phe Asp Ile Leu
    50                  55                  60

Ser Pro Ala Phe Gln Tyr Gly Asn Arg Thr Phe Thr Lys Tyr Pro Glu
65                  70                  75                  80

Asp Ile Ser Asp Phe Phe Ile Gln Ser Phe Pro Ala Gly Phe Val Tyr
                85                  90                  95

Glu Arg Thr Leu Arg Tyr Glu Asp Gly Gly Leu Val Glu Ile Arg Ser
            100                 105                 110

Asp Ile Asn Leu Ile Glu Gly Met Phe Val Tyr Arg Val Glu Tyr Lys
        115                 120                 125

Gly Ser Asn Phe Pro Asn Asp Gly Pro Val Met Lys Asn Thr Ile Thr
    130                 135                 140

Gly Leu Gln Pro Ser Phe Glu Val Val Tyr Met Asn Asp Gly Val Leu
145                 150                 155                 160

Val Gly Gln Val Ile Leu Val Tyr Arg Leu Asn Ser Gly Lys Phe Tyr
                165                 170                 175

Ser Cys His Met Arg Thr Leu Met Lys Ser Lys Gly Val Val Lys Asp
            180                 185                 190

Phe Pro Glu Tyr His Phe Ile Gln His Arg Leu Glu Lys Thr Tyr Val
        195                 200                 205

Glu Asp Gly Gly Phe Val Glu Glu His Glu Thr Ala Ile Ala Gln Leu
    210                 215                 220

Thr Ser Leu Gly Lys Pro Leu Gly Ser Leu His Glu Trp Val
225                 230                 235

<210> SEQ ID NO 45
<211> LENGTH: 714
<212> TYPE: DNA
<213> ORGANISM: Renilla reniformis

<400> SEQUENCE: 45
```

```
atgagtaaac aaatattgaa gaacactgga ttgcaggaga tcatgtcgtt taaagtgaat     60

ctggaaggtg tagtaaacaa tcatgtgttc acaatggaag gttgtggaaa aggaaatatt    120

ttattcggaa accaactggt tcagattcgt gtcacaaaag ggctccgct tccatttgca    180

tttgatattc tctcaccagc tttccaatac ggcaaccgta cattcacgaa atacccggag    240

gatatatcag actttttat acaatcattt ccagcgggat ttgtatacga aagaacgttg    300

cgtttcgaag atggtggact ggttgaaatc cgttcagata taaatttaat cgaggagatg    360

tttgtctaca gagtggaata taaaggtagt aacttcccga atgatggtcc agtgatgaag    420

aagacaatca caggattaca accttcgttc gaagttgtgt atatgaacga tggcgtcttg    480

gttggccaag tcattcttgt ttatagatta aactctggca aattttattc gtgtcacatg    540

agaacactga tgaaatcaaa gggtgtagtg aaggattttc ccgaatacca tttcattcaa    600

catcgtttag agaagacgta tgtggaagac ggaggttttg ttgaggaaca cgagacggcc    660

attgctcaac tgacatcgct ggggaaacca cttggatcct tacacgaatg ggtt          714
```

<210> SEQ ID NO 46
<211> LENGTH: 238
<212> TYPE: PRT
<213> ORGANISM: Renilla reniformis

<400> SEQUENCE: 46

```
Met Ser Lys Gln Ile Leu Lys Asn Thr Gly Leu Gln Glu Ile Met Ser
1               5                   10                  15

Phe Lys Val Asn Leu Glu Gly Val Val Asn Asn His Val Phe Thr Met
            20                  25                  30

Glu Gly Cys Gly Lys Gly Asn Ile Leu Phe Gly Asn Gln Leu Val Gln
        35                  40                  45

Ile Arg Val Thr Lys Gly Ala Pro Leu Pro Phe Ala Phe Asp Ile Leu
    50                  55                  60

Ser Pro Ala Phe Gln Tyr Gly Asn Arg Thr Phe Thr Lys Tyr Pro Glu
65                  70                  75                  80

Asp Ile Ser Asp Phe Phe Ile Gln Ser Phe Pro Ala Gly Phe Val Tyr
                85                  90                  95

Glu Arg Thr Leu Arg Phe Glu Asp Gly Gly Leu Val Glu Ile Arg Ser
            100                 105                 110

Asp Ile Asn Leu Ile Glu Glu Met Phe Val Tyr Arg Val Glu Tyr Lys
        115                 120                 125

Gly Ser Asn Phe Pro Asn Asp Gly Pro Val Met Lys Lys Thr Ile Thr
    130                 135                 140

Gly Leu Gln Pro Ser Phe Glu Val Val Tyr Met Asn Asp Gly Val Leu
145                 150                 155                 160

Val Gly Gln Val Ile Leu Val Tyr Arg Leu Asn Ser Gly Lys Phe Tyr
                165                 170                 175

Ser Cys His Met Arg Thr Leu Met Lys Ser Lys Gly Val Val Lys Asp
            180                 185                 190

Phe Pro Glu Tyr His Phe Ile Gln His Arg Leu Glu Lys Thr Tyr Val
        195                 200                 205

Glu Asp Gly Gly Phe Val Glu Glu His Glu Thr Ala Ile Ala Gln Leu
    210                 215                 220

Thr Ser Leu Gly Lys Pro Leu Gly Ser Leu His Glu Trp Val
225                 230                 235
```

<210> SEQ ID NO 47
<211> LENGTH: 714
<212> TYPE: DNA
<213> ORGANISM: Renilla reniformis

<400> SEQUENCE: 47

```
atgagtaaac aaatattgaa gaacactgga ttgcaggaga tcatgtcgtt taaagtgaat     60
ctggaaggtg tagtaaacaa tcatgtgttc ccaatggaag gttgtggaaa aggaaatatt    120
ttattcggaa accaactggt tcagattcgt gtcacaaaag ggctccgct tccatttgca     180
tttgatattc tctcaccagc tttccaatac ggcaaccgta cattcacgaa atacccggag    240
gatatatcag actttttat acaatcattt ccagcgggat ttgtatacga aagaacgttg     300
cgtttcgaag atggtggact ggttgaaatc cgttcagata taaatttaat cgaggagatg    360
tttgtctaca gagtggaata taaaggtagt aacttcccga atgatggtcc agtgatgaag    420
aagacaatca caggattaca accttcgttc gaagttgtgt atatgaacga tggcgtcttg    480
gttggccaag tcattcttgt ttatagatta aactctggca aattttattc gtgtcacatg    540
agaacactga tgaaatcaaa gggtgtagtg aaggattttc ccgaatacca tttcattcaa    600
catcgtttag agaagacgta tgtggaagac ggaggttttg ttgaggaaca cgagacggcc    660
attgctcaac tgacatcgct ggggaaacca cttggatcct tacacgaatg ggtt          714
```

<210> SEQ ID NO 48
<211> LENGTH: 238
<212> TYPE: PRT
<213> ORGANISM: Renilla reniformis

<400> SEQUENCE: 48

```
Met Ser Lys Gln Ile Leu Lys Asn Thr Gly Leu Gln Glu Ile Met Ser
1               5                   10                  15

Phe Lys Val Asn Leu Glu Gly Val Val Asn Asn His Val Phe Pro Met
            20                  25                  30

Glu Gly Cys Gly Lys Gly Asn Ile Leu Phe Gly Asn Gln Leu Val Gln
        35                  40                  45

Ile Arg Val Thr Lys Gly Ala Pro Leu Pro Phe Ala Phe Asp Ile Leu
    50                  55                  60

Ser Pro Ala Phe Gln Tyr Gly Asn Arg Thr Phe Thr Lys Tyr Pro Glu
65                  70                  75                  80

Asp Ile Ser Asp Phe Phe Ile Gln Ser Phe Pro Ala Gly Phe Val Tyr
                85                  90                  95

Glu Arg Thr Leu Arg Phe Glu Asp Gly Gly Leu Val Glu Ile Arg Ser
            100                 105                 110

Asp Ile Asn Leu Ile Glu Glu Met Phe Val Tyr Arg Val Glu Tyr Lys
        115                 120                 125

Gly Ser Asn Phe Pro Asn Asp Gly Pro Val Met Lys Lys Thr Ile Thr
    130                 135                 140

Gly Leu Gln Pro Ser Phe Glu Val Val Tyr Met Asn Asp Gly Val Leu
145                 150                 155                 160

Val Gly Gln Val Ile Leu Val Tyr Arg Leu Asn Ser Gly Lys Phe Tyr
                165                 170                 175

Ser Cys His Met Arg Thr Leu Met Lys Ser Lys Gly Val Val Lys Asp
            180                 185                 190

Phe Pro Glu Tyr His Phe Ile Gln His Arg Leu Glu Lys Thr Tyr Val
        195                 200                 205

Glu Asp Gly Gly Phe Val Glu Glu His Glu Thr Ala Ile Ala Gln Leu
```

-continued

```
    210                 215                 220

Thr Ser Leu Gly Lys Pro Leu Gly Ser Leu His Glu Trp Val
225                 230                 235
```

<210> SEQ ID NO 49
<211> LENGTH: 714
<212> TYPE: DNA
<213> ORGANISM: Renilla reniformis

<400> SEQUENCE: 49

```
atgagtaaac aaatattgaa gaacactgga ttgcaggaga tcatgtcgtt taaagtgaat     60

ctggaaggtg tagtaaacaa tcatgtgttc acaatggaag gttgtggaaa aggaaatatt    120

ttattcggaa accaactggt tcagattcgt gtcacaaaag ggctccgct tccatttgca     180

tttgatattc tctcaccagc tttccaatac ggcaaccgta cattcacgaa atacccggag    240

gatatatcag actttttat acaatcattt ccagcgggat ttgtatacga aagaacgttg     300

cgttacgaag atggtggact ggttgaaatc cgttcagata taaatttaat cgaggggatg    360

tttgtctaca gagtggaata taaaggtagt aacttcccga atgatggtcc agtgatgaag    420

aagacaatca caggattaca accttcgttc gaagttgtgt atatgaacga tggcgtcttg    480

gttggccaag tcattcttgt ttatagatta aactctggca aattttattc gtgtcacatg    540

agaacactga tgaaatcaaa gggtgtagtg aaggattttc ccgaatacca tttcattcaa    600

catcgtttag agaagacgta tgtggaagac ggaggttttg ttgaggaaca cgagacggcc    660

attgctcaac tgacatcgct ggggaaacca cttggatcct tacacgaatg ggtt          714
```

<210> SEQ ID NO 50
<211> LENGTH: 238
<212> TYPE: PRT
<213> ORGANISM: Renilla reniformis

<400> SEQUENCE: 50

```
Met Ser Lys Gln Ile Leu Lys Asn Thr Gly Leu Gln Glu Ile Met Ser
1               5                   10                  15

Phe Lys Val Asn Leu Glu Gly Val Val Asn Asn His Val Phe Thr Met
            20                  25                  30

Glu Gly Cys Gly Lys Gly Asn Ile Leu Phe Gly Asn Gln Leu Val Gln
        35                  40                  45

Ile Arg Val Thr Lys Gly Ala Pro Leu Pro Phe Ala Phe Asp Ile Leu
    50                  55                  60

Ser Pro Ala Phe Gln Tyr Gly Asn Arg Thr Phe Thr Lys Tyr Pro Glu
65                  70                  75                  80

Asp Ile Ser Asp Phe Phe Ile Gln Ser Phe Pro Ala Gly Phe Val Tyr
                85                  90                  95

Glu Arg Thr Leu Arg Tyr Glu Asp Gly Gly Leu Val Glu Ile Arg Ser
            100                 105                 110

Asp Ile Asn Leu Ile Glu Gly Met Phe Val Tyr Arg Val Glu Tyr Lys
        115                 120                 125

Gly Ser Asn Phe Pro Asn Asp Gly Pro Val Met Lys Lys Thr Ile Thr
    130                 135                 140

Gly Leu Gln Pro Ser Phe Glu Val Val Tyr Met Asn Asp Gly Val Leu
145                 150                 155                 160

Val Gly Gln Val Ile Leu Val Tyr Arg Leu Asn Ser Gly Lys Phe Tyr
                165                 170                 175

Ser Cys His Met Arg Thr Leu Met Lys Ser Lys Gly Val Val Lys Asp
```

-continued

```
        180                 185                 190

Phe Pro Glu Tyr His Phe Ile Gln His Arg Leu Glu Lys Thr Tyr Val
        195                 200                 205

Glu Asp Gly Gly Phe Val Glu Glu His Glu Thr Ala Ile Ala Gln Leu
    210                 215                 220

Thr Ser Leu Gly Lys Pro Leu Gly Ser Leu His Glu Trp Val
225                 230                 235


<210> SEQ ID NO 51
<211> LENGTH: 714
<212> TYPE: DNA
<213> ORGANISM: Renilla reniformis

<400> SEQUENCE: 51

atgagtaaac aaatattgaa gaacactgga ttgcaggaga tcatgtcgtt taaagtgaat      60

ctggaaggtg tagtaaacaa tcatgtgttc acaatggaag gttgtggaaa aggaaatatt     120

ttatccggaa accaactggt tcagattcgt gtcacaaaag gggctccgct tccatttgca     180

tttgatattc tctcaccagc tttccaatac ggcaaccgta cattcacgaa atacccggag     240

gatatatcag actttttat acaatcattt ccagcgggat ttgtatacga aagaacgttg      300

cgtttcgaag atggtggact ggttgaaatc cgttcagata taaatttaat cgaggagatg     360

tttgagtaca gagtggaata taaaggtagt aacttcccga atgatggtcc agtgatgaag     420

aagacaatca caggattaca accttcgttc gaagttgtgt atatgaacga tggcgtcttg     480

gttggccaag tcattcttgt ttatagatta aactctggca aattttattc gtgtcacatg     540

agaacactga tgaaatcaaa gggtgtagtg aaggattttc ccgaatacca tttcattcaa     600

catcgtttag agaagacgta tgtggaagac ggaggttttg tagaggaaca cgagacggcc     660

attgctcaac tgacatcgct ggggaaacca cttggatcct tacacgaatg ggtt           714


<210> SEQ ID NO 52
<211> LENGTH: 238
<212> TYPE: PRT
<213> ORGANISM: Renilla reniformis

<400> SEQUENCE: 52

Met Ser Lys Gln Ile Leu Lys Asn Thr Gly Leu Gln Glu Ile Met Ser
1               5                   10                  15

Phe Lys Val Asn Leu Glu Gly Val Val Asn Asn His Val Phe Thr Met
            20                  25                  30

Glu Gly Cys Gly Lys Gly Asn Ile Leu Ser Gly Asn Gln Leu Val Gln
        35                  40                  45

Ile Arg Val Thr Lys Gly Ala Pro Leu Pro Phe Ala Phe Asp Ile Leu
    50                  55                  60

Ser Pro Ala Phe Gln Tyr Gly Asn Arg Thr Phe Thr Lys Tyr Pro Glu
65                  70                  75                  80

Asp Ile Ser Asp Phe Phe Ile Gln Ser Phe Pro Ala Gly Phe Val Tyr
                85                  90                  95

Glu Arg Thr Leu Arg Phe Glu Asp Gly Gly Leu Val Glu Ile Arg Ser
            100                 105                 110

Asp Ile Asn Leu Ile Glu Glu Met Phe Glu Tyr Arg Val Glu Tyr Lys
        115                 120                 125

Gly Ser Asn Phe Pro Asn Asp Gly Pro Val Met Lys Lys Thr Ile Thr
    130                 135                 140

Gly Leu Gln Pro Ser Phe Glu Val Val Tyr Met Asn Asp Gly Val Leu
```

-continued 145 150 155 160

Val Gly Gln Val Ile Leu Val Tyr Arg Leu Asn Ser Gly Lys Phe Tyr
165 170 175

Ser Cys His Met Arg Thr Leu Met Lys Ser Lys Gly Val Val Lys Asp
180 185 190

Phe Pro Glu Tyr His Phe Ile Gln His Arg Leu Glu Lys Thr Tyr Val
195 200 205

Glu Asp Gly Gly Phe Val Glu Glu His Glu Thr Ala Ile Ala Gln Leu
210 215 220

Thr Ser Leu Gly Lys Pro Leu Gly Ser Leu His Glu Trp Val
225 230 235

<210> SEQ ID NO 53
<211> LENGTH: 714
<212> TYPE: DNA
<213> ORGANISM: Renilla reniformis

<400> SEQUENCE: 53
atgagtaaac aaatattgaa gaacactgga ttgcaggaga tcatgtcgtt taaagtgaat 60
ctggaaggtg tagtaaacaa tcatgtgttc acaatggaag gttgtggaaa aggaaatatt 120
ttatccggaa accaactggt tcagattcgt gtcacaaaag ggctccgct tccatttgca 180 tttgatattc tctcaccagc tttccaatac ggcaaccgta cattcacgaa atacccggag 240
gatatatcag actttttat acaatcattt ccagcgggat ttgtatacga aagaacgttg 300
cgtttcgaag atggtggact ggttgaaatc cgttcagata taaatttaat cgaggagatg 360
tttgagtaca gagtggaata taaaggtagt aacttcccga atgatggtcc agtgatgaag 420
aagacaatca caggattaca accttcgttc gaagttgtgt atatgaacga tggcgtcttg 480
gttggccaag tcattcttgt ttatagatta aactctggca aattttattc gtgtcacatg 540
agaacactga tgaaatcaaa gggtgtagtg aaggattttc ccgaatacca tttcattcaa 600
catcgtttag agaagacgta tgtggaagac ggaggttttg ttgaggaaca cgagacggcc 660
attgctcaac tgacatcgct ggggaaacca cttggatcct tacacgaatg ggtt 714

<210> SEQ ID NO 54
<211> LENGTH: 238
<212> TYPE: PRT
<213> ORGANISM: Renilla reniformis

<400> SEQUENCE: 54

Met Ser Lys Gln Ile Leu Lys Asn Thr Gly Leu Gln Glu Ile Met Ser
1 5 10 15

Phe Lys Val Asn Leu Glu Gly Val Val Asn Asn His Val Phe Thr Met
20 25 30

Glu Gly Cys Gly Lys Gly Asn Ile Leu Ser Gly Asn Gln Leu Val Gln
35 40 45

Ile Arg Val Thr Lys Gly Ala Pro Leu Pro Phe Ala Phe Asp Ile Leu
50 55 60

Ser Pro Ala Phe Gln Tyr Gly Asn Arg Thr Phe Thr Lys Tyr Pro Glu
65 70 75 80

Asp Ile Ser Asp Phe Phe Ile Gln Ser Phe Pro Ala Gly Phe Val Tyr
85 90 95

Glu Arg Thr Leu Arg Phe Glu Asp Gly Gly Leu Val Glu Ile Arg Ser
100 105 110

Asp Ile Asn Leu Ile Glu Glu Met Phe Glu Tyr Arg Val Glu Tyr Lys

-continued

```
        115                 120                 125

Gly Ser Asn Phe Pro Asn Asp Gly Pro Val Met Lys Lys Thr Ile Thr
    130                 135                 140

Gly Leu Gln Pro Ser Phe Glu Val Val Tyr Met Asn Asp Gly Val Leu
145                 150                 155                 160

Val Gly Gln Val Ile Leu Val Tyr Arg Leu Asn Ser Gly Lys Phe Tyr
                165                 170                 175

Ser Cys His Met Arg Thr Leu Met Lys Ser Lys Gly Val Val Lys Asp
            180                 185                 190

Phe Pro Glu Tyr His Phe Ile Gln His Arg Leu Glu Lys Thr Tyr Val
        195                 200                 205

Glu Asp Gly Gly Phe Val Glu Glu His Glu Thr Ala Ile Ala Gln Leu
    210                 215                 220

Thr Ser Leu Gly Lys Pro Leu Gly Ser Leu His Glu Trp Val
225                 230                 235


<210> SEQ ID NO 55
<211> LENGTH: 714
<212> TYPE: DNA
<213> ORGANISM: Renilla reniformis

<400> SEQUENCE: 55

atgagtaaac aaatattgaa gaacactgga ttgcaggaga tcatgtcgtt taaagtgatt      60

ctggaaggtg tagtaaacaa tcatgtgttc acaatggaag gttgtggaaa aggaaatatt     120

ttattcggaa accaactggt tcagattcgt gtcacaaaag ggctccgct tccatttgca     180

tttgatattc tctcaccagc tttccaatac ggcaaccgta cattcacgaa atacccggag     240

gatatatcag actttttat acaatcattt ccagcgggat ttgtatacga aagaacgttg     300

cgtttcgaag atggtggact ggttgaaatc cgttcagata taaatttaat cgaggggatg     360

tttgtctaca gagtggaata taaaggtagt aacttcccga atgatggtcc agtgatgaag     420

aatacaatca caggattaca accttcgttc gaagttgtgt atatgaacga tggcgtcttg     480

gttggccaag tcattcttgt ttatagatta aactctggca aattttattc gtgtcacatg     540

agaacactga tgaaatcaaa gggtgtagtg aaggattttc ccgaatacca tttcattcaa     600

catcgtttag agaaggcgta tgtggaagac ggaggtattg ttgaggaaca cgagacggcc     660

attgctcaac tgacatcgct ggggaaacca cttggatcct tacacgaatg ggtt           714


<210> SEQ ID NO 56
<211> LENGTH: 238
<212> TYPE: PRT
<213> ORGANISM: Renilla reniformis

<400> SEQUENCE: 56

Met Ser Lys Gln Ile Leu Lys Asn Thr Gly Leu Gln Glu Ile Met Ser
1               5                   10                  15

Phe Lys Val Ile Leu Glu Gly Val Val Asn Asn His Val Phe Thr Met
            20                  25                  30

Glu Gly Cys Gly Lys Gly Asn Ile Leu Phe Gly Asn Gln Leu Val Gln
        35                  40                  45

Ile Arg Val Thr Lys Gly Ala Pro Leu Pro Phe Ala Phe Asp Ile Leu
    50                  55                  60

Ser Pro Ala Phe Gln Tyr Gly Asn Arg Thr Phe Thr Lys Tyr Pro Glu
65                  70                  75                  80

Asp Ile Ser Asp Phe Phe Ile Gln Ser Phe Pro Ala Gly Phe Val Tyr
```

-continued

```
                85                  90                  95

Glu Arg Thr Leu Arg Phe Glu Asp Gly Gly Leu Val Glu Ile Arg Ser
            100                 105                 110

Asp Ile Asn Leu Ile Glu Gly Met Phe Val Tyr Arg Val Glu Tyr Lys
        115                 120                 125

Gly Ser Asn Phe Pro Asn Asp Gly Pro Val Met Lys Asn Thr Ile Thr
    130                 135                 140

Gly Leu Gln Pro Ser Phe Glu Val Val Tyr Met Asn Asp Gly Val Leu
145                 150                 155                 160

Val Gly Gln Val Ile Leu Val Tyr Arg Leu Asn Ser Gly Lys Phe Tyr
                165                 170                 175

Ser Cys His Met Arg Thr Leu Met Lys Ser Lys Gly Val Val Lys Asp
            180                 185                 190

Phe Pro Glu Tyr His Phe Ile Gln His Arg Leu Glu Lys Ala Tyr Val
        195                 200                 205

Glu Asp Gly Gly Ile Val Glu Glu His Glu Thr Ala Ile Ala Gln Leu
    210                 215                 220

Thr Ser Leu Gly Lys Pro Leu Gly Ser Leu His Glu Trp Val
225                 230                 235


<210> SEQ ID NO 57
<211> LENGTH: 714
<212> TYPE: DNA
<213> ORGANISM: Renilla reniformis

<400> SEQUENCE: 57

atgagtaaac aaatattgaa gaacactgga ttgcaggaga tcatgtcgtt taaagtgaat     60

ctggaaggtg tagtaaacaa tcatgtgttc acaatggaag gttgtggaaa aggaaatatt    120

ttattcggaa accaactggt tcagattcgt gtcacaaaag ggctccgct  tccatttgca    180

tttgatattc tctcaccagc tttccaatac ggcaaccgta cattcacgaa atacccggag    240

gatatatcag actttttat  acaatcattt ccagcgggat ttgtatacga aagaacgttg    300

cgttacgaag atggtggact ggctgaaatc cgttcagata taaatttaat cgaggggatg    360

tttgtctaca gagtggaata taaaggtagt aacttcccga atgatggtcc agtgatgaag    420

aatacaatca caggattaca accttcgttc gaagttgtgt atatgaacga tggcgtcttg    480

gttggccaag tcattcttgt ttatagatta aactctggca aattttattc gtgtcacatg    540

agaacactga tgaaatcaaa gggtgtagtg aaggattttc ccgaatacca tttcattcaa    600

catcgtttag agaagacgta tgtggaagac ggaggttttg ttgaggaaca cgagacggcc    660

attgctcaac tgacatcgct ggggaaacca cttggatcct tacacgaatg ggtt          714


<210> SEQ ID NO 58
<211> LENGTH: 238
<212> TYPE: PRT
<213> ORGANISM: Renilla reniformis

<400> SEQUENCE: 58

Met Ser Lys Gln Ile Leu Lys Asn Thr Gly Leu Gln Glu Ile Met Ser
1               5                   10                  15

Phe Lys Val Asn Leu Glu Gly Val Val Asn Asn His Val Phe Thr Met
            20                  25                  30

Glu Gly Cys Gly Lys Gly Asn Ile Leu Phe Gly Asn Gln Leu Val Gln
        35                  40                  45

Ile Arg Val Thr Lys Gly Ala Pro Leu Pro Phe Ala Phe Asp Ile Leu
```

-continued

```
    50                  55                  60

Ser Pro Ala Phe Gln Tyr Gly Asn Arg Thr Phe Thr Lys Tyr Pro Glu
65                  70                  75                  80

Asp Ile Ser Asp Phe Phe Ile Gln Ser Phe Pro Ala Gly Phe Val Tyr
                85                  90                  95

Glu Arg Thr Leu Arg Tyr Glu Asp Gly Gly Leu Ala Glu Ile Arg Ser
            100                 105                 110

Asp Ile Asn Leu Ile Glu Gly Met Phe Val Tyr Arg Val Glu Tyr Lys
        115                 120                 125

Gly Ser Asn Phe Pro Asn Asp Gly Pro Val Met Lys Asn Thr Ile Thr
    130                 135                 140

Gly Leu Gln Pro Ser Phe Glu Val Val Tyr Met Asn Asp Gly Val Leu
145                 150                 155                 160

Val Gly Gln Val Ile Leu Val Tyr Arg Leu Asn Ser Gly Lys Phe Tyr
                165                 170                 175

Ser Cys His Met Arg Thr Leu Met Lys Ser Lys Gly Val Val Lys Asp
            180                 185                 190

Phe Pro Glu Tyr His Phe Ile Gln His Arg Leu Glu Lys Thr Tyr Val
        195                 200                 205

Glu Asp Gly Gly Phe Val Glu Glu His Glu Thr Ala Ile Ala Gln Leu
    210                 215                 220

Thr Ser Leu Gly Lys Pro Leu Gly Ser Leu His Glu Trp Val
225                 230                 235


<210> SEQ ID NO 59
<211> LENGTH: 714
<212> TYPE: DNA
<213> ORGANISM: Renilla reniformis

<400> SEQUENCE: 59

atgagtaaac aaatattgaa gaacactgga ttgcaggaga tcgtgtcgtt taaagtgatt      60

ctggaaggtg tagtaaacaa tcatgtgttc acaatggaag gttgtggaaa aggaaatatt     120

ttattcggaa accaactggt tcagattcgt gtcacaaaag gggctccgct tccatttgca     180

tttgatattc tctcaccagc tttccaatac ggcaaccgta cattcacgaa atacccggag     240

gatatatcag actttttat acaatcattt ccagcgggat ttgtatacga aagaacgttg      300

cgttacgaag atggtggact ggttgaaatc cgttcagata taaatttaat cgaggggatg     360

tttgtctaca gagtggaata taaaggtagt aacttcccga atgatggtcc agtgatgaag     420

aatacaatca caggattaca accttcgttc gaagttgtgt atatgaacga tggcgtcttg     480

gttggccaag tcattcttgt ttatagatta aactgtggca aattttattc gtgtcacatg     540

agaacactga tgaaatcaaa gggtgtagtg aaggattttc ccgaatacca tttcattcaa     600

catcgtttag agaagacgta tgtggaagac ggaggttttg ttgaggaaca cgagacggcc     660

attgctcaac tgacatcgct ggggaaacca cttggatcct tacacgaatg ggtt           714


<210> SEQ ID NO 60
<211> LENGTH: 238
<212> TYPE: PRT
<213> ORGANISM: Renilla reniformis

<400> SEQUENCE: 60

Met Ser Lys Gln Ile Leu Lys Asn Thr Gly Leu Gln Glu Ile Val Ser
1               5                   10                  15

Phe Lys Val Ile Leu Glu Gly Val Val Asn Asn His Val Phe Thr Met
```

-continued

```
            20                  25                  30

Glu Gly Cys Gly Lys Gly Asn Ile Leu Phe Gly Asn Gln Leu Val Gln
        35                  40                  45

Ile Arg Val Thr Lys Gly Ala Pro Leu Pro Phe Ala Phe Asp Ile Leu
    50                  55                  60

Ser Pro Ala Phe Gln Tyr Gly Asn Arg Thr Phe Thr Lys Tyr Pro Glu
65                  70                  75                  80

Asp Ile Ser Asp Phe Phe Ile Gln Ser Phe Pro Ala Gly Phe Val Tyr
                85                  90                  95

Glu Arg Thr Leu Arg Tyr Glu Asp Gly Gly Leu Val Glu Ile Arg Ser
            100                 105                 110

Asp Ile Asn Leu Ile Glu Gly Met Phe Val Tyr Arg Val Glu Tyr Lys
        115                 120                 125

Gly Ser Asn Phe Pro Asn Asp Gly Pro Val Met Lys Asn Thr Ile Thr
    130                 135                 140

Gly Leu Gln Pro Ser Phe Glu Val Val Tyr Met Asn Asp Gly Val Leu
145                 150                 155                 160

Val Gly Gln Val Ile Leu Val Tyr Arg Leu Asn Cys Gly Lys Phe Tyr
                165                 170                 175

Ser Cys His Met Arg Thr Leu Met Lys Ser Lys Gly Val Val Lys Asp
            180                 185                 190

Phe Pro Glu Tyr His Phe Ile Gln His Arg Leu Glu Lys Thr Tyr Val
        195                 200                 205

Glu Asp Gly Gly Phe Val Glu Glu His Glu Thr Ala Ile Ala Gln Leu
    210                 215                 220

Thr Ser Leu Gly Lys Pro Leu Gly Ser Leu His Glu Trp Val
225                 230                 235
```

<210> SEQ ID NO 61
<211> LENGTH: 714
<212> TYPE: DNA
<213> ORGANISM: Renilla reniformis

<400> SEQUENCE: 61

```
atgagtaaac aaatattgaa gaacactgga ttgcaggaga tcatgtcgtt taaagtgaat     60

ctggaaggtg tagtaaacaa tcatgtgttc acaatggaag gttgtggaaa aggaaatatt    120

ttattcggaa accaactggt tcagattcgt gtcacaaaag ggctccgct tccatttgca    180

tttgatattc tctcaccagc cttccaatac ggcaaccgta cattcacgaa atacccggag    240

gatatatcag actttttat acaatcattt ccagcgggat ttgtatacga aagagcgttg    300

cgttacgaag atggtggact ggttgaaatc cgttcagata taaatttaat cgaggagatg    360

tttgtctaca gagtggaata taaaggtagt aacttcccga atgatggtcc agtgatgaag    420

aagacaatca caggattaca accttcgttc gaagttgtgt atatgaacga tggcgtcttg    480

gttggccaag tcattcttgt ttatagatta aactctggca aattttattc gtgtcacatg    540

agaacactga tgaaatcaaa gggtgtagtg aaggattttc ccgaatacca tttcattcaa    600

catcgtttag agaagacgta tgtggaagac ggaggttttg ttgaggaaca cgagacggcc    660

attgctcaac tgacatcgct ggggaaacca cttggatcct tacacgaatg ggtt          714
```

<210> SEQ ID NO 62
<211> LENGTH: 238
<212> TYPE: PRT
<213> ORGANISM: Renilla reniformis

<400> SEQUENCE: 62

```
Met Ser Lys Gln Ile Leu Lys Asn Thr Gly Leu Gln Glu Ile Met Ser
1               5                   10                  15

Phe Lys Val Asn Leu Glu Gly Val Val Asn Asn His Val Phe Thr Met
            20                  25                  30

Glu Gly Cys Gly Lys Gly Asn Ile Leu Phe Gly Asn Gln Leu Val Gln
        35                  40                  45

Ile Arg Val Thr Lys Gly Ala Pro Leu Pro Phe Ala Phe Asp Ile Leu
    50                  55                  60

Ser Pro Ala Phe Gln Tyr Gly Asn Arg Thr Phe Thr Lys Tyr Pro Glu
65                  70                  75                  80

Asp Ile Ser Asp Phe Phe Ile Gln Ser Phe Pro Ala Gly Phe Val Tyr
                85                  90                  95

Glu Arg Ala Leu Arg Tyr Glu Asp Gly Gly Leu Val Glu Ile Arg Ser
            100                 105                 110

Asp Ile Asn Leu Ile Glu Glu Met Phe Val Tyr Arg Val Glu Tyr Lys
        115                 120                 125

Gly Ser Asn Phe Pro Asn Asp Gly Pro Val Met Lys Lys Thr Ile Thr
    130                 135                 140

Gly Leu Gln Pro Ser Phe Glu Val Val Tyr Met Asn Asp Gly Val Leu
145                 150                 155                 160

Val Gly Gln Val Ile Leu Val Tyr Arg Leu Asn Ser Gly Lys Phe Tyr
                165                 170                 175

Ser Cys His Met Arg Thr Leu Met Lys Ser Lys Gly Val Val Lys Asp
            180                 185                 190

Phe Pro Glu Tyr His Phe Ile Gln His Arg Leu Glu Lys Thr Tyr Val
        195                 200                 205

Glu Asp Gly Gly Phe Val Glu Glu His Glu Thr Ala Ile Ala Gln Leu
    210                 215                 220

Thr Ser Leu Gly Lys Pro Leu Gly Ser Leu His Glu Trp Val
225                 230                 235
```

<210> SEQ ID NO 63
<211> LENGTH: 36
<212> TYPE: DNA
<213> ORGANISM: Artificial
<220> FEATURE:
<223> OTHER INFORMATION: PCR primer

<400> SEQUENCE: 63
attattattg aattcatgag caagcagatc ctgaag 36

<210> SEQ ID NO 64
<211> LENGTH: 37
<212> TYPE: DNA
<213> ORGANISM: Artificial
<220> FEATURE:
<223> OTHER INFORMATION: PCR Primer

<400> SEQUENCE: 64
attattatta agcttctatt acacccactc gtgcagg 37

<210> SEQ ID NO 65
<211> LENGTH: 17
<212> TYPE: DNA
<213> ORGANISM: Artificial
<220> FEATURE:
<223> OTHER INFORMATION: ERFP1 Sequencing primer

<400> SEQUENCE: 65
cttcgacatc ctgagcc 17

<210> SEQ ID NO 66
<211> LENGTH: 19
<212> TYPE: DNA
<213> ORGANISM: Artificial
<220> FEATURE:
<223> OTHER INFORMATION: ERFP2 sequencing primer

<400> SEQUENCE: 66
cgcatgtggc agctgtaga 19

<210> SEQ ID NO 67
<211> LENGTH: 33
<212> TYPE: DNA
<213> ORGANISM: Artificial
<220> FEATURE:
<223> OTHER INFORMATION: Oligonucleotide Primer for Introduction of hrGFP Mutations into Mammalian Expression Vectors

<400> SEQUENCE: 67
aagggcaaca tcctgttagg caaccagctg gtg 33

<210> SEQ ID NO 68
<211> LENGTH: 33
<212> TYPE: DNA
<213> ORGANISM: Artificial
<220> FEATURE:
<223> OTHER INFORMATION: Oligonucleotide Primer for Introduction of hrGFP Mutations into Mammalian Expression Vectors

<400> SEQUENCE: 68
acatcaacct gatcgagggg atgttcgtgt acc 33

<210> SEQ ID NO 69
<211> LENGTH: 32
<212> TYPE: DNA
<213> ORGANISM: Renilla reniformis

<400> SEQUENCE: 69
aggacggcgg cttcgtagag cagcacgaga cc 32

<210> SEQ ID NO 70
<211> LENGTH: 32
<212> TYPE: DNA
<213> ORGANISM: Artificial
<220> FEATURE:
<223> OTHER INFORMATION: Oligonucleotide Primer for Introduction of hrGFP Mutations into Mammalian Expression Vectors

<400> SEQUENCE: 70
tgtacgagcg caccatgcgc tacgaggacg gc 32

<210> SEQ ID NO 71
<211> LENGTH: 33
<212> TYPE: DNA
<213> ORGANISM: Artificial
<220> FEATURE:
<223> OTHER INFORMATION: Oligonucleotide Primer for Introduction of hrGFP Mutations into Mammalian Expression Vectors

<400> SEQUENCE: 71
aagggcaaca tcctgtccgg caaccagctg gtg 33

-continued

<210> SEQ ID NO 72
<211> LENGTH: 32
<212> TYPE: DNA
<213> ORGANISM: Artificial
<220> FEATURE:
<223> OTHER INFORMATION: Oligonucleotide Primer for Introduction of hrGFP Mutations into Mammalian Expression Vectors

<400> SEQUENCE: 72
tgtacgagcg caccctgtgc tacgaggacg gc 32

<210> SEQ ID NO 73
<211> LENGTH: 33
<212> TYPE: DNA
<213> ORGANISM: Artificial
<220> FEATURE:
<223> OTHER INFORMATION: Oligonucleotide Primer for Introduction of hrGFP Mutations into Mammalian Expression Vectors

<400> SEQUENCE: 73
atgttcgtgt accacgtgga gtacaagggc cgc 33

<210> SEQ ID NO 74
<211> LENGTH: 32
<212> TYPE: DNA
<213> ORGANISM: Artificial
<220> FEATURE:
<223> OTHER INFORMATION: Oligonucleotide Primer for Introduction of hrGFP Mutations into Mammalian Expression Vectors

<400> SEQUENCE: 74
tgaccagcct gggcaatccc ctgggcagcc tg 32

<210> SEQ ID NO 75
<211> LENGTH: 33
<212> TYPE: DNA
<213> ORGANISM: Artificial
<220> FEATURE:
<223> OTHER INFORMATION: Oligonucleotide Primer for Introduction of hrGFP Mutations into Mammalian Expression Vectors

<400> SEQUENCE: 75
atgagcttca aggtgatcct ggagggcgtg gtg 33

<210> SEQ ID NO 76
<211> LENGTH: 32
<212> TYPE: DNA
<213> ORGANISM: Artificial
<220> FEATURE:
<223> OTHER INFORMATION: Oligonucleotide Primer for Introduction of hrGFP Mutations into Mammalian Expression Vectors

<400> SEQUENCE: 76
acggccccgt gatgaagaat accatcaccg gc 32

<210> SEQ ID NO 77
<211> LENGTH: 31
<212> TYPE: DNA
<213> ORGANISM: Artificial
<220> FEATURE:
<223> OTHER INFORMATION: Oligonucleotide Primer for Introduction of hrGFP Mutations into Mammalian Expression Vectors

<400> SEQUENCE: 77
tacgagcgca ccctgcgctt cgaggacggc g 31

<210> SEQ ID NO 78

-continued

```
<211> LENGTH: 32
<212> TYPE: DNA
<213> ORGANISM: Artificial
<220> FEATURE:
<223> OTHER INFORMATION: Oligonucleotide Primer for Introduction of
      hrGFP Mutations into Mammalian Expression Vectors

<400> SEQUENCE: 78

acaaccacgt gttccccatg gagggctgcg gc                              32


<210> SEQ ID NO 79
<211> LENGTH: 30
<212> TYPE: DNA
<213> ORGANISM: Renilla reniformis

<400> SEQUENCE: 79

ggcctgcagg agatcgtgag cttcaaggtg                                 30


<210> SEQ ID NO 80
<211> LENGTH: 30
<212> TYPE: DNA
<213> ORGANISM: Artificial
<220> FEATURE:
<223> OTHER INFORMATION: Oligonucleotide Primer for Introduction of
      hrGFP Mutations into Mammalian Expression Vectors

<400> SEQUENCE: 80

taccgcctga actgcggcaa gttctacagc                                 30
```

*RENILLA* GFP MUTANTS WITH INCREASED FLUORESCENT INTENSITY AND SPECTRAL SHIFT

RELATED APPLICATION

This application claims the benefit of U.S. Provisional Application No. 60/460,432, filed on Apr. 4, 2003. The entire teachings of the above application are incorporated herein by reference.

BACKGROUND

The green fluorescent protein (GFP) from the jellyfish *Aequorea victoria* has become an extremely useful tool for tracking and quantifying biological entities in the fields of biochemistry, molecular and cell biology, and medical diagnostics (Chalfie et al., 1994, *Science* 263:802–805; Tsien, 1998, *Ann. Rev. Biochem.* 67:509–544). There are no cofactors or substrates required for fluorescence, thus the protein can be used in a wide variety of organisms and cell types. GFP has been used as a reporter gene to study gene expression in vivo by insertion downstream of a test promoter. The protein has also been used to study the subcellular localization of a number of proteins by direct fusion of the test protein to GFP, and GFP has become the reporter of choice for monitoring the infection efficiency of viral vectors both in cell culture and in animals. In addition, a number of genetic modifications have been made to GFP resulting in variants for which spectral shifts correspond to changes in the cellular environment such as pH, ion flux, and the phosphorylation state of the cell. Perhaps the most promising role for GFP as a cellular indicator is its application to fluorescence resonance energy transfer (FRET) technology. FRET occurs with fluorophores for which the emission spectrum of one overlaps with the excitation spectrum of the second. When the fluorophores are brought into close proximity, excitation of the "donor" fluorophore results in emission from the "acceptor". Pairs of such fluorophores are thus useful for monitoring molecular interactions. Fluorescent proteins such as GFP are useful for analysis of protein: protein interactions in vivo or in vitro if their fluorescent emission and excitation spectra overlap to allow FRET. The donor and acceptor fluorescent proteins may be produced as fusions with the proteins one wishes to analyze for interactions. These types of applications of GFPs are particularly appealing for high throughput analyses, since the readout is direct and independent of subcellular localization.

Purified *A. victoria* GFP is a monomeric protein of about 27 kDa that absorbs blue light with excitation wavelength maximum of 395 nm, with a minor peak at 470 nm, and emits green fluorescence with an emission wavelength of about 510 nm and a minor peak near 540 nm (Ward et al., 1979, *Photochem. Photobiol. Rev.* 4:1–57). The excitation maximum of *A. victoria* GFP is not within the range of wavelengths of standard fluorescein detection optics. Further, the breadth of the excitation and emission spectra of the *A. victoria* GFP are not well suited for use in applications involving FRET. In order to be useful in FRET applications, the excitation and emission spectra of the fluorophores are preferably tall and narrow, rather than low and broad. There is a need in the art for GFP proteins that are amenable to the use of standard fluorescein excitation and detection optics. There is also a need in the art for GFP proteins with narrow, preferably non-overlapping spectral peaks.

The use of *A. victoria* GFP as a reporter for gene expression studies, while very popular, is hindered by relatively low quantum yield (the brightness of a fluorophore is determined as the product of the extinction coefficient and the fluorescence quantum yield). Generally, the *A. victoria* GFP coding sequences must be linked to a strong promoter, such as the CMV promoter or strong exogenous regulators such as the tetracycline transactivator system, in order to produce readily detectable signal. This makes it difficult to use GFP as a reporter for examining the activity of native promoters responsive to endogenous regulators. Higher intensity would obviously also increase the sensitivity of other applications of GFP technology. There is a need in the art for GFP proteins with higher quantum yield.

Another disadvantage of *A. victoria* GFP involves fluctuations in its spectral characteristics with changes in pH. At high pH (pH 11–12), the wild-type *A. victoria* GFP loses absorbance and excitation amplitude at 395 nm and gains amplitude at 470 nm (Ward et al., 1982, *Photochem. Photobiol.* 35:803–808). *A. victoria* fluorescence is also quenched at acid pH, with a pKa around 4.5. There is a need in the art for GFPs exhibiting fluorescence that is less sensitive to pH fluctuations.

Further, in order to be more useful in a broad range of applications, there is a need in the art for GFP proteins exhibiting increased stability of fluorescence characteristics relative to *A. victoria* GFP, with regard to organic solvents, detergents and proteases often used in biological studies. There is also a need in the art for GFP proteins that are more likely to be soluble in a wider range of cell types and less likely to interfere non-specifically with endogenous proteins.

A number of modifications to *A. victoria* GFP have been made with the aim of enhancing the usefulness of the protein. For example, modifications aimed at enhancing the brightness of the fluorescence emissions or the spectral characteristics of either the excitation or emission spectra or both have been made. It is noted that the stated aim of several of these modification approaches was to make an *A. victoria* GFP that is more similar to *R. reniformis* GFP in its excitation and emission spectra and fluorescence intensity.

Literature references relating to *A. victoria* mutants exhibiting altered fluorescence characteristics include, for example, the following. Heim et al. (1995, *Nature* 373: 663–664) relates to mutations at S65 of *A. victoria* that enhance fluorescence intensity of the polypeptide. The S65T mutation to the *A. victoria* GFP is said to "ameliorate its main problems and bring its spectra much closer to that of *Renilla*".

A review by Chalfie (1995, *Photochem. Photobiol.* 62:651–656) notes that an S65T mutant of *A. victoria*, the most intensely fluorescent mutant of *A. victoria* known at the time, is not as intense as the *R. reniformis* GFP.

Further references relating to *A. victoria* mutants include, for example, Ehrig et al., 1995, *FEBS Lett.* 367:163–166); Surpin et al., 1987, *Photochem. Photobiol.* 45(Suppl):95S; Delagrave et al., 1995, *BioTechnology* 13:151–154; and Yang et al., 1996, *Gene* 173:19–23.

Patent and patent application references relating to *A. victoria* GFP and mutants thereof include the following. U.S. Pat. No. 5,874,304 discloses *A. victoria* GFP mutants said to alter spectral characteristics and fluorescence intensity of the polypeptide. U.S. Pat. No. 5,968,738 discloses *A. victoria* GFP mutants said to have altered spectral characteristics. One mutation, V163A, is said to result in increased fluorescence intensity. U.S. Pat. No. 5,804,387 discloses *A. victoria* mutants said to have increased fluorescence intensity, particularly in response to excitation with 488 nm laser light. U.S. Pat. No. 5,625,048 discloses *A. victoria* mutants said to have altered spectral characteristics as well as several mutants said to have increased fluorescence intensity. Related U.S. Pat. No. 5,777,079 discloses further combinations of mutations said to provide *A. victoria* GFP polypeptides with increased fluorescence intensity. International Patent Application (PCT) No. WO 98/21355 discloses *A. victoria* GFP mutants said to have increased fluorescence intensity, as do WO 97/20078, WO 97/42320 and WO 97/11094. PCT Application No. WO 98/06737 discloses mutants said to have altered spectral characteristics, several of which are said to have increased fluorescence intensity.

In addition to *A. victoria*, GFPs and other fluorescent proteins have been identified in a variety of other coelenterates and anthazoa. Other GFPs cloned include *A. victoria* (Prasher, 1992, *Gene* 111:229–233) and *Renilla mulleri* (WO 99/49019). A red-shifted fluorescent protein cloned from the coral *Discosoma* (Matz, M. V. et al., 1999, *Nat. Biotechnol.* 17:969–973) and named DsRed. Biochemical properties of DsRed and a mutant of DsRed are reported in Baird, G. S. et al. (2000, *Proc. Natl. Acad. Sci. USA* 97:11984–89).

The native *R. reniformis* protein was purified and characterized by Ward, W. et al. (*J. Biol. Chem.* 254 3:781–788) in 1979. The native protein was found to have a 5 fold greater extinction coefficient than native *A. victoria* GFP. In addition the *R. reniformis* GFP forms a non-dissociable homodimer, shows a broad range of pH stability, is resistant to organic solvents, detergents, and proteases, and has a narrow excitation and emission spectra. RT-PCR with gene specific primers has revealed the presence of two distinct isoforms of *R. reniformis* GFP (WO 01/68824) and (WO 01/64843).

SUMMARY OF THE INVENTION

Disclosed herein are the polynucleotide and polypeptide sequences for a series of mutants of *R. reniformis* GFP that display increased fluorescence intensity and/or alterations to the fluorescence spectra. Also disclosed are humanized versions of the polynucleotides encoding those mutants.

The invention features mutant Green Fluorescent Protein (GFP) sequences, and nucleic acids encoding them, and particularly humanized forms of the nucleic acids.

The invention also features a mutant Green Fluorescent Protein (GFP) from *Renilla reniformis*, where the mutation includes an amino acid substitution in the Beta Strand 4 portion of the protein, relative to the wild-type form of the protein, and where the mutant GFP protein has one or more of the following characteristics: (a) enhanced emission intensity, relative to wild-type GFP protein from *Renilla reniformis*; (b) a narrower or broader emission spectrum, relative to wild-type GFP protein from *Renilla reniformis*; and (c) a shift in excitation or emission maxima, relative to wild-type GFP protein from *Renilla reniformis*; (d) a shift in maturation rate, relative to wild-type GFP protein from *Renilla reniformis*; and (e) exhibiting less quenching of fluorescence at acidic pH, relative to wild-type GFP protein from *Renilla reniformis.*

The invention also features a mutant Green Fluorescent Protein (GFP) from *Renilla reniformis*, where the mutation includes an amino acid substitution in the loop region of the protein between Beta Strand 2 and Beta Strand 3, relative to the wild-type form of the protein, and where the mutant GFP protein has one or more of the following characteristics: (a) enhanced emission intensity, relative to wild-type GFP protein from *Renilla reniformis*; (b) a narrower or broader emission spectrum, relative to wild-type GFP protein from *Renilla reniformis*; and (c) a shift in excitation or emission maxima, relative to wild-type GFP protein from *Renilla reniformis*; (d) a shift in maturation rate, relative to wild-type GFP protein from *Renilla reniformis*; and (e) exhibiting less quenching of fluorescence at acidic pH, relative to wild-type GFP protein from *Renilla reniformis.*

The invention additionally features a mutant Green Fluorescent Protein (GFP) from *Renilla reniformis*, where the mutation includes an amino acid substitution in the loop region of the protein between Beta Strand 5 and Beta Strand 6, relative to the wild-type form of the protein, and where the mutant GFP protein has one or more of the following characteristics: (a) enhanced emission intensity, relative to wild-type GFP protein from *Renilla reniformis*; (b) a narrower or broader emission spectrum, relative to wild-type GFP protein from *Renilla reniformis*; and (c) a shift in excitation or emission maxima, relative to wild-type GFP protein from *Renilla reniformis*; (d) a shift in maturation rate, relative to wild-type GFP protein from *Renilla reniformis*; and (e) exhibiting less quenching of fluorescence at acidic pH, relative to wild-type GFP protein from *Renilla reniformis.*

In another aspect, the invention features a mutant Green Fluorescent Protein (GFP) from *Renilla reniformis*, where the mutation includes an amino acid substitution in the region of the protein extending from the beginning of Beta Strand 1 through the end of the loop region between Beta Strands 2 and 3, relative to the wild-type form of the protein, and where the mutant GFP protein has one or more of the following characteristics: (a) enhanced emission intensity, relative to wild-type GFP protein from *Renilla reniformis*; (b) a narrower or broader emission spectrum, relative to wild-type GFP protein from *Renilla reniformis*; and (c) a shift in excitation or emission maxima, relative to wild-type GFP protein from *Renilla reniformis*; (d) a shift in maturation rate, relative to wild-type GFP protein from *Renilla reniformis*; and (e) exhibiting less quenching of fluorescence at acidic pH, relative to wild-type GFP protein from *Renilla reniformis.*

The invention also features a mutant Green Fluorescent Protein (GFP) from *Renilla reniformis*, where the mutation includes an amino acid substitution in the region of the protean extending from the beginning of Beta Strand 4 through the end of Beta Strand 6, relative to the wild-type form of the protein, and where the mutant GFP protein has one or more of the following characteristics: (a) enhanced emission intensity, relative to wild-type GFP protein from *Renilla reniformis*; (b) a narrower or broader emission spectrum, relative to wild-type GFP protein from *Renilla reniformis*; and (c) a shift in excitation or emission maxima, relative to wild-type GFP protein from *Renilla reniformis*; (d) a shift in maturation rate, relative to wild-type GFP protein from *Renilla reniformis*; and (e) exhibiting less quenching of fluorescence at acidic pH, relative to wild-type GFP protein from *Renilla reniformis.*

The invention also features a polynucleotide encoding the mutant *Renilla reniformis* Green Fluorescent Proteins (GFPs) as described above. The polynucleotide can be humanized. The polynucleotide can be in a vector, and the vector can be contained in a host cell.

The invention also features a mutant Green Fluorescent Protein (GFP) from *Renilla reniformis*, selected from the group consisting of: (a) the amino acid sequence of mutant GM1; (b) the amino acid sequence of mutant GM2; (c) the amino acid sequence of mutant GM3; (d) the amino acid sequence of mutant GM4; (e) the amino acid sequence of mutant GM6; (f) the amino acid sequence of mutant T1; (g)

the amino acid sequence of mutant T6; (h) the amino acid sequence of mutant T8; (i) the amino acid sequence of mutant T11; (j) the amino acid sequence of mutant T12; (k) the amino acid sequence of mutant T13; (1) the amino acid sequence of mutant T14; (m) the amino acid sequence of mutant T15; and (n) the amino acid sequence of mutant T17. The amino acid substitutions making up these mutants are described herein.

The invention also features a polynucleotide encoding a mutant Green Fluorescent Protein (GFP) from *Renilla reniformis*, selected from the group consisting of: (a) a polynucleotide encoding the amino acid sequence of mutant GM1; (b) a polynucleotide encoding the amino acid sequence of mutant GM2; (c) a polynucleotide encoding the amino acid sequence of mutant GM3; (d) a polynucleotide encoding the amino acid sequence of mutant GM4; (e) a polynucleotide encoding the amino acid sequence of mutant GM6; (f) a polynucleotide encoding the amino acid sequence of mutant T1; (g) a polynucleotide encoding the amino acid sequence of mutant T6; (h) a polynucleotide encoding the amino acid sequence of mutant T8; (i) a polynucleotide encoding the amino acid sequence of mutant T11; (j) a polynucleotide encoding the amino acid sequence of mutant T12; (k) a polynucleotide encoding the amino acid sequence of mutant T13; (l) a polynucleotide encoding the amino acid sequence of mutant T14; (m) a polynucleotide encoding the amino acid sequence of mutant T15; and (n) a polynucleotide encoding the amino acid sequence of mutant T17. The polynucleotide can be humanized. The polynucleotide can be in a vector, and the vector can be contained in a host cell.

In an additional aspect, the invention features a mutant Green Fluorescent Protein (GFP) from *Renilla reniformis*, selected from the group consisting of: (a) the amino acid sequence of SEQ ID NO:34; (b) the amino acid sequence of SEQ ID NO:36; (c) the amino acid sequence of SEQ ID NO:38; (d) the amino acid sequence of SEQ ID NO:40; (e) the amino acid sequence of SEQ ID NO:42; (f) the amino acid sequence of SEQ ID NO:44; (g) the amino acid sequence of SEQ ID NO:46; (h) the amino acid sequence of SEQ ID NO:48; (i) the amino acid sequence of SEQ ID NO:50; (j) the amino acid sequence of SEQ ID NO:52; (k) the amino acid sequence of SEQ ID NO:54; (l) the amino acid sequence of SEQ ID NO:56; (m) the amino acid sequence of SEQ ID NO:58; and (n) the amino acid sequence of SEQ ID NO:60.

The invention also features a polynucleotide encoding a mutant Green Fluorescent Protein (GFP) from *Renilla reniformis*, selected from the group consisting of: (a) the polynucleotide sequence of SEQ ID NO:33; (b) the polynucleotide sequence of SEQ ID NO:35; (c) the polynucleotide sequence of SEQ ID NO:37; (d) the polynucleotide sequence of SEQ ID NO:39; (e) the polynucleotide sequence of SEQ ID NO:41; (f) the polynucleotide sequence of SEQ ID NO:43; (g) the polynucleotide sequence of SEQ ID NO:45; (h) the polynucleotide sequence of SEQ ID NO:47; (i) the polynucleotide sequence of SEQ ID NO:49; (j) the polynucleotide sequence of SEQ ID NO:51; (k) the polynucleotide sequence of SEQ ID NO:53; (l) the polynucleotide sequence of SEQ ID NO:55; (m) the polynucleotide sequence of SEQ ID NO:57; and (n) the polynucleotide sequence of SEQ ID NO:59. The polynucleotide can be humanized. The polynucleotide can be in a vector, and the vector can be contained in a host cell.

The invention features a mutant Green Fluorescent Protein (GFP) from *Renilla reniformis*, selected from the group consisting of: (a) the amino acid sequence of SEQ ID NO:4; (b) the amino acid sequence of SEQ ID NO:6; (c) the amino acid sequence of SEQ ID NO:8; (d) the amino acid sequence of SEQ ID NO:10; (e) the amino acid sequence of SEQ ID NO:12; (f) the amino acid sequence of SEQ ID NO:14; (g) the amino acid sequence of SEQ ID NO:16; (h) the amino acid sequence of SEQ ID NO:18; (i) the amino acid sequence of SEQ ID NO:20; (j) the amino acid sequence of SEQ ID NO:22; (k) the amino acid sequence of SEQ ID NO:24; (l) the amino acid sequence of SEQ ID NO:26; (m) the amino acid sequence of SEQ ID NO:28; and (n) the amino acid sequence of SEQ ID NO:30.

Another feature of the invention is a polynucleotide encoding a mutant Green Fluorescent Protein (GFP) from *Renilla reniformis*, selected from the group consisting of: (a) the polynucleotide sequence of SEQ ID NO:3; (b) the polynucleotide sequence of SEQ ID NO:5; (c) the polynucleotide sequence of SEQ ID NO:7; (d) the polynucleotide sequence of SEQ ID NO:9; (e) the polynucleotide sequence of SEQ ID NO:11; (f) the polynucleotide sequence of SEQ ID NO:13; (g) the polynucleotide sequence of SEQ ID NO:15; (h) the polynucleotide sequence of SEQ ID NO:17; (i) the polynucleotide sequence of SEQ ID NO:19; (j) the polynucleotide sequence of SEQ ID NO:21; (k) the polynucleotide sequence of SEQ ID NO:23; (l) the polynucleotide sequence of SEQ ID NO:25; (m) the polynucleotide sequence of SEQ ID NO:27; and (n) the polynucleotide sequence of SEQ ID NO:29. The polynucleotide can be in a vector, and the vector can be contained in a host cell.

The invention also features a method of producing mutant *Renilla reniformis* GFP, including the steps of: (a) culturing a cell containing a recombinant vector including a wild type or humanized polynucleotide sequence encoding mutant *Renilla reniformis* GFP under conditions where the mutant *Renilla reniformis* GFP protein is expressed; and (b) isolating the mutant *Renilla reniformis* GFP protein from the cell; thereby producing mutant *Renilla reniformis* GFP.

In another aspect, the invention features a method of producing a *Renilla reniformis* fusion protein, the method including the steps of: culturing a cell containing a polynucleotide sequence encoding the polypeptide of interest linked with a humanized polynucleotide encoding mutant *Renilla reniformis* GFP wherein the linked polynucleotide sequences are fused in frame, under conditions where the mutant *Renilla reniformis* GFP protein is expressed. A method of determining the location of a polypeptide of interest in a cell can use the production method described above.

An additional feature of the invention is a method of identifying a cell into which a recombinant vector has been introduced, the method including the steps of: (a) providing a cell containing a recombinant vector including a humanized polynucleotide which encodes mutant *Renilla reniformis* GFP, wherein the cell permits expression of the humanized polynucleotide; (b) illuminating the population with light within the excitation spectrum of mutant *Renilla reniformis* GFP; and (c) detecting fluorescence in the emission spectrum of mutant *Renilla reniformis* GFP in the population, where detection of fluorescence in the cell indicates that the recombinant vector has been introduced into the cell; thereby identifying a cell into which the recombinant vector has been introduced. In these methods, the GFP can be expressed as a fusion polypeptide, or a distinct polypeptide. The cells can be identified by FACS analysis.

Another feature of the invention is a method of detecting the activity of a transcriptional regulatory sequence, the method including the steps of: (a) culturing a cell containing a nucleic acid sequence including the transcriptional regulatory sequence operably linked to a humanized nucleic acid sequence encoding mutant *Renilla reniformis* GFP to form a reporter construct, under conditions where the mutant *Renilla reniformis* GFP is expressed; and (b) detecting mutant *Renilla reniformis* GFP fluorescence in the cell, wherein detection of fluorescence indicates activity of the transcriptional regulatory sequence; thereby detecting the activity of a transcriptional regulatory sequence.

The invention also features a method of detecting the presence of a modulator of a transcriptional regulatory sequence, the method including the steps of: (a) culturing a cell containing a nucleic acid sequence including the transcriptional regulatory sequence operably linked to a humanized nucleic acid sequence encoding mutant *Renilla reniformis* GFP to form a reporter construct, under conditions where the mutant *Renilla reniformis* GFP is expressed; and (b) detecting mutant *Renilla reniformis* GFP fluorescence in the cell, wherein the fluorescence indicates the presence of the modulator; thereby detecting the presence of a modulator of a transcriptional regulatory sequence.

The invention additionally features a method of screening for an inhibitor of a transcriptional regulatory sequence, the method including the steps of: (a) culturing a cell containing a nucleic acid sequence including the transcriptional regulatory sequence operably linked to a humanized nucleic acid sequence encoding mutant *Renilla reniformis* GFP to form a reporter construct, under conditions where the mutant *Renilla reniformis* GFP is expressed; (b) contacting the cell with a candidate inhibitor of the transcriptional regulatory sequence; and (c) detecting mutant *Renilla reniformis* GFP fluorescence in the cell, wherein a decrease in the fluorescence relative to that detected in the absence of the candidate inhibitor indicates that the candidate inhibitor inhibits the activity of the transcriptional regulatory sequence.

In another aspect, the invention features a method of producing a fluorescent molecular weight marker, the method including the steps of: (a) culturing a cell containing a humanized nucleic acid sequence encoding mutant *Renilla reniformis* GFP linked in frame to a nucleic acid sequence encoding a polypeptide of known relative molecular weight such that the linked molecules encode a fusion polypeptide, under conditions where the mutant *Renilla reniformis* GFP is expressed; (b) isolating the fusion polypeptide from the cell, wherein the fusion polypeptide is a relative molecular weight marker.

In the above methods, the cell can be a mammalian cell. The cell can also be a human cell. In the above methods, the mutant *Renilla reniformis* GFP can be selected from the group consisting of: SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28 and SEQ ID NO:30. The nucleic acid sequence encoding mutant *Renilla reniformis* GFP can be selected from the group consisting of: SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 and SEQ ID NO:29.

The invention additionally features a mutant Green Fluorescent Protein (GFP) from *Renilla reniformis*, where the mutation comprises an amino acid substitution in one of the following regions of the protein, relative to the wild-type form of the protein: (a) the Beta Strand 4 region of the protein; (b) the loop region of the protein between Beta Strand 2 and Beta Strand 3; (c) the loop region of the protein between Beta Strand 5 and Beta Strand 6; (d) the region of the protein extending from the beginning of Beta Strand 1 through the end of the loop region between Beta Strands 2 and 3; and (e) the region of the protein extending from the beginning of Beta Strand 4 through the end of Beta Strand 6; and where the mutant GFP protein also has one or more of the following characteristics: (r) exhibiting less quenching over a broad pH range, relative to wild-type GFP protein from *Renilla reniformis*.; (s) exhibiting greater resistance to one or more of the following: proteases, solvents, detergents and chaotropic agents; and (t) exhibiting reduced tendency to oligomerize.

The invention also features a mutant Green Fluorescent Protein (GFP) from *Renilla reniformis*, wherein the mutation comprises an amino acid substitution at one or more of the following residues: (a) F43; (b) E120; (c) L101; and (d) Y103.

By "mutant GFP protein" is meant that the protein contains an amino acid substitution at one or more amino acid residues relative to the reference GFP protein, and that the resulting protein displays one or more of the following characteristics: (a) enhanced emission intensity, (b) a narrower emission spectrum, and/or (c) exhibiting less quenching of fluorescence at acidic pH, relative to the reference GFP protein. By "reference GFP protein" is meant the protein from which the mutant GFP was derived. For example, one can begin with a wild type GFP nucleic acid sequence, introduce one or more mutations that produce amino acid substitution(s), and produce a mutant GFP protein. One can also humanize the nucleic acid sequence encoding a GFP protein, and then introduce one or more mutations that produce amino acid substitution(s).

The mutant proteins as described herein also include those proteins that contain more than one of the amino acid substitutions as described here, or specific combinations of those amino acid substitutions, or one or more of those amino acid substitutions in combination with other amino acid substitutions. Some specific combinations of amino acid substitutions confer beneficial properties to the resulting mutant GFP. For instance, as shown herein, a mutant GFP containing the combination of E120G, F43L and R125H matures faster than wild type hrGFP at 37° C., that is, it is brighter earlier at elevated incubation temperature.

The mutant proteins as described herein also include other amino acid substitutions made at the sites described herein.

The term "humanized GFP sequence" or "humanized mutant GFP sequence" refers to a polynucleotide coding sequence in which one or more codons of the polynucleotide have been altered to codons which are more preferred for expression in mammalian cells. Methods of humanizing proteins are well known in the art, and such a humanized GFP nucleic acid sequence is provided herein as SEQ ID NO:1. For example, in human genes the preferred codon for alanine is "GCC". The codon "GCG", which also codes for alanine, can therefore be changed to "GCC" to enhance expression of the overall protein in mammalian cells. Other codons can also be replaced, and preferred human codons and other changes to enhance protein expression in human and mammalian systems are discussed further below.

Preferably, the amount of fluorescent polypeptide expressed in a human cell from a humanized GFP polynucleotide sequence is at least two-fold greater, on either a mass or a fluorescence intensity scale per cell, than the amount expressed from an equal amount or number of copies of a wild type *R. reniformis* GFP polynucleotide.

As used herein, the term "humanized codon" means a codon, within a polynucleotide sequence encoding a non-human polypeptide, that has been changed to a codon that is more preferred for expression by human cells relative to that codon encoded by the non-human organism from which the non-human polypeptide is derived. Species-specific codon preferences stem in part from differences in the expression of tRNA molecules with the appropriate anticodon sequence. That is, one factor in the species-specific codon preference is the relationship between a codon and the amount of corresponding anticodon tRNA expressed.

By saying that a protein (e.g., a test protein, e.g., a mutant *Renilla reniformis* GFP) has "enhanced emission intensity", or "increased fluorescence intensity" or "increased brightness" relative to another protein (e.g., a reference GFP protein), means that the fluorescence intensity of the test protein is greater than that of the reference protein, that is, the mutant protein is "brighter" than the reference protein under a given set of conditions. Brightness is measured as the product of the molar extinction coefficient and quantum yield (see, e.g., the spectroscopic studies in Baird, G. S. et al., 2000*, Proc. Natl. Acad. Sci. USA* 97(22)11984–11989). For example, the brightness for wild-type *A. victoria* GFP is generally (9500)(0.8)=7600 units $M^{-1}$ $cm^{-1}$. For EGFP (Clontech, Palo Alto, Calif., USA), the brightness is (55000)(0.6)=40600 units $M^{-1}$ $cm^{-1}$.

For spectral analysis with pure proteins, the spectral analysis is performed as described in Example 4, below, using quantitated purified proteins. The fluorescence intensity divided by the amount of protein is calculated, and the values compared between those of hrGFP and the mutant protein. A mutant protein with greater than 1-fold higher value over the wild type hrGFP is considered "brighter".

The cells expressing the various wild-type and mutant proteins can also be assayed by FACS analysis, and the mean value calculated for each, as described in Example 7, below. A mutant protein with greater than 1-fold higher value over the wild type hrGFP is considered, "brighter".

Preferably, the fluorescence intensity of the test protein is at least twice that of the wild-type GFP protein (i.e., 15200), more preferably, at least three times (i.e., 22800), and most preferably, at least four times (i.e., 30400) that of the wild type GFP protein.

By saying that a protein (e.g., a test protein, e.g., a mutant *Renilla reniformis* GFP) has "narrower emission spectrum" relative to another protein (e.g., a reference protein, e.g., wild-type *Renilla reniformis* GFP), means that the emission spectrum of the test protein is narrower than that of the reference protein, that is, that the spectrum for the test has narrower shoulders than the spectrum for the reference protein. "Narrower shoulders" refers to the wavelength maximum ±75 nm, preferably the wavelength maximum ±50 nm, and most preferably the wavelength maximum ±25 nm.

By saying that a protein (e.g., a test protein, e.g., a mutant *Renilla reniformis* GFP) "exhibits less quenching of fluorescence at acidic pH" relative to another protein (e.g., a reference protein, e.g., wild-type *Renilla reniformis* GFP), means that, under a given set of acidic conditions, the fluorescence intensity of the test protein exhibits less of a decrease than that of the reference protein. By saying that a protein (e.g., a test protein, e.g., a mutant *Renilla reniformis* GFP) "exhibits less quenching over a broad pH range" relative to another protein (e.g., a reference protein, e.g., wild-type *Renilla reniformis* GFP), means that, as the pH of the test protein's immediate environment deviates from neutral, the fluorescence intensity of the test protein exhibits less of a decrease than that of the reference protein. "Less quenching" in this regard means that a decrease in fluorescence intensity of 100% would be completely quenched, a decrease of 50% would be less quenced, a decrease of 10% would beneven less quenched, and most preferably, a decrease of 0% would be no quenching. Preferably, such a protein exhibits less quenching over a broad pH range, maintaining its general intensity over a more broad pH range relative to the wild-type hrGFP.

The mutant proteins as described herein can also exhibit greater resistance to proteases (e.g., proteinase K, trypsin, chymotrypsin, papain, pronase), solvents (e.g., ethanol, methanol, acetonitride), detergents (e.g., SDS, Tween 20, Trition X-100), and/or chaotropic agents (e.g., 8M urea, 4M guanidine HCl). By "exhibits greater resistance" to these agents, it is meant that the protein tends to function more normally relative to the reference protein under those same conditions, e.g., preferably there is no substantial decrease in intensity of the protein, or change in excitation or emission maxima.

The mutant proteins as described herein can also show reduced tendency to oligomerize, that is, a monomer being more preferred than a dimer, which would be more preferred than a trimer), as determined by analytical gradient ultracentrifugation and native protein gels.

The mutant protein can also exhibit a shift in in vivo maturation time relative to the wild-type version of the protein, as determined by examination of transfected cells by fluorescence microscopy. Maturation at 36 hours post-transfection is preferred, maturation at 24 hours post-transfection is more preferred, and maturation at 12 hours or less post-transfection is most preferred.

The term "variant thereof" when used in reference to an *R. reniformis* GFP means that the amino acid sequence bears one or more residue differences relative to the wild type *R. reniformis* GFP sequence and has at least the same, preferably improved (as described herein) biological activity (fluorescence intensity) of the wild type polypeptide.

As used herein, the term "increased fluorescence intensity" or "increased brightness" refers to fluorescence intensity or brightness that is greater than that exhibited by wild-type *R. reniformis* GFP under a given set of conditions. Generally, an increase in fluorescence intensity or brightness means that fluorescence of a variant is at least 5% or more, and preferably 10%, 20%, 50%, 75%, 100% or more, up to even 5 times, 10 times, 20 times, 50 times or 100 times or more intense or bright than wild-type *R. reniformis* GFP under a given set of conditions.

Assays can also be performed to determine color shift of the mutant proteins. A spectral analysis can be performed (e.g., as described in Example 4, below). Bacterial colonies expressing the hrGFP proteins and the mutant proteins can be observed with filters and various lens combinations (e.g., as described in Example 2, below), to determine the different color emitted by the mutant protein. Mammalian cells expressing the hrGFP proteins and the mutant proteins can be observed under a fluorescent microscope equipped with different fluorescent filter cubes (Omega Optical) to determine if the mutant emits a different color relative to the green of standard hrGFP (e.g., SEQ ID NO:2). If the emission maximum for a given mutant protein is 21 nm or greater than the emission spectrum of the wild type hrGFP, then the mutant protein is color-shifted to the red side of the spectrum. If the emission maximum for a given mutant protein is 29 nm or less than the emission spectrum of the wild type hrGFP, then the mutant protein is color-shifted to the blue side of the spectrum.

As used herein, the term "fused heterologous polypeptide domain" refers to an amino acid sequence of two or more amino acids fused in frame to *R. reniformis* GFP. A fused heterologous domain may be linked to the N or C terminus of the *R. reniformis* GFP polypeptide.

As used herein, the term "fused to the amino-terminal end" refers to the linkage of a polypeptide sequence to the amino terminus of another polypeptide. The linkage may be direct or may be mediated by a short (e.g., about 2–20 amino acids) linker peptide.

As used herein, the term "fused to the carboxy-terminal end" refers to the linkage of a polypeptide sequence to the carboxyl terminus of another polypeptide. The linkage may be direct or may be mediated by a linker peptide.

As used herein, the term "linker sequence" refers to a short (e.g., about 1–20 amino acids) sequence of amino acids that is not part of the sequence of either of two polypeptides being joined. A linker sequence is attached on its amino-terminal end to one polypeptide or polypeptide domain and on its carboxyl-terminal end to another polypeptide or polypeptide domain.

As used herein, the term "excitation spectrum" refers to the wavelength or wavelengths of light that, when absorbed by a fluorescent polypeptide molecule of the invention, causes fluorescent emission by that molecule.

As used herein, the term "emission spectrum" refers to the wavelength or wavelengths of light emitted by a fluorescent polypeptide.

As used herein, the terms "distinguishable" or "detectably distinct" mean that standard filter sets allow either the excitation of one form of a polypeptide without excitation of another given polypeptide, or similarly, that standard filter sets allow the distinction of the emission from one polypeptide form from the emission spectrum of another. Generally, distinguishable or detectably distinct excitation or emission spectra have peaks that vary by more than 1 nm, and preferably vary by more than 2, 3, 4, 5, 10 or more nm.

As used herein, the term "fusion polypeptide" refers to a polypeptide that is comprised of two or more amino acid sequences, from two or more proteins that are not found linked in nature, that are physically linked by a peptide bond. As used herein, only one protein which comprises a "fusion polypeptide" of the present invention is a fluorescent protein.

As used herein, the term "emission spectrum overlaps the excitation spectrum" means that light emitted by one fluorescent polypeptide is of a wavelength or wavelengths that causes excitation and emission by another fluorescent polypeptide.

As used herein, the term "population of cells" refers to a plurality of cells, preferably, but not necessarily of same type or strain.

As used herein, the term "FACS analysis" refers to the method of sorting cells, fluorescence activated cell sorting, wherein cells are stained with or express one or more fluorescent markers. In this method, cells are passed through an apparatus that excites and detects fluorescence from the marker(s). Upon detection of fluorescence in a given portion of the spectrum by a cell, the FACS apparatus allows the separation of that cell from those not expressing that fluorescence spectrum.

As used herein, the term "operably linked" means that a given coding sequence is joined to a given transcriptional regulatory sequence such that transcription of the coding sequence occurs and is regulated by the regulatory sequence.

As used herein, the term "reporter construct" refers to a polynucleotide construct encoding a detectable molecule, linked to a transcriptional regulatory sequence conferring regulated transcription upon the polynucleotide encoding the detectable molecule. A detectable molecule is preferably an *R. reniformis* GFP.

As used herein, the term "responsive to the presence of a modulator" means that a given transcriptional regulatory sequence is either turned on or turned off in the presence of a given compound. As used herein, gene expression is "turned on" when the polypeptide encoded by the gene sequence (e.g., a GFP polypeptide) is detectable over background, or alternatively, when the polypeptide is detectable in an increased amount over the amount detected in the absence of a given modulator compound. In this context, "increased amount" means at least 10%, preferably 20%, 50%, 75%, 100% or more, up to even 5 times, 10 times, 20 times, 50 times, or 100 times or more higher than background detection, with background detection being the amount of signal observed in the absence of the modulator compound.

As used herein, the term "modulator of a transcriptional regulatory sequence" refers to a compound or chemical moiety that causes a change in the level of expression from a transcriptional regulatory sequence. Preferably, the change is detectable as an increase or decrease in the detection of a reporter molecule or reporter molecule activity, with at least 10%, 20%, 50%, 75%, 100%, or even 5 times, 10 times, 20 times, 50 times or 100 times or more increased or decreased level of reporter signal relative to the absence of a given modulator.

As used herein the term "inhibitor of a transcriptional regulatory sequence" refers to a compound or chemical moiety that causes a decrease in the amount of a reporter molecule or reporter molecule activity expressed from a given transcriptional regulatory sequence. As used herein, the term "decrease" when used in reference to the detection of a reporter molecule or reporter molecule activity means that detectable activity is reduced by at least 10%, 20%, 50%, 75%, or even 100% (i.e., no expression), relative to the amount detected in the absence of a given compound or chemical moiety. As used herein the term "candidate inhibitor" refers to a compound or chemical moiety being tested for inhibitory activity in an assay.

An advantage of the present invention is that it provides a method for the improved expression of a GFP in mammalian, particularly human cells both in vivo and in vitro. A further advantage of the present invention is that it provides a method of providing a humanized *R. reniformis* GFP which, due to enhanced expression will produce a stronger fluorescent signal in cells in which it is expressed. The invention also provides additional GFP mutant polynucleotides, which can be either humanized for optimal expression in mammalian systems, or not humanized, leaving the mutant polynucleotides in a form for expression in bacterial systems.

Figure 3A:
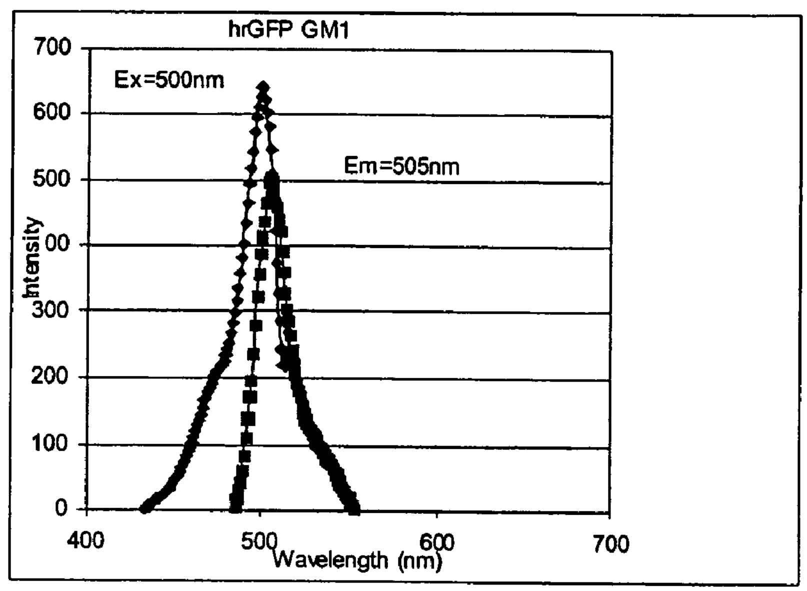
FIGS. 3A–3J are graphs showing the excitation (♦) and emission (■) spectra of hrGFP mutant GM1 (FIG. 3A), hrGFP mutant GM3 (FIG. 3B), hrGFP mutant GM4 (FIG. 3C), hrGFP mutant GM6 (FIG. 3D), hrGFP mutant T1 (FIG.
Figure 3B:
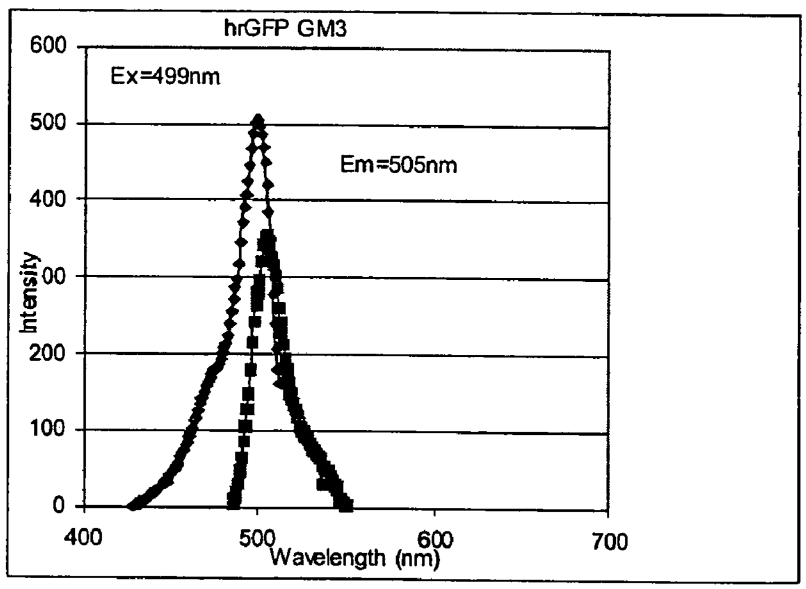
Figure 3C:
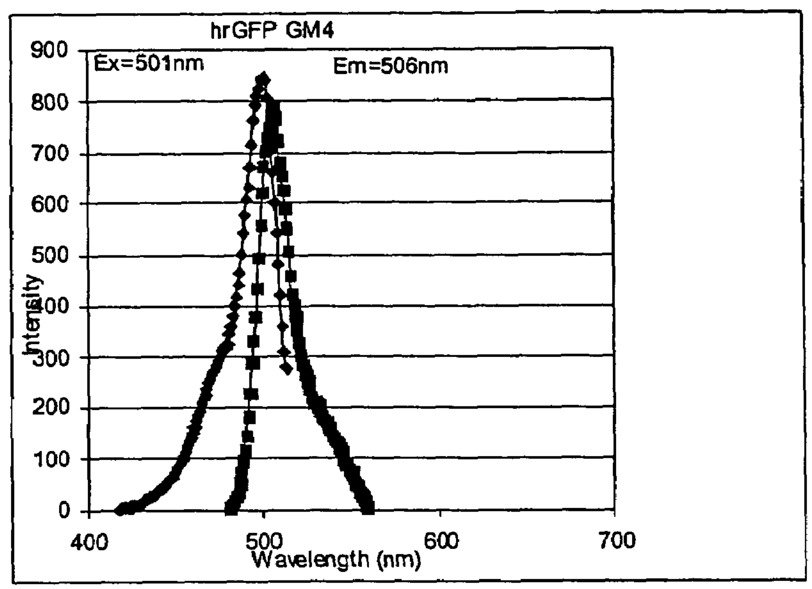
Figure 3D:
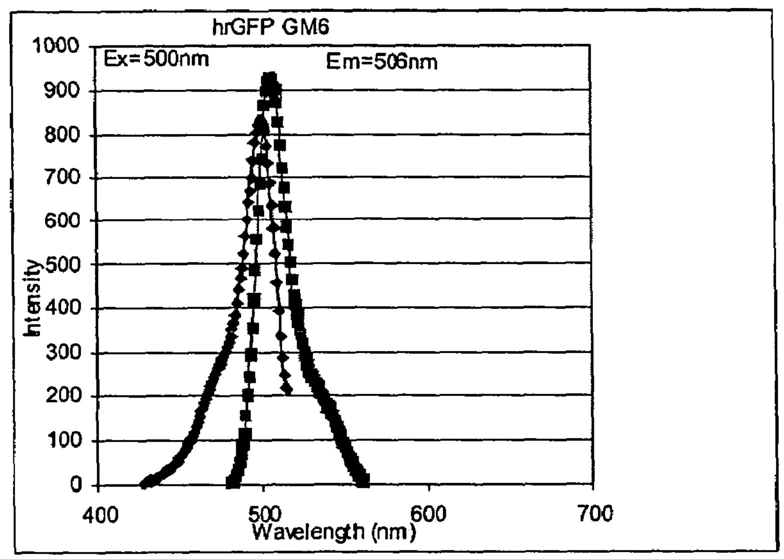
Figure 3E:
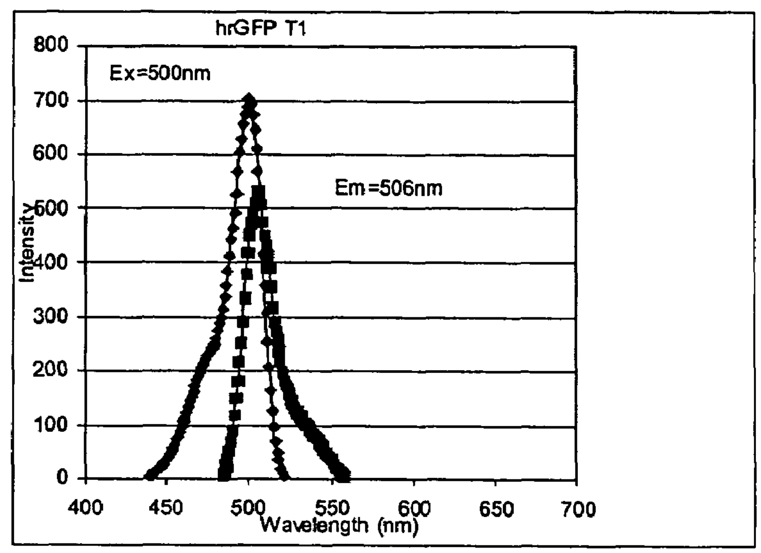
Figure 3F:
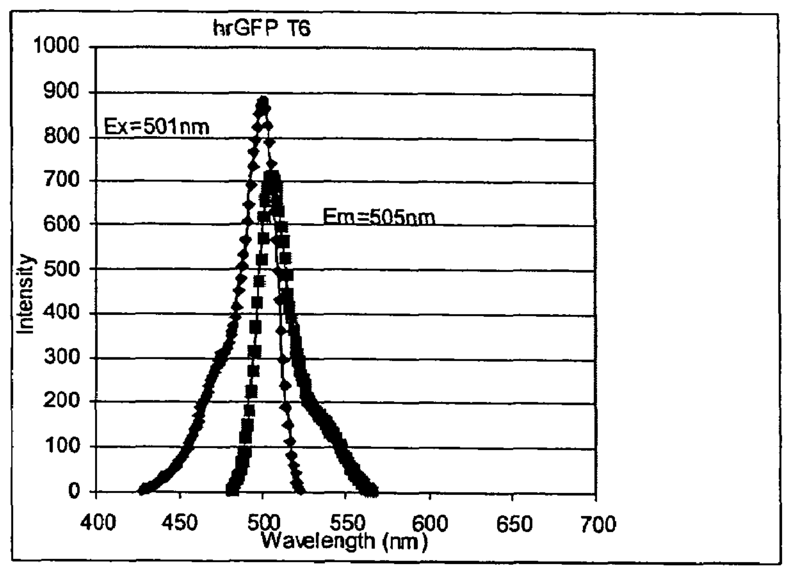
Figure 3G:
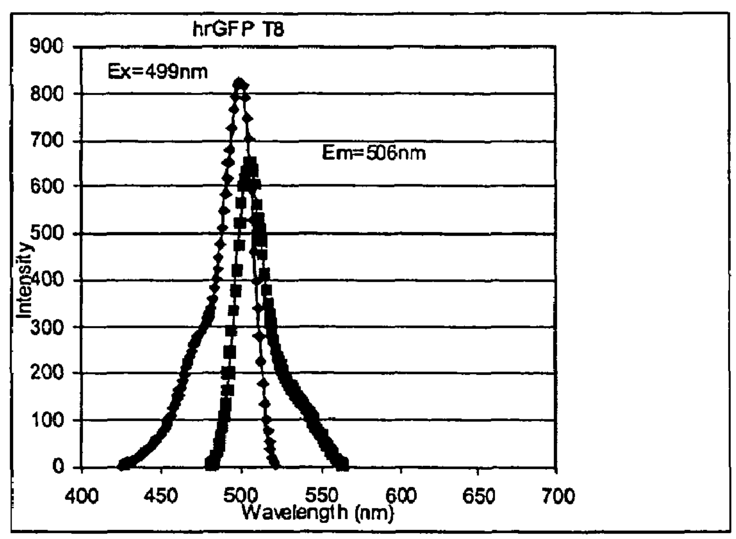
Figure 3H:
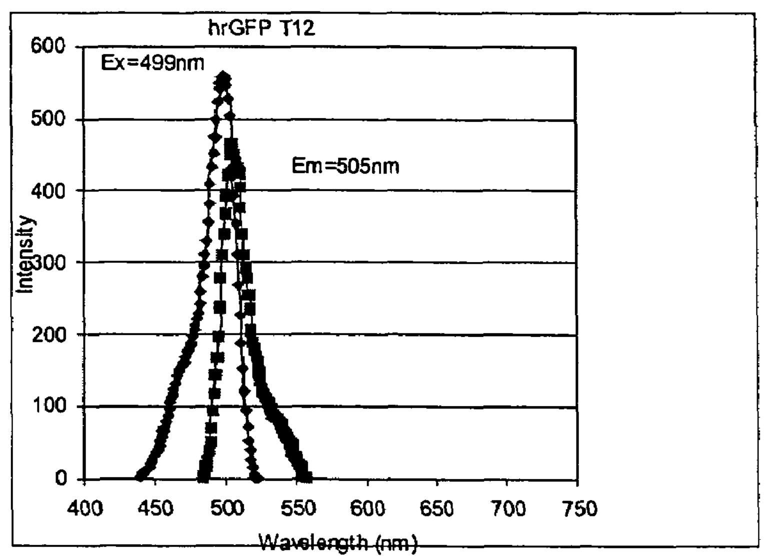
Figure 3:
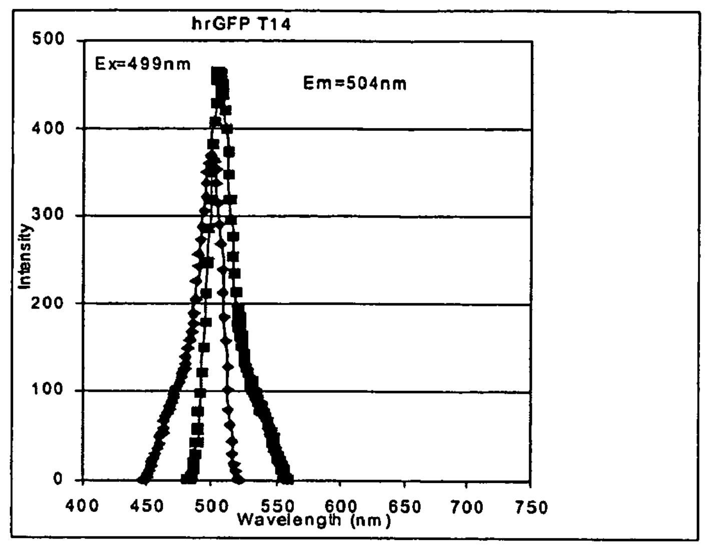
Figure 3J:
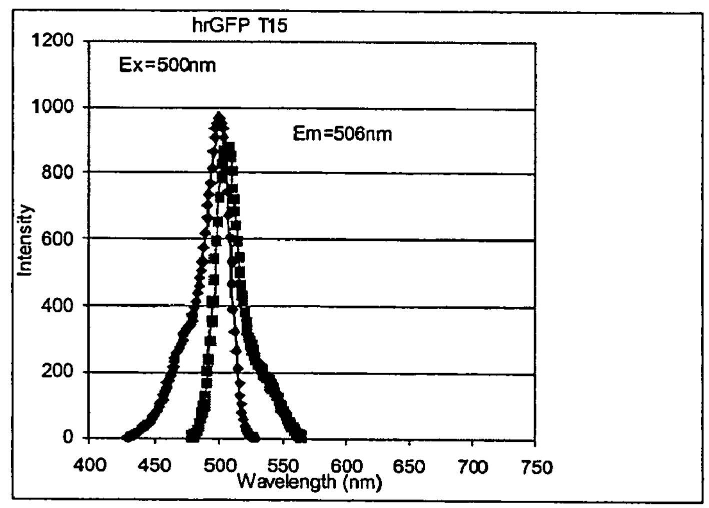

3E), hrGFP mutant T6 (FIG. 3F), hrGFP mutant T8 (FIG. 3G), hrGFP mutant T12 (FIG. 3H), hrGFP mutant T14 (FIG. 3I) and hrGFP mutant T15 (FIG. 3J).

FIG. 4 shows the nucleic acid (SEQ ID NO:1) and amino acid (SEQ ID NO:2) sequences for hrGFP.

FIG. 5 shows the nucleic acid (SEQ ID NO:3) and amino acid (SEQ ID NO:4) sequences for humanized mutant GFP GM1.

FIG. 6 shows the nucleic acid (SEQ ID NO:5) and amino acid (SEQ ID NO:6) sequences for humanized mutant GFP GM2.

FIG. 7 shows the nucleic acid (SEQ ID NO:7) and amino acid (SEQ ID NO:8) sequences for humanized mutant GFP GM3.

FIG. 8 shows the nucleic acid (SEQ ID NO:9) and amino acid (SEQ ID NO:10) sequences for humanized mutant GFP GM4.

FIG. 9 shows the nucleic acid (SEQ ID NO:11) and amino acid (SEQ ID NO:12) sequences for humanized mutant GFP GM6.

FIG. 10 shows the nucleic acid (SEQ ID NO:13) and amino acid (SEQ ID NO:14) sequences for humanized mutant GFP T1.

FIG. 11 shows the nucleic acid (SEQ ID NO:15) and amino acid (SEQ ID NO:16) sequences for humanized mutant GFP T6.

FIG. 12 shows the nucleic acid (SEQ ID NO:17) and amino acid (SEQ ID NO:18) sequences for humanized mutant GFP T8.

FIG. 13 shows the nucleic acid (SEQ ID NO:19) and amino acid (SEQ ID NO:20) sequences for humanized mutant GFP T11.

FIG. 14 shows the nucleic acid (SEQ ID NO:21) and amino acid (SEQ ID NO:22) sequences for humanized mutant GFP T12.

FIG. 15 shows the nucleic acid (SEQ ID NO:23) and amino acid (SEQ ID NO:24) sequences for humanized mutant GFP T13.

FIG. 16 shows the nucleic acid (SEQ ID NO:25) and amino acid (SEQ ID NO:26) sequences for humanized mutant GFP T14.

FIG. 17 shows the nucleic acid (SEQ ID NO:27) and amino acid (SEQ ID NO:28) sequences for humanized mutant GFP T15.

FIG. 18 shows the nucleic acid (SEQ ID NO:29) and amino acid (SEQ ID NO:30) sequences for humanized mutant GFP T17.

FIG. 19 shows the nucleic acid (SEQ ID NO:31) and amino acid (SEQ ID NO:32) sequences for wild type (non-humanized) GFP.

FIG. 20 shows the nucleic acid (SEQ ID NO:33) and amino acid (SEQ ID NO:34) sequences for mutant non-humanized GFP GM1.

FIG. 21 shows the nucleic acid (SEQ ID NO:35) and amino acid (SEQ ID NO:36) sequences for mutant non-humanized GFP GM2.

FIG. 22 shows the nucleic acid (SEQ ID NO:37) and amino acid (SEQ ID NO:38) sequences for mutant non-humanized GFP GM3.

FIG. 23 shows the nucleic acid (SEQ ID NO:39) and amino acid (SEQ ID NO:40) sequences for humanized mutant non-humanized GFP GM4.

FIG. 24 shows the nucleic acid (SEQ ID NO:41) and amino acid (SEQ ID NO:42) sequences for non-humanized mutant non-humanized GFP GM6.

FIG. 25 shows the nucleic acid (SEQ ID NO:43) and amino acid (SEQ ID NO:44) sequences for non-humanized mutant non-humanized GFP T1.

FIG. 26 shows the nucleic acid (SEQ ID NO:45) and amino acid (SEQ ID NO:46) sequences for non-humanized mutant non-humanized GFP T6.

FIG. 27 shows the nucleic acid (SEQ ID NO:47) and amino acid (SEQ ID NO:48) sequences for non-humanized mutant non-humanized GFP T8.

FIG. 28 shows the nucleic acid (SEQ ID NO:49) and amino acid (SEQ ID NO:50) sequences for non-humanized mutant non-humanized GFP T11.

FIG. 29 shows the nucleic acid (SEQ ID NO:51) and amino acid (SEQ ID NO:52) sequences for non-humanized mutant non-humanized GFP T12.

FIG. 30 shows the nucleic acid (SEQ ID NO:53) and amino acid (SEQ ID NO:54) sequences for non-humanized mutant non-humanized GFP T13.

FIG. 31 shows the nucleic acid (SEQ ID NO:55) and amino acid (SEQ ID NO:56) sequences for non-humanized mutant non-humanized GFP T14.

FIG. 32 shows the nucleic acid (SEQ ID NO:57) and amino acid (SEQ ID NO:58) sequences for non-humanized mutant non-humanized GFP T15.

FIG. 33 shows the nucleic acid (SEQ ID NO:59) and amino acid (SEQ ID NO:60) sequences for non-humanized mutant non-humanized GFP T17.

FIG. 34 shows the nucleic acid (SEQ ID NO:61) and amino acid (SEQ ID NO:62) sequences for an alternate wild type (non-humanized) GFP.

FIGS. 35A–E show use of FACS analysis to assess improved brightness of several of the proteins in vivo.

DETAILED DESCRIPTION

Polynucleotide and polypeptide sequences are disclosed, for a series of mutants of *R. reniformis* GFP that display increased fluorescence intensity and/or alterations to the fluorescence spectra. Also disclosed are humanized versions of the polynucleotides encoding those mutants.

Also disclosed herein are methods of using a humanized *R. reniformis* GFP gene to produce an *R. reniformis* GFP polypeptide, the methods comprising introducing an expression vector containing a humanized coding sequence for *R. reniformis* GFP into a cell, culturing the cell, and isolating the GFP polypeptide.

The *Renilla* GFP has eleven Beta strands, with loop regions connecting each beta strand to the next. Alpha helices are also located in the loop regions between beta strands 3 and 4 and 6 and 7. Mutations can be introduced at a number of different points in the GFP protein to produce mutant proteins with spectral properties and intensities different from the wild type form of the protein. A number of mutations, and the regions in which they occur, are listed below in Table 1.

TABLE 1

Regions of the *R. reniformis* Green Fluorescent Protein and mutations within each region.

| Region* | Amino Acid Residues | Mutations |
|---|---|---|
| B1 | 16–27 | M16V, N21I |
| B2 | 29–40 | T32P |
| L2–3 | 41–43 | F43L, F43S |
| B3 | 44–52 | |
| B4 | 95–103 | L101M, R102C, Y103F |

TABLE 1-continued

Regions of the *R. reniformis* Green Fluorescent Protein and mutations within each region.

| Region* | Amino Acid Residues | Mutations |
|---|---|---|
| B5 | 108–118 | V109A |
| L5–6 | 119–120 | E120G |
| B6 | 121–131 | V123E, R125H |
| L6–7 | 132–148 | K142N |
| B7 | 149–155 | |
| B8 | 161–170 | |
| L8–9 | 171–174 | S173C |
| B9 | 175–186 | |
| B10 | 198–207 | T207A |
| L10–11 | 208–214 | F214I |
| B11 | 215–224 | V215V |
| C-terminal tail | 225–239 | K230N |

*"B" = Beta strand, "L" = Loop region between two beta strands.

As can be seen, the mutations producing higher-intensity clones cluster in beta strand 4 (which includes substitutions L101M, R102C and Y103F), in the loop region between beta strands 2 and 3 (which includes substitutions F43L and F43S), and in the loop region between beta strand 5 and beta strand 6. There is also a more dispersed cluster of mutations extending from beta strand 1 through the loop between beta strands 2 and 3 (which includes substitutions M16V, N21I, T32P, F43L and F43S), and in the region extending from beta strand 4 through beta strand 6 (which includes substitutions L101M, R102C, Y103F, V109A, E120G, V123E and R125H). These regions appear especially promising locations in which to induce amino acid substitutions.

In addition, one can also mutate these regions via saturation mutagenesis, such as by the methods described in Myers R. M. et al. (1985, *Science* 229:242–247). Saturation mutagenesis is a method that is used in replacing a selected codon by a set of codons that, upon translation, should yield all 20 amino acids in the mutant population. Saturation mutagenesis provides a much more comprehensive analysis of structure-function relationships than can be achieved by single-amino acid replacements. Error-prone PCR strategies involving compromised enzymes and stressful PCR conditions randomly generate single-base changes throughout a gene sequence. However, a large number of mutation types are not adequately represented, in particular, mutations requiring 2–3 base pair changes per codon (primarily non-conservative amino acid substitutions) in random mutant collections. To access a larger fraction of protein sequence space, site-specific saturation mutagenesis is commonly used to introduce all possible mutations at key sites or adjacent sites.

A list of hrGFP mutants and the specific amino acid substitutions they contain is provided in Table 5. All of the amino acid substitutes listed in Table 5 should be decreased by one residue when making the same substitutions in the wild type (i.e., non-humanized) GFP sequence. This is because the hrGFP protein sequence has a valine inserted at position two. Therefore, for instance, the M16V substitution of the hrGFP mutant T17 would be M15V in the wild-type protein.

The terms "GM1 mutant", "GM2 mutant", etc., are therefore intended to include the equivalent amino acid substitutions in both the wild type GFP and the humanized GFP. For instance, the term "GM1 mutant" includes both (1) a protein with a valine at residue number 2 and an amino acid substitution of phenylalanine to leucine at position 43 (as shown in SEQ ID NO:4), and also (2) a protein with no valine at residue number 2 and having an amino acid substitution of phenylalanine to leucine at position 42 (as shown in SEQ ID NO:20). The terms also refers to nucleic acid sequences encoding such mutant proteins.

Key sites for saturation mutagenesis are F43, L101, R102, Y103 and E120 (referring to the positions in the 239-amino acid long hrGFP (SEQ ID NO:2)). Such mutations, as well as those described herein, can then be shuffled, that is, random combinations can be made of the point mutations, creating all possible combinations of double mutants, triple mutants, quadruple mutants, etc.

Specific mutations described herein are made by using primers with altered GFP sequences, as described in the Examples below. Representative primers are shown in Table 7, below. Using these techniques, any amino acid substitution can be made in the GFP protein. The mutant GFP nucleic acid and protein sequences disclosed herein are shown in Table 2, below.

TABLE 2

GFP sequences and mutants.

| Sequence | SEQ ID NO | FIG. |
|---|---|---|
| hrGFP DNA; humanized nucleic acid sequence encoding *Renilla reniformis* Green Fluorescent Protein (GFP) | SEQ ID NO: 1 | 4 |
| hrGFP protein; protein encoded by SEQ ID NO: 1 (humanized nucleic acid sequence encoding *Renilla reniformis* Green Fluorescent Protein (GFP)) | SEQ ID NO: 2 | 4 |
| Mutant GM1 DNA; humanized nucleic acid sequence encoding mutant GM1 Renilla reniformis Green Fluorescent Protein (GFP) | SEQ ID NO: 3 | 5 |
| Mutant GM1 protein; protein encoded by SEQ ID NO: 3 (humanized nucleic acid sequence encoding mutant GM1 *Renilla reniformis* Green Fluorescent Protein (GFP)) | SEQ ID NO: 4 | 5 |
| Mutant GM2 DNA; humanized nucleic acid sequence encoding mutant GM2 *Renilla reniformis* Green Fluorescent Protein (GFP) | SEQ ID NO: 5 | 6 |
| Mutant GM2 protein; protein encoded by SEQ ID NO: 5 (humanized nucleic acid sequence encoding mutant GM2 *Renilla reniformis* Green Fluorescent Protein (GFP)) | SEQ ID NO: 6 | 6 |
| Mutant GM3 DNA; humanized nucleic acid sequence encoding mutant GM3 *Renilla reniformis* Green Fluorescent Protein (GFP) | SEQ ID NO: 7 | 7 |
| Mutant GM3 protein; protein encoded by SEQ ID NO: 7 | SEQ ID NO: 8 | 7 |

TABLE 2-continued

GFP sequences and mutants.

| Sequence | SEQ ID NO | FIG. |
|---|---|---|
| (humanized nucleic acid sequence encoding mutant GM3 *Renilla reniformis* Green Fluorescent Protein (GFP)) | | |
| Mutant GM4 DNA; humanized nucleic acid sequence encoding mutant GM4 *Renilla reniformis* Green Fluorescent Protein (GFP) | SEQ ID NO: 9 | 8 |
| Mutant GM4 protein; protein encoded by SEQ ID NO: 9 (humanized nucleic acid sequence encoding mutant GM4 *Renilla reniformis* Green Fluorescent Protein (GFP)) | SEQ ID NO: 10 | 8 |
| Mutant GM6 DNA; humanized nucleic acid sequence encoding mutant GM6 *Renilla reniformis* Green Fluorescent Protein (GFP) | SEQ ID NO: 11 | 9 |
| Mutant GM6 protein; protein encoded by SEQ ID NO: 11 (humanized nucleic acid sequence encoding mutant GM6 *Renilla reniformis* Green Fluorescent Protein (GFP)) | SEQ ID NO: 12 | 9 |
| Mutant T1 DNA; humanized nucleic acid sequence encoding mutant T1 *Renilla reniformis* Green Fluorescent Protein (GFP) | SEQ ID NO: 13 | 10 |
| Mutant T1 protein; protein encoded by SEQ ID NO: 13 (humanized nucleic acid sequence encoding mutant T1 *Renilla reniformis* Green Fluorescent Protein (GFP)) | SEQ ID NO: 14 | 10 |
| Mutant T6 DNA; humanized nucleic acid sequence encoding mutant T6 *Renilla reniformis* Green Fluorescent Protein (GFP) | SEQ ID NO: 15 | 11 |
| Mutant T6 protein; protein encoded by SEQ ID NO: 15 (humanized nucleic acid sequence encoding mutant T6 *Renilla reniformis* Green Fluorescent Protein (GFP)) | SEQ ID NO: 16 | 11 |
| Mutant T8 DNA; humanized nucleic acid sequence encoding mutant T8 *Renilla reniformis* Green Fluorescent Protein (GFP) | SEQ ID NO: 17 | 12 |
| Mutant T8 protein; protein encoded by SEQ ID NO: 17 (humanized nucleic acid sequence encoding mutant T8 *Renilla reniformis* Green Fluorescent Protein (GFP)) | SEQ ID NO: 18 | 12 |
| Mutant T11 DNA; humanized nucleic acid sequence encoding mutant T11 *Renilla reniformis* Green Fluorescent Protein (GFP) | SEQ ID NO: 19 | 13 |
| Mutant T11 protein; protein encoded by SEQ ID NO: 19 (humanized nucleic acid sequence encoding mutant T11 *Renilla reniformis* Green Fluorescent Protein (GFP)) | SEQ ID NO: 20 | 13 |
| Mutant T12 DNA; humanized nucleic acid sequence encoding mutant T12 *Renilla reniformis* Green Fluorescent Protein (GFP) | SEQ ID NO: 21 | 14 |
| Mutant T12 protein; protein encoded by SEQ ID NO: 21 (humanized nucleic acid sequence encoding mutant T12 *Renilla reniformis* Green Fluorescent Protein (GFP)) | SEQ ID NO: 22 | 14 |
| Mutant T13 DNA; humanized nucleic acid sequence encoding mutant T13 *Renilla reniformis* Green Fluorescent Protein (GFP) | SEQ ID NO: 23 | 15 |
| Mutant T13 protein; protein encoded by SEQ ID NO: 23 (humanized nucleic acid sequence encoding mutant T13 *Renilla reniformis* Green Fluorescent Protein (GFP)) | SEQ ID NO: 24 | 15 |
| Mutant T14 DNA; humanized nucleic acid sequence encoding mutant T14 *Renilla reniformis* Green Fluorescent Protein (GFP) | SEQ ID NO: 25 | 16 |
| Mutant T14 protein; protein encoded by SEQ ID NO: 25 (humanized nucleic acid sequence encoding mutant T14 *Renilla reniformis* Green Fluorescent Protein (GFP)) | SEQ ID NO: 26 | 16 |
| Mutant T15 DNA; humanized nucleic acid sequence encoding mutant T15 *Renilla reniformis* Green Fluorescent Protein (GFP) | SEQ ID NO: 27 | 17 |
| Mutant T15 protein; protein encoded by SEQ ID NO: 27 (humanized nucleic acid sequence encoding mutant T15 *Renilla reniformis* Green Fluorescent Protein (GFP)) | SEQ ID NO: 28 | 17 |
| Mutant T17 DNA; humanized nucleic acid sequence encoding mutant T17 *Renilla reniformis* Green Fluorescent Protein (GFP) | SEQ ID NO: 29 | 18 |
| Mutant T17 protein; protein encoded by SEQ ID NO: 29 (humanized nucleic acid sequence encoding mutant T17 *Renilla* reniformis Green Fluorescent Protein (GFP)) | SEQ ID NO: 30 | 18 |
| WT GFP DNA; nucleic acid sequence encoding *Renilla reniformis* Green Fluorescent Protein (GFP) | SEQ ID NO: 31 | 19 |
| WT GFP protein; protein encoded by SEQ ID NO: 31 (WT nucleic acid sequence encoding *Renilla reniformis* Green Fluorescent Protein (GFP)) | SEQ ID NO: 32 | 19 |
| WT Mutant GM1 DNA; nucleic acid sequence encoding mutant GM1 *Renilla reniformis* Green Fluorescent Protein (GFP) | SEQ ID NO: 33 | 20 |
| WT Mutant GM1 protein; protein encoded by SEQ ID NO: 33 (nucleic acid sequence encoding mutant GM1 *Renilla reniformis* Green Fluorescent Protein (GFP)) | SEQ ID NO: 34 | 20 |
| WT Mutant GM2 DNA; nucleic acid sequence encoding mutant GM2 *Renilla reniformis* Green Fluorescent Protein (GFP) | SEQ ID NO: 35 | 21 |
| WT Mutant GM2 protein; protein encoded by SEQ ID NO: 35 (nucleic acid sequence encoding mutant GM2 *Renilla reniformis* Green Fluorescent Protein (GFP)) | SEQ ID NO: 36 | 21 |
| WT Mutant GM3 DNA; nucleic acid sequence encoding mutant GM3 *Renilla reniformis* Green Fluorescent Protein (GFP) | SEQ ID NO: 37 | 22 |

TABLE 2-continued

GFP sequences and mutants.

| Sequence | SEQ ID NO | FIG. |
|---|---|---|
| WT Mutant GM3 protein; protein encoded by SEQ ID NO: 37 (nucleic acid sequence encoding mutant GM3 *Renilla reniformis* Green Fluorescent Protein (GFP)) | SEQ ID NO: 38 | 22 |
| WT Mutant GM4 DNA; nucleic acid sequence encoding mutant GM4 *Renilla reniformis* Green Fluorescent Protein (GFP) | SEQ ID NO: 39 | 23 |
| WT Mutant GM4 protein; protein encoded by SEQ ID NO: 39 (nucleic acid sequence encoding mutant GM4 *Renilla reniformis* Green Fluorescent Protein (GFP)) | SEQ ID NO: 40 | 23 |
| WT Mutant GM6 DNA; nucleic acid sequence encoding mutant GM6 *Renilla reniformis* Green Fluorescent Protein (GFP) | SEQ ID NO: 41 | 24 |
| WT Mutant GM6 protein; protein encoded by SEQ ID NO: 41 (nucleic acid sequence encoding mutant GM6 *Renilla reniformis* Green Fluorescent Protein (GFP)) | SEQ ID NO: 42 | 24 |
| WT Mutant T1 DNA; nucleic acid sequence encoding mutant T1 *Renilla reniformis* Green Fluorescent Protein (GFP) | SEQ ID NO: 43 | 25 |
| WT Mutant T1 protein; protein encoded by SEQ ID NO: 43 (nucleic acid sequence encoding mutant T1 *Renilla reniformis* Green Fluorescent Protein (GFP)) | SEQ ID NO: 44 | 25 |
| WT Mutant T6 DNA; nucleic acid sequence encoding mutant T6 *Renilla reniformis* Green Fluorescent Protein (GFP) | SEQ ID NO: 45 | 26 |
| WT Mutant T6 protein; protein encoded by SEQ ID NO: 45 (nucleic acid sequence encoding mutant T6 *Renilla reniformis* Green Fluorescent Protein (GFP)) | SEQ ID NO: 46 | 26 |
| WT Mutant T8 DNA; nucleic acid sequence encoding mutant T8 *Renilla reniformis* Green Fluorescent Protein (GFP) | SEQ ID NO: 47 | 27 |
| WT Mutant T8 protein; protein encoded by SEQ ID NO: 47 (nucleic acid sequence encoding mutant T8 *Renilla reniformis* Green Fluorescent Protein (GFP)) | SEQ ID NO: 48 | 27 |
| WT Mutant T11 DNA; nucleic acid sequence encoding mutant T11 *Renilla reniformis* Green Fluorescent Protein (GFP) | SEQ ID NO: 49 | 28 |
| WT Mutant T11 protein; protein encoded by SEQ ID NO: 49 (nucleic acid sequence encoding mutant T11 *Renilla reniformis* Green Fluorescent Protein (GFP)) | SEQ ID NO: 50 | 28 |
| WT Mutant T12 DNA; nucleic acid sequence encoding mutant T12 *Renilla reniformis* Green Fluorescent Protein (GFP) | SEQ ID NO: 51 | 29 |
| WT Mutant T12 protein; protein encoded by SEQ ID NO: 51 (nucleic acid sequence encoding mutant T12 *Renilla reniformis* Green Fluorescent Protein (GFP)) | SEQ ID NO: 52 | 29 |
| WT Mutant T13 DNA; nucleic acid sequence encoding mutant T13 *Renilla reniformis* Green Fluorescent Protein (GFP) | SEQ ID NO: 53 | 30 |
| WT Mutant T13 protein; protein encoded by SEQ ID NO: 53 (nucleic acid sequence encoding mutant T13 *Renilla reniformis* Green Fluorescent Protein (GFP)) | SEQ ID NO: 54 | 30 |
| WT Mutant T14 DNA; nucleic acid sequence encoding mutant T14 *Renilla reniformis* Green Fluorescent Protein (GFP)) | SEQ ID NO: 55 | 31 |
| WT Mutant T14 protein; protein encoded by SEQ ID NO: 55 (nucleic acid sequence encoding mutant T14 *Renilla reniformis* Green Fluorescent Protein (GFP)) | SEQ ID NO: 56 | 31 |
| WT Mutant T15 DNA; nucleic acid sequence encoding mutant T15 *Renilla reniformis* Green Fluorescent Protein (GFP) | SEQ ID NO: 57 | 32 |
| WT Mutant T15 protein; protein encoded by SEQ ID NO: 57 (nucleic acid sequence encoding mutant T15 *Renilla reniformis* Green Fluorescent Protein (GFP)) | SEQ ID NO: 58 | 32 |
| WT Mutant T17 DNA; nucleic acid sequence encoding mutant T17 *Renilla reniformis* Green Fluorescent Protein (GFP) | SEQ ID NO: 59 | 33 |
| WT Mutant T17 protein; protein encoded by SEQ ID NO: 59 (nucleic acid sequence encoding mutant T17 *Renilla reniformis* Green Fluorescent Protein (GFP)) | SEQ ID NO: 60 | 33 |
| Alt WT GFP DNA; alternate form of nucleic acid sequence encoding *Renilla reniformis* Green Fluorescent Protein (GFP) | SEQ ID NO: 61 | 34 |
| Alt WT GFP protein; protein encoded by SEQ ID NO: 61 (alternate form of WT nucleic acid sequence encoding *Renilla reniformis* Green Fluorescent Protein (GFP)) | SEQ ID NO: 62 | 34 |

The mutagenesis primers shown in Table 7 were designed to introduce mutations into the humanized version of the GFP nucleotide sequence. To introduce the same amino acid substitutions to the wild type nucleotide sequence, different primers need to be used, which match the non-humanized GFP nucleotide sequence, and introduce a codon coding for the desired amino acid substitution. Methods for designing and making such primers are well-known.

Using the methods described herein, or other methods known in the art, one can produce other mutant GFP proteins, either humanized or unhumanized.

I. How to Make a Humanized *R. reniformis* GFP Polynucleotide and Produce a *R. reniformis* GFP Polypeptide According to the Invention A number of methodologies were combined to provide the invention disclosed herein, including molecular, cellular and biochemical approaches. Polynucleotides encoding *R. reniformis* GFP or a variant GFP sequence to which a humanized sequence is desired are obtained in any of several different ways know to those of skill in the art, including direct chemical synthesis, library screening and PCR amplification.

A. Polynucleotide Sequence Encoding Wild Type *R. reniformis* GFP.

The wild type polynucleotide sequence of *R. reniformis* is provided herein as SEQ ID NO:31. Accordingly one of skill in the art may generate a polynucleotide sequence encoding a wild type *R. reniformis* GFP by synthesizing the sequence of SEQ ID NO:31, using methods known in the art (Alvarado-Urbina et al., 1981, Science 214:270). A polynucleotide sequence encoding wild type *R. reniformis* GFP may also be generated as described below.

1. *R. reniformis* cDNA Library Preparation.

Construction methods for libraries in a variety of different vectors, including, for example, bacteriophage, plasmids, and viruses capable of infecting eukaryotic cells are well known in the art. Any known library production method resulting in largely full-length clones of expressed genes may be used to provide a template for the isolation of wild type GFP-encoding polynucleotides from *R. reniformis.*

For the library used to isolate the GFP-encoding polynucleotides disclosed herein, the following method may be used. Poly(A) RNA can be prepared from *R. reniformis* organisms as described by Chomczynski, P. and Sacchi, N. (1987*, Anal. Biochem.* 162:156–159). cDNA is prepared using the ZAP-cDNA Synthesis Kit (Stratagene cat.# 200400, Stratagene, La Jolla, Calif., USA) according to the manufacturer's recommended protocols and inserted between the EcoRI and XhoI sites in the vector Lambda ZAP II. The resulting library contained $5\times10^6$ individual primary clones, with an insert size range of 0.5–3.0 kb and an average insert size of 1.2 kb. The library is amplified once prior to use as template for PCR reactions.

2. Isolation of *R. reniformis* GFP Polynucleotide Coding Sequence By PCR.

The *R. reniformis* GFP coding sequence can be isolated by polymerase chain reaction (PCR) amplification of the sequence from within the cDNA library described herein. A large number of PCR methods are known to those skilled in the art. Thermal-cycled PCR (Mullis and Faloona, 1987, *Methods Enzymol.* 155:335–350; see also, *PCR Protocols,* 1990, Academic Press, San Diego, Calif., USA for a review of PCR methods) uses multiple cycles of DNA replication catalyzed by a thermostable, DNA-dependent DNA polymerase to amplify the target sequence of interest. Briefly, oligonucleotide primers are selected such that they anneal on either side and on opposite strands of a sequence to be amplified. The primers are annealed and extended using a template-dependent thermostable DNA polymerase, followed by thermal denaturation and annealing of primers to both the original template sequence and the newly-extended template sequences, after which primer extension is performed. Repeating such cycles results in exponential amplification of the sequences between the two primers.

In addition to thermal cycled PCR, there are a number of other nucleic acid sequence amplification methods that may be used to amplify and isolate a GFP-encoding polypeptide according to the invention from a *R. reniformis* cDNA library. These include, for example, isothermal 3SR (Gingeras et al., 1990*, Annales de Biologie Clinique* 48(7): 498–501; Guatelli et al., 1990*, Proc. Natl. Acad. Sci. USA* 87:1874), and the DNA ligase amplification reaction (LAR), which permits the exponential increase of specific short sequences through the activities of any one of several bacterial DNA ligases (Wu and Wallace, 1989*, Genomics* 4:560). The contents of both of these references are incorporated herein in their entirety by reference.

To amplify a sequence encoding *R. reniformis* GFP from an *R. reniformis* cDNA library, the following approach can be taken. The *R. reniformis* GFP coding sequence can be amplified using 5' and 3' primers adjacent the coding region. Oligonucleotides may be purchased from any of a number of commercial suppliers (for example, Life Technologies, Inc., Operon Technologies, etc.). Alternatively, oligonucleotide primers may be synthesized using methods well known in the art, including, for example, the phosphotriester (see Narang, S. A., et al., 1979*, Meth. Enzymol.* 68:90; and U.S. Pat. No. 4,356,270), phosphodiester (Brown, et al., 1979*, Meth. Enzymol.* 68:109), and phosphoramidite (Beaucage, 1993*, Meth. Mol. Biol.* 20:33) approaches. Each of these references is incorporated herein in its entirety by reference.

PCR is carried out in a 50 μl reaction volume containing 1×TaqPlus Precision buffer (Stratagene, La Jolla, Calif., USA), 250 μM of each dNTP, 200 nM of each PCR primer, 2.5 U TaqPlus Precision enzyme (Stratagene) and approximately $3\times10^7$ lambda phage particles from the amplified cDNA library described above. Reactions can be carried out in a Robocycler Gradient 40 (Stratagene) as follows: 1 minute at 95° C. (1 cycle), 1 minute at 95° C., 1 minute at 53° C., 1 minute at 72° C. (40 cycles), and 1 minute at 72° C. (1 cycle). Reaction products are resolved on a 1% agarose gel, and a band of approximately 700 bp is then excised and purified using the StrataPrep DNA Gel Extraction Kit (Stratagene). Other methods of isolating and purifying amplified nucleic acid fragments are well known to those skilled in the art. The PCR fragment is then subcloned by digestion to completion with EcoRI and XhoI and insertion into the retroviral expression vector pFB (Stratagene) to create the vector pFB-rGFP. Both strands of the cloned GFP fragment are then completely sequenced.

3. Isolation of *R. reniformis* GFP-Encoding Polynucleotides By Library Screening.

An alternative method of isolating GFP-encoding polynucleotides according to the invention involves the screening of an expression library, such as a lambda phage expression library, for clones exhibiting fluorescence within the emission spectrum of GFP when illuminated with light within the excitation spectrum of GFP. In this way clones may be directly identified from within a large pool. Standard methods for plating lambda phage expression libraries and inducing expression of polypeptides encoded by the inserts are well established in the art. Screening by fluorescence excitation and emission is carried out as described herein below using either a spectrofluorometer or even visual identification of fluorescing plaques. With either method, fluorescent plaques are picked and used to re-infect fresh cultures one or more times to provide pure cultures, from which GFP insert sequences may be determined and subcloned.

As another alternative, if a sequence is available for the polynucleotide one wishes to obtain, the polynucleotide may be chemically synthesized by one of skill in the art. The same synthetic methods used for the preparation of oligonucleotide primers (described above) may be used to synthesize gene coding sequences for GFPs of the invention. Generally this would be performed by synthesizing several shorter sequences (about 100 nt or less), followed by annealing and ligation to produce the full length coding sequence.

B. Production of Humanized Polynucleotides Encoding *R. reniformis*.

The present invention provides a modified nucleic acid sequence which represents a humanized form of *R. reniformis* GFP polynucleotide, which provides of enhanced expression of the encoded GFP polypeptide in human cells. To generate a humanized polynucleotide encoding *R. reniformis* GFP, useful in the present invention, the nucleic acid sequence encoding the polypeptide may be modified to enhance its expression in mammalian or human cells. The codon usage of *R. reniformis* is optimal for expression in *R. reniformis*, but not for expression in mammalian or human systems. Therefore, the adaptation of the sequence isolated from the sea pansy for expression in higher eukaryotes involves the modification of specific codons to change those less favored in mammalian or human systems to those more commonly used in these systems. This so-called "humanization" is accomplished by site-directed mutagenesis of the less favored codons as described herein below or as known in the art. The preferred codons for human gene expression are listed in Table 3, below. The codons in the table are arranged from left to right in descending order of relative use in human genes.

Humanized nucleotide sequences encoding *R. reniformis* may be generated by site directed mutagenesis. The humanized nucleotide sequences disclosed herein may, of course, be varied slightly by altering several humanized codons to be non-preferential codons in a mammalian or human cell and such slight alterations are considered to be equivalent as long as they do not reduce the level of expression of the humanized gene in mammalian cells by more than 5 or 10% relative to the expression of the sequence of SEQ ID NO:1.

There are 64 possible combinations of the 4 DNA nucleotides in codon groups of 3, and the genetic code is redundant for many of the 20 amino acids. Each of the different codons for a given amino acid encodes the incorporation of that amino acid into a polypeptide. However, within a given species there tends to be a preference for certain of the redundant codons to encode a given amino acid. The "codon preference" of *R. reniformis* is different from that of humans (this codon preference is usually based upon differences in the level of expression of the tRNAs containing the corresponding anticodon sequences). Table 3, below, shows the preferred codons for human gene expression. A codon sequence is preferred for human expression if it occurs to the left of a given codon sequence in the table. Optimally, but not necessarily, less preferred codons in a non-human polynucleotide coding sequence are humanized by altering them to the codon most preferred for that amino acid in human gene expression.

TABLE 3

Preferred DNA Codons For Human Use

| Amino Acids | | | Codons Preferred in Human Genes |
|---|---|---|---|
| Alanine | Ala | A | GCC GCT GCA GCG |
| Cysteine | Cys | C | TGC TGT |
| Aspartic acid | Asp | D | GAC GAT |
| Glutamic acid | Glu | E | GAG GAA |
| Phenylalanine | Phe | F | TTC TTT |
| Glycine | Gly | G | GGC GGG GGA GGT |
| Histidine | His | H | CAC CAT |
| Isoleucine | Ile | I | ATC ATT ATA |
| Lysine | Lys | K | AAG AAA |
| Leucine | Leu | L | CTG TTG CTT cta tta |
| Methionine | Met | M | ATG |
| Asparagine | Asn | N | AAC AAT |
| Proline | Pro | P | CCC CCT CCA CCG |
| Glutamine | Gln | Q | CAG CAA |
| Arginine | Arg | R | CGC AGG CGG AGA CGA CGT |
| Serine | Ser | S | AGC TCC TCT AGT TCA tcg |
| Threonine | Thr | T | ACC ACA ACT ACG |
| Valine | Val | V | GTG GTC GTT gta |
| Tryprophan | Trp | W | TGG |
| Tyrosine | Tyr | Y | TAC TAT |

The codons at the left represent those most preferred for use in human genes, with human usage decreasing towards the right. Codons in lower case are almost never used in human genes.

C. Production of *R. reniformis* GFP Polypeptides.

The production of *R. reniformis* GFP polypeptides from recombinant vectors comprising humanized GFP-encoding polynucleotides of the invention may be effected in a number of ways known to those skilled in the art. For example, plasmids, bacteriophage or viruses may be introduced to prokaryotic or eukaryotic cells by any of a number of ways known to those skilled in the art. Following introduction of *R. reniformis* GFP-encoding polynucleotides to a prokaryotic or eukaryotic cell, expressed GFP polypeptides may be isolated using methods known in the art or described herein below. Useful vectors, cells, methods of introducing vectors to cells and methods of detecting and isolating GFP polypeptides are also described herein below.

1. Vectors Useful According to the Invention.

There is a wide array of vectors known and available in the art that are useful for the expression of GFP polypeptides according to the invention. The selection of a particular vector clearly depends upon the intended use of the GFP polypeptide. For example, the selected vector must be capable of driving expression of the polypeptide in the desired cell type, whether that cell type be prokaryotic or eukaryotic. Many vectors comprise sequences allowing both prokaryotic vector replication and eukaryotic expression of operably linked gene sequences.

Vectors useful according to the invention may be autonomously replicating, that is, the vector, for example, a plasmid, exists extrachromosomally and its replication is not necessarily directly linked to the replication of the host cell's genome. Alternatively, the replication of the vector may be linked to the replication of the host's chromosomal DNA, for example, the vector may be integrated into the chromosome of the host cell as achieved by retroviral vectors.

Vectors useful according to the invention preferably comprise sequences operably linked to the GFP coding sequences that permit the transcription and translation of the GFP sequence. Sequences that permit the transcription of the linked GFP sequence include a promoter and optionally also include an enhancer element or elements permitting the strong expression of the linked sequences. The term "transcriptional regulatory sequences" refers to the combination of a promoter and any additional sequences conferring desired expression characteristics (e.g., high level expression, inducible expression, tissue- or cell-type-specific expression) on an operably linked nucleic acid sequence.

The selected promoter may be any DNA sequence that exhibits transcriptional activity in the selected host cell, and may be derived from a gene normally expressed in the host cell or from a gene normally expressed in other cells or organisms. Examples of promoters include, but are not limited to prokaryotic promoters and eukaryotic promoters. Prokaryotic promoters include, but are not limited to, *E. coli* lac, tac, or trp promoters, lambda phage $P_R$ or $P_L$ promoters, bacteriophage T7, T3, Sp6 promoters, *B. subtilis* alkaline protease promoter, and the *B. stearothermophilus* maltogenic amylase promoter, etc. Eukaryotic promoters include, but are not limited to, yeast promoters, such as GAL1, GAL4 and other glycolytic gene promoters (see for example, Hitzeman et al., 1980, *J. Biol. Chem.* 255:12073–12080; Alber & Kawasaki, 1982, *J. Mol. Appl. Gen.* 1:419–434), LEU2 promoter (Martinez-Garcia et al., 1989, *Mol. Gen. Genet.* 217:464–470), alcohol dehydrogenase gene promoters (Young et al., 1982, in: *Genetic Engineering of Microorganisms for Chemicals*, Hollaender et al., eds., Plenum Press, NY), or the TPI1 promoter (U.S. Pat. No. 4,599,311); insect promoters, such as the polyhedrin promoter (U.S. Pat. No. 4,745,051; Vasuvedan et al., 1992, *FEBS Lett.* 311:7–11), the P10 promoter (Vlak et al., 1988, *J. Gen. Virol.* 69:765–776), the *Autographa californica* polyhedrosis virus basic protein promoter (EP 397485), the baculovirus immediate-early gene promoter gene 1 promoter (U.S. Pat. Nos. 5,155,037 and 5,162,222), the baculovirus 39K delayed-early gene promoter (also U.S. Pat. Nos. 5,155,037 and 5,162,222) and the OpMNPV immediate early promoter 2; mammalian promoters—the SV40 promoter (Subramani et al., 1981, *Mol. Cell. Biol.* 1:854–864), metallothionein promoter (MT-1; Palmiter et al., 1983, *Science* 222:809–814), adenovirus 2 major late promoter (Yu et al., 1984, *Nuc. Acids Res.* 12:9309–21), cytomegalovirus (CMV) or other viral promoter (Tong et al., 1998, *Anticancer Res.* 18:719–725), or even the endogenous promoter of a gene of interest in a particular cell type.

A selected promoter may also be linked to sequences rendering it inducible or tissue-specific. For example, the addition of a tissue-specific enhancer element upstream of a selected promoter may render the promoter more active in a given tissue or cell type. Alternatively, or in addition, inducible expression may be achieved by linking the promoter to any of a number of sequence elements permitting induction by, for example, thermal changes (temperature sensitive), chemical treatment (for example, metal ion- or IPTG-inducible), or the addition of an antibiotic inducing agent (for example, tetracycline).

Regulatable expression is achieved using, for example, expression systems that are drug inducible (e.g., tetracycline, rapamycin or hormone-inducible). Drug-regulatable promoters that are particularly well suited for use in mammalian cells include the tetracycline regulatable promoters, and glucocorticoid steroid-, sex hormone steroid-, ecdysone-, lipopolysaccharide (LPS)- and isopropylthiogalactoside (IPTG)-regulatable promoters. A regulatable expression system for use in mammalian cells should ideally, but not necessarily, involve a transcriptional regulator that binds (or fails to bind) non-mammalian DNA motifs in response to a regulatory agent, and a regulatory sequence that is responsive only to this transcriptional regulator.

One inducible expression system that is well suited for the regulated expression of a GFP polypeptide of the invention, is the tetracycline-regulatable expression system, which is founded on the efficiency of the tetracycline resistance operon of *E. coli*. The binding constant between tetracycline and the tet repressor is high while the toxicity of tetracycline for mammalian cells is low, thereby allowing for regulation of the system by tetracycline concentrations in eukaryotic cell culture or within a mammal that do not affect cellular growth rates or morphology. Binding of the tet repressor to the operator occurs with high specificity.

Versions of the tet-regulatable system exist that allow either positive or negative regulation of gene expression by tetracycline. In the absence of tetracycline or a tetracycline analog, the wild-type bacterial tet repressor protein causes negative regulation of genes driven by promoters containing repressor binding elements from the tet operator sequences. Gossen & Bujard (1995, *Science* 268:1766–1769; also International patent application No. WO 96/01313) describe a tet-regulatable expression system that exploits this positive regulation by tetracycline. In this system, tetracycline binds to a tet repressor fusion protein, rtTA, and prevents it from binding to the tet operator DNA sequence, thus allowing transcription and expression of the linked gene only in the presence of the drug.

This positive tetracycline-regulatable system provides one means of stringent temporal regulation of the GFP polypeptide of the invention (Gossen & Bujard, 1995, supra). The tet operator (tet O) sequence is now well known to those skilled in the art. For a review, the reader is referred to Hillen & Wissmann (1989) in "*Protein-Nucleic Acid Interaction, Topics in Molecular and Structural Biology*", eds. Saenger & Heinemann, (Macmillan, London), Vol. 10, pp 143–162. Typically the nucleic acid sequence encoding the GFP polypeptide is placed downstream of a plurality of tet O sequences: generally 5 to 10 such tet O sequences are used, in direct repeats.

In addition to the tetracycline-regulatable systems, a number of other options exist for the regulated or inducible expression of a GFP polypeptide according to the invention. For example, the *E. coli* lac promoter is responsive to lac repressor (lacI) DNA binding at the lac operator sequence. The elements of the operator system are functional in heterologous contexts, and the inhibition of lacI binding to the lac operator by IPTG is widely used to provide inducible expression in both prokaryotic, and more recently, eukaryotic cell systems. In addition, the rapamycin-controlled transcriptional activator system described by Rivera et al. (1996, *Nature Med.* 2:1028–1032) provides transcriptional activation dependent on rapamycin. That system has low baseline expression and a high induction ratio.

Another option for regulated or inducible expression of a GFP polypeptide involves the use of a heat-responsive promoter. Activation is induced by incubation of cells, transfected with a GFP construct regulated by a temperature-sensitive transactivator, at the permissive temperature prior to administration. For example, transcription regulated by a co-transfected, temperature sensitive transcription factor active only at 37° C. may be used if cells are first grown at, for example, 32° C., and then switched to 37° C. to induce expression.

Tissue-specific promoters may also be used to advantage in GFP-encoding constructs of the invention. A wide variety of tissue-specific promoters is known. As used herein, the term "tissue-specific" means that a given promoter is transcriptionally active (i.e., directs the expression of linked sequences sufficient to permit detection of the polypeptide product of the promoter) in less than all cells or tissues of an organism. A tissue specific promoter is preferably active in only one cell type, but may, for example, be active in a particular class or lineage of cell types (e.g., hematopoietic cells). A tissue specific promoter useful according to the invention comprises those sequences necessary and sufficient for the expression of an operably linked nucleic acid sequence in a manner or pattern that is essentially the same as the manner or pattern of expression of the gene linked to that promoter in nature. The following is a non-exclusive list of tissue specific promoters and literature references containing the necessary sequences to achieve expression characteristic of those promoters in their respective tissues; the entire content of each of these literature references is incorporated herein by reference. Examples of tissue specific promoters useful with the *R. reniformis* GFP of the invention are as follows: Bowman et al., 1995, *Proc. Natl. Acad. Sci. USA* 92:12115–12119 describe a brain-specific transferrin promoter; the synapsin I promoter is neuron specific (Schoch et al., 1996, *J. Biol. Chem.* 271:3317–3323); the nestin promoter is post-mitotic neuron specific (Uetsuki et al., 1996, *J. Biol. Chem.* 271:918–924); the neurofilament light promoter is neuron specific (Charron et al., 1995, *J. Biol. Chem.* 270:30604–30610); the acetylcholine receptor promoter is neuron specific (Wood et al., 1995, *J. Biol. Chem.* 270:30933–30940); the potassium channel promoter is high-frequency firing neuron specific (Gan et al., 1996, *J. Biol. Chem.* 271:5859–5865); the chromogranin A promoter is neuroendocrine cell specific (Wu et al., 1995, *Amer. J. Clin. Invest.* 96:568–578); the Von Willebrand factor promoter is brain endothelium specific (Aird et al., 1995, *Proc. Natl. Acad. Sci. USA* 92:4567–4571); the flt-1 promoter is endothelium specific (Morishita et al., 1995, *J. Biol. Chem.* 270:27948–27953); the preproendothelin-1 promoter is endothelium, epithelium and muscle specific (Harats et al., 1995, *J. Clin. Invest.* 95:1335–1344); the GLUT4 promoter is skeletal muscle specific (Olson and Pessin, 1995, *J. Biol. Chem.* 270:23491–23495); the Slow/fast troponins promoter is slow/fast twitch myofibre specific (Corin et al., 1995, *Proc. Natl. Acad. Sci. USA* 92:6185–6189); the beta-Actin promoter is smooth muscle specific (Shimizu et al., 1995, *J. Biol. Chem.* 270:7631–7643); the Myosin heavy chain promoter is smooth muscle specific (Kallmeier et al., 1995, *J. Biol. Chem.* 270:30949–30957); the E-cadherin promoter is epithelium specific (Hennig et al., 1996, *J. Biol. Chem.* 271:595–602); the cytokeratins promoter is keratinocyte specific (Alexander et al., 1995, *B. Hum. Mol. Genet.* 4:993–999); the transglutaminase 3 promoter is keratinocyte specific (J. Lee et al., 1996, *J. Biol. Chem.* 271:4561–4568); the bullous pemphigoid antigen promoter is basal keratinocyte specific (Tamai et al., 1995, *J. Biol. Chem.* 270: 7609–7614); the keratin 6 promoter is proliferating epidermis specific (Ramirez et al., 1995, *Proc. Natl. Acad. Sci. USA* 92:4783–4787); the collagen 1 promoter is hepatic stellate cell and skin/tendon fibroblast specific (Houglum et al., 1995, *J. Clin. Invest.* 96:2269–2276); the type X collagen promoter is hypertrophic chondrocyte specific (Long & Linsenmayer, 1995, *Hum. Gene Ther.* 6:419–428); the Factor VII promoter is liver specific (Greenberg et al., 1995, *Proc. Natl. Acad. Sci. USA* 92:12347–1235); the fatty acid synthase promoter is liver and adipose tissue specific (Soncini et al., 1995, *J. Biol. Chem.* 270:30339–3034); the carbamoyl phosphate synthetase I promoter is portal vein hepatocyte and small intestine specific (Christoffels et al., 1995, *J. Biol. Chem.* 270:24932–24940); the Na—K—Cl transporter promoter is kidney (loop of Henle) specific (Igarashi et al., 1996, *J. Biol. Chem.* 271:9666–9674); the scavenger receptor A promoter is macrophages and foam cell specific (Horvai et al., 1995, *Proc. Natl. Acad. Sci. USA* 92:5391–5395); the glycoprotein IIb promoter is megakaryocyte and platelet specific (Block & Poncz, 1995, *Stem Cells* 13:135–145); the yc chain promoter is hematopoietic cell specific (Markiewicz et al., 1996, J. Biol. Chem. 271: 14849–14855); and the CD11b promoter is mature myeloid cell specific (Dziennis et al., 1995, *Blood* 85:319–329).

Any tissue specific transcriptional regulatory sequence known in the art may be used to advantage with a vector encoding *R. reniformis* GFP.

In addition to promoter/enhancer elements, vectors useful according to the invention may further comprise a suitable terminator. Such terminators include, for example, the human growth hormone terminator (Palmiter et al., 1983, *Science* 222:809–814), or, for yeast or fungal hosts, the TPI1 (Alber & Kawasaki, 1982, *J. Mol. Appl. Gen.* 1:419–434) or ADH3 terminator (McKnight et al., 1985, *EMBO J.* 4:2093–2099).

Vectors useful according to the invention may also comprise polyadenylation sequences (e.g., the SV40 or Ad5E1b poly(A) sequence), and translational enhancer sequences (e.g., those from Adenovirus VA RNAs). Further, a vector useful according to the invention may encode a signal sequence directing the recombinant polypeptide to a particular cellular compartment or, alternatively, may encode a signal directing secretion of the recombinant polypeptide.

Coordinate expression of different genes from the same promoter in a recombinant vector maybe achieved by using an IRES element, such as the internal ribosomal entry site of Poliovirus type 1 from pSBC-1 (Dirks et al., 1993, *Gene* 128:247–9). Internal ribosome binding site (IRES) elements are used to create multigenic or polycistronic messages. IRES elements are able to bypass the ribosome scanning mechanism of 5' methylated Cap-dependent translation and begin translation at internal sites (Pelletier and Sonenberg, 1988, *Nature* 334:320–325). IRES elements from two members of the picanovirus family (polio and encephalomyocarditis) have been described (Pelletier and Sonenberg, 1988, supra), as well an IRES from a mammalian message (Macejak and Sarnow, 1991 *Nature* 353:90–94). Any of the foregoing may be used in an *R. reniformis* GFP vector in accordance with the present invention.

IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. In this manner, multiple genes, one of which will be an *R.*

*reniformis* GFP gene, can be efficiently expressed using a single promoter/enhancer to transcribe a single message. Any heterologous open reading frame can be linked to IRES elements. In the present context, this means any selected protein that one desires to express and any second reporter gene (or selectable marker gene). In this way, the expression of multiple proteins could be achieved, for example, with concurrent monitoring through GFP production.

A vector useful according to the invention may also comprise a selectable marker allowing identification of a cell that has received a functional copy of the GFP-encoding gene construct. In its simplest form, the GFP sequence itself, linked to a chosen promoter may be considered a selectable marker, in that illumination of cells or cell lysates with the proper wavelength of light and measurement of emitted fluorescence at the expected wavelength allows detection of cells that express the GFP construct. In other forms, the selectable marker may comprise an antibiotic resistance gene, such as the neomycin, bleomycin, zeocin or phleomycin resistance genes, or it may comprise a gene whose product complements a defect in a host cell, such as the gene encoding dihydrofolate reductase (DHFR), or, for example, in yeast, the Leu2 gene. Alternatively, the selectable marker may, in some cases be a luciferase gene or a chromogenic substrate-converting enzyme gene such as the beta-galactosidase gene.

GFP-encoding sequences according to the invention may be expressed either as free-standing polypeptides or frequently as fusions with other polypeptides. It is assumed that one of skill in the art can, given the polynucleotide sequences disclosed herein, readily construct a gene comprising a sequence encoding *R. reniformis* GFP and a sequence comprising one or more polypeptides or polypeptide domains of interest. It is understood that the fusion of GFP coding sequences and sequences encoding a polypeptide of interest maintains the reading frame of all polypeptide sequences involved. As used herein, the term "polypeptide of interest" or "domain of interest" refers to any polypeptide or polypeptide domain one wishes to fuse to a GFP molecule of the invention. The fusion of a GFP polypeptide of the invention with a polypeptide of interest may be through linkage of the GFP sequence to either the N or C terminus of the fusion partner, or the GFP sequence may even be inserted in frame between the N and C termini of the polypeptide of interest, if so desired. Fusions comprising GFP polypeptides of the invention need not comprise only a single polypeptide or domain in addition to the GFP. Rather, any number of domains of interest may be linked in any way as long as the GFP coding region retains its reading frame and the encoded polypeptide retains fluorescence activity under at least one set of conditions. One non-limiting example of such conditions includes physiological salt concentration (i.e., about 90 mM), pH near neutral and 37° C.

a. Plasmid Vectors.

Any plasmid vector that allows expression of a humanized GFP coding sequence of the invention in a selected host cell type is acceptable for use according to the invention. A plasmid vector useful in the invention may have any or all of the above-noted characteristics of vectors useful according to the invention. Plasmid vectors useful according to the invention include, but are not limited to the following examples: Bacterial—pQE70, pQE60, pQE-9 (Qiagen, Hilden, Germany) pBs, phagescript, psiX174, pBluescript SK, pBsKS, pNH8a, pNH16a, pNH18a, pNH46a (Stratagene, La Jolla, Calif., USA); pTrc99A, pKK223-3, pKK233-3, pDR540, and pRIT5 (Pharmacia Biotech, Inc., Piscataway, N.J., USA); Eukaryotic—pWLneo, pSV2cat, pOG44, pXT1, pSG (Stratagene) pSVK3, pBPV, pMSG, and pSVL (Pharmacia). However, any other plasmid or vector may be used as long as it is replicable and viable in the host.

b. Bacteriophage Vectors.

There are a number of well known bacteriophage-derived vectors useful according to the invention. Foremost among these are the lambda-based vectors, such as Lambda Zap II or Lambda-Zap Express vectors (Stratagene, La Jolla, Calif., USA) that allow inducible expression of the polypeptide encoded by the insert. Others include filamentous bacteriophage such as the M13-based family of vectors.

c. Viral Vectors.

A number of different viral vectors are useful according to the invention, and any viral vector that permits the introduction and expression of humanized sequences encoding *R. reniformis* GFP thereof in cells is acceptable for use in the methods of the invention. Viral vectors that can be used to deliver foreign nucleic acid into cells include but are not limited to retroviral vectors, adenoviral vectors, adeno-associated viral vectors, herpesviral vectors, and Semliki forest viral (alphaviral) vectors. Defective retroviruses are well characterized for use in gene transfer (for a review see Miller, A. D., 1990, *Blood* 76:271). Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14, and other standard laboratory manuals.

In addition to retroviral vectors, adenovirus can be manipulated such that it encodes and expresses a gene product of interest but is inactivated in terms of its ability to replicate in a normal lytic viral life cycle (see for example Berkner et al., 1988, *BioTechniques* 6:616; Rosenfeld et al., 1991, *Science* 252:431–434; and Rosenfeld et al., 1992, *Cell* 68:143–155). Suitable adenoviral vectors derived from the adenovirus strain Ad type 5d1324 or other strains of adenovirus (e.g., Ad2, Ad3, Ad7 etc.) are well known to those skilled in the art. Adeno-associated virus (AAV) is a naturally occurring defective virus that requires another virus, such as an adenovirus or a herpes virus, as a helper virus for efficient replication and a productive life cycle. For a review see Muzyczka et al., 1992, *Curr. Topics in Micro. and Immunol.* 158:97–129. An AAV vector such as that described in Traschin et al. (1985, *Mol. Cell. Biol.* 5:3251–3260) can be used to introduce nucleic acid into cells. A variety of nucleic acids have been introduced into different cell types using AAV vectors (see, for example, Hermonat et al., 1984, *Proc. Natl. Acad. Sci. USA* 81:6466–6470; and Traschin et al., 1985, *Mol. Cell. Biol.* 4:2072–2081).

Finally, the introduction and expression of foreign genes is often desired in insect cells because high level expression may be obtained, the culture conditions are simple relative to mammalian cell culture, and the post-translational modifications made by insect cells closely resemble those made by mammalian cells. For the introduction of foreign DNA to insect cells, such as *Drosophila* S2 cells, infection with baculovirus vectors is widely used. Other insect vector systems include, for example, the expression plasmid pIZ/V5-His (InVitrogen Corporation, Carlsbad, Calif., USA) and other variants of the pIZ/V5 vectors encoding other tags and selectable markers. Insect cells are readily transfectable using lipofection reagents, and there are lipid-based transfection products specifically optimized for the transfection of insect cells (for example, from PanVera Corporation, Madison, Wis., USA).

2. Host Cells Useful According to the Invention.

Any cell into which a recombinant vector carrying a gene encoding *R. reniformis* GFP or humanized version may be introduced and wherein the vector is permitted to drive the expression of the GFP is useful according to the invention. That is, because of the wide variety of uses for the GFP molecules of the invention, any cell in which a GFP molecule of the invention may be expressed and preferably detected is a suitable host, wherein the host cell is preferably a mammalian cell and more preferably a human cell. Vectors suitable for the introduction of GFP-encoding sequences to host cells from a variety of different organisms, both prokaryotic and eukaryotic, are described herein above or known to those skilled in the art.

Host cells may be prokaryotic, such as any of a number of bacterial strains, or may be eukaryotic, such as yeast or other fungal cells, insect or amphibian cells, or mammalian cells including, for example, rodent, simian or human cells. Cells expressing GFPs of the invention may be primary cultured cells, for example, primary human fibroblasts or keratinocytes, or may be an established cell line, such as NIH3T3, 293T or CHO cells. Further, mammalian cells useful for expression of GFPs of the invention may be phenotypically normal or oncogenically transformed. It is assumed that one skilled in the art can readily establish and maintain a chosen host cell type in culture.

It is preferable that host cells of the present invention be human cells, as expression of a humanized GFP of the invention is particularly enhanced in human cells. Human cells which into which humanized *R. reniformis* GFP may be introduced include any cell in the human body. Introduction of humanized GFP, by any method described herein or known in the art, may be into human cells maintained in culture, human cell lines (i.e., HEK 293 cells), or may be into cells maintained in vivo in a human.

3. Introduction of GFP-Encoding Vectors to Host Cells.

GFP-encoding vectors may be introduced to selected host cells by any of a number of suitable methods known to those skilled in the art. For example, GFP constructs may be introduced to appropriate bacterial cells by infection, in the case of *E. coli* bacteriophage vector particles such as lambda or M13, or by any of a number of transformation methods for plasmid vectors or for bacteriophage DNA. For example, standard calcium-chloride-mediated bacterial transformation is still commonly used to introduce naked DNA to bacteria (Sambrook et al., 1989, *Molecular Cloning, A Laboratory Manual*, Cold Spring Harbor Laboratory Press, Cold Spring Harbor, N.Y.), but electroporation may also be used (Ausubel et al., 1988, *Current Protocols in Molecular Biology*, (John Wiley & Sons, Inc., NY, N.Y.)).

For the introduction of GFP-encoding constructs to yeast or other fungal cells, chemical transformation methods are generally used (e.g. as described by Rose et al., 1990, *Methods in Yeast Genetics*, Cold Spring Harbor Laboratory Press, Cold Spring Harbor, N.Y.). For transformation of *S. cerevisiae*, for example, the cells are treated with lithium acetate to achieve transformation efficiencies of approximately $10^4$ colony-forming units (transformed cells)/μg of DNA. Transformed cells are then isolated on selective media appropriate to the selectable marker used. Alternatively, or in addition, plates or filters lifted from plates may be scanned for GFP fluorescence to identify transformed clones.

For the introduction of *R. reniformis* GFP-encoding vectors to mammalian cells, the method used will depend upon the form of the vector. For plasmid vectors, humanized DNA encoding *R. reniformis* GFP may be introduced by any of a number of transfection methods, including, for example, lipid-mediated transfection ("lipofection"), DEAE-dextran-mediated transfection, electroporation or calcium phosphate precipitation. These methods are detailed, for example, in *Current Protocols in Molecular Biology* (Ausubel et al., 1988, John Wiley & Sons, Inc., NY, N.Y.).

Lipofection reagents and methods suitable for transient transfection of a wide variety of transformed and non-transformed or primary cells are widely available, making lipofection an attractive method of introducing constructs to eukaryotic, and particularly mammalian cells in culture. For example, LipofectAMINE™ (Life Technologies, Gibco, Invitrogen Corporation, Carlsbad, Calif., USA) or LipoTaxi™ (Stratagene, La Jolla, Calif., USA) kits are available. Other companies offering reagents and methods for lipofection include Bio-Rad Laboratories (Hercules, Calif., USA), CLONTECH (Palo Alto, Calif., USA), Glen Research Corp. (Sterling, Va., USA), JBL Scientific, MBI Fermentas (Hanover, Md., USA), PanVera Corporation (Madison, Wis., USA), Promega (Madison, Wis., USA), Qbiogene, Inc. (Carlsbad, Calif., USA), Sigma-Aldrich (St. Louis, Mo., USA), and Wako Chemicals USA (Richmond, Va., USA).

For the introduction of *R. reniformis* GFP-encoding vectors to insect cells, such as *Drosophila* Schneider 2 cells (S2) cells, Sf9 or Sf21cells, transfection is also performed by lipofection.

Following transfection with an *R. reniformis* GFP-encoding vector of the invention, eukaryotic (e.g., human) cells successfully incorporating the construct (intra- or extrachromosomally) may be selected, as noted above, by either treatment of the transfected population with a selection agent, such as an antibiotic whose resistance gene is encoded by the vector, or by direct screening using, for example, FACS of the cell population or fluorescence scanning of adherent cultures. Frequently, both types of screening may be used, wherein a negative selection is used to enrich for cells taking up the construct and FACS or fluorescence scanning is used to further enrich for cells expressing GFPs or to identify specific clones of cells, respectively. For example, a negative selection with the neomycin analog G418 (Life Technologies, Inc., Gibco, Invitrogen Corporation, Carlsbad, Calif., USA) may be used to identify cells that have received the vector, and fluorescence scanning may be used to identify those cells or clones of cells that express the humanized *R. reniformis* GFP to the greatest extent.

4. Preparation of Antibodies Reactive with *R. reniformis* GFP

Antibodies that bind to a GFP polypeptide encoded by a polynucleotide of the invention are useful, for example, in protein purification and in protein association assays. An antibody useful in the invention may comprise a whole antibody, an antibody fragment, a polyfunctional antibody aggregate, or in general a substance comprising one or more specific binding sites from an antibody. The antibody fragment may be a fragment such as an Fv, Fab or $F(ab')_2$ fragment or a derivative thereof, such as a single chain Fv fragment. The antibody or antibody fragment may be non-recombinant, recombinant or humanized. The antibody may be of an immunoglobulin isotype, e.g., IgG, IgM, and so forth. In addition, an aggregate, polymer, derivative and conjugate of an immunoglobulin or a fragment thereof can be used where appropriate.

GFP-derived peptides used to induce specific antibodies preferably have an amino acid sequence consisting of at least five amino acids and more conveniently at least ten amino acids. It is advantageous for such peptides to be identical to a region of the natural *R. reniformis* GFP protein, and they may even contain the entire amino acid sequence of *R. reniformis* GFP.

For the production of antibodies, various hosts including goats, rabbits, rats, mice, etc., may be immunized by injection with peptides or polypeptides having sequences derived from the GFP polypeptides of the invention. Depending on the host species, various adjuvants may be used to increase the immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol.

To generate polyclonal antibodies, the antigen (i.e., an *R. reniformis* GFP polypeptide, or peptide fragment derived therefrom) may be conjugated to a conventional carrier in order to increase its immunogenicity, and an antiserum to the peptide-carrier conjugate raised. Short stretches of amino acids corresponding to a GFP polypeptide of the invention may be fused, either by expression as a fusion product or by chemical linkage, with amino acids from another protein such as keyhole limpet hemocyanin or GST, with antibodies then being raised against the chimeric molecule. Coupling of a peptide to a carrier protein and immunizations may be performed as described in Dymecki et al., 1992*, J. Biol. Chem.* 267:4815. The serum can be titered against polypeptide antigen by ELISA or alternatively by dot or spot blotting (Boersma & Van Leeuwen, 1994*, J. Neurosci. Methods* 51:317). A useful serum will react strongly with the appropriate peptides by ELISA, for example, following the procedures of Green et al. (1982*, Cell* 28:477).

Techniques for preparing monoclonal antibodies are well known, and monoclonal antibodies may be prepared using an antigen, preferably bound to a carrier, as described by Arnheiter et al., (1981*, Nature* 294:278). Monoclonal antibodies are typically obtained from hybridoma tissue cultures or from ascites fluid obtained from animals into which the hybridoma tissue was introduced. Monoclonal antibody-producing hybridomas (or polyclonal sera) can be screened for antibody binding to the target protein according to methods known in the art.

5. Purification of *R. reniformis* GFP.

The proteins described herein can be purified by any means known in the art. In one such method, *R. reniformis* GFP is purified from *R. reniformis* organisms as described by Ward and Cormier (1979*, J. Biol. Chem.* 254:781–788) and by Matthews et al. (1977*, Biochemistry* 16:85–91), the contents of both of which are herein incorporated by reference. Similar procedures may be applied by one of skill in the art to bacterially expressed *R. reniformis* GFP following freeze-thaw lysis and preparation of a clarified lysate by centrifugation at 14,000×g. Briefly, the methods employed by Matthews et al. and Ward and Cormier involve successive chromatography over DEAE-cellulose, Sephadex G-100, and DTNB (5,5'-dithiobis(2-nitrobenzoic acid))-Sepharose columns, and dialysis against 1 mM Tris (pH 8.0), 0.1 mM EDTA. The dialyzed fractions containing GFP (identified by fluorescence) are then acid treated to precipitate contaminants, followed by neutralization of the supernatant, which is lyophilized. Low salt (10 mM to 1 mM initially) and pH ranging from 7.5 to 8.5 are critical to maintaining activity upon lyophilization. The lyophilized sample is re-suspended in water, immediately centrifuged to remove less-soluble contaminants and applied to a Sephadex G-75 column. GFP is eluted in 1.0 mM Tris (pH 8.0), 0.1 mM EDTA. Samples are concentrated by partial lyophilization and dialyzed against 5 mM sodium acetate, 5 mM imidazole, 1 mM EDTA, pH 7.5, followed by chromatography over a DEAE-BioGel-A column equilibrated in the same dialysis buffer. GFP is eluted with a continuous acidic gradient from pH 6.0 to 4.9 in the same acetate/imidizole buffer. Following dialysis of GFP-containing fractions against 1.0 mM Tris-HCl, 0.1 mM EDTA, pH 8.0, the sample is partially lyophilized to concentrate and passed over a Sephadex G-75 (Superfine) column. The GFP-containing fractions are then loaded onto a DEAE-BioGel A column in Tris/EDTA buffer at pH 8.0, followed by elution in a continuous alkaline gradient from pH 8.5 to 10.5 formed with 20 mM glycine, 5 mM Tris-HCl and 5 mM EDTA. GFP-containing fractions contain essentially homogeneous *R. reniformis* GFP.

In screening applications requiring less pure GFP preparations, recombinant *R. reniformis* can be purified from bacteria as follows. Bacteria transformed with a recombinant GFP-encoding vector of the invention are grown in Luria-Bertani medium containing the appropriate selective antibiotic (e.g., ampicillin at 50 μg/ml). If the vector permits, recombinant polypeptide expression is induced by the addition of the appropriate inducer (e.g., IPTG at 1 mM). Bacteria are harvested by centrifugation and lysed by freeze-thaw of the cell pellet. Debris is removed by centrifugation at 14,000×g, and the supernatant is loaded onto a Sephadex G-75 (Pharmacia, Piscataway, N.J.) column equilibrated with 10 mM phosphate buffered saline, pH 7.0. Fractions containing GFP are identified by fluorescence emission at 506 nm when excited by 500 nm light.

II. How to Use Humanized Polynucleotides Encoding *R. reniformis* GFP According to the Invention Humanized polynucleotide sequences encoding *R. reniformis* GFP are useful in a number of different ways. Generally, a polynucleotide sequence encoding *R. reniformis* GFP is useful in any process or assay that can be performed with *A. victoria* GFP. Further, because of its enhanced expression in mammalian cells and fluorescent intensity, a humanized polynucleotide sequence encoding *R. reniformis* GFP is useful in processes and assays beyond those that can be performed with *A. victoria* GFP.

Humanized polynucleotide sequences encoding *R. reniformis* GFP may be used as selectable markers for the identification of cells transfected or infected with a gene transfer vector. In this aspect, cells transfected with a humanized construct encoding GFP may be identified over a background of non-transfected or infected cells by illumination of the cells with light within the excitation spectrum and detection of fluorescent emission in the emission spectrum of the GFP.

Humanized *R. reniformis* GFP genes can be used to identify transformed mammalian cells (e.g., by fluorescence-activated cell sorting (FACS) or fluorescence microscopy), particularly human cells, to measure gene expression in vitro and in vivo, to label specific cells in multicellular organisms (e.g., to study cell lineages), to label and locate fusion proteins, and to study intracellular protein trafficking.

*R. reniformis* GFPs may also be used for standard biological applications. For example, they may be used as molecular weight markers on protein gels and Western blots, in calibration of fluorometers and FACS equipment and as a marker for micro injection into cells and tissues. In methods to produce fluorescent molecular weight markers, an *R. reniformis* GFP gene sequence is fused to one or more DNA sequences that encode proteins having defined amino acid sequences, and the fusion proteins are expressed from an expression vector. Expression results in the production of fluorescent proteins of defined molecular weight or weights that may be used as markers.

Preferably, purified fluorescent proteins are subjected to size-fractionation, such as by using a gel. A determination of the molecular weight of an unknown protein is then made by compiling a calibration curve from the fluorescent standards and reading the unknown molecular weight from the curve.

A. Use of Humanized Polynucleotides Encoding *R. Reniformis* GFP in the Identification of Transfected Cells.

A humanized polynucleotide sequence encoding *R. reniformis* GFP may be introduced as a selectable marker to identify transfected mammalian cells from a background of non-transfected cells. Alternatively, humanized *R. reniformis* GFP transfection may be used to pre-label isolated cells or a population of similar cells prior to exposing the cells to an environment in which different cell types are present. Detection of GFP in only the original cells allows the location of such cells to be determined and compared with the total population.

Mammalian cells that have been transfected with exogenous DNA can be identified with polynucleotide sequence encoding *R. reniformis* GFPs of the invention without creating a fusion protein. The method relies on the identification of cells that have received a plasmid or vector that comprises at least two transcriptional or translational units. A first unit will encode and direct expression of the desired protein, while the second unit will direct expression of humanized polynucleotide sequences encoding *R. reniformis* GFP. Co-expression of GFP from the second transcriptional or translational unit ensures that cells containing the vector are detected and differentiated from cells that do not contain the vector.

The humanized *R. reniformis* GFP sequences of the invention may also be fused to a DNA sequence encoding a selected protein in order to directly label the encoded protein with GFP. Expressing such an *R. reniformis* GFP fusion protein in a human cell results in the production of fluorescently-tagged proteins that can be readily detected. This is useful in confirming that a protein is being produced by a chosen host cell. It also allows the location of the selected protein to be determined, whether this represents a natural location or whether the protein has been artificially targeted to another location.

B. Use Of Humanized Polynucleotides Encoding *R. reniformis* for Analysis of Transcriptional Regulatory Sequences.

The humanized *R. reniformis* GFP genes of the invention allow a range of transcriptional regulatory sequences to be tested for their suitability for use with a given gene, cell, or system, but preferably for use with mammalian cells, preferably human cells. This applies to in vitro uses, such as in identifying a suitable transcriptional regulatory sequence for use in recombinant expression and high level protein production, as well as in vivo uses, such as in pre-clinical testing or in gene therapy in human subjects.

In order to analyze a transcriptional regulatory sequence, one must first establish a control cell or system. In the control, a positive result is established by using a known and effective promoter, such as the CMV promoter. To test a candidate transcriptional regulatory sequence, another cell or system, or a second population of the same cell type used as control, is established in which all conditions are the same except for there being different transcriptional regulatory sequences in the expression vector or genetic construct. After running the assay for the same period of time and under the same conditions as in the control, the expression levels of polynucleotide sequences encoding GFP are determined. This allows one to make a comparison of the strength or suitability of the candidate transcriptional regulatory sequence with the standard or control transcriptional regulatory sequence.

Transcriptional regulatory sequences that can be tested in this manner also include candidate tissue-specific promoters and candidate-inducible promoters. Testing of tissue-specific promoters allows the identification of optimal transcriptional regulatory sequences for use with a given cell. Again, this is useful both in vitro and in vivo. Optimizing the combination of a given transcriptional regulatory sequence and a given cell type in recombinant expression and protein production is often necessary to ensure that the highest possible expression levels are achieved.

The humanized GFP encoded by a regulatory sequence testing construct may optionally have a secretion signal fused to it, such that GFP secreted to the medium is detected.

The use of tissue-specific promoters and inducible promoters is particularly powerful in vivo embodiments. When used in the context of expressing a therapeutic gene in a human, the use of such transcriptional regulatory sequences allows expression only in a given tissue or tissues, at a given site and/or under defined conditions. Achieving tissue-specific expression is particularly important in certain gene therapy applications, such as in the expression of a cytotoxic agent, as is often employed in approaches to the treatment of cancer. In expressing other therapeutic genes with a beneficial effect, rather than a cytotoxic effect, tissue-specific expression is also preferred since it can optimize the effect of the treatment. Appropriate tissue-specific and inducible transcriptional regulatory sequences are known to those of skill in the art, or, for example, described herein above.

C. Use of Humanized Polynucleotide Sequences Encoding *R. reniformis* GFP In Assays for Compounds that Modulate Transcription.

Humanized polynucleotide sequences encoding *R. reniformis* GFP are useful in screening assays to detect compounds that modulate transcription. In this aspect of the invention, humanized *R. reniformis* GFP coding sequences are positioned downstream of a promoter that is known to be inducible by the agent that one wishes to detect. Expression of GFP in the cells will normally be silent, and is activated by exposing the cell to a composition that contains the selected agent. In using a promoter that is responsive to, for example, a lipid soluble transcriptional modulator, a toxin, a hormone, a cytokine, a growth factor or other defined molecule, the presence the particular defined molecule can be determined. For example, an estrogen-responsive regulatory sequence may be linked to GFP in order to test for the presence of estrogen in a sample.

It will be clear to one of skill in the art that any of the detection assays may be used in the context of screening for agents that inhibit, suppress or otherwise down regulate gene expression from a given transcriptional regulatory sequence. Such negative effects are detectable by decreased GFP fluorescence that results when gene expression is down-regulated in response to the presence of an inhibitory agent.

D. Use of Humanized Polynucleotide Sequences Encoding *R. reniformis* GFP in FACS Analyses.

Many conventional FACS methods require the use of fluorescent dyes conjugated to purified antibodies. Fusion proteins tagged with a fluorescent label are preferred over antibodies in FACS applications because the cells do not have to be incubated with the fluorescent-tagged reagent and because there is no background due to nonspecific binding of an antibody conjugate. GFP is particularly suitable for use in FACS as fluorescence is stable and species-independent and does not require any substrates or cofactors.

As with other expression embodiments, a desired protein may be directly labeled with GFP by preparing a fusion protein comprising a humanized polynucleotide sequence encoding GFP for expression in a cell; preferably a humanized GFP fusion protein in a human cell. A humanized polynucleotide sequence encoding GFP can also be co-expressed from a second transcriptional or translational unit within the expression vector that expresses desired protein, as described above. Cells expressing the GFP-tagged protein or cells co-expressing GFP are then detected and sorted by FACS analysis.

E. Other Uses of Humanized Polynucleotide Sequences Encoding *R. reniformis* GFP Fusion Proteins.

Humanized *R. reniformis* GFP genes can be used as one portion of a fusion protein, allowing the location of the tagged protein to be identified. Fusions of GFP with an exogenous protein should preserve both the fluorescence of GFP and functions of the host protein, such as physiological functions and/or targeting functions.

Both the amino and carboxyl termini of GFP may be fused to virtually any desired protein to create an identifiable GFP-fusion, and fusion may be mediated by a linker sequence if necessary to preserve the function of the fusion partner. However, it is preferable that the protein fused to GFP not possess fluorescent properties of its own (e.g., a luciferase protein) to prevent interference in screening for GFP expression.

*R. reniformis* GFP fusions are useful for subcellular localization studies. Localization studies have previously been carried out by subcellular fractionation and by immunofluorescence. However, these techniques can give only a static representation of the position of the protein at one instant in the cell cycle. In addition, artifacts can be introduced when cells are fixed for immunofluorescence. Using GFP to visualize proteins in living cells, which allows proteins to be followed throughout the cell cycle in an individual cell, is thus an important technique.

EXAMPLES

Example 1

Generation of Random Mutant hrGFP Libraries

The template used was hrGFP (described in PCT WO 01/64843) cloned into the SacI/HindIII restriction enzyme sites of the pMalc2e vector (New England BioLabs, Beverly, Mass., USA). Mutagenesis of the hrGFP template was performed with either the GeneMorph™ PCR Mutagenesis Kit (Stratagene, La Jolla, Calif., USA) according to manufacturer's instructions or by error prone-PCR conditions with Taq DNA polymerase (Cadwell, R. C. and Joyce, G. F., 1992, *PCR Methods and Applications* 2:28–33) using the following PCR primers:

```
hrGFPEF:
5'-ATTATTATTGAATTCATGAGCAAGCAGATC  (SEQ ID NO: 63)

CTGAAG-3' and

hrGFPHR:
5'-ATTATTATTAAGCTTCTATTACACCCACTC  (SEQ ID NO: 64)

GTGCAGG-3'.
```

Amplification reactions with the GeneMorph™ PCR Mutagenesis Kit (Stratagene) consisted of 1×Mutazyme™ reaction buffer, four different amounts of template DNA (100 ng, 10 ng, 1 ng, or 100 pg), 250 ng of each primer, 200 μM each dNTP, and 2.5U of Mutazyme™ DNA polymerase. Amplification reactions under EP-PCR conditions, modified from Zhao et al. (1998, *Nature Biotechnology* 16:258–261), consisted of 10 mM Tris pH 8.3, 50 mM KCl, 7 mM $MgCl_2$, 0.2 mM dGTP, 0.2 mM dATP, 1 mM dCTP, 1 mM dTTP, four different amounts of template DNA (100 ng, 10 ng, 1 ng, or 100 pg), 250 ng of each primer, 2.5U Taq 2000™ DNA Polymerase (Stratagene), and 0.15 mM $MnCl_2$. Amplification was performed using a RoboCycler® gradient 96 temperature cycler (Stratagene) with the following program: (1 cycle) 95° C. for 1 minute; (30 cycles) 95° C. for 1 minute, 50° C. for 1 minute, 72° C. for 1 minute; (1 cycle) 72° C. for 10 minutes. The PCR products were purified with StrataPrep® PCR Purification kit, digested with HindIII and EcoRI restriction enzymes, and subjected to electrophoresis on a 0.8% agarose gel. The 700 bp band was excised from the gel and purified from the agarose using the StrataPrep® Gel Extraction Kit (Stratagene). The library of gel purified inserts were ligated to the HindIII/EcoRI digested, gel purified pMalc2e vector backbone using the DNA ligation kit (Stratagene). Following overnight incubation at 16° C., 1.5 μl of each ligation reaction was transformed into 40 μl of XL10-Gold® ultracompetent cells (Stratagene) and plated on 10 cm LB/100 μg/ml amp plates to determine library size ($2.3\times10^4$–$2.8\times10^5$).

Example 2

Screening of Random Mutant hrGFP Libraries

Following titration of the library, each of the remaining ligation reactions was transformed into XL10-Gold® ultracompetent cells (Stratagene) and plated out on 15 cm LB/100 μg/ml amp plates. The plates were incubated at 30° C. overnight followed by incubation at room temperature for 12–48 hours. The plates were sprayed with 100 mM IPTG to induce protein expression and incubated at room temperature overnight. The plates were incubated at 4° C. for 24–72 hrs. The plates were screened for fluorescent bacterial colonies by holding the plate up to a slide projector equipped with different excitation lenses (Omega Optical, Inc., Brattleboro, Vt., USA) and viewing the plates with safety goggles covered with different WRATTEN emission filters (Kodak) listed in Table 4, below (Bevis, B. J. and Glick, B. J., 2002, *Nature Biotechnology* 20:83–87).

TABLE 4

Excitation Lenses and Emission Filters for Screening Mutant hrGFP Library Plates.

| | Wavelengths |
|---|---|
| Excitation Lenses | |
| 380BP10 | 375–385 nm |
| 470DF10 | 465–475 nm |
| 514.5DF10 | 509.5–519.5 nm |
| 540DF10 | 535–545 nm |
| Emission Filters | |
| No. 12 | >380 nm |
| No. 22 | >470 nm |
| No. 47 | >514 nm |
| No. 99 | >540 nm |

Bacterial colonies with an increase in green fluorescence intensity and/or a different emission color were picked for sequence analysis.

Example 3

Sequence Analysis of the Mutant hrGFP Clones

Each clone was grown up overnight in 2 mls of LB/100 μg/ml ampicillin and the DNA was isolated using the StrataPrep Plasmid Miniprep Kit (Stratagene). Both strands of each clone was sequenced with primers: (ERFP1) 5'-CT-TCGACATCCTGAGCC-3' (SEQ ID NO:65) and (ERFP2) 5'-CGCATGTGGCAGCTGTAGA-3' (SEQ ID NO:66) by Sequetech (Mountain View, Calif., USA).

The full-length sequence of each mutant clone was compared to the wild-type sequence of hrGFP. The mutations responsible for the observed phenotypic changes observed for the mutant clones are reported in Table 5, below.

TABLE 5

Amino acid mutations identified for each hrGFP mutant clone.

| Clone ID | AA Mutation | SEQ ID NOs of Polynucleotide and Polypeptide Sequences |
|---|---|---|
| GM1 | F43L | SEQ ID NO: 3 and SEQ ID NO: 4 |
| GM2 | E120G, V215V* | SEQ ID NO: 5 and SEQ ID NO: 6 |
| GM3 | L101M | SEQ ID NO: 7 and SEQ ID NO: 8 |
| GM4 | F43S | SEQ ID NO: 9 and SEQ ID NO: 10 |
| GM6 | R102C, R125H, K230N | SEQ ID NO: 11 and SEQ ID NO: 12 |
| T1 | N21I, E120G, K142N | SEQ ID NO: 13 and SEQ ID NO: 14 |
| T6 | Y103F | SEQ ID NO: 15 and SEQ ID NO: 16 |
| T8 | T32P, Y103F | SEQ ID NO: 17 and SEQ ID NO: 18 |
| T11 | E120G | SEQ ID NO: 19 and SEQ ID NO: 20 |
| T12 | F43S, Y103F, V123E, V215V* | SEQ ID NO: 21 and SEQ ID NO: 22 |
| T13 | F43S, Y103F, V123E | SEQ ID NO: 23 and SEQ ID NO: 24 |
| T14 | N21I, Y103F, E120G, K142N, T207A, F214I | SEQ ID NO: 25 and SEQ ID NO: 26 |
| T15 | V109A, E120G, K142N | SEQ ID NO: 27 and SEQ ID NO: 28 |
| T17 | M16V, N21I, E120G, K142N, S173C | SEQ ID NO: 29 and SEQ ID NO: 30 |

Each mutation lists the original and the substituted amino acid, e.g., "F43L" denotes an animo acid substitution wherein the phenylalanine at position 43 was replaced with leucine.
*"V215V" denotes a nucleotide substitution G645A.

All of the amino acid substitutions listed above should be decreased by one residue when referring to the wild type GFP sequence. The valine at position two in the hrGFP sequence is absent from the wild-type GFP sequence (i.e., the wild type sequence begins "Met Ser Lys Gln", while the hrGFP sequence begins "Met Val Ser Lys Gln"). Therefore, for instance, the M16V substitution of the hrGFP mutant T17 would be M15V in the wild-type protein.

Example 4

Spectral Analysis of Bacterial Lysates of Mutant hrGFP Clones

Crude bacterial lysates were prepared from cells expressing either wild-type or mutant hrGFP protein using the B-Per Bacterial Protein Extraction Reagent (Pierce Chemical Co., Rockford, Ill., USA). Briefly, cells expressing a single fluorescent protein (determined by plate screening method in Example 2) were transferred to a 1.5 ml microcentrifuge tube containing 0.5 ml LB. The tube was centrifuged for 1 minute at 13,000 rpm. The supernate was removed, 0.3 ml of B-Per Reagent was added to the pellet and the tube was vortexed for 1 minute. The tube was incubated on dry ice for 10 minutes, allowed to thaw at room temperature, then centrifuged for 10 minutes at 13,000 rpm. The lysate was collected and analyzed on a SHIMADZU Spectrofluorophotometer RF-1501. For wild-type hrGFP and every mutant hrGFP clone except T11 and T17 the excitation spectrum was collected holding the emission constant at 550 nm and the emission spectrum was collected holding the excitation constant at 450 nm. For clones T11 and T17 the excitation spectrum was collected at a constant emission of 650 nm and the emission spectrum was collected at a constant excitation of 585 nm.

Figure 1A:
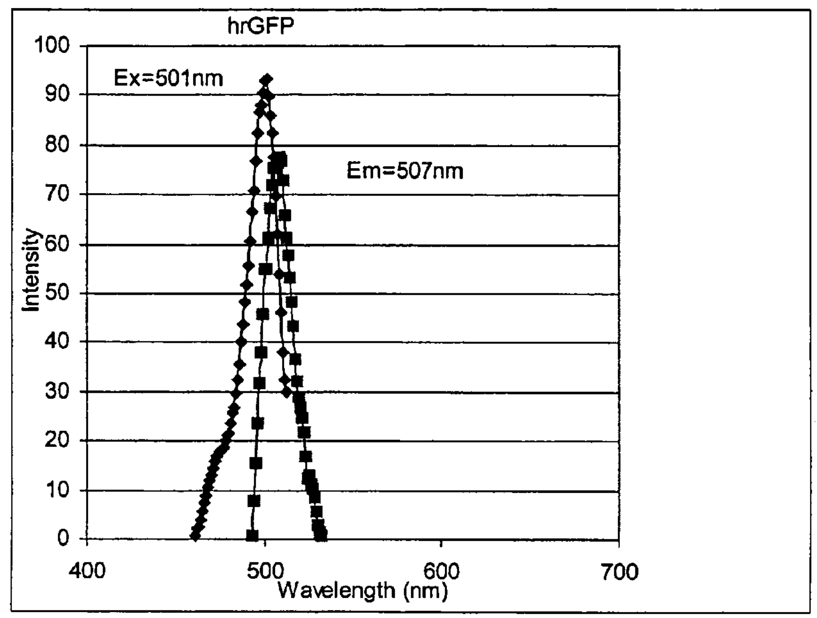
FIGS. 1A, 1B, 1C and 1D are graphs showing the excitation (♦) and emission (■) spectra of hrGFP (FIG. 1A), hrGFP mutant GM2 (FIG. 1B), hrGFP mutant T11 (FIG. 1C) and hrGFP mutant T17 (FIG. 1D).
Figure 1B:
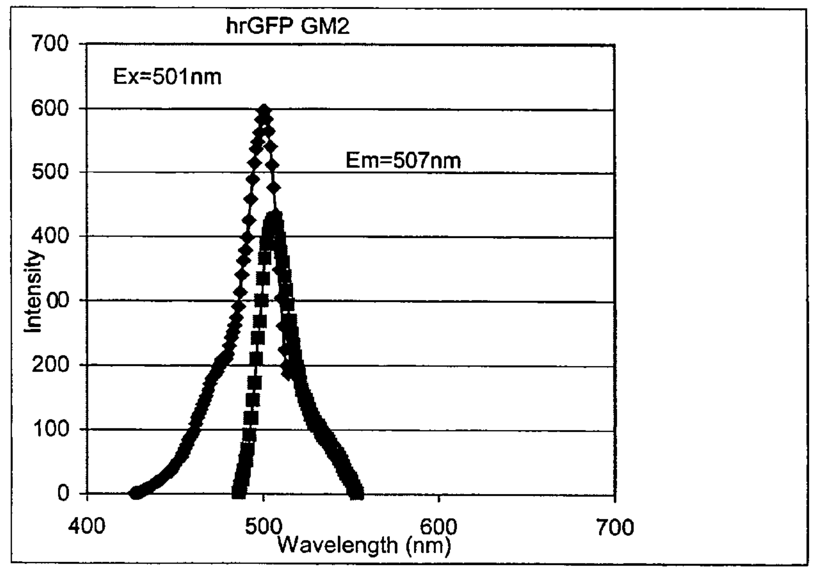
Figure 1C:
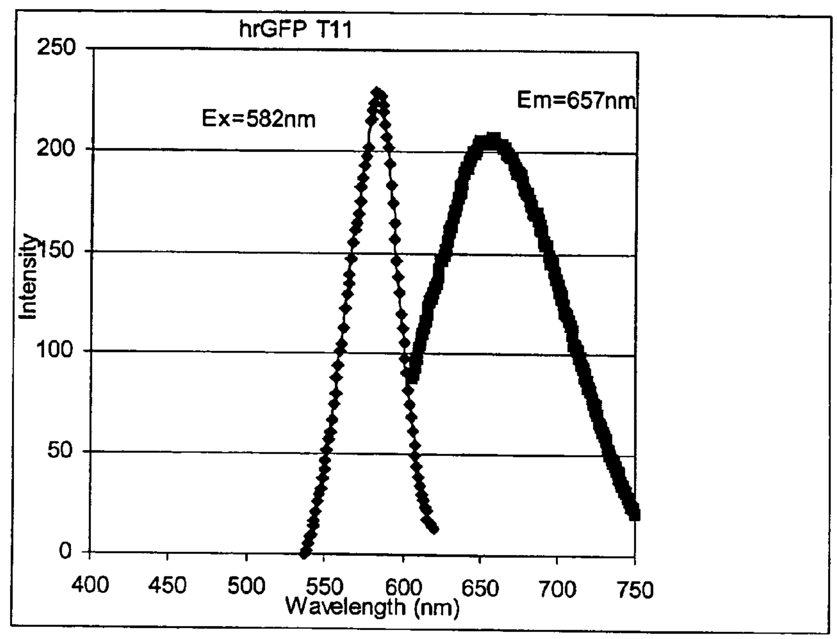
Figure 1D:
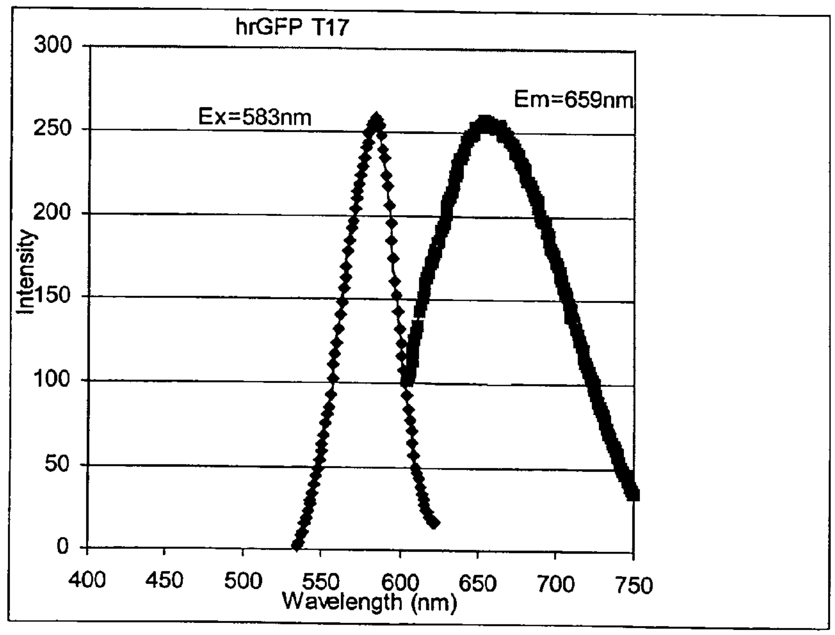

The spectral profiles are shown in FIGS. 1A–1D for wild-type hrGFP (FIG. 1A), clone GM2 (FIG. 1B), an example of a brighter/yellow-shifted mutant, and both red-shifted clones T11 (FIG. 1C) and T17 (FIG. 1D). The hrGFP profile is characterized by a narrow excitation and emission spectra with excitation and emission maximums of 501 nm and 507 nm, respectively. In comparison, the spectra for the brighter/yellow-shifted GM2 clone shows a slight broadening of both the excitation and emission spectrums while the excitation and emission maximums are unchanged. The spectral profiles for the two red-shifted clones, T11 and T17, are also shown in FIG. 1. Both T11 and T17 mutants show similar spectrums and maximums and are characterized by narrow excitation and broader emission spectrums. The excitation and emission maximums for each clone are reported in Table 6, below.

TABLE 6

Excitation and Emission Maximums for hrGFP and each hrGFP Mutant Clone.

| Clone ID | Excitation Maximum | Emission Maximum |
|---|---|---|
| WT | 501 mm | 507 nm |
| GM1 | 500 nm | 505 nm |
| GM2 | 501 mm | 507 nm |
| GM3 | 499 nm | 505 nm |
| GM4 | 501 mm | 506 nm |
| GM6 | 500 nm | 506 nm |
| T1 | 500 nm | 506 nm |
| T6 | 501 mm | 505 nm |
| T8 | 499 nm | 506 nm |
| T11 | 582 nm | 657 nm |
| T12 | 499 nm | 505 nm |
| T13 | 500 nm | 507 nm |
| T14 | 499 nm | 504 nm |
| T15 | 500 nm | 506 nm |
| T17 | 583 nm | 659 nm |

Example 5

Introduction and Verification of hrGFP Mutations Into hrGFP Mammalian Expression Vectors The QuikChange® Multi Site-Directed Mutagenesis kit (Stratagene) was used to introduce the mutations previously identified by sequencing the hrGFP mutant clones (Table 5, above) into two different Vitality™ hrGFP Mammalian Expression Vectors (Stratagene). One (or more) phosphorylated mutagenic primers (Table 7, below) were incorporated into the pFBhrGFP and/or the phrGFP-C vector (Stratagene).

TABLE 7

Oligonucleotide Primers for Introduction of hrGFP Mutations into Mammalian Expression Vectors.

| AA Mutation | QuikChange Multi Primer |
|---|---|
| F43L | 5'-(Phosphate)AAGGGCAACATC (SEQ ID NO: 67) CTGTTAGGCAACCAGCTGGTG-3' |
| E120G | 5'-(Phosphate)ACATCAACCTGA (SEQ ID NO: 68) TCGAGGGGATGTTCGTGTACC-3' |
| V215V | 5'-(Phosphate)AGGACGGCGGCT (SEQ ID NO: 69) TCGTAGAGCAGCACGAGACC-3' |
| L101M | 5'-(Phosphate)TGTACGAGCGCA (SEQ ID NO: 70) CCATGCGCTACGAGGACGGC-3' |
| F43S | 5'-(Phosphate)AAGGGCAACATC (SEQ ID NO: 71) CTGTCCGGCAACCAGCTGGTG-3' |
| R102C | 5'-(Phosphate)TGTACGAGCGCA (SEQ ID NO: 72) CCCTGTGCTACGAGGACGGC-3' |
| R125H | 5'-(Phosphate)ATGTTCGTGTAC (SEQ ID NO: 73) CACGTGGAGTACAAGGGCCGC-3' |
| K230N | 5'-(Phosphate)TGACCAGCCTGG (SEQ ID NO: 74) GCAATCCCCTGGGCAGCCTG-3' |
| N21I | 5'-(Phosphate)ATGAGCTTCAAG (SEQ ID NO: 75) GTGATCCTGGAGGGCGTGGTG-3' |
| K142N | 5'-(Phosphate)ACGGCCCCGTGA (SEQ ID NO: 76) TGAAGAATACCATCACCGGC-3' |
| Y103F | 5'-(Phosphate)TACGAGCGCACC (SEQ ID NO: 77) CTGCGCTTCGAGGACGGCG-3' |
| T32P | 5'-(Phosphate)ACAACCACGTGT (SEQ ID NO: 78) TCCCCATGGAGGGCTGCGGC-3' |
| M16V | 5'-(Phosphate)GGCCTGCAGGAG (SEQ ID NO: 79) ATCGTGAGCTTCAAGGTG-3' |
| S173C | 5'-(Phosphate)TACCGCCTGAAC (SEQ ID NO: 80) TGCGGCAAGTTCTACAGC-3' |

The mutagenesis primers shown in Table 7 were designed to introduce mutations into the humanized version of the GFP nucleotide sequence. To introduce the same amino acid substitutions to the wild type nucleotide sequence, different primers need to be used, which match the non-humanized GFP nucleotide sequence, and introduce a codon coding for the desired amino acid substitution. Methods for designing and making such primers are well-known.

Clones were sequenced to verify positive clones using primers ERFP1 and ERFP2 (Example 3, above) and ultrapure DNA of each vector was prepared using the QIAfilter Plasmid Midi kit (Qiagen, Hilden, Germany) following the manufacturer's directions.

Example 6

Transient Transfection of Mutant hrGFP Clones in Mammalian Cells

To test the phenotype of the hrGFP mutants in mammalian cells, CHO, 293, and HeLa cells were transfected with the pFBhrGFP and/or the phrGFP-C mutant vectors generated in Example 5 using GeneJammer® transfection reagent (Stratagene) according to the manufacturer's instructions. The transfected cells were observed and photographed 24–72 hours post-transfection using the B2A/DM51 and G2A/DM580 fluorescent filter set (Omega Optical, Inc., Brattleboro, Vt., USA) on a Nikon Diaphot Microscope.

Figure 2A:
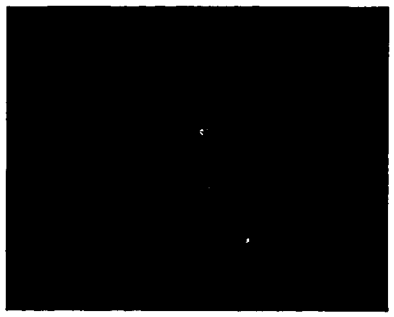
FIGS. 2A and 2B are photomicrographs showing the expression of wild type hrGFP (FIG. 2A) and hrGFP mutant GM2 (FIG. 2B) in CHO cells.
Figure 2B:
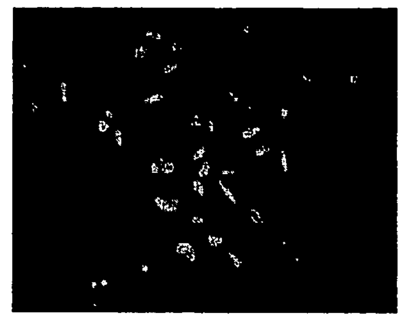

Pictures of CHO cells transfected with either phrGFP-C or phrGFP-C GM2 are shown in FIGS. 2A (wild type) and 2B (mutant GM2). This comparison clearly shows the GM2 clone is significantly brighter in fluorescence intensity than the wild-type hrGFP. A summary of the phenotype of each hrGFP mutant observed in prokaryotic and eukaryotic cells is presented in Table 8, below.

TABLE 8

Phenotype of hrGFP Mutants Expressed in Prokaryotic or Eukaryotic Cells

| Clone ID | Prokaryotic Phenotype | Eukaryotic Phenotype |
|---|---|---|
| GM1 | Brighter/Yellow-Shifted | Brighter Green |
| GM2 | Brighter/Yellow-Shifted | Brightest Green |
| GM3 | Brighter/Yellow-Shifted | Brighter Green |
| GM4 | Brighter/Yellow-Shifted | Brighter Green |
| GM6 | Brighter/Yellow-Shifted | Brighter Green |
| T1 | Brighter/Yellow-Shifted | Brighter Green |
| T6 | Brighter/Yellow-Shifted | Brighter Green |
| T8 | Brighter/Yellow-Shifted | Brighter Green |
| T11 | Red | Brighter Green |
| T12 | Brighter/Yellow-Shifted | In Progress |
| T13 | Brighter/Yellow-Shifted | In Progress |
| T14 | Brighter/Yellow-Shifted | In Progress |
| T15 | Brighter/Yellow-Shifted | In Progress |
| T17 | Red | Brighter Green |

While every brighter green/yellow-shifted mutant shows the same phenotype in both cell types, clones T11 and T17 only appear red-shifted in prokaryotic cells.

Example 7

FACS Analysis of Mammalian Cells Expressing hrGFP and the GM2 Mutant

Cells were transfected and observed for fluorescence according to Example 6. At appropriate time points cells were harvested for FACS analysis by incubation with 0.05%

Trypsin until the cells detached from the bottom of the tissue culture plate. The cells were collected by centrifugation and resuspended in 0.5 ml Phosphate Buffered Saline pH 7.4. Each sample was analyzed for green fluorescence on a Flow Cytometer by Cytometry Research, LLC (San Diego, Calif., USA).

FIGS. 35A–C show the results of the FACS analysis at 48 hours post-transfection. The results show HeLa cells alone (FIG. 35A) and HeLa cells expressing hrGFP (FIG. 35B) or the hrGFPGM2 Mutant (FIG. 35C). The graphs show the number of cells (counts) on the y-axis verses the fluorescent intensity (log scale) of each cell on the x-axis. Statistical analysis of each sample is based on the number of cells that fall within region M1 (defined by a background of 1.08% of total cells collected in the negative control 1C and by a cell having a fluorescent intensity from 10–10,000.) The Mean reflects the total fluorescence intensity observed in M1 divided by the number of cells in M1, which controls for differences in transfection efficiency between samples. The cells transfected with hrGFP (FIG. 35B) have a Mean in M1 of 1328.43 and the cells transfected with GM2 (FIG. 35C) have a Mean in M1 of 2455.40, this is a 1.8 fold increase in fluorescence intensity for the GM2 mutant. The results are also shown in Table 9, below.

TABLE 9

Improved brightness of several of the proteins in vivo.

| Cell Line | FP | Time Point | Mean | GM2/hrGFP at 48 hr | GM2/EGFP at 48 hr |
|---|---|---|---|---|---|
| HeLa | hrGFP | 24 hr | 904 | | |
| | hrGFP | 48 hr | 1328 | | |
| | GM2 | 24 hr | 2013 | | |
| | GM2 | 48 hr | 2455 | 1.8× | 3.4× |
| | EGFP | 24 hr | 665 | | |
| | EGFP | 48 hr | 704 | | |
| 293 | hrGFP | 24 hr | 1992 | | |
| | hrGFP | 48 hr | 2614 | | |
| | GM2 | 24 hr | 3049 | | |
| | GM2 | 48 hr | 3400 | 1.3× | 1.9× |
| | EGFP | 24 hr | 2061 | | |
| | EGFP | 48 hr | 1774 | | |
| COS | hrGFP | 24 hr | 2239 | | |
| | hrGFP | 48 hr | 3326 | | |
| | GM2 | 24 hr | 3433 | | |
| | GM2 | 48 hr | 4215 | 1.2× | 1.2× |
| | EGFP | 24 hr | 3104 | | |
| | EGEP | 48 hr | 3290 | | |

Example 8

Comparison of Expression of Humanized Versus Wild Type Genes Encoding *R. reniformis* GFP The humanized *R. reniformis* GFP coding sequence can be tested for expression in several human, rodent and monkey cell lines. Fluoresence levels are expected to be substantially higher for the humanized rGFP (hrGFP) gene compared with that for rGFP. In a direct comparison between cell populations harboring single copy proviral expression cassettes encoding either hrGFP or the humanized, red-shifted *Aequorea* GFP (EGFP), relative fluorescence intensity is expected to be comparable between the two genes.

Viral Transduction. One day prior to transduction, 293 cells (human) or CHO cells (hamster) are plated in DMEM supplemented with 10% FBS at $1\times10^5$ cells/well in a 6 well tissue culture dish. The following day the viral supernatants are serially diluted in DMEM+10% FBS to a final volume of 1.0 ml/sample, and supplemented with DEAE-Dextran (Sigma, St. Louis, Mo., catalog #D-9885) to a final concentration of 10 μg/ml. Culture medium is then removed from the target cells and replaced with 1 ml of viral dilution. Each diluted viral sample is applied to a well containing the target cells, and incubated for 3 hour, after which 1 ml of pre-warmed DMEM+10% FBS can be added to each well, and the plates are then incubated for 2 days. After 2 days the plates are washed twice with PBS, trypsinized, pelleted by centrifugation, and resuspended in 1.0 ml PBS. Cell suspensions can be stored on ice and analyzed by Fluorescence Activated Cell Sorting (FACS) within one hour. FACS analysis may optionally be performed by Cytometry Research Services (Sorrento Valley, Calif.).

Comparison of rGFP and hrGFP expression in vivo. To determine whether the sequence alterations introduced into the *R. reniformis* GFP gene results in enhanced expression, the hrGFP coding sequence may be inserted into the vector pFB, and the resulting vector pFB-hrGFP is then transfected side-by-side with the parental vector pFB-rGFP gene into CHO cells. Visual inspection of the transfected cells by fluorescence microscopy (excitation 450–490 nm; emission 520 nm) can be performed. CHO cells can then be infected with virus derived from the two vectors at equivalent multiplicities of infection (MOI), and two days following infection the transduced cells can be analyzed by fluorescence-activated cell sorting (FACS; excitation 488 nm, emission 515–545 nm).

The relative fluorescence can be compared from cells harboring single-copy proviral integrants encoding rGFP, hrGFP or EGFP. 293 cells are infected at low MOI, and two days post-infection the fluoresence levels are analysed by FACS. In the transduced populations, the overall fluorescence intensity of the populations is expected to be comparable for the hrGFP and EGFP expression vectors. Fluorescence for rGFP is expected to be significantly lower than for the latter two genes. Similar results are anticipated for experiments involving the transduction of HeLa, CHO, COS7 and NIH3T3 cells.

Example 9

Expression of Humanized *R. reniformis* GFP in Human Cells

Enhanced Expression. To confirm enhanced expression of a humanized *R. reniformis* GFP nucleic acid sequence in human cells, nucleic acid encoding the humanized sequence is expressed in human HeLa cells. Production of viral particles encoding the humanized GFP for transduction of human cells is carried out by co-transfecting 293 cells with 3 μg each of the retroviral packaging vectors pVPack-GP, pVPack-VSV-G (Stratagene) and pCFB-hrGFP (humanized *R. reniformis* GFP). The transfections are carried out according to Pear et al. (1997, *Methods in Molecular Medicine: Gene Therapy Protocols*, Robbind (Ed.) Humana Press, Totawa, N.J.), but modified by using the MBS Transfection Kit (Stratagene). Subsequently, $2\times10^5$ HeLa cells are infected with tissue culture supernatant containing no virus or containing virus prepared using pCFB-hrGFP. After 72 hours, cells are trypsinized and analyzed by FACS (Cytometry Research Services, Sorrento Valley, Calif.) using standard FITC filters.

Fluroescence Spectra. To confirm that the fluorescence spectra for the cloned, humanized gene encoding *R. reniformis* GFP is identical to that previously reported for the native protein, the fluorescence spectra of human cells expressing the humanized GFP is examined. HeLa cells transduced with the hrGFP-expressing retrovirus, described above, are lysed in PBS by three cycles of freeze-thawing using liquid nitrogen and a 37° C. water bath. The lysates are cleared by high-speed centrifugation, and the supernatants are then used for spectral analysis. Excitation and emission spectral analysis is determined using a Shimadzu RF-1501 Spectrofluorophotometer. Excitation and emission scans are performed on equal amounts of total protein prepared from transfected or untransfected HeLa cells. Background fluorescence is subtracted from the scans of the GFP-containing (transfected) extract by normalization to the scans of the untransfected extracts.

All patents, patent applications; and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A mutant Green Fluorescent Protein (GFP) from *Renilla reniformis*, selected from the group consisting of:

(a) the amino acid sequence of mutant GM1;
(b) the amino acid sequence of mutant GM2;
(c) the amino acid sequence of mutant GM3;
(d) the amino acid sequence of mutant GM4;
(e) the amino acid sequence of mutant GM6;
(f) the amino acid sequence of mutant T1;
(g) the amino acid sequence of mutant T6;
(h) the amino acid sequence of mutant T8;
(i) the amino acid sequence of mutant T11;
(j) the amino acid sequence of mutant T12;
(k) the amino acid sequence of mutant T13;
(l) the amino acid sequence of mutant T14;
(m) the amino acid sequence of mutant T15; and
(n) the amino acid sequence of mutant T17.

2. A polynucleotide encoding a mutant Green Fluorescent Protein (GFP) from *Renilla reniformis*, selected from the group consisting of:

(a) a polynucleotide encoding the amino acid sequence of mutant GM1;
(b) a polynucleotide encoding the amino acid sequence of mutant GM2;
(c) a polynucleotide encoding the amino acid sequence of mutant GM3;
(d) a polynucleotide encoding the amino acid sequence of mutant GM4;
(e) a polynucleotide encoding the amino acid sequence of mutant GM6;
(f) a polynucleotide encoding the amino acid sequence of mutant T1;
(g) a polynucleotide encoding the amino acid sequence of mutant T6;
(h) a polynucleotide encoding the amino acid sequence of mutant T8;
(i) a polynucleotide encoding the amino acid sequence of mutant T11;
(j) a polynucleotide encoding the amino acid sequence of mutant T12;
(k) a polynucleotide encoding the amino acid sequence of mutant T13;
(l) a polynucleotide encoding the amino acid sequence of mutant T14;
(m) a polynucleotide encoding the amino acid sequence of mutant T15; and
(n) a polynucleotide encoding the amino acid sequence of mutant T17.

3. The polynucleotide of claim 2, said polynucleotide being humanized.

4. A vector comprising the polynucleotide of claim 3.

5. A host cell containing the vector of claim 4.

6. A mutant Green Fluorescent Protein (GFP) from *Renilla reniformis*, selected from the group consisting of:

(a) the amino acid sequence of SEQ ID NO:34;
(b) the amino acid sequence of SEQ ID NO:36;
(c) the amino acid sequence of SEQ ID NO:38;
(d) the amino acid sequence of SEQ ID NO:40;
(e) the amino acid sequence of SEQ ID NO:42;
(f) the amino acid sequence of SEQ ID NO:44;
(g) the amino acid sequence of SEQ ID NO:46;
(h) the amino acid sequence of SEQ ID NO:48;
(i) the amino acid sequence of SEQ ID NO:50;
(j) the amino acid sequence of SEQ ID NO:52;
(k) the amino acid sequence of SEQ ID NO:54;
(l) the amino acid sequence of SEQ ID NO:56;
(m) the amino acid sequence of SEQ ID NO:58; and
(n) the amino acid sequence of SEQ ID NO:60.

7. A polynucleotide encoding a mutant Green Fluorescent Protein (GFP) from *Renilla reniformis*, selected from the group consisting of:

(a) the polynucleotide sequence of SEQ ID NO:33;
(b) the polynucleotide sequence of SEQ ID NO:35;
(c) the polynucleotide sequence of SEQ ID NO:37;
(d) the polynucleotide sequence of SEQ ID NO:39;
(e) the polynucleotide sequence of SEQ ID NO:41;
(f) the polynucleotide sequence of SEQ ID NO:43;
(g) the polynucleotide sequence of SEQ ID NO:45;
(h) the polynucleotide sequence of SEQ ID NO:47;
(i) the polynucleotide sequence of SEQ ID NO:49;
(j) the polynucleotide sequence of SEQ ID NO:51;
(k) the polynucleotide sequence of SEQ ID NO:53;
(l) the polynucleotide sequence of SEQ ID NO:55;
(m) the polynucleotide sequence of SEQ ID NO:57; and
(n) the polynucleotide sequence of SEQ ID NO:59.

8. The polynucleotide of claim 7, said polynucleotide being humanized.

9. A vector comprising the polynucleotide of claim 8.

10. A host cell containing the vector of claim 9.

11. A mutant Green Fluorescent Protein (GFP) from *Renilla reniformis*, selected from the group consisting of:

(a) the amino acid sequence of SEQ ID NO:4;
(b) the amino acid sequence of SEQ ID NO:6;
(c) the amino acid sequence of SEQ ID NO:8;
(d) the amino acid sequence of SEQ ID NO:10;
(e) the amino acid sequence of SEQ ID NO:12;
(f) the amino acid sequence of SEQ ID NO:14;
(g) the amino acid sequence of SEQ ID NO:16;
(h) the amino acid sequence of SEQ ID NO:18;
(i) the amino acid sequence of SEQ ID NO:20;
(j) the amino acid sequence of SEQ ID NO:22;
(k) the amino acid sequence of SEQ ID NO:24;
(l) the amino acid sequence of SEQ ID NO:26;
(m) the amino acid sequence of SEQ ID NO:28; and
(n) the amino acid sequence of SEQ ID NO:30.

12. A polynucleotide encoding a mutant Green Fluorescent Protein (GFP) from *Renilla reniformis*, selected from the group consisting of:

(a) the polynucleotide sequence of SEQ ID NO:3;
(b) the polynucleotide sequence of SEQ ID NO:5;
(c) the polynucleotide sequence of SEQ ID NO:7;
(d) the polynucleotide sequence of SEQ ID NO:9;
(e) the polynucleotide sequence of SEQ ID NO:11;
(f) the polynucleotide sequence of SEQ ID NO:13;
(g) the polynucleotide sequence of SEQ ID NO:15;
(h) the polynucleotide sequence of SEQ ID NO:17;
(i) the polynucleotide sequence of SEQ ID NO:19;
(j) the polynucleotide sequence of SEQ ID NO:21;
(k) the polynucleotide sequence of SEQ ID NO:23;
(l) the polynucleotide sequence of SEQ ID NO:25;
(m) the polynucleotide sequence of SEQ ID NO:27; and
(n) the polynucleotide sequence of SEQ ID NO:29.

13. A vector comprising the polynucleotide of claim 12.

14. A host cell containing the vector of claim 13.

15. A method of producing mutant *Renilla reniformis* GFP comprising the steps of:

(a) culturing a cell containing a recombinant vector comprising a wild type or humanized polynucleotide sequence encoding mutant *Renilla reniformis* GFP under conditions where the mutant *Renilla reniformis* GFP protein is expressed, wherein said polynucleotide sequence is selected from the group consisting of SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 and SEQ ID NO:29; and (b) isolating said mutant *Renilla reniformis* GFP protein from said cell, wherein said mutant *Renilla reniformis* GFP has a sequence selected from the group consisting of SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28 and SEQ ID NO:30;

thereby producing mutant *Renilla reniformis* GFP.

16. A method of producing a *Renilla reniformis* fusion protein, said method comprising the steps of: culturing a cell containing a polynucleotide sequence encoding said polypeptide of interest linked with a humanized polynucleotide encoding mutant *Renilla reniformis* GFP wherein said humanized polynucleotide is selected from the group consisting of SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 and SEQ ID NO:29, and wherein the linked polynucleotide sequences are fused in frame, under conditions where the mutant *Renilla reniformis* GFP protein is expressed.

17. A method of determining the location of a polypeptide of interest in a cell, said method comprising determining the location of the fusion protein of claim 16.

18. A method of identifying a cell into which a recombinant vector has been introduced, said method comprising the steps of:

(a) providing a cell containing a recombinant vector comprising a humanized polynucleotide which encodes mutant *Renilla reniformis* GFP, wherein said humanized polynucleotide is selected from the group consisting of SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 and SEQ ID NO:29, and wherein said cell permits expression of said humanized polynucleotide;

(b) illuminating said population with light within the excitation spectrum of mutant *Renilla reniformis* GFP; and (c) detecting fluorescence in the emission spectrum of mutant *Renilla reniformis* GEP in said population, where detection of fluorescence in the cell indicates that the recombinant vector has been introduced into the cell;

thereby identifying a cell into which said recombinant vector has been introduced.

19. The method of claim 18, wherein said GFP is expressed as a fusion polypeptide.

20. The method of claim 18, wherein said GFP is expressed as a distinct polypeptide.

21. The method of claim 18, wherein said cells are identified by FACS analysis.

22. A method of detecting the activity of a transcriptional regulatory sequence, said method comprising the steps of:

(a) culturing a cell containing a nucleic acid sequence comprising said transcriptional regulatory sequence operably linked to a humanized nucleic acid sequence encoding mutant *Renilla reniformis* GFP to form a reporter construct, under conditions where the mutant *Renilla reniformis* GFP is expressed, wherein said humanized nucleic acid sequence is selected from the group consisting of SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 and SEQ ID NO:29; and (b) detecting mutant *Renilla reniformis* GFP fluorescence in said cell, wherein detection of fluorescence indicates activity of said transcriptional regulatory sequence; thereby detecting the activity of a transcriptional regulatory sequence.

23. A method of detecting the presence of a modulator of a transcriptional regulatory sequence, said method comprising the steps of:

(a) culturing a cell containing a nucleic acid sequence comprising said transcriptional regulatory sequence operably linked to a humanized nucleic acid sequence encoding mutant *Renilla reniformis* GFP to form a reporter construct, under conditions where the mutant *Renilla reniformis* GFP is expressed, wherein said humanized nucleic acid sequence is selected from the group consisting of SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 and SEQ ID NO:29; and (b) detecting mutant *Renilla reniformis* GFP fluorescence in said cell, wherein said fluorescence indicates the presence of said modulator;

thereby detecting the presence of a modulator of a transcriptional regulatory sequence.

24. A method of screening for an inhibitor of a transcriptional regulatory sequence, said method comprising the steps of:

(a) culturing a cell containing a nucleic acid sequence comprising said transcriptional regulatory sequence operably linked to a humanized nucleic acid sequence encoding mutant *Renilla reniformis* GFP to form a reporter construct, under conditions where the mutant *Renilla reniformis* GFP is expressed, wherein said humanized nucleic acid sequence is selected from the group consisting of SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 and SEQ ID NO:29;

(b) contacting said cell with a candidate inhibitor of said transcriptional regulatory sequence; and (c) detecting mutant *Renilla reniformis* GFP fluorescence in said cell, wherein a decrease in said fluorescence relative to that detected in the absence of said candidate inhibitor indicates that said candidate inhibitor inhibits the activity of said transcriptional regulatory sequence.

25. A method of producing a fluorescent molecular weight marker, said method comprising the steps of:

(a) culturing a cell containing a humanized nucleic acid sequence encoding mutant *Renilla reniformis* GFP linked in frame to a nucleic acid sequence encoding a polypeptide of known relative molecular weight such that said linked molecules encode a fusion polypeptide, under conditions where the mutant *Renilla reniformis* GFP is expressed, wherein said humanized nucleic acid sequence is selected from the group consisting of SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27 and SEQ ID NO:29;

(b) isolating said fusion polypeptide from said cell, wherein said fusion polypeptide is a relative molecular weight marker.

26. The method of claims 15, 16, 18 or 22–25, wherein said cell is a mammalian cell.

27. The method of claims 15, 16, 18 or 22–25, wherein said cell is a human cell.

28. A mutant Green Fluorescent Protein (GFP) from *Renilla reniformis*, wherein the mutation comprises an amino acid substitution at one or more of the following residues:

(a) F43;

(b) E120;

(c) L101; and (d) Y103.

29. The mutant GFP of claim 28, wherein said mutation is E120G.

* * * * *